(12) United States Patent
Monahan et al.

(10) Patent No.: US 10,660,970 B2
(45) Date of Patent: May 26, 2020

(54) NUCLEIC ACID CONSTRUCTS AND METHODS OF USING THE SAME

(71) Applicant: GENEVANT SCIENCES GMBH, Basel (CH)

(72) Inventors: Sean D. Monahan, Lake Forest Park, WA (US); Michael S. DeClue, Seattle, WA (US); Pierrot Harvie, Seattle, WA (US); Russell N. Johnson, Seattle, WA (US); Amber E. Paschal, Redmond, WA (US); Mary G. Prieve, Lake Forest Park, WA (US); Debashish Roy, Seattle, WA (US); Charbel Diab, Tustin, CA (US); Michael E. Houston, Jr., Kirkland, WA (US); Anna Galperin, Seatlle, WA (US); Maher Qabar, Sammamish, WA (US)

(73) Assignee: Genevant Sciences GmbH, Basel (CH)

( * ) Notice: Subject to any disclaimer, the term of this patent is extended or adjusted under 35 U.S.C. 154(b) by 0 days.

(21) Appl. No.: 16/543,324

(22) Filed: Aug. 16, 2019

(65) Prior Publication Data

US 2019/0388551 A1 Dec. 26, 2019

Related U.S. Application Data

(63) Continuation of application No. 15/827,793, filed on Nov. 30, 2017, which is a continuation of application No. 14/908,351, filed as application No. PCT/US2014/048839 on Jul. 30, 2014, now Pat. No. 9,867,885.

(60) Provisional application No. 61/868,122, filed on Aug. 21, 2013, provisional application No. 61/860,136, filed on Jul. 30, 2013.

(51) Int. Cl.
| | |
|---|---|
| *A61K 47/64* | (2017.01) |
| *A01K 67/027* | (2006.01) |
| *A61K 38/08* | (2019.01) |
| *A61K 38/44* | (2006.01) |
| *A61K 47/54* | (2017.01) |
| *A61K 47/58* | (2017.01) |
| *A61K 48/00* | (2006.01) |
| *C08F 293/00* | (2006.01) |
| *C12N 15/113* | (2010.01) |
| *C12N 15/87* | (2006.01) |

(52) U.S. Cl.
CPC ........ *A61K 47/6455* (2017.08); *A01K 67/027* (2013.01); *A61K 38/08* (2013.01); *A61K 38/44* (2013.01); *A61K 47/549* (2017.08); *A61K 47/58* (2017.08); *A61K 48/0041* (2013.01); *C08F 293/005* (2013.01); *C12N 15/113* (2013.01); *C12N 15/87* (2013.01); *A01K 2207/05* (2013.01); *C12N 2310/14* (2013.01); *C12N 2310/351* (2013.01); *C12N 2320/32* (2013.01); *C12Y 113/12007* (2013.01)

(58) Field of Classification Search
None
See application file for complete search history.

(56) References Cited

U.S. PATENT DOCUMENTS

| | | | |
|---|---|---|---|
| 6,359,054 B1 | 3/2002 | Lemieux et al. | |
| 6,383,811 B2 | 5/2002 | Wolff et al. | |
| 6,410,057 B1 | 6/2002 | Kweon-Choi et al. | |
| 6,780,428 B2 | 8/2004 | Ranger et al. | |
| 6,835,393 B2 | 12/2004 | Hoffman et al. | |
| 6,919,091 B2 | 7/2005 | Trubetskoy et al. | |
| 6,939,564 B2 | 9/2005 | Ranger et al. | |
| 7,033,607 B2 | 4/2006 | Trubetskoy et al. | |
| 7,098,032 B2 | 8/2006 | Trubetskoy et al. | |
| 7,217,776 B1 | 5/2007 | Mallapragada et al. | |
| 7,524,680 B2 | 4/2009 | Wolff et al. | |
| 7,718,193 B2 | 5/2010 | Stayton et al. | |
| 7,737,108 B1 | 6/2010 | Hoffman et al. | |
| 8,962,757 B2 | 2/2015 | Devore et al. | |
| 9,006,193 B2 | 4/2015 | Stayton et al. | |
| 9,211,250 B2 | 12/2015 | Johnson et al. | |
| 2003/0134420 A1 | 7/2003 | Lollo et al. | |
| 2003/0191081 A1 | 10/2003 | Lemieux et al. | |

(Continued)

FOREIGN PATENT DOCUMENTS

| | | |
|---|---|---|
| EP | 2922554 A1 | 9/2015 |
| WO | WO 1999029303 A1 | 6/1999 |

(Continued)

OTHER PUBLICATIONS

Mori, et al. (1982) "Ornithine transcarbamylase in liver mitochondria", Molecular and Cellular Biochemistry, 49(2): 97-111 (Abstract Only), 2 pages long. (Year: 1982).*

(Continued)

*Primary Examiner* — Robert M Kelly
(74) *Attorney, Agent, or Firm* — Sterne, Kessler, Goldstein & Fox P.L.L.C.

(57) ABSTRACT

Described herein are block copolymers, and methods of making and utilizing such copolymers. The described block copolymers are disruptive of a cellular membrane, including an extracellular membrane, an intracellular membrane, a vesicle, an organelle, an endosome, a liposome, or a red blood cell. Preferably, in certain instances, the block copolymer disrupts the membrane and enters the intracellular environment. In specific examples, the block copolymer is endosomolytic and capable of delivering an oligonucleotide (e.g., an mRNA) to a cell. Compositions comprising a block copolymer and an oligonucleotide (e.g., an mRNA) are also disclosed.

30 Claims, 29 Drawing Sheets

Specification includes a Sequence Listing.

(56) References Cited

U.S. PATENT DOCUMENTS

| | | |
|---|---|---|
| 2004/0072784 A1 | 4/2004 | Sant et al. |
| 2004/0151775 A1 | 8/2004 | Rozema et al. |
| 2004/0162235 A1 | 8/2004 | Trubetskoy et al. |
| 2005/0260276 A1 | 11/2005 | Yang et al. |
| 2007/0003609 A1 | 1/2007 | Collin-Djangone et al. |
| 2007/0037891 A1 | 2/2007 | Esfand et al. |
| 2007/0059271 A1 | 3/2007 | Kataoka et al. |
| 2007/0110709 A1 | 5/2007 | Ranger et al. |
| 2008/0069902 A1 | 3/2008 | Zhao et al. |
| 2008/0171067 A1 | 7/2008 | Govindan et al. |
| 2010/0150952 A1 | 6/2010 | Stayton et al. |
| 2011/0123636 A1 | 5/2011 | Stayton et al. |
| 2011/0281934 A1 | 11/2011 | Johnson et al. |
| 2011/0286957 A1 | 11/2011 | Prieve et al. |
| 2012/0251618 A1 | 10/2012 | Schrum et al. |
| 2013/0011362 A1 | 1/2013 | Monahan et al. |
| 2014/0155472 A1 | 6/2014 | Bancel et al. |
| 2015/0238619 A1 | 8/2015 | Stayton et al. |
| 2015/0283254 A1 | 10/2015 | Duvall et al. |
| 2016/0206750 A1 | 7/2016 | Monahan et al. |
| 2018/0243433 A1 | 8/2018 | Monahan et al. |
| 2018/0311381 A1 | 11/2018 | Bancel et al. |
| 2019/0030129 A1 | 1/2019 | Schrum et al. |

FOREIGN PATENT DOCUMENTS

| | | | |
|---|---|---|---|
| WO | WO 2003087188 A1 | 10/2003 | |
| WO | WO 2005108614 A2 | 11/2005 | |
| WO | WO 2009016166 A1 | 1/2006 | |
| WO | WO 2007008300 A2 | 1/2007 | |
| WO | WO 2008004978 A1 | 1/2008 | |
| WO | WO 2008022309 A2 | 2/2008 | |
| WO | WO 2008071009 A1 | 6/2008 | |
| WO | WO 2008153940 A1 | 12/2008 | |
| WO | WO 2009009025 A1 | 1/2009 | |
| WO | WO 2009021728 A2 | 2/2009 | |
| WO | WO 2009140421 A2 | 11/2009 | |
| WO | WO 2009140427 A2 | 11/2009 | |
| WO | WO 2009140429 A2 | 11/2009 | |
| WO | WO 2009140432 A2 | 11/2009 | |
| WO | WO 2010021770 A1 | 2/2010 | |
| WO | WO 2010053596 A1 | 5/2010 | |
| WO | WO 2010053597 A2 | 5/2010 | |
| WO | WO 2010054266 A2 | 5/2010 | |
| WO | WO 2010077678 A2 | 7/2010 | |
| WO | WO 2011060281 A1 | 5/2011 | |
| WO | WO 2011062965 A2 | 5/2011 | |
| WO | WO-2012019168 A2 | 2/2012 | |
| WO | WO-2013071047 A1 | 5/2013 | |
| WO | WO-2015138348 A1 | 9/2015 | |
| WO | WO-2015138357 A2 | 9/2015 | |
| WO | WO-2017201349 A1 | 11/2017 | |
| WO | WO-2018129586 A1 | 7/2018 | |
| WO | WO-2018183808 A1 | 10/2018 | |
| WO | WO-2019089818 A1 | 5/2019 | |
| WO | WO-2019104152 A1 | 5/2019 | |
| WO | WO-2019104195 A1 | 5/2019 | |

OTHER PUBLICATIONS

Wang, et al. (2017) "AAV Gene Therapy Corrects OTC Deficiency and Prevents Liver Fibrosis in Aged OTC-Knock Out Heterozygous Mice", Molecular Genetics and Metabolism, 120(4): 299-305. (Year: 2017).*

Hengge, et al. (2000) "Adeno-Associated Virus Expresses Transgenes in Hair Follicles and Epidermis", Molecular Therapy, 2(3): 188-94. (Year: 2000).*

Agarwal, A. et al., "Dual-Role Self-Assembling Nanoplexes for Efficient Gene Transfection and Sustained Gene Delivery," *Biomaterials* vol. 29, pp. 607-617 (2008).

Benoit, D.S.W. et al., "Resensitizing Multidrug Resistant Cells to Doxorubicin Through plk 1 Knockdown Using a Novel pH-Responsive Micelle siRNA Delivery System," *Abstracts of Society for Biomaterials Meeting*, 1 pg. (Apr. 22, 2009).

Boeckle, S. et al., "Purification of Polyethylenimine Polyplexes Highlights the Role of Free Polycations in Gene Transfer," *J. Gene Med.*, vol. 6, pp. 1102-1111 (2004).

Bulmus, V. et al., "A New pH-Responsive and Glutathione-Reactive, Endosomal Membrane-Disruptive Polymeric Carrier for Intracellular Delivery of Biomolecular Drugs," *Journal of Controlled Release* vol. 93, pp. 105-120 (Dec. 2003).

Cho, Y.W. et al., "Polycation Gene Delivery Systems: Escape from Endosomes to Cytosol," *Journal of Pharmacy and Pharmacology*, vol. 55, pp. 721-734 (2003).

Convertine, a.J. et al., "Development of a Novel Endosomolytic Diblock Copolymer for siRNA Delivery," *Journal of Controlled Release*, vol. 133, pp. 221-229 (Feb. 2009).

Dufresne, M-H. et al., "Characterization of Polyion Complex Micelles Designed to Address the Challenges of Oligonucleotide Delivery," *Pharmaceutical Research*, vol. 25, pp. 2083-2093 (Sep. 2008).

Duvall, C.L. et al., "Polymer Enhanced Intracellular Delivery of a Pro-apoptotic Peptide for Cancer Therapy," *Abstracts of Society for Biomaterials Meeting*, 1 pg. (Apr. 22, 2009).

Eliyahu, H. et al., "Novel Dextran-Spermine Conjugates as Transfecting Agents: Comparing Water-Soluble and Micellar Polymers," *Gene Therapy.*, vol. 12, pp. 494-503 (2005).

El-Sayed, M.E.H. et al., "Smart Polymeric Carriers for Enhanced Intracellular Delivery of Therapeutic Macromolecules," *Expert Opinion on Biological Therapy*, vol. 5, pp. 23-32 (Jan. 2005).

El-Sayed, M.E.H. et al., "Rational Design of Composition and Activity Correlations for pH-Sensitive and Glutathione-Reactive Polymer Therapeutics," *Journal of Controlled Release*, vol. 101, pp. 47-58 (2005).

Funhoff, A.J. et al., "Endosomal Escape of Polymeric Gene Delivery Complexes Is Not Always Enhanced by Polymers Buffering at Low pH," *Biomacromolecules*, vol. 5, pp. 32-39 (2004).

Gary, D.J. et al., "Polymer-Based siRNA Delivery: Perspectives on the Fundamental and Phenomenological Distinctions from Polymer-Based DNA Delivery," *J. Control. Release*, vol. 121, pp. 64-73 (2007).

Gaucher, G. et al., "Block Copolymer Micelles: Preparation, Characterization and Application in Drug Delivery," *J. Control. Release*, vol. 109, pp. 169-188 (Dec. 2005).

Germershaus, O. et al., "Gene Delivery Using Chitosan, Trimethyl Chitosan or Polyethylenglycoi-Graft-Trimethyl Chitosan Block Copolymers: Establishment of Structure-Activity Relationships in vitro," *J. Control. Release*, vol. 125, pp. 145-154 (2008).

Glinel, K. et al., "Responsive Polyelectrolyte Multilayers," *Colloids and Surfaces A: Physiochemical and Engineering Aspects*, vol. 303, pp. 3-13 (Aug. 2007).

Guo, Y. et al., "Capillary Electrophoresis Analysis of Poly( ethylene glycol) and Ligand-Modified Polylysine Gene Delivery Vectors," *Anal. Biochem.*, vol. 363, pp. 204-209 (2007).

Henry, S.M. et al., "pH-Responsive Poly(styrene-alt-maleic anhydride) Alkylamide Copolymers for Intracellular Drug Delivery," *Biomacromolecules*, vol. 7, pp. 2407-2414 (Aug. 2006).

Heredia, K.L. et al., "Reversible siRNA-Polymer Conjugates by RAFT Polymerization," *Chemical Communications*, vol. 28, pp. 3245-3247 (Jul. 2008).

Jensen, K.D. et al., "Antisense Oligonucleotides Delivered to the Lysosome Escape and Actively Inhibit the Hepatitis B Virus," *Bioconjugate Chemistry*, vol. 13, pp. 975-984 (Sep.-Oct. 2002).

Jeong, J.H. et al., "siRNA Conjugate Delivery Systems," *Bioconjugate Chemistry*, vol. 20, pp. 5-14 (Jan. 2009).

Jeong, Y.H. et al., "Cellular Recognition of Paclitaxel-Loaded Polymeric Nanoparticles Composed of Poly(γ-benzyl L-glutamate) and Poly( ethylene glycol) Diblock Copolymer Endcapped with Galactose Moiety," *International Journal of Pharmaceutics*, vol. 296, pp. 151-161 (Apr. 2005).

Kataoka, K. et al., "Smart Polymeric Micelles as Nanocarriers for Oligonucleotides and siRNA Delivery," *Nucleic Acids Symposium Series*, vol. 49, pp. 17-18 (Sep. 2005).

Lam, J. K.W. et al., "Phosphocoline-polycation Diblock Copolymers as Synthetic Vectors for Gene Delivery," *J. Control. Release*, vol. 100, pp. 293-312 (2004).

(56) References Cited

OTHER PUBLICATIONS

Lee, E. S. et al., "Super pH-Sensitive Multifunctional Polymeric Micelle," *Nano Letters*, vol. 5, pp. 325-329 (Feb. 2005).
Lomas, H. et al., "Biomimetic pH Sensitive Polymersomes for Efficient DNA Encapsulation and Delivery," *Adv. Mater.*, vol. 19, pp. 4238-4243 (2007).
Lundy, B. B. et al., "Neutral Polymeric Micelles for RNA Delivery," *Bioconjugate Chemistry*, vol. 24(3), pp. 398-407 (Mar. 20, 2013).
Meyer, M. et al., "Synthesis and Biological Evaluation of a Bioresponsive and Endosomolytic siRNA-Polymer Conjugate," *Molecular Pharmaceutics*, vol. 6, pp. 752-762 (May-Jun. 2009).
Murthy, N. N et al., "The Design and Synthesis of Polymers for Eukaryotic Membrane Disruption," *J. Control. Release*, vol. 61, pp. 137-143 (Aug. 1999).
Murthy, N. et al., "Bioinspired pH-Responsive Polymers for the Intracellular Delivery of Biomolecular Drugs," *Bioconjugate Chemistry*, vol. 14, pp. 412-419 (Mar.-Apr. 2003).
Nagasaki, Y. et al., "Sugar-Installed Block Copolymer Micelles: Their Preparation and Specific Interaction with Lectin Molecules," *Biomacromolecules*, vol. 2, pp. 1067-1070 (Winter 2001).
Nelson, C.E. et al., "Balancing Cationic and Hydrophobic Content of PEGylated siRNA Polyplexes Enhances Endosome Escape, Stability, Blood Circulation Time, and Bioactivity in Vivo," *ACS Nano*, vol. 7, pp. 8870-8880 (2013).
Neu, M. et al., "Recent Advances in Rational Gene Transfer Vector Design Based on Poly( ethylene imine) and its Derivatives," *J. Gene Med.*, vol. 7, pp. 992-1009 (2005).
Ogris, M. et al., "PEGylated DNA/transferrin-PEI Complexes: Reduced Interaction with Blood Components, Extended Circulation in Blood and Potential for Systemic Gene Delivery," *Gene. Ther.*, vol. 6, pp. 595-605 (1999).
Oishi, M. et al., "Lactosylated Poly(ethylene glycol)-siRNA Conjugate Through Acid-Labile b-Thiopropionate Linkage to Construct pH-Sensitive Polyion Complex Micelles Achieving Enhanced Gene Silencing in Hepatoma Cells," *Journal of the American Chemical Society*, vol. 127, pp. 1624-1625 (Feb. 2005).
Oishi, M. et al., "pH-Responsive Oligodeoxynucleotide (ODN)-Poly(Ethylene Glycol) Conjugate through Acid-Labile beta-Thiopropionate Linkage: Preparation and Polyion Complex Micelle Formation," *Biomacromolecules*, vol. 4, pp. 1426-1432 (Aug. 2003).
Oupicky, D. et al., "DNA Delivery Systems Based on Complexes of DNA with Synthetic Polycations and their Copolymers," *J. Control. Release*, vol. 65, pp. 149-171 (2000).
International Search Report and Written Opinion for PCT Application No. PCT/US2014/048839, United States Patent Office, United States, dated Oct. 27, 2014, 14 pages.
Read, M.L. et al., "Physiochemical and Biological Characterisation of an Antisense Oligonucleotide Targeted Against the bcl-2 mRNA Complexed with Cationic-Hydrophilic Copolymers," *European Journal of Pharmaceutical Sciences*, vol. 10, pp. 169-177 (May 2000).
Satturwar, P. et al., "pH-Responsive Polymeric Micelles of Poly-(ethylene glycol)-bpoly(alkyl(meth)acrylate-co-methacrylic acid): Influence of the Copolymer Composition on Self-Assembling Properties and Release of Candesartan Cilexetil," *European Journal of Pharmaceutics and Biopharmaceutics*, vol. 65, pp. 379-387(2007).
Sawant, R.M. et al., "'SMART' Drug Delivery Systems: Double-Targeted pH-Responsive Pharmaceutical Nanocarriers," *Bioconjugate Chemistry*, vol. 17, pp. 943-949 (Jun. 2006).
Scales, C.W. et al., "Corona-Stabilized lnterpolyelectrolyte Complexes of SiRNA with Nonimmunogenic, Hydrophilic/Cationic Block Copolymers Prepared by Aqueous RAFT Polymerization," *Macromolecules*, vol. 39, pp. 6871-6881 (2006).
Schellinger, J.G. et al., "Melittin-Grafted HPMA-Oligolysine Based Copolymers for Gene Delivery," *Biomaterials*, vol. 34(9), pp. 2318-2326 (Mar. 2013).
Segura, T. et al., "Synthesis and In Vitro Characterization of an ABC Triblock Copolymer for siRNA Delivery," *Bioconjugate Chemistry*, vol. 18, pp. 736-745 (May 2007).
Shi, J. et al., "Influence of Histidine Incorporation on Buffer Capacity and Gene Transfection Efficiency of HPMA-co-oligolysine Brush Polymers," *Biomacromolecules*, vol. 14(6), pp. 1961-1970 (Jun. 10, 2013).
Stayton, P.S. et al., "Intelligent Biohybrid Materials for Therapeutic and Imaging Agent Delivery," *Proceeding of the IEEE*, vol. 93, pp. 726-736 (Apr. 2005).
Stayton, P.S., "Smart pH-Responive Carriers for Intracellular Delivery of Biomolecular Drugs," in *"Fundamental Biomedical Technologies: Multifunctional Pharmaceutical Nanocarriers,"* vol. 4, V. Torchilin, ed., pp. 143-159, Springer Science+Business Media, LLC, New York (May 2008)
Torchilin, V.P., "Micellar Nanocarriers: Pharmaceutical Perspectives," *Pharmaceutical Research.* vol. 24, pp. 1-16 (Jan. 2007).
Wakebayashi, D. et al., "Lactose-Conjugated Polyion Complex Micelles Incorporating Plasmid DNA as a Targetable Gene Vector System: Their Preparation and Gene Transfecting Efficiency Against Cultured HepG2 cells," *J. Control. Release* vol. 95, pp. 653-664 (Mar. 2004).
Wang, L. et al., "Delivery of Antisense Oligonucleotides Using HPMA Polymer: Synthesis of a Thiol Polymer and its Conjugation to Water-soluble Molecules," *Bioconjugate Chemistry*, vol. 9, pp. 749-757 (Nov.-Dec. 1998).
Wilson, J.T. et al., "pH-Responsive Nanoparticle Vaccines for Dual-Delivery of Antigens and Immunostimulatory Oligonucleotides," *ACS Nano*, vol. 7(5), pp. 3912-3925, (May 28, 2013).
Yamamoto, S. et al. "Temperature and pH-Responsive Dense Copolymer Brushes Prepared by ATRP," *Macromolecules*, vol. 41, pp. 7013-7020 (Oct. 2008).
Yasugi, K. et al., "Sugar-Installed Polymer Micelles: Synthesis and Micellization of Poly( ethylene glycol)-Poly(D,L-lactide) Block Copolymers Having Sugar Groups at the PEG Chain End," *Macromolecules*, vol. 32, pp. 8024-8032 (Nov. 1999).
Yessine, M.A. et al., "Proton-Actuated Membrane-Destabilizing Polyion Complex Micelles," *Bioconjugate Chemistry*, vol. 18, pp. 1010-1014 (May-Jun. 2007).
Zhao, X. et al., "Nanostructure of Polyplexes Formed Between Cationic Diblock Copolymer and Antisense Oligodeoxynucleotide and its Influence on Cell Transfection Efficiency," *Biomacromolecules*, vol. 8, pp. 3493-3502 (2007).

\* cited by examiner

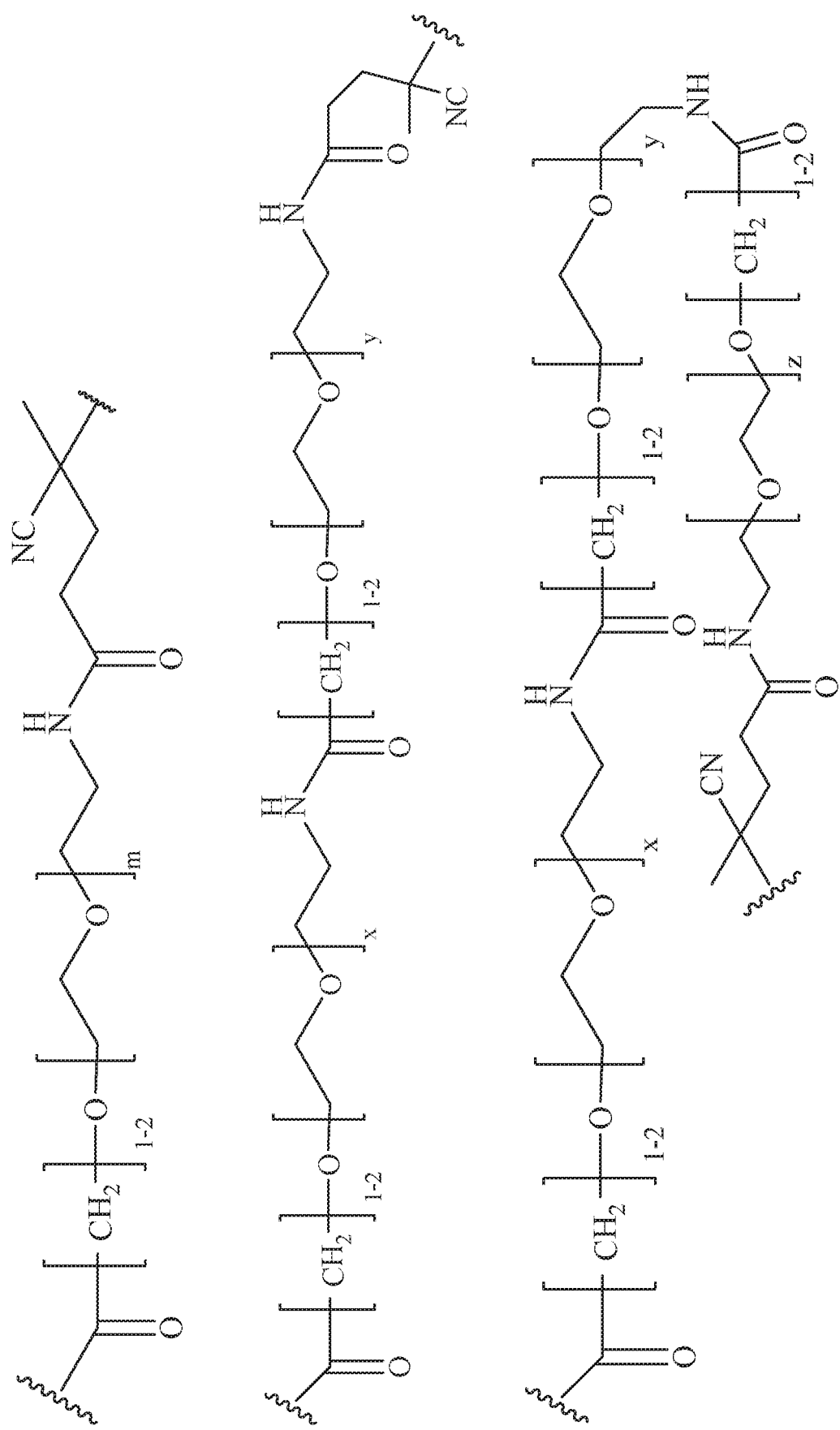
FIG. 10B (Cont. 1)

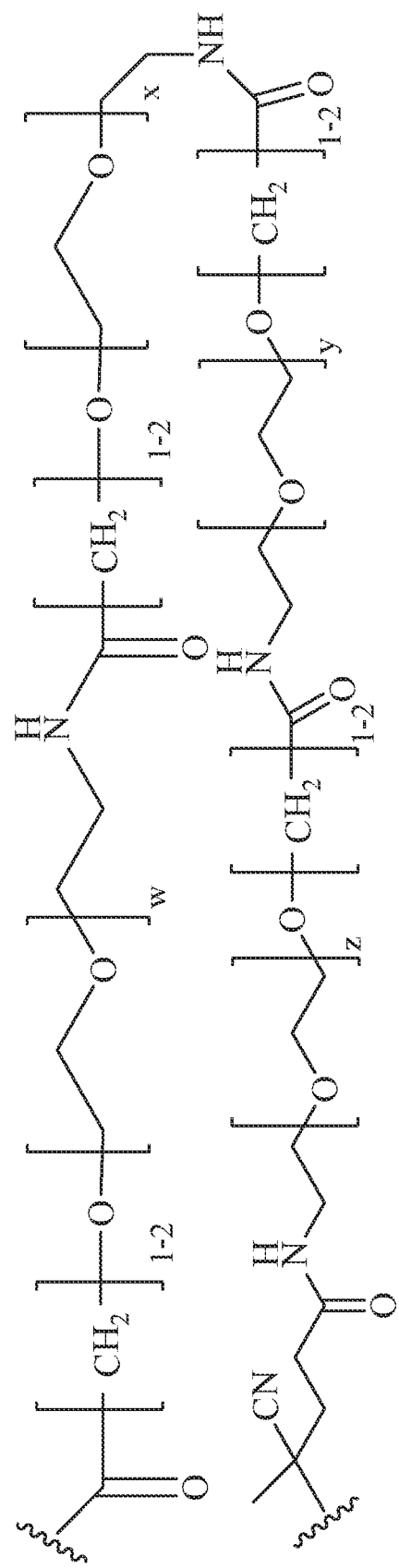
FIG. 10B (Cont. 2)

NUCLEIC ACID CONSTRUCTS AND METHODS OF USING THE SAME

CROSS-REFERENCE TO RELATED APPLICATIONS

This application is a continuation of U.S. application Ser. No. 15/827,793, filed Nov. 30, 2017, which is a continuation of U.S. application Ser. No. 14/908,351, filed Jan. 28, 2016, which is the National Stage of International Application No. PCT/US14/48839, filed Jul. 30, 2014, now issued as U.S. Pat. No. 9,867,885, which claims the benefit of U.S. Application No. 61/868,122, filed Aug. 21, 2013, and U.S. Application No. 61/860,136, filed Jul. 30, 2013, each of which is incorporated in its entirety by reference.

FIELD

This invention relates to the fields of organic chemistry, polymer chemistry, biochemistry, molecular biology and medicine. More particularly, this invention relates to copolymers, conjugates of copolymers with oligonucleotides, and complexes of copolymers with oligonucleotides to be used for delivery of oligonucleotides into cells.

SEQUENCE LISTING

This application contains a Sequence Listing electronically submitted in ASCII format via EFS-Web to the United States Patent and Trademark Office. Said ASCII Copy, created on Aug. 16, 2019, is named "4170_0030004_SL_ST25" and is 113,271 bytes in size. Due to the electronic filing of the Sequence Listing, the electronically submitted Sequence Listing serves as both the paper copy required by 37 C.F.R. § 1.821(c) and the CRF required by 37 C.F.R. § 1.821(e). The information contained in the Sequence Listing is hereby incorporated herein by reference.

BACKGROUND OF THE INVENTION

Various diseases today require a treatment which involves administration of peptide-, protein-, and nucleic acid-based drugs, particularly the transfection of nucleic acids into cells or tissues. The full therapeutic potential of peptide-, protein-, and nucleic acid-based drugs is currently compromised by their limited ability to cross the plasma membrane of mammalian cells, resulting in poor therapeutic efficacy.

RNA molecules have the capacity to act as potent modulators of gene expression in vitro and in vivo and therefore have great potential as nucleic acid based drugs. These molecules can function through a number of mechanisms utilizing either specific interactions with cellular proteins or base pairing interactions with other RNA molecules. RNA interference is a process of gene silencing that plays an important role in development and maintenance of the genome. The RNAi pathway is complex. It is initiated by the enzyme dicer which cleaves double stranded RNA (dsRNA) into fragments. An RNA-induced silencing complex (RISC) is then formed by base pairing between complementary mRNA and the guide strand of each new fragment. The passenger strand of each fragment is degraded. This formation of the RISC complex leads to translational silencing or degradation of the complementary mRNA by the endonuclease argonaute. Argonaute is the catalytic component of the complex. The short fragments are known as small interfering RNA (siRNA) and microRNA (miRNA) for example. Modulation of gene expression via RNA effector molecules, such as siRNA, has great therapeutic potential as the modulatory complexes formed, be they RNA-protein complexes or RNA-RNA complexes, are often highly specific. However, in order for such RNA effector molecules to modulate gene expression they must be present in the cell's cytoplasm to enter into the RISC Complex.

The delivery of exogenous oligonucleotides such as RNA molecules and other membrane impermeable compounds into living cells is highly restricted by the complex membrane systems of the cell. Typically, molecules used in antisense and gene therapies are large, negatively charged and hydrophilic molecules. These characteristics preclude their direct diffusion across the cell membrane to the cytoplasm. For this reason, the major barrier to the therapeutic use of oligonucleotides for modulation of gene expression is the delivery of the oligonucleotide to the cytoplasm. Transfection agents used in the art today typically comprise peptides, polymers, and lipids of a cationic nature as well as nano- and microparticles. These transfection agents typically have been used successfully only in in vitro reactions as the cationic nature of these systems, while facilitating both cell binding and binding of the oligonucleotide, renders them ineffective or toxic in vivo. Furthermore, the cationic charge of these systems causes interaction with serum components, which causes destabilization of the oligonucleotide-transfection reagent interaction and poor bioavailability and targeting. When transfecting nucleic acids in vivo further requirements have to be fulfilled. For example, the complex should not interact with parts of the complement system of the host. Additionally, the complex should protect the nucleic acid from early extracellular degradation by ubiquitously occurring nucleases. Furthermore, the carrier should not be recognized by the adaptive immune system (immunogenicity) and should not stimulate an acute immune response.

Although high transfection efficiencies are possible in vitro, achieving similar extents of transfection without toxicity is difficult in vivo. In general, exogenous unmodified nucleic acid molecules, particularly viral nucleic acids, introduced into the cell induce an innate immune response which results in cytokine and interferon (IFN) production and ultimately cell death. It is of great interest for therapeutics, diagnostics, reagents and for biological assays to be able to deliver a nucleic acid, e.g., a ribonucleic acid (RNA), into a cell, such as to cause intracellular translation of the nucleic acid and production of the encoded protein instead of generating an innate immune response. This delivery issue is currently the major prohibitive factor for the application of nucleic acid-based drugs, particularly RNA based therapeutics, in vivo. Thus, there remains a need for an effective delivery system for efficiently delivering nucleic acid-based drugs, particularly RNA based therapeutics, to cells and tissues. The present invention provides compositions and methods for the delivery and release of an oligonucleotide to a cell.

BRIEF SUMMARY

The present disclosure provides block copolymers for the effective delivery of an oligonucleotide to a cell. The present disclosure also provides for methods of using the block copolymers, methods of treatment using the block copolymers, processes for preparing the block copolymers and pharmaceutical compositions including the block copolymers.

In one example, the disclosure provides a block co-polymer of the formula I

T1-L1-[A]$_x$-[B]$_y$-Z        I where
T1 is absent or a first targeting moiety;
L1 is absent or a linking moiety;
A is a first block that is a polymer formed from monomers comprising formula A2 or a random copolymer formed from monomers comprising formulae A1, A2 and A3; A1 and A2; A2, A4 and A5; A2 and A5; or A4 and A5;

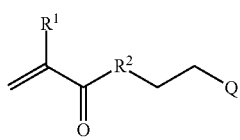

where $R^1$ is H or $C_1$-$C_6$ alkyl, $R^2$ is O, S, NH, N($C_1$-$C_6$ alkyl), or (OCH$_2$CH$_2$)$_{1-120}$, and Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, (OCH$_2$CH$_2$)$_{1-50}$, $C_1$-$C_6$ alkyl-(OCH$_2$CH$_2$)$_{1-50}$, or thioether,

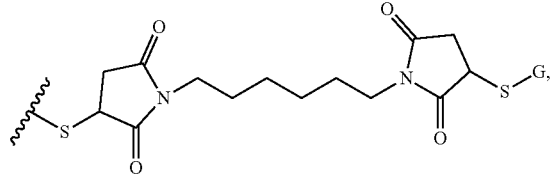

(v)

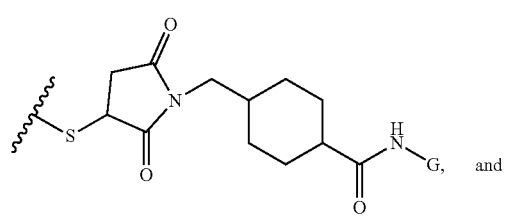

(vi)

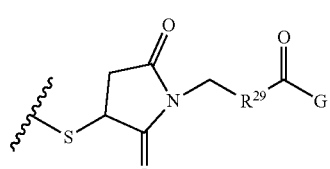

(vii)

where $R^{29}$ is $C_1$-$C_6$ alkyl, (OCH$_2$CH$_2$)$_{1-50}$, $C_1$-$C_6$ alkyl-(OCH$_2$CH$_2$)$_{1-50}$, O, NH, or N($C_1$-$C_6$ alkyl), (viii) S-S-L2-G wherein L2 is

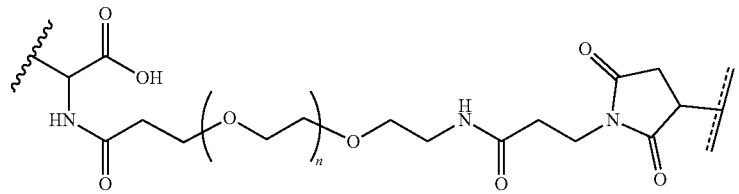

where n=1-35 and ===== designates a point of attachment of L2 to G,
where G is an oligonucleotide, cationic peptide, polyamine, or polycation;

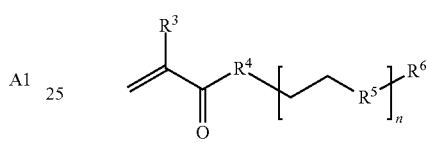

A2 where n is 1-120, $R^3$ is H or $C_1$-$C_6$ alkyl, $R^4$ is S, O, NH or N($C_1$-$C_6$ alkyl), $R^5$ is O or S and $R^6$ is H, $C_1$-$C_6$ alkyl, $C_1$-$C_6$ alkyl-NH$_2$, $C_1$-$C_6$ alkyl-NH($C_1$-$C_6$ alkyl), $C_1$-$C_6$ alkyl-N($C_1$-$C_6$ alkyl)$_2$;

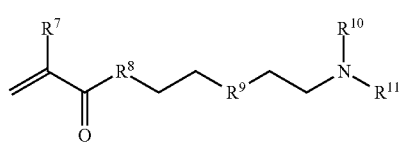

A3 where $R^7$ and $R^{10}$ are independently H or $C_1$-$C_6$ alkyl, $R^8$ is S, O, NH or N($C_1$-$C_6$ alkyl), and $R^9$ is O or S and $R^{11}$ is an amine protecting group;

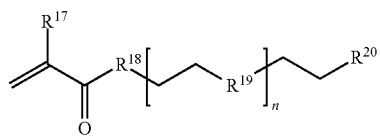

A4 where n is 1-230, $R^{17}$ is H or $C_1$-$C_6$ alkyl, $R^{18}$ is O, S, NH or N($C_1$-$C_6$ alkyl), $R^{19}$ is O or S, and $R^{20}$ is OH, NH, H, T2, or $C_1$-$C_6$ alkyl, where T2 is a second targeting moiety;

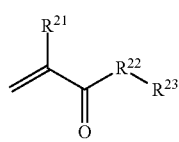

A5 where $R^{21}$ is H or $C_1$-$C_6$ alkyl, $R^{22}$ is O, NH or N($C_1$-$C_6$ alkyl), $R^{23}$ is H, aryl, arylhalide, alkyl, alkyl alcohol;

B is a second block that is a random copolymer formed from monomers comprising formulae B1, B2, B3 and B4 or B1, B2 and B3

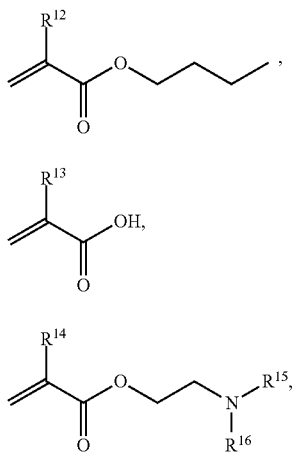

B1

B2

B3

-continued

B4

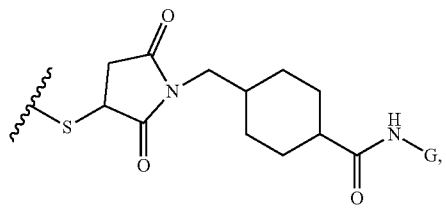

(vi)

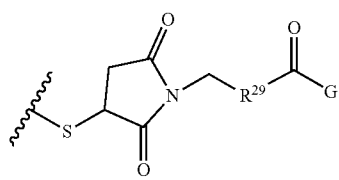

(vii)

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

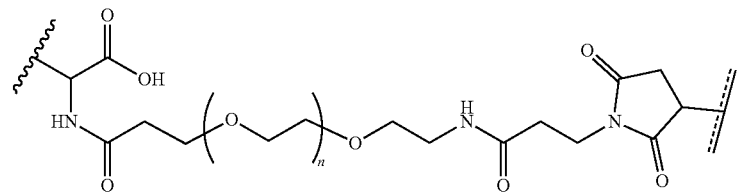

where n=1-35 and ===== designates a point of attachment of L2 to G, where G is an oligonucleotide, cationic peptide, polyamine, or polycation;

x is 2-20 kDa;

y is 2-20 kDa;

Z is H, SH, $C(CH_3)_2CN$,

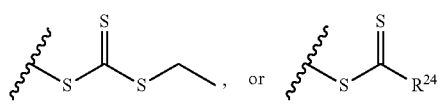

where $R^{24}$ is S—($C_1$-$C_{12}$ alkyl), aryl, arylhalide, O—($C_1$-$C_{12}$ alkyl), $NR^{25}R^{26}$ where $R^{25}$ and $R^{26}$ are independently H, alkyl, aryl, or heteroaryl;

the ratio of x to y is from 2:1 to 1:4; and

∿∿∿ designates a point of attachment.

In some embodiments of a copolymer of Formula I above, the monomer of formula A2 is

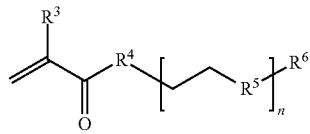

A2

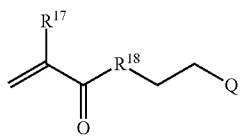

where $R^{12}$, $R^{13}$, $R^{14}$, $R^{15}$, $R^{16}$ and $R^{17}$ are independently H or $C_1$-$C_6$ alkyl, $R^{18}$ is O, S, NH, $N(C_1$-$C_6$ alkyl), or $(OCH_2CH_2)_{1-120}$, and Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, (v)

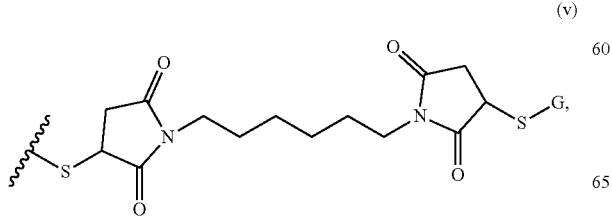

where n is 1-20, $R^3$ is H or $C_1$-$C_6$ alkyl, $R^4$ is S, O, NH or N($C_1$-$C_6$ alkyl), $R^5$ is O or S and $R^6$ is H, $C_1$-$C_6$ alkyl, $C_1$-$C_6$ alkyl-$NH_2$, $C_1$-$C_6$ alkyl-NH($C_1$-$C_6$ alkyl), $C_1$-$C_6$ alkyl-N($C_1$-$C_6$ alkyl)$_2$.

In another example, the disclosure provides a method for the intracellular delivery of an oligonucleotide comprising: a) contacting a block copolymer of Formula I as described above, where G is present and is an oligonucleotide, with a cell where the copolymer is introduced into an endosomal membrane within the cell through endocytosis; and b) destabilizing the endosomal membrane, whereby the copolymer or the oligonucleotide is delivered to the cytosol of the cell.

In another example, the disclosure provides a method of treating hepatocellular carcinoma, cholangiocarcinoma, hepatitis, hypercholesterolemia, liver fibrosis, pulmonary fibrosis or haemochromatosis comprising administering to a mammal in need thereof a therapeutically effective amount of a block copolymer of Formula I as described above, wherein Q is S-S-oligonucleotide,

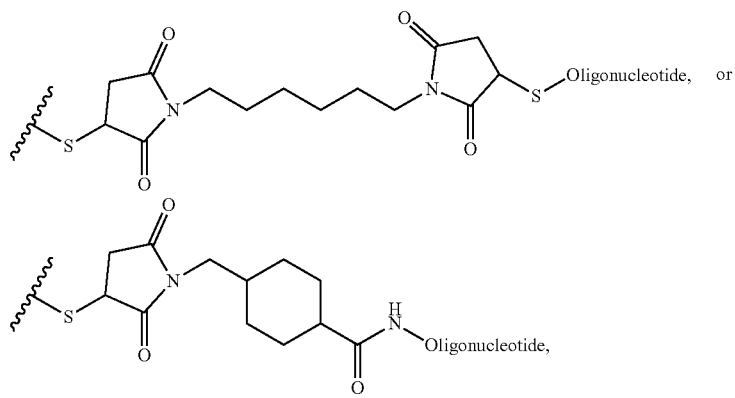

and ～～ designates a point of attachment.

In another example, the disclosure provides a pharmaceutical composition comprising a block copolymer of Formula I as described above and a pharmaceutically acceptable diluent or carrier, wherein Q is S-S-oligonucleotide,

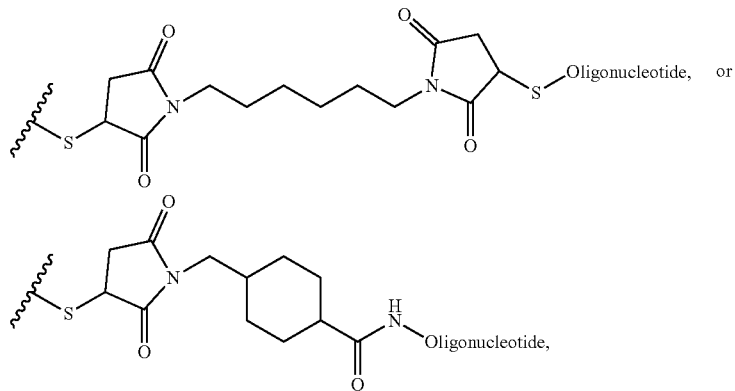

and ～～ designates a point of attachment.

In yet another example, the disclosure provides a pharmaceutical composition comprising a (a) block copolymer of Formula I wherein G is present and is cationic peptide, (b) an mRNA molecule, and (c) a pharmaceutically acceptable diluent or carrier.

In yet another example, the disclosure provides a process for preparation of the polymer of Formula I as described above including the steps of:

a) contacting a compound of Structure Va, Vb, Vc, or Vd,

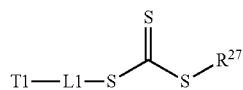
Va where $R^{27}=C_1-C_{12}$ alkyl,

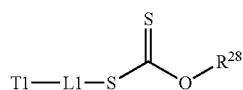
Vb where $R^{28}=C_1-C_{12}$ alkyl,

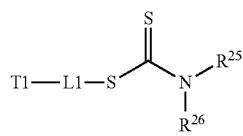
Vc where $R^{25}$ and $R^{26}$ are independently H, alkyl, aryl, or heteroaryl,

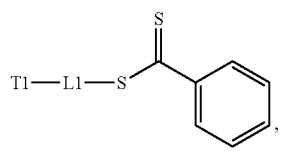
Vd where T1 is absent or a first targeting moiety and L1 is absent or a linking moiety; with one or more monomers selected from monomers of the formulae A1, A2 and A3,

A1 where $R^1$ is H or $C_1-C_6$ alkyl, $R^2$ is O, S, NH, N($C_1-C_6$ alkyl), or $[O(CH_2CH_2)]_{1-120}$, Q is —$SR^{20}$ or S-S-pyridyl, and $R^{20}$ is a thiol-protecting group;

A2 where n is 1-120, $R^3$ is H or $C_1-C_6$ alkyl, $R^4$ is S, O, NH or N($C_1-C_6$ alkyl), $R^5$ is O or S and $R^6$ is H, $C_1-C_6$ alkyl, $C_1-C_6$ alkyl-NH$_2$, $C_1-C_6$ alkyl-NH($C_1-C_6$ alkyl), $C_1-C_6$ alkyl-N($C_1-C_6$ alkyl)$_2$;

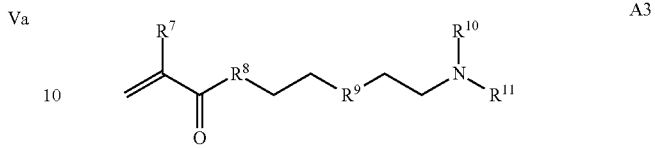
A3 where $R^7$ and $R^{10}$ are independently H or $C_1-C_6$ alkyl, $R^8$ is S, O, NH or N($C_1-C_6$ alkyl), and $R^9$ is O or S and $R^{11}$ is an amine protecting group; in the presence of a free radical;

b) contacting the product of step a) with monomers of formulae B1, B2 and B3,

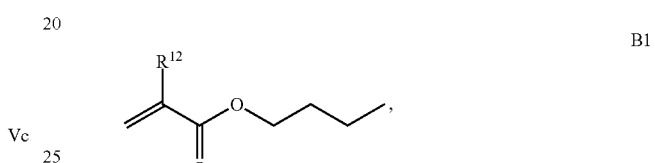
B1

B2

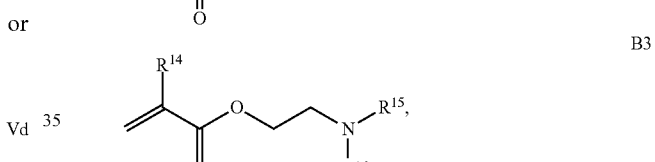
B3 where $R^{12}$, $R^{13}$, $R^{14}$, $R^{15}$ and $R^{16}$ are independently H or $C_1-C_6$ alkyl; in the presence of a free radical; and c) deprotecting the product of step b) and contacting it with an oligonucleotide, cationic peptide, polyamine, or polycation comprising a thiol-reactive or amine-reactive group; or contacting the product of step b) with an oligonucleotide, cationic peptide, polyamine, or polycation comprising a thiol group. In some embodiments where the product of step b) is contacted with a cationic peptide, polyamine, or polycation comprising a thiol-reactive or amine-reactive group, or with a cationic peptide, polyamine, or polycation comprising a thiol group, the process further includes contacting the product of step c) with a polynucleotide (e.g., an mRNA) to form a complex comprising the block copolymer of Formula I and the polynucleotide. In particular variations of a method as above, $R^{25}$ and/or $R^{26}$ is a heteroaryl having the structure:

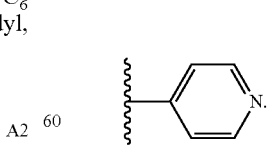

In some embodiments of a method as above, for the monomer of formula A2, n is 1-20.

In yet another example, the disclosure provides a process for preparation of the polymer of Formula I as described above including the steps of:

a) contacting a compound of Structure Va, Vb, Vc, or Vd,

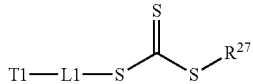
Va where $R^{27}=C_1$-$C_{12}$ alkyl,

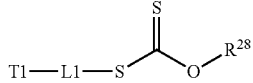
Vb where $R^{28}=C_1$-$C_{12}$ alkyl,

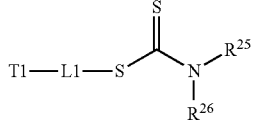
Vc where $R^{25}$ and $R^{26}$ are independently H, alkyl, aryl, or heteroaryl,

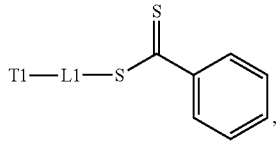
Vd where T1 is absent or a first targeting moiety and L1 is absent or a linking moiety; with one or more monomers selected from monomers of the formulae A2, A4 and A5,

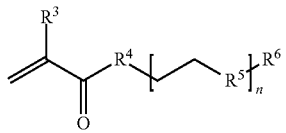
A2 where n is 1-120, $R^3$ is H or $C_1$-$C_6$ alkyl, $R^4$ is S, O, NH or N($C_1$-$C_6$ alkyl), $R^5$ is O or S and $R^6$ is H or $C_1$-$C_6$ alkyl;

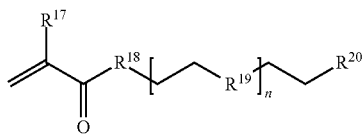
A4 where $R^{17}$ is H or $C_1$-$C_6$ alkyl, $R^{18}$ is O, S, NH or N($C_1$-$C_6$ alkyl), $R^{19}$ is O or N, $R^{20}$ is H, T2, or $C_1$-$C_6$ alkyl, where T2 is a second targeting moiety;

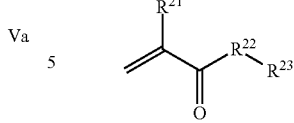
A5 where $R^{21}$ is H or $C_1$-$C_6$ alkyl, $R^{22}$ is O, NH or N($C_1$-$C_6$ alkyl), $R^{23}$ is H, aryl, arylhalide, alkyl, alkyl alcohol;

b) contacting the product of step a) with monomers of formulae B1, B2, B3, and B4,

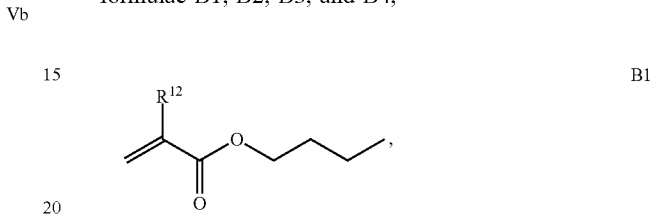
B1

B2

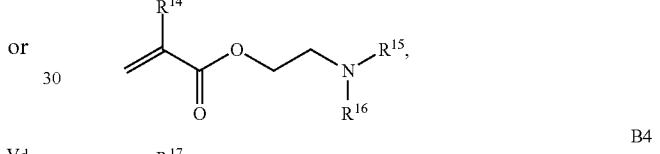
B3

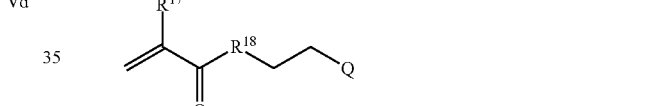
B4 where $R^{12}$, $R^{13}$, $R^{14}$, $R^{15}$, $R^{16}$ and $R^{17}$ are independently H or $C_1$-$C_6$ alkyl, $R^{18}$ is O, S, NH or N($C_1$-$C_6$ alkyl), and Q is —$SR^{20}$ or S-S-pyridyl, and $R^{20}$ is a thiol-protecting group; and c) deprotecting the product of step b) and contacting it with an oligonucleotide, cationic peptide, polyamine, or polycation comprising a thiol-reactive or amine-reactive group; or contacting the product of step b) with an oligonucleotide, cationic peptide, polyamine, or polycation comprising a thiol group. In some embodiments where the product of step b) is contacted with a cationic peptide, polyamine, or polycation comprising a thiol-reactive or amine-reactive group, or with a cationic peptide, polyamine, or polycation comprising a thiol group, the process further includes contacting the product of step c) with a polynucleotide (e.g., an mRNA) to form a complex comprising the block copolymer of Formula I and the polynucleotide. In particular variations of a method as above, $R^{25}$ and/or $R^{26}$ is a heteroaryl having the structure

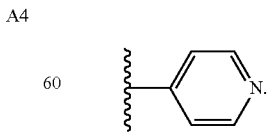

In some embodiments of a method as above, for the monomer of formula A2, n is 1-20.

In yet another example, the disclosure provides a compound of the formula

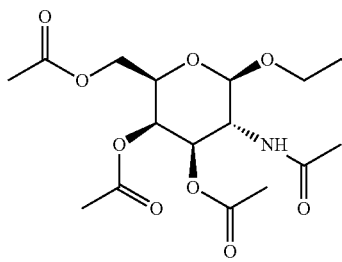
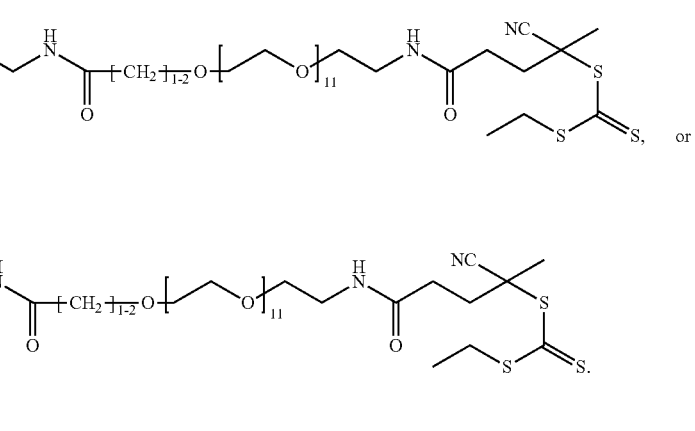
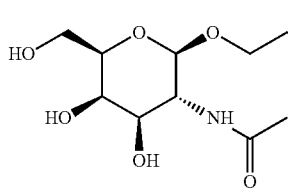

BRIEF DESCRIPTION OF THE FIGURES

The disclosure may be more completely understood in consideration of the following detailed description of various embodiments of the disclosure in connection with the accompanying Figures, in which.

DETAILED DESCRIPTION

Figure 1:
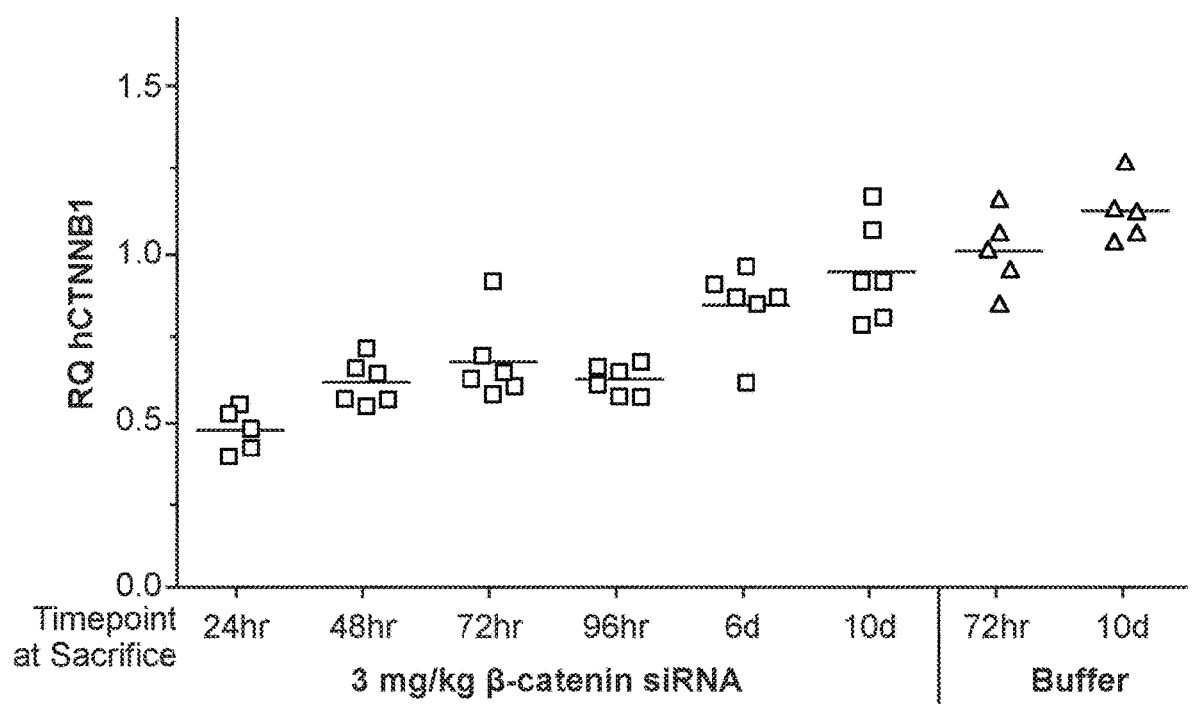
FIG. 1 is a graph demonstrating human β-catenin mRNA knockdown relative to human MET mRNA after β-catenin siRNA (si033)/polymer dosing.

The present invention is directed to copolymers, compositions, and methods useful for delivering oligonucleotides or other cell-impermeable molecules to mammalian cells. The following detailed description is not to be taken in a limiting sense. Unless defined otherwise, all technical and scientific terms used herein have the same meaning as commonly understood by one of ordinary skill in the art pertinent to the methods and compositions described. The definitions provided herein are to facilitate understanding of certain terms used frequently herein and are not meant to limit the scope of the present disclosure.

As used herein the term "alkyl" as used herein refers to a monovalent straight or branched hydrocarbon of from 1 to 12 carbon atoms. Examples of alkyl groups include, but are not limited to methyl, ethyl, n-propyl, isopropyl, n-butyl, sec-butyl, isobutyl, tert-butyl, n-pentyl, and n-hexyl.

As used herein, the term "block copolymer" refers to two or more homopolymer or copolymer subunits linked by covalent bonds. Block copolymers with two or three distinct blocks are called diblock copolymers and triblock copolymers, respectively. A schematic generalization of a diblock copolymer is represented by the formula $[F_fG_gH_h \ldots ]_q$-$[J_jK_kL_l \ldots ]_r$, wherein each letter stands for a constitutional unit derived from polymerization of a corresponding monomer and wherein each subscript to a constitutional unit represents the mole fraction of that unit in the particular block, the three dots indicate that there may be more (there may also be fewer) constitutional units in each block and q and r indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units and the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: f-f-g-h-f-g-g-h-g-h-h-h . . . . An exemplary alternating random configuration may have the non-limiting form: f-g-f-h-g-f-g-h-g-f-h . . . , and an exemplary regular alternating configuration may have the non-limiting form: f-g-h-f-g-h-f-g-h . . . . An exemplary regular block configuration may have the following non-limiting configuration: . . . f-f-f-g-g-g-h-h-h-f-f . . . , while an exemplary random block configuration may have the non-limiting configuration: f-f-f-h-h-f-f-g-g-g-h-h-h-f-f-h-h-h . . . . In a gradient polymer, the content of one or more monomeric units increases or decreases in a gradient manner from the α-end of the polymer to the ω-end. In none of the preceding generic examples is the particular juxtaposition of individual constitutional units or blocks or the number of constitutional units in a block or the number of blocks meant nor should they be construed as in any manner bearing on or limiting the actual structure of block copolymers described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers.

As used herein, the term "molecular weight" for a polymer or polymer block is the number average molecular weight. It is understood in the art that a population of polymer molecules will have a distribution of different molecular weights. This distribution of molecular weights can be described by the term dispersity index or polydispersity index (PI or PDI), which is the weight average molecular weight/number average molecular weight.

As used herein, the term heteroaryl is an aromatic heterocyclic ring. The heteroatom in a heteroaryl can be O, N, or S. Examples of heteroaryl include pyridyl or pyridine, imidazole, and oxazole.

As used herein, the term "antibody" refers to any immunoglobulin protein that specifically binds to an antigen, as well as antigen-binding fragments thereof and engineered variants thereof. Hence, the term "antibody" includes, for example, polyclonal antibodies, monoclonal antibodies, and antigen-binding antibody fragments that contain the paratope of an intact antibody, such as Fab, Fab', F(ab')$_2$ and F(v) fragments. Genetically engineered intact antibodies and fragments, such as chimeric antibodies, humanized antibodies, single-chain Fv fragments, single-chain antibodies, diabodies, minibodies, linear antibodies, multivalent or multispecific hybrid antibodies, and the like are also included. Thus, the term "antibody" is used expansively to include any protein that comprises an antigen binding site of an antibody and is capable of binding to its antigen. In some embodiments, an antibody has affinity to a cell surface molecule.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with cells and other effector functions. Typically, changes in the variable region will be made in order to improve the antigen binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, J. Mol. Recog. 12:131-140, 1999; Nguyen et al., EMBO J. 19:921-930, 2000) or from $V_H$ domains of other species to produce single-domain antibodies ("dAbs"; see Ward et al., Nature 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., Nature 362: 367-369, 1993; Qiu et al., Nature Biotechnol. 25:921-929, 2007). More commonly, an antigen-binding site of an antibody comprises both a heavy chain variable domain and a light chain variable domain that bind to a common epitope. Examples of molecules comprising an antigen-binding site of an antibody are known in the art and include, for example, Fv fragments, single-chain Fv fragments (scFv), Fab fragments, diabodies, minibodies, Fab-scFv fusions, bispecific (scFv)$_4$-IgG, and bispecific (scFv)$_2$-Fab. (See, e.g., Hu et al., Cancer Res. 56:3055-3061, 1996; Atwell et al., Molecular Immunology 33:1301-1312, 1996; Carter and Merchant, Curr. Opin. Biotechnol. 8:449-454, 1997; Zuo et al., Protein Engineering 13:361-367, 2000; and Lu et al., J. Immunol. Methods 267:213-226, 2002.)

As used herein, the terms "single-chain Fv" and "single-chain antibody" refer to antibody fragments that comprise, within a single polypeptide chain, the variable regions from both heavy and light chains, but lack constant regions. In general, a single-chain antibody further comprises a polypeptide linker between the $V_H$ and $V_L$ domains, which enables it to form the desired structure that allows for antigen binding. Single-chain antibodies are discussed in detail by, for example, Pluckthun in The Pharmacology of Monoclonal Antibodies, vol. 113 (Rosenburg and Moore eds., Springer-Verlag, New York, 1994), pp. 269-315. (See also WIPO Publication WO 88/01649; U.S. Pat. Nos. 4,946,778 and 5,260,203; Bird et al., Science 242:423-426, 1988.) Single-chain antibodies can also be bi-specific and/or humanized.

As used herein the term "oligonucleotide" refers to a polymer comprising 7-20,000 nucleotide monomeric units (i.e., from 7 nucleotide monomeric units to 20,000 nucleotide monomeric units, inclusive). Typical oligonucleotides in accordance with certain embodiments of the present invention include those comprising 7-20,000 nucleotide monomeric units, 7-15,000 nucleotide monomeric units, 7-10,000 nucleotide monomeric units, 7-5,000 nucleotide monomeric units and 7-1000 nucleotide monomeric units. Oligonucleotides include deoxyribonucleic acid (DNA) and ribonucleic acid (RNA), or their derivatives, and combinations of DNA, RNA. DNA may be in form of cDNA, in vitro polymerized DNA, plasmid DNA, parts of a plasmid DNA, genetic material derived from a virus, linear DNA, vectors (P1, PAC, BAC, YAC, and artificial chromosomes), expression vectors, expression cassettes, chimeric sequences, recombinant DNA, chromosomal DNA, anti-sense DNA, or derivatives of these groups. RNA may be in the form of messenger RNA (mRNA), in vitro polymerized RNA, recombinant RNA, transfer RNA (tRNA), small nuclear RNA (snRNA), ribosomal RNA (rRNA), chimeric sequences, dicer substrate and the precursors thereof, locked nucleic acids, anti-sense RNA, interfering RNA (RNAi), asymmetric interfering RNA (aiRNA), small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or their derivatives. In addition, DNA and RNA may be single, double, triple, or quadruple stranded. Double stranded RNA (dsRNA) and siRNA are of interest particularly in connection with the phenomenon of RNA interference. Examples of oligonucleotides as used herein include, but are not limited to, siRNA, an antisense oligonucleotide, a dicer substrate, a miRNA, an aiRNA or an shRNA. Further examples of oligonucleotides as used herein include, but are not limited to dsRNA having a length of from 17 to 29 nucleotides, or from 19 to 25 nucleotides, and being at least 90 percent, or 95 percent or 100 percent (of the nucleotides of a dsRNA) complementary to a coding or a non-coding section of the nucleic acid sequence of a therapeutically relevant protein or antigen. Ninety percent complementary means that a 20 nucleotide length of a dsRNA contains not more than 2 nucleotides without a corresponding complementarity with the corresponding section of the mRNA. Yet further examples of oligonucleotides as used herein include, but are not limited to single stranded mRNA which can be modified or unmodified. Modified mRNA includes those with at least two modifications and a translatable region. The modifications may be located on the backbone and/or a nucleoside of the nucleic acid molecule. The modifications may be located on both a nucleoside and a backbone linkage. Typically, mRNAs in accordance with certain compositions and methods of the present invention include those comprising 300-20,000 nucleotide monomeric units, 300-15,000 nucleotide monomeric units, 300-10,000 nucleotide monomeric units, 300-5,000 nucleotide monomeric units, 300-2000 nucleotide monomeric units, 300-1,500 nucleotide monomeric units, and 300-1000 nucleotide monomeric units. In some variations, an mRNA in accordance with compositions and methods of the present disclosure is at least 500, at least 1,000, at least 1,200, or at least 1,500 nucleotide monomeric units (e.g., from 500 to 20,000 nucleotide monomeric units; from 1,000 to 20,000 nucleotide monomeric units; from 1,200 to 20,000 nucleotide monomeric units; from 1,500 to 20,000 nucleotide monomeric units; from 500 to 15,000 nucleotide monomeric units; from 1000 to 15,000 nucleotide monomeric units; from 1,200 to 15,000 nucleotide monomeric units; from 1,500 to 15,000 nucleotide monomeric units; from 500 to 10,000 nucleotide monomeric units; from 1,000 to 10,000 nucleotide monomeric units; from 1,200 to 10,000 nucleotide monomeric units; from 1,500 to 10,000 nucleotide monomeric units; from 500 to 5,000 nucleotide monomeric units; from 1,000 to 5,000 nucleotide monomeric units; from 1,200 to 5,000 nucleotide monomeric units; from 1,500 to 5,000 nucleotide monomeric units; from 500 to 2,000 nucleotide monomeric units; from 1,000 to 2,000 nucleotide monomeric units; or from 1,200 to 2,000 nucleotide monomeric units).

As used herein the term "cationic peptide" refers to a polymer comprising 2-100 amino acid monomers whose overall charge is positive.

As used herein, the term "polycation" refers to a moiety having positive charges at a plurality of sites and whose overall charge is positive. Examples of polycations include but are not limited to spermine, spermidine, pentaethylenehexamine, tetraethylenepentamine, 1,4-bis(3-aminopropyl) piperazine, linear or branched polyethyleneimine, chitosan, polyvinylamine, poly(vinylpyridine), and amino cyclodextrins.

As used herein, a "targeting moiety" refers to a moiety that is capable of specifically binding to (i) a molecule on the surface of a target cell or (ii) a molecule that is capable of specifically binding to a molecule on the surface of a target cell, such as a cell within a target tissue of a subject. A molecule (e.g., cell surface molecule) that specifically binds to a targeting moiety is also referred to herein as a "binding partner." In some embodiments of copolymers and related compositions and methods as described herein, a targeting moiety specifically binds to a molecule on the surface of the target cell. Particularly suitable targeting moieties include antibodies, antibody-like molecules, polypeptides, proteins (e.g., insulin-like growth factor II (IGF-II)), peptides (e.g., an integrin-binding peptide such as an RGD-containing peptide), and small molecules such as, for example, sugars (e.g., lactose, galactose, N-acetyl galactoseamine (NAG), mannose, mannose-6-phosphate (M6P)) or vitamins (e.g., folate). In some variations, a targeting moiety is a protein derived from a natural ligand of a cell-surface molecule (e.g., derived from a cytokine or from the extracellular domain of a cell-surface receptor that binds to a cell surface counter-receptor). Examples of cell surface molecules that may be targeted by a targeting moiety of a copolymer provided herein include, but are not limited to, the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, the asialoglycoprotein receptor, mannose receptor, and the cation-independent mannose-6-phosphate/IGF-II receptor.

A "polypeptide" is a polymer of amino acid residues joined by peptide bonds, whether produced naturally or synthetically.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Some proteins are defined herein in terms of their amino acid backbone structures.

As used herein the term "peptide" refers to a polypeptide having 2-100 amino acid monomers.

A polypeptide that is a targeting moiety (e.g., T1 and/or T2) is also referred to herein as a "targeting polypeptide." A "targeting peptide" is a targeting polypeptide that has 2-100 amino acid monomers. Typically, targeting polypeptides as used herein target or deliver copolymers to target cells or tissues, or specific cells types and enhance the association of molecules with the target cells. Examples of targeting polypeptides as used herein include, but are not limited to, signal peptides, cell penetrating peptides such as TAT or KALA for example, integrin-binding peptides such as RGD-containing peptides, NL4, neurotensin, secretin, LOX-1 binding insulin, EGF, IGF-II, GE7 and transferrin. In some embodiments, a targeting polypeptide is a single-chain antibody.

As used herein the term "sugar" refers to saccharides such as monosaccharides, disaccharides, oligosaccharides, and polysaccharides for example. Typically, sugars as used herein target or deliver copolymers to target cells or tissues, or specific cells types and enhance the association of molecules with the target cells. For example, liver hepatocytes contain asialoglycoprotein (ASGP) receptors. Therefore, galactose-containing targeting groups may be used to target hepatocytes. Examples of galactose containing targeting groups include, but are not limited to, galactose or galactose derivatives such as its protected analogs, N-acetylgalactosamine or N-acetylgalactosamine derivatives such as its protected analogs, oligosaccharides, and saccharide clusters such as Tyr-Glu-Glu-(aminohexyl GalNAc)3, lysine-based galactose clusters, and cholane-based galactose clusters. Other examples of sugars include, but are not limited to, mannose and mannose derivatives such as its protected analogs. In some variations, a sugar is a multivalent structure comprising two or more sugar moieties (e.g., three or four moieties). In some such multivalent sugar embodiments, each moiety is connected to a common branching point via a linker. An exemplary multivalent sugar is a tri-N-acetylgalactosamine (tri-NAG) structure having three NAG moieties. Tri-NAG structures are generally known in the art and are described, for example, in Lee et al., *Carbohydrates and Chemistry and Biology* (B. Ernst, G. W. Hart, & P. Sinay, Eds., Wiley-WCH: Weinheim, 2000), Vol. 4, p 459 (and references cited therein); Biessen et al. *J. Med. Chem.* 38:1538, 1995; Sliedregt et al., *J. Med. Chem.* 42:609, 1999; Rensen et al., *J. Med. Chem.* 47:5798, 2004; Khorev et al., *Bioorg. Med. Chem.* 16:5216, 2008. Another exemplary multivalent sugar is a bis-mannose-6-phosphate (bis-M6P) structure having two mannose-6-phosphate moieties (see, e.g., U.S. Pat. No. 8,399,657 to Zhu et al.).

As used herein the term "vitamin" refers to Vitamin A (Retinol), Vitamin B1 (Thiamine), Vitamin C (Ascorbic acid), Vitamin D (Calciferol), Vitamin B2 (Riboflavin), Vitamin E (Tocopherol), Vitamin B12 (Cobalamins), Vitamin K1 (Phylloquinone), Vitamin B5 (Pantothenic acid), Vitamin B7 (Biotin), Vitamin B6 (Pyridoxine), Vitamin B3 (Niacin), Vitamin B9 (Folic acid) and their derivatives for example. Typically, vitamins as used herein target or deliver copolymers to target cells or tissues, or specific cells types and enhance the association of molecules with the target cells. An example of a vitamin as used herein includes Vitamin $B_9$, including folic acid, folate and their derivatives.

When a functional group, such as an amine, is termed "protected", this means that the group is in modified form to preclude undesired side reactions at the protected site. Suitable protecting groups for the copolymers of the present disclosure will be recognized from the present application taking into account the level of skill in the art, and with reference to standard textbooks, such as Greene, T. W. et al. Protective Groups in Organic Synthesis Wiley, New York (1991). Carboxy groups can be protected as esters thereof, for example methyl, ethyl, tert-butyl, benzyl, and 4-nitrobenzyl esters. Hydroxy groups can be protected as ethers or esters thereof, for example methoxymethyl ethers, tetrahydropyranyl ethers, benzyl ethers, acetates or benzoates. Mercapto groups can be protected as thioethers or thioesters, for example pyridyl thioethers, maleimide thioethers, tert-butyl thioethers, thioacetates or thiobenzoates. Amino groups can be protected as carbamates, such as tert-butoxycarbonyl derivatives, or as amides, such as acetamides and benzamides.

As is well-known in the art, nomenclature of PEG molecular weight can use the overall molecular weight (including the PEG end groups) or the number of repeat units. For example $PEG_{12}$ is also known as $PEG_{0.6kDa}$ or $PEG_{0.6k}$. $PEG_{36}$ is also known as $PEG_{1.6kDa}$ or $PEG_{1.6k}$. $PEG_{48}$ is also known as $PEG_{2.2kDa}$ or $PEG_{2.2k}$. A particular form of $PEG_{48}$ is also known as $PEG_{24}$-amido-$PEG_{24}$, but has also been generally described as $PEG_{2.2kDa}$ or $PEG_{2.2k}$.

$PEGMA_{4-5}$ (Poly(ethylene glycol) methyl ether methacrylate, average Mn=300) is also known as $PEGMA_{0.3kDA}$ or $PEGMA_{0.3k}$ or $PEGMA_{300}$, which is the average molecular weight of a mixture of $PEGMA_4$ and $PEGMA_5$. Similarly, $PEGMA_{7-9}$ (Poly(ethylene glycol) methyl ether methacrylate, average Mn=500) is also known as $PEGMA_{0.5kDA}$ or $PEGMA_{0.5k}$ or $PEGMA_{500}$, which is the average molecular weight of a mixture of $PEG_7$ and $PEG_9$. Similarly, $PEGMA_{17-19}$ (Poly(ethylene glycol) methyl ether methacrylate, average Mn=1000) is also known as $PEGMA_{1kDA}$ or $PEGMA_{1k}$ or $PEGMA_{1000}$, which is the average molecular weight of a mixture of $PEGMA_{17}$ and $PEGMA_{19}$.

As used herein the term "treating" refers to the administration of a copolymer that eliminates, alleviates, inhibits the progression of, or reverses progression of, in part or in whole, any one or more of the pathological hallmarks or symptoms of any one of the diseases and disorders being treated. Such disease include, but are not limited to liver cancer, for example hepatocellular carcinoma, cholangiocarcinoma, hepatitis, hypercholesterolemia, liver fibrosis, pulmonary fibrosis, haemochromatosis cancers of the breast, ovaries, pancreas, endometrium, lungs, kidneys, colon, brain, or myeloid cells of hematopoietic origin. Other diseases include ornithine transcarbamylase deficiency (OTCD), alpha-1-antitrypsin deficiency (A1ATD), cystic fibrosis (CF) and hyperoxaluria.

The phrase "therapeutically effective" as used herein is intended to qualify the amount of copolymer or pharmaceutical composition, or the combined amount of active ingredients in the case of combination therapy. This amount or combined amount will achieve the goal of treating the relevant condition.

As used herein the symbols  and ===== designate a point of attachment of one molecular moiety to another.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise.

The present disclosure provides for block co-polymers of the formula I $$T1\text{-}L1\text{-}[A]_x\text{-}[B]_y\text{-}Z \qquad\qquad I$$

where
T1 is absent or a first targeting moiety;
L1 is absent or a linking moiety;
A, also referred to as block A or the first block, is a first block that is a polymer formed from monomers comprising formula A2 or a random copolymer formed from monomers comprising formulae A1, A2 and A3; A1 and A2; A2, A4, and A5; A2 and A5; or A4 and A5;

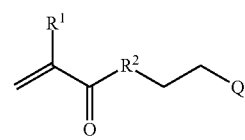

A1 where $R^1$ is H or $C_1$-$C_6$ alkyl, $R^2$ is O, S, NH, N($C_1$-$C_6$ alkyl), or $(OCH_2CH_2)_{1-120}$, and Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, (v)

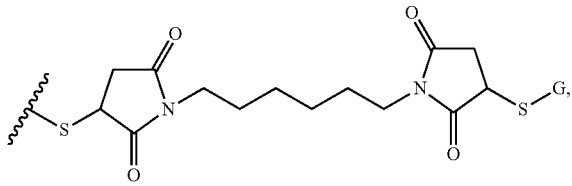

(vi)

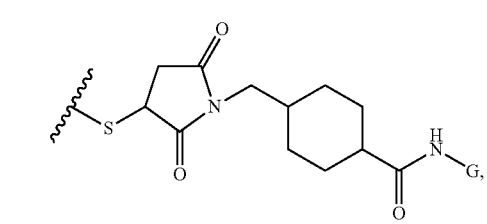

(vii)

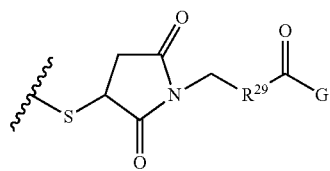

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

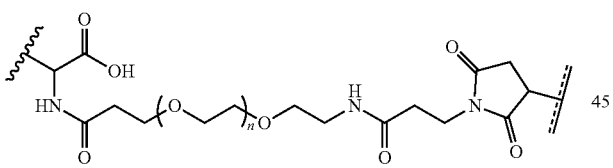

where n=1-35 and ----- designates a point of attachment of L2 to G, where G is an oligonucleotide, cationic peptide, polyamine, or polycation;

A2

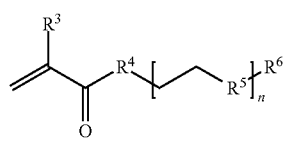

where n is 1-120, $R^3$ is H or $C_1$-$C_6$ alkyl, $R^4$ is S, O, NH or $N(C_1$-$C_6$ alkyl), $R^5$ is O or S and $R^6$ is H, $C_1$-$C_6$ alkyl, $C_1$-$C_6$ alkyl-$NH_2$, $C_1$-$C_6$ alkyl-$NH(C_1$-$C_6$ alkyl), $C_1$-$C_6$ alkyl-$N(C_1$-$C_6$ alkyl)$_2$;

A3

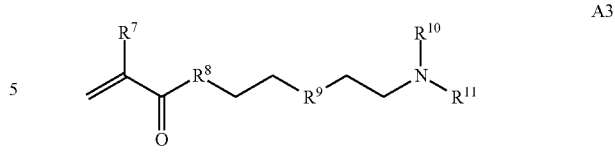

where $R^7$ and $R^{19}$ are independently H or $C_1$-$C_6$ alkyl, $R^8$ is S, O, NH or $N(C_1$-$C_6$ alkyl), and $R^9$ is O or S and $R^{11}$ is an amine protecting group;

A4

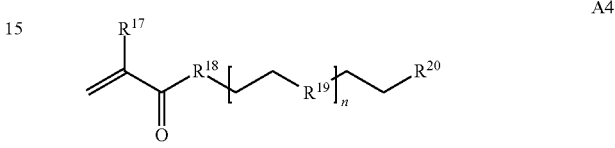

where n is 1-230, $R^{17}$ is H or $C_1$-$C_6$ alkyl, $R^{18}$ is O, S, NH or $N(C_1$-$C_6$ alkyl), $R^{19}$ is O or S, and $R^{29}$ is OH, NH, H, T2, or $C_1$-$C_6$ alkyl, where T2 is a second targeting moiety;

A5

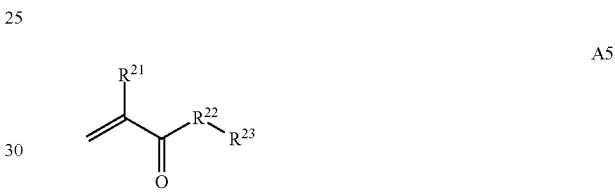

where $R^{21}$ is H or $C_1$-$C_6$ alkyl, $R^{22}$ is O, NH or $N(C_1$-$C_6$ alkyl), $R^{23}$ is H, aryl, arylhalide, alkyl, alkyl alcohol;

B is a second block that is a random copolymer formed from monomers comprising formulae B1, B2, B3 and B4 or B1, B2 and B3

B1

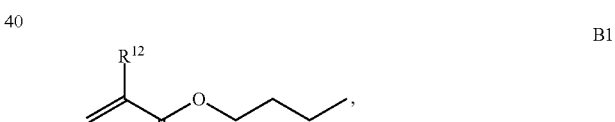

B2

B3

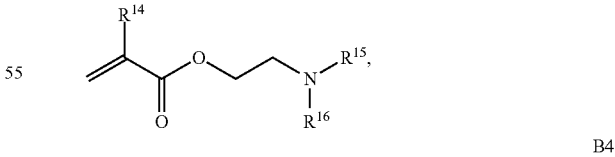

B4

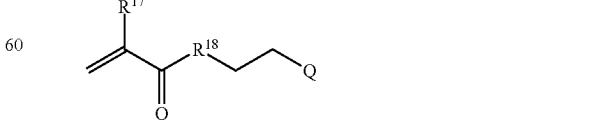

where $R^{12}$, $R^{13}$, $R^{14}$, $R^{15}$, $R^{16}$ and $R^{17}$ are independently H or $C_1$-$C_6$ alkyl, $R^{18}$ is O, S, NH, $N(C_1$-$C_6$ alkyl), or $(OCH_2CH_2)_{1-120}$, and Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether,

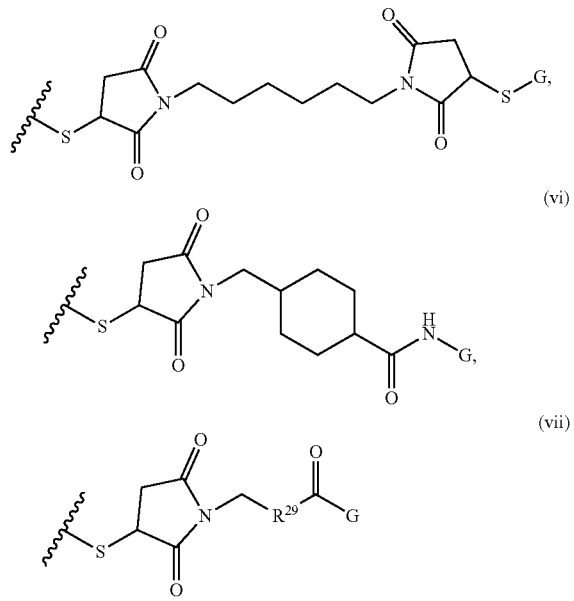

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

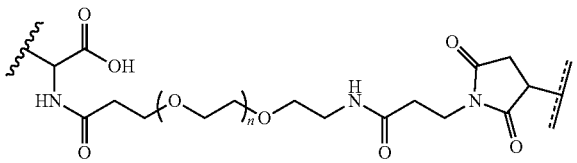

where n=1-35 and ===== designates a point of attachment of L2 to G,
where G is an oligonucleotide, cationic peptide, polyamine, or polycation;
x is 2-20 kDa;
y is 2-20 kDa;
Z is H, SH, $C(CH_3)_2CN$,

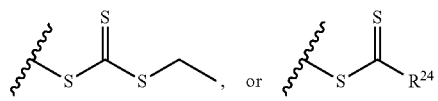

where $R^{24}$ is S—($C_1$-$C_{12}$ alkyl), aryl, arylhalide, O—($C_1$-$C_{12}$ alkyl), $NR^{25}R^{26}$ where $R^{25}$ and $R^{26}$ are independently H, alkyl, aryl, or heteroaryl;
the ratio of x to y is from 2:1 to 1:4; and
⌇⌇⌇ designates a point of attachment.

In some embodiments of a copolymer of Formula I above, the monomer of formula A2 is $$A2$$

where n is 1-20, $R^3$ is H or $C_1$-$C_6$ alkyl, $R^4$ is S, O, NH or $N(C_1$-$C_6$ alkyl), $R^5$ is O or S and $R^6$ is H, $C_1$-$C_6$ alkyl, $C_1$-$C_6$ alkyl-$NH_2$, $C_1$-$C_6$ alkyl-$NH(C_1$-$C_6$ alkyl), $C_1$-$C_6$ alkyl-$N(C_1$-$C_6$ alkyl)$_2$.

In some embodiments of a copolymer of Formula I above, Q is not S-S-pyridyl and G is a cationic peptide, polyamine, or polycation. In some such variations, an mRNA molecule is complexed to the cationic peptide, polyamine, or polycation.

In particular variations of a block copolymer of Formula I as above, T1 and/or T2 is selected from the group consisting of an antibody, a peptide, a sugar, and a vitamin. In some embodiments, each of T1 and T2 is independently selected from an antibody, a peptide, a sugar, and a vitamin (i.e., T1 is a first antibody, peptide sugar, or vitamin, and T2 is a second antibody, peptide, sugar, or vitamin, where T1 and T2 may be the same or different). In some such embodiments as above, the block copolymer of Formula I is a copolymer of formula VII as described hereinbelow.

In some embodiments of a block copolymer of Formula I as above where T1 and T2 are both present, T1 and T2 are the same. In other embodiments of a block copolymer of Formula I as above where T1 and T2 are both present, T1 and T2 are different. In certain variations where T1 and T2 are both present and are different, T1 and T2 are both capable of specifically binding to the same binding partner on the surface of a cell. In other variations where T1 and T2 are both present and are different, T1 and T2 are both capable of specifically binding to different binding partners on the surface of the same cell, e.g., the same cell within a target tissue of a subject. In some such embodiments as above, the block copolymer of Formula I is a copolymer of formula VII as described hereinbelow.

In some embodiments of block copolymers of Formula I as above, x is 2-15, 2-10 kDa, 3-10 kDa, 3-9 kDa, 3-8 kDa, 3-7 kDa, 3-6 kDa, 4-8 kDa, 4-7 kDa, or 4-6 kDa. In some embodiments, y is 2-10 kDa, 3-7 kDa, 3-6 kDa, 4-6 kDa, 4.5-5.5 kDa, or 3-5 kDa. In more particular variations, x is 2-15 kDa and y is 3-7 kDa; x is 2-15 kDa and y is 3-6 kDa; x is 2-15 kDa and y is 4-6 kDa; x is 2-15 kDa and y is 4.5-5.5 kDa; x is 2-15 kDa and y is 3-5 kDa; x is 2-10 kDa and y is 3-7 kDa; x is 2-10 kDa and y is 3-6 kDa; x is 2-10 kDa and y is 4-6 kDa; x is 2-10 kDa and y is 4.5-5.5 kDa; x is 2-10 and y is 3-5 kDa; x is 3-10 kDa and y is 3-7 kDa; x is 3-10 kDa and y is 3-6 kDa; x is 3-10 kDa and y is 4-6 kDa; x is 3-10 kDa and y is 4.5-5.5 kDa; x is 3-10 kDa and y is 3-5 kDa; x is 3-9 kDa and y is 3-7 kDa; x is 3-9 kDa and y is 3-6 kDa; x is 3-9 kDa and y is 4-6 kDa; x is 3-9 kDa and y is 4.5-5.5 kDa; x is 3-9 kDa and y is 3-5 kDa; x is 3-8 kDa and y is 3-7 kDa; x is 3-8 kDa and y is 3-6 kDa; x is 3-8 kDa and y is 4-6 kDa; x is 3-8 kDa and y is 4.5-5.5 kDa; x is 3-8 kDa and y is 3-5 kDa; x is 3-7 kDa and y is 3-7 kDa; x is 3-7 kDa and y is 3-6 kDa; x is 3-7 kDa and y is 4-6 kDa; x is 3-7 kDa and y is 4.5-5.5 kDa; x is 3-7 kDa and y is 3-5 kDa; x is 3-6 kDa and y is 3-7 kDa; x is 3-6 kDa and y is 3-6 kDa; x is 3-6 kDa and y is 4-6 kDa; x is 3-6 kDa and y is 4.5-5.5 kDa; x is 3-6 kDa and y is 3-5 kDa; x is 4-7 kDa and y is 3-7 kDa; x is 4-7 kDa and y is 3-6 kDa; x is 4-7 kDa and y is 4-6 kDa; x is 4-7 kDa and y is 4.5-5.5 kDa; x is 4-7 kDa and y is 3-5 kDa; x is 4-6 kDa and y is 3-7 kDa; x is 4-6 kDa and y is 3-6 kDa; x is 4-6 kDa and y is 4-6 kDa; x is 4-6 kDa and y is 4.5-5.5 kDa; x is 4-6 kDa and y is 3-5 kDa.

Examples of block copolymers of Formula I include those where A is a first block that is a random copolymer formed from monomers of formulae A1, A2 and A3 as described above. Additional examples of block copolymers of Formula I include those where A is a first block that is a random copolymer formed from monomers comprising formulae A1 and A2 as described above. Additional examples of block copolymers of Formula I include those where A is a first block that is a polymer formed from monomer A2 as described above. Additional examples of block copolymers of Formula I include those where A is a first block that is a random copolymer formed from monomers comprising formulae A2, A4 and A5 as described above. In some such embodiments as above in which A1 is absent, the block copolymer of Formula I is a copolymer of formula VII as described hereinbelow.

An example of a monomer of formula A1 is 2-(pyridin-2-yldisulfanyl)ethyl methacrylate. 2-(Pyridin-2-yldisulfanyl)ethyl methacrylate is also referred to herein as PDSMA. Another example of a monomer of formula A1 is

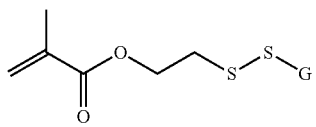

where G is an oligonucleotide, cationic peptide, polyamine, or polycation.

Examples of monomers of formula A2 include those of formula A2a

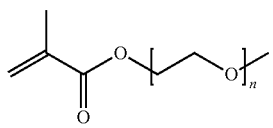

A2a where n is 1-120. Other examples of monomers of formula A2 include those of formula A2a where n is 1-10 or 3-20. Other examples of monomers of formula A2 include those of formula A2a where n is 3-6. Yet other examples of monomer of formula A2 include those of formula A2a where n is 7-20. Additional examples of monomers of formula A2 include those of formula A2a where n is 4 or 5, n is 7-9, or n is 17-19.

Examples of monomers of formula A3 include those of formula A3a

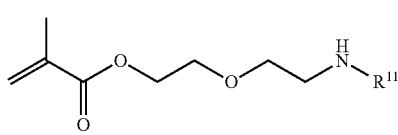

A3a where $R^{11}$ is an amine protecting group. Other examples of monomers of formula A3 include those of formula A3a where $R^{11}$ is tert-butyloxycarbonyl. An example of monomer A3 is 2-(2-((tert-Butoxycarbonyl)amino)ethoxy)ethyl methacrylate which is also referred to herein as BPAM.

A particular example of a block copolymer of Formula I is that where the monomer of formula A1 is

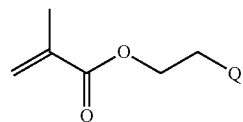

where Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether,

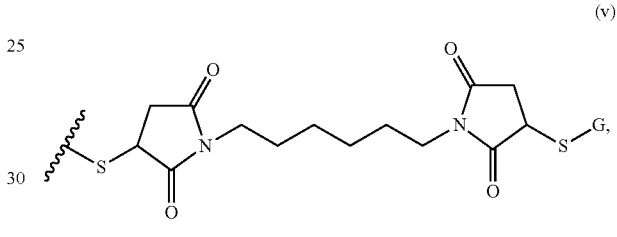

(v)

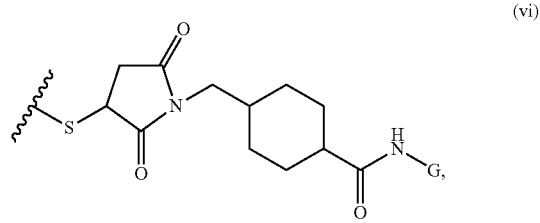

(vi)

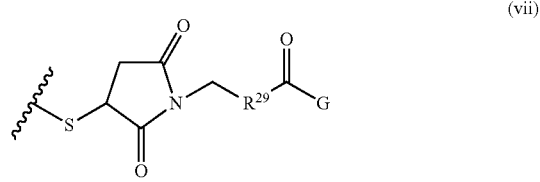

(vii)

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

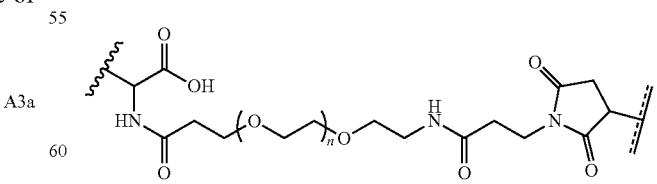

where n=1-35 and ═══ designates a point of attachment of L2 to G, where G is an oligonucleotide, cationic peptide, polyamine, or polycation, the monomer of formula A2 is

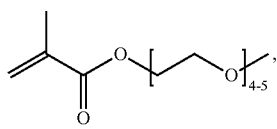

the monomer of formula A3 is absent or 2-(2-((tert-butoxy-carbonyl)amino)ethoxy)ethyl methacrylate, and ∿∿ designates a point of attachment.

An additional example of a block copolymer of Formula I is that where the monomer of formula A1 is

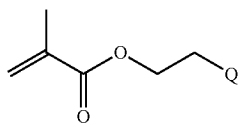

wherein Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, (v)

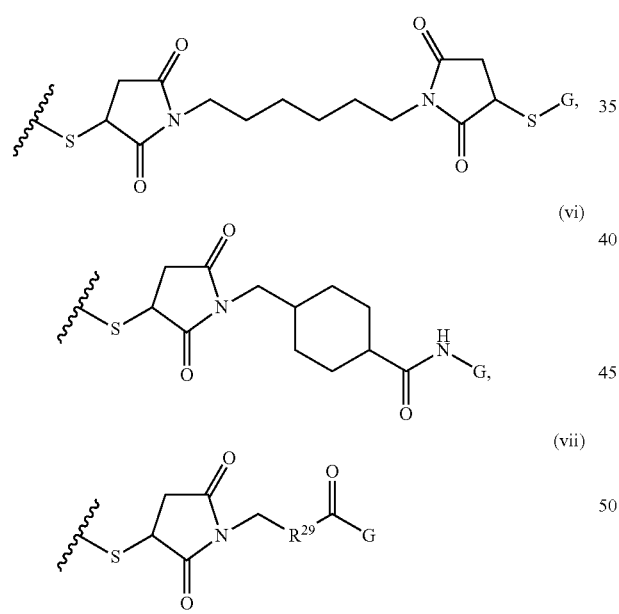

(vi)

(vii)

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), or
(viii) S-S-L2-G wherein L2 is

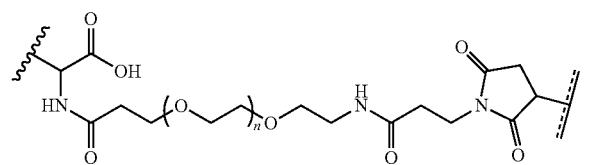

where n=1-35 and ≡≡≡ designates a point of attachment of L2 to G;

wherein G is an oligonucleotide, cationic peptide, polyamine, or polycation, the monomer of formula A2 is

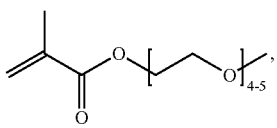

the monomer of formula A3 is absent or 2-(2-((tert-butoxycarbonyl)amino)ethoxy)ethyl methacrylate, and ∿∿ designates a point of attachment.

An additional example of a block copolymer of Formula I is that the monomer of formula A1 is absent, the monomer of formula A2 has the formula A2a where n is 1-120 (e.g., wherein n is 1-10, 3-20, or 7-20), and the monomer of formula A3 is absent. In some variations, the monomer of formula A1 is absent, the monomer of formula A2 is

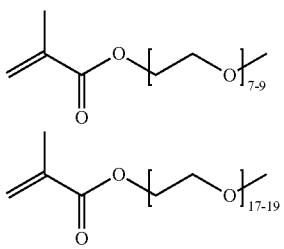

and the monomer of formula A3 is absent. In other variations, the monomer of A1 is absent, the monomer of formula A2 is selected from the group consisting of and the monomer of A3 is absent. In some such embodiments as above, the block copolymer of Formula I is a copolymer of formula VII as described hereinbelow.

An example of a monomer of formula B1 is butyl methacrylate. Butyl methacrylate is also referred to herein as BMA.

An example of a monomer of formula B2 is 2-propyl acrylic acid. 2-Propyl acrylic acid is also referred to as 2-n-propyl acrylic acid and 2-methylenepentanoic acid. 2-Propyl acrylic acid is also referred to herein as PAA.

An example of a monomer of formula B3 is 2-(dimethylamino)ethyl methacrylate. 2-(dimethylamino)ethyl methacrylate is also commonly referred to as 2-dimethylaminoethylester, dimethylaminoethyl methacrylate, N,N-diemthylaminoethyl methacrylate and methacrylic acid 2-(dimethylamino)ethyl ester. 2-(dimethylamino)ethyl methacrylate acid is also referred to herein as DMAEMA.

An example of a monomer of formula B4 is 2-(pyridin-2-yldisulfanyl)ethyl methacrylate or

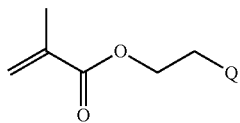

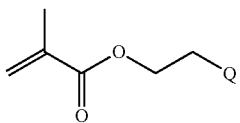

where Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, wherein Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether,

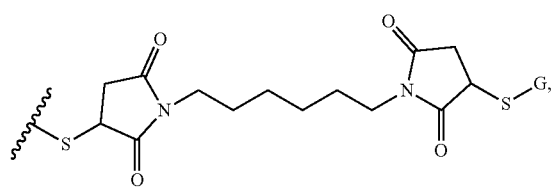
(v)

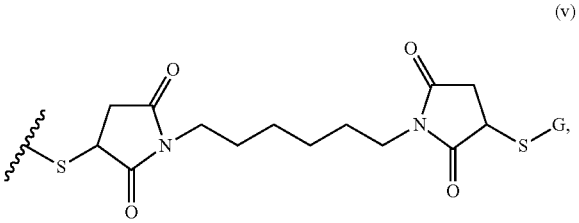
(v)

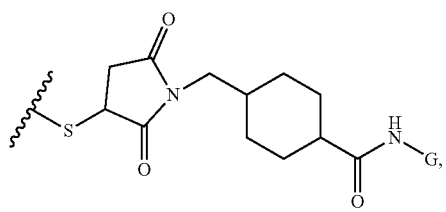
(vi)

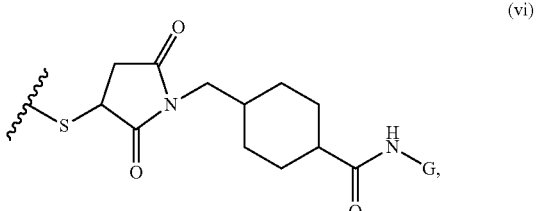
(vi)

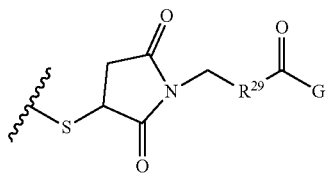
(vii)

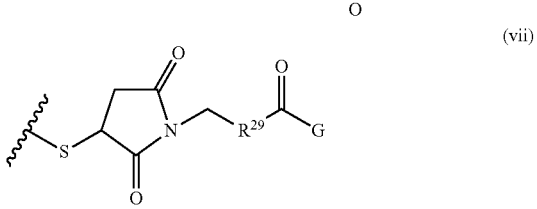
(vii)

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and
(viii) S-S-L2-G wherein L2 is where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and
(viii) S-S-L2-G wherein L2 is

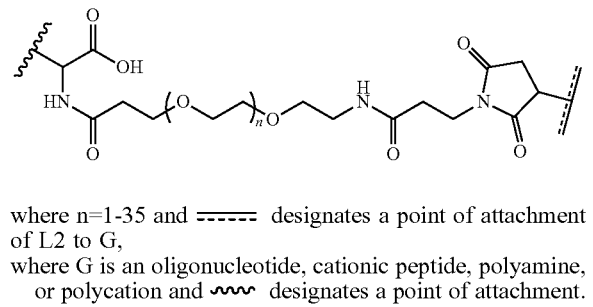

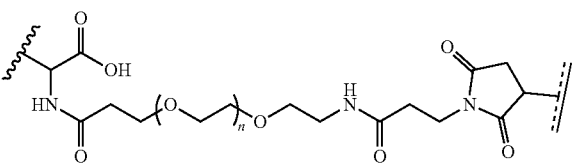

where n=1-35 and ===== designates a point of attachment of L2 to G,
where G is an oligonucleotide, cationic peptide, polyamine, or polycation and ∿∿∿ designates a point of attachment.

An example of a block copolymer of Formula I is that where the monomer of formula B1 is butyl methacrylate, the monomer of formula B2 is 2-propyl acrylic acid, the monomer of formula B3 is 2-(dimethylamino)ethyl methacrylate, and the monomer B4 is absent.

An example of a block copolymer of Formula I is that where the monomer of formula B1 is butyl methacrylate, the monomer of formula B2 is 2-propyl acrylic acid, the monomer of formula B3 is 2-(dimethylamino)ethyl methacrylate, and the monomer B4 is where n=1-35 and ===== designates a point of attachment of L2 to G,
where G is an oligonucleotide, cationic peptide, polyamine, or polycation and ∿∿∿ designates a point of attachment.
In some such embodiments as above, the block copolymer of Formula I is a copolymer of formula VII as described hereinbelow.

Examples of block copolymers of Formula I include those where T1 specifically binds to the asialoglycoprotein (ASGP) receptor. Particularly suitable are structures having one or more N-acetyl galactoseamine (NAG) moieties. For example, in some variations, T1 is

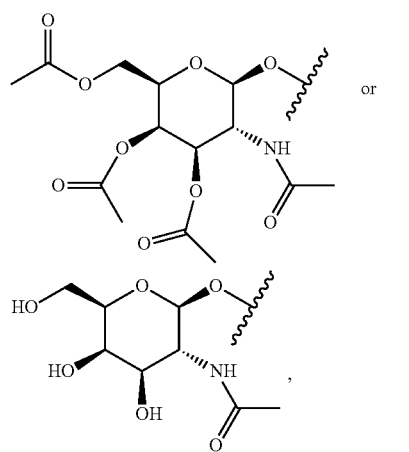

and ∿∿∿ designates a point of attachment. In some variations where has multiple NAG moieties, T1 is a tri-N-acetylgalactosamine (tri-NAG) structure. In one such embodiment, T1 is

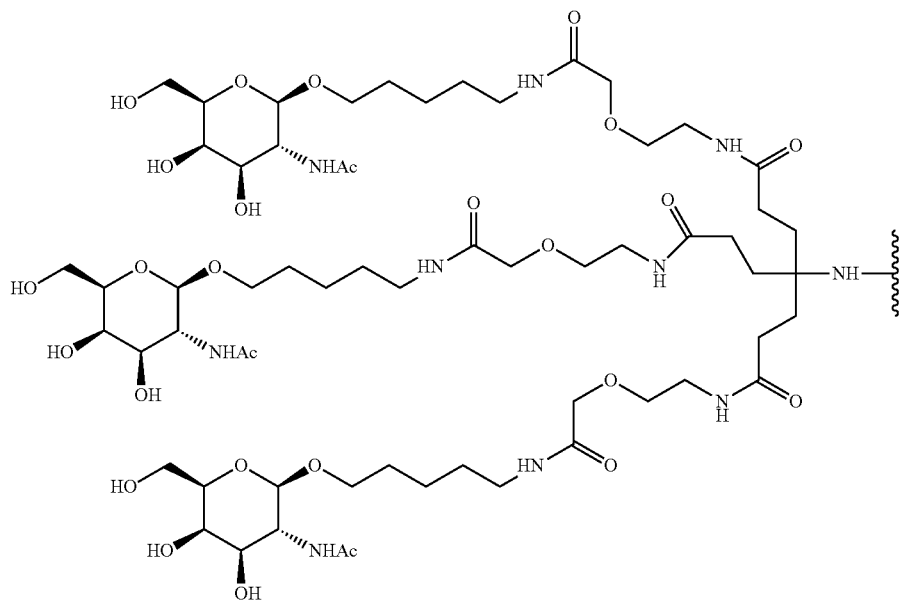 [SMILES: *NC(CCC(=O)NCCOCC(=O)NCCCCCO[C@@H]1O[C@H](CO)[C@H](O)[C@H](O)[C@H]1NC(C)=O)(CCC(=O)NCCOCC(=O)NCCCCCO[C@@H]1O[C@H](CO)[C@H](O)[C@H](O)[C@H]1NC(C)=O)CCC(=O)NCCOCC(=O)NCCCCCO[C@@H]1O[C@H](CO)[C@H](O)[C@H](O)[C@H]1NC(C)=O]

and ∿∿∿ designates a point of attachment. In some such embodiments as above, the block copolymer of Formula I is a copolymer of formula VII as described hereinbelow.

Examples of block copolymers of Formula I include those where L1 is

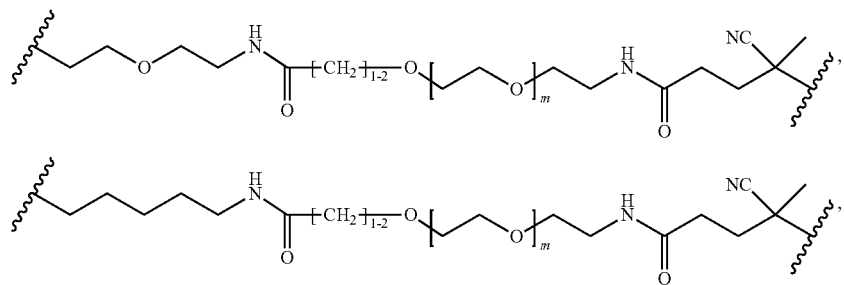

-continued

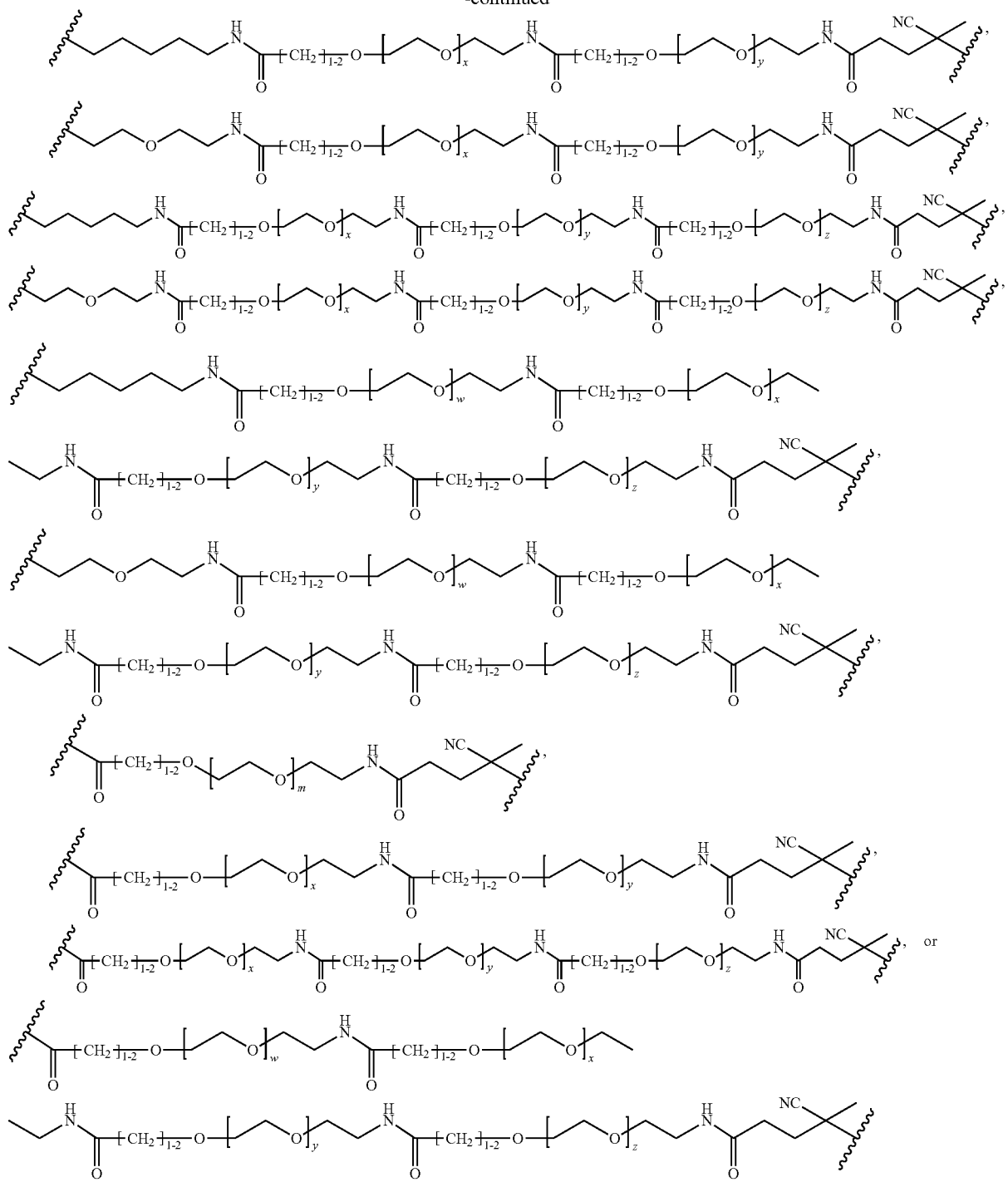

where m is 1-100 or 10-460 and each of w, x, y, and z is independently 1-48. In certain variations of L1 comprising m as above, m is 1-15, 10-20, 20-30, 20-25, 11 or 12. In other variations of L1 comprising m as above, m is 20-60, 25-60, 25-55, 25-50, 25-48, 30-60, 30-55, 30-50, 30-48, 34-60, 34-55, 34-50, 34-48, 36-60, 36-55, 36-50, 36-48, 36, or 48. In yet other embodiments of L1 comprising m as above, m is 60-460, 100-460, 150-460, 200-460, 60-250, 100-250, 150-250, or 200-250. In certain variations of L1 comprising x and y, x, y and z, or w, x, y and z as above, each of w, x, y, and z is independently 20-30, 20-25, or 23. In other variations of L1 comprising x and y, x, y and z, or w, x, y and z as above, each of w, x, y, and z is independently 1-12, 1-24, 1-36, 8-16, 10-14, 20-28, 22-26, 32-40, 34-38, 8-48, 10-48, 20-48, 22-48, 32-48, 34-48, or 44-48. In some such embodiments as above, the block copolymer of Formula I is a copolymer of formula VII as described hereinbelow.

Other examples of L1 include —CO—$(CH_2CH_2)_{1-460}$—$CH_2CH_2NHCO$-Ph-C=N—O—$(CH_2CH_2)_{2-20}$—

CH₂CH₂NH—CO—CH₂CH₂C(CH₃)(CN)—. Another example of L1 includes —CO—(CH₂CH₂)₁₋₄₆₀—CH₂CH₂NH—CO—CH₂CH₂C(CH₃)(CN)—. Yet another example of L1 includes —CO—(CH₂CH₂)₁₋₄₆₀—CH₂CH₂NH—CO—(CH₂CH₂)₁₋₅₀—CH₂CH₂NH—CO—CH₂CH₂C(CH₃)(CN)—. In yet other examples, L1 is —CO—(CH₂CH₂)₁₋₄₆₀—CH₂CH₂-x-(CH₂CH₂)₁₋₅₀—CH₂CH₂NH—CO—CH₂CH₂C(CH₃)(CN)—, or —CO—(CH₂CH₂)₁₄₆₀—CH₂CH₂-x -CH₂CH₂C(CH₃)(CN)—, where x is an ester, imine, oxime, thioester, product of a [3+2] cycloaddition, product of a [4+1] cycloaddition, carbonate, carbamate, urea, acetal, ketal, or hydrazine. In some such embodiments as above, the block copolymer of Formula I is a copolymer of formula VII as described hereinbelow.

Examples of block copolymers of Formula I include those where T1-L1-together are

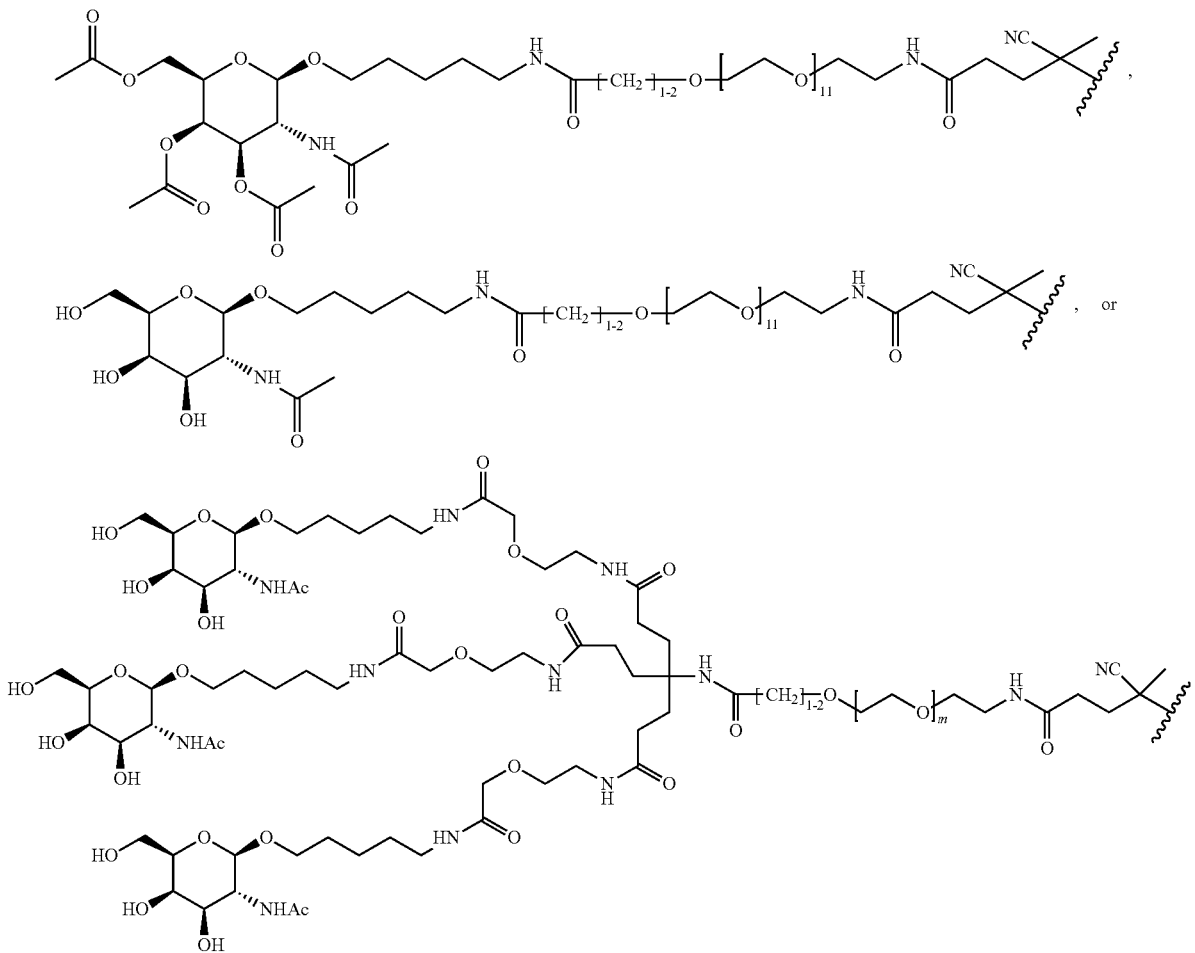

wherein m=11 and ∿∿ designates a point of attachment. In some such embodiments, the block copolymer of Formula I is a copolymer of formula VII as described hereinbelow.

Additional examples of block copolymers of Formula I include those where T1-L1-together are selected from the group consisting of

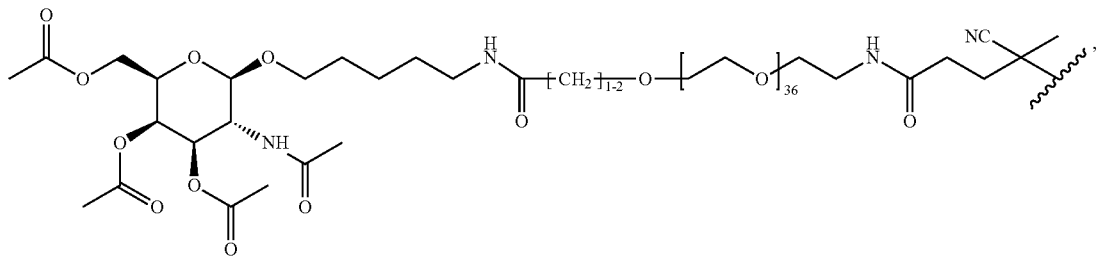

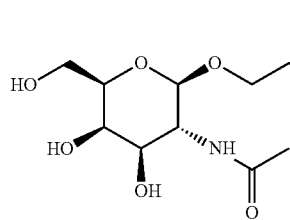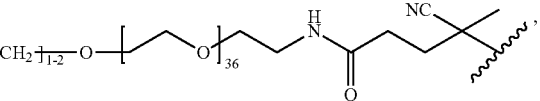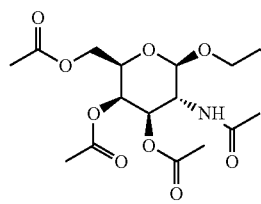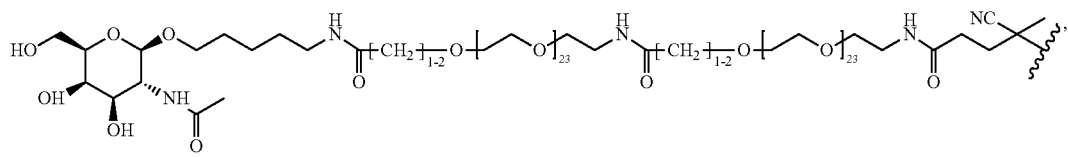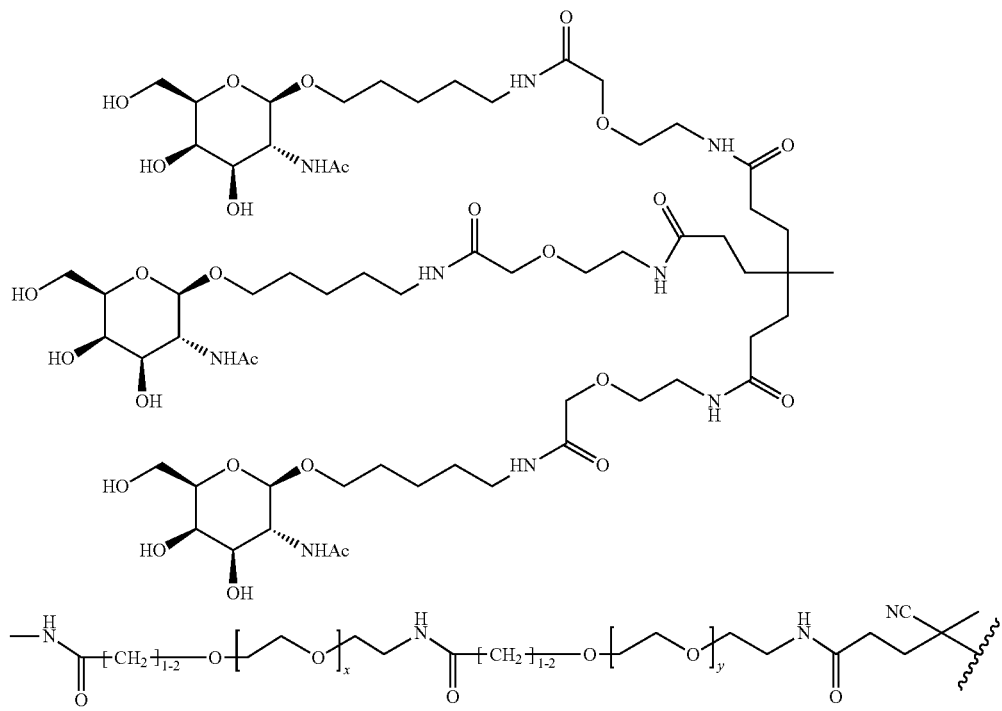
wherein x = y = z = 23,

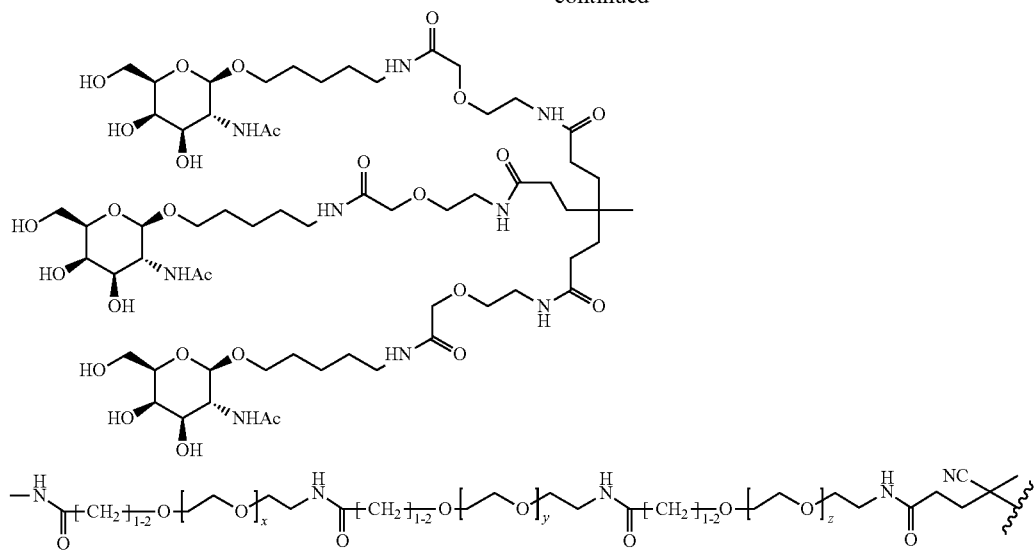
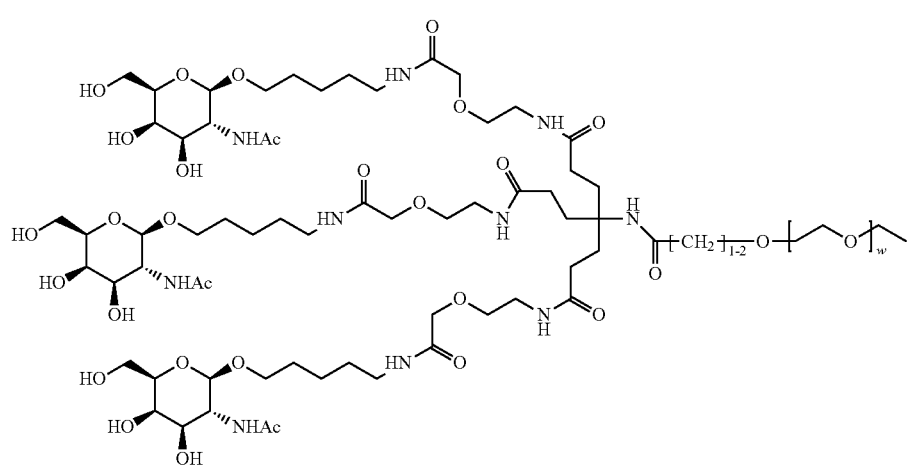
wherein x = y = z = 23,
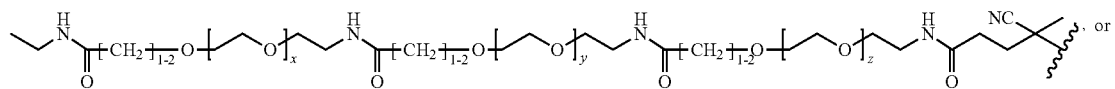
, or
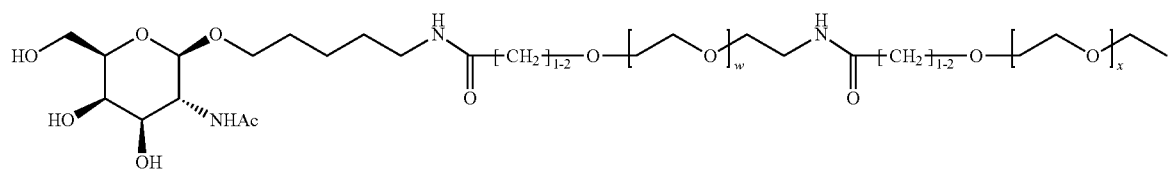
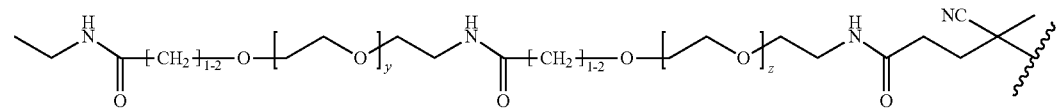

and ᨒ designates a point of attachment. In some such embodiments, the block copolymer of Formula I is a copolymer of formula VII as described hereinbelow.

Examples of block copolymers of Formula I include those where the monomer of formula A1 is

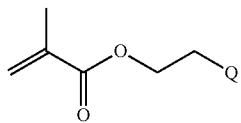

where Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is C$_1$-C$_6$ alkyl, (OCH$_2$CH$_2$)$_{1-50}$, C$_1$-C$_6$ alkyl-(OCH$_2$CH$_2$)$_{1-50}$, or thioether, (v)

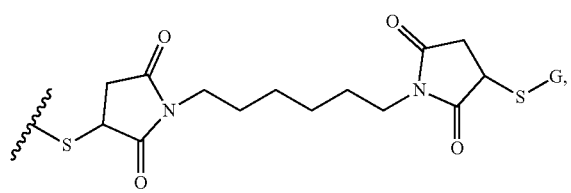

(vi)

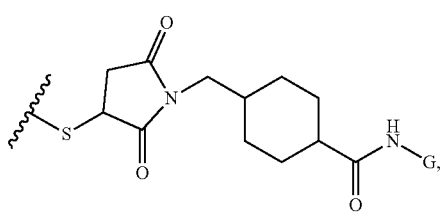

(vii)

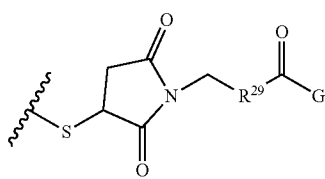

where R$^{29}$ is C$_1$-C$_6$ alkyl, (OCH$_2$CH$_2$)$_{1-50}$, C$_1$-C$_6$ alkyl-(OCH$_2$CH$_2$)$_{1-50}$, O, NH, or N(C$_1$-C$_6$ alkyl), and (viii) S-S-L2-G wherein L2 is

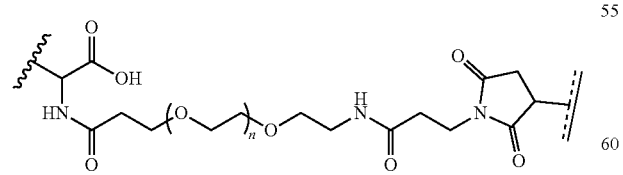

where n=1-35 and ===== designates a point of attachment of L2 to G, where G is an oligonucleotide, cationic peptide, polyamine, or polycation, the monomer of formula A2 is

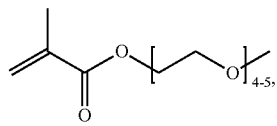

the monomer of formula A3 is absent or 2-(2-((tert-butoxycarbonyl)amino)ethoxy)ethyl methacrylate, the monomer of formula B1 is butyl methacrylate, the monomer of formula B2 is 2-propyl acrylic acid, the monomer of formula B3 is 2-(dimethylamino)ethyl methacrylate, and ᨒ designates a point of attachment.

Additional examples of block copolymers of Formula I include those where the monomer of formula A1 is

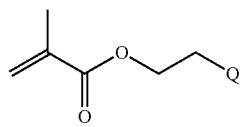

where Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is C$_1$-C$_6$ alkyl, (OCH$_2$CH$_2$)$_{1-50}$, C$_1$-C$_6$ alkyl-(OCH$_2$CH$_2$)$_{1-50}$, or thioether, (v)

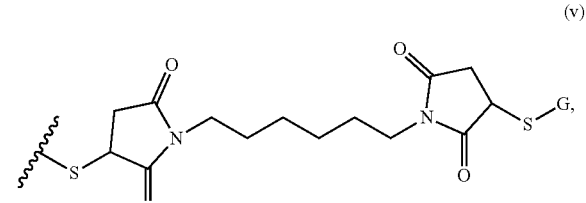

(vi)

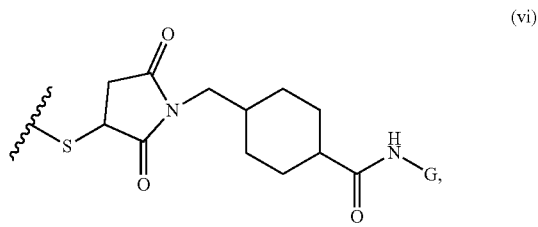

(vii)

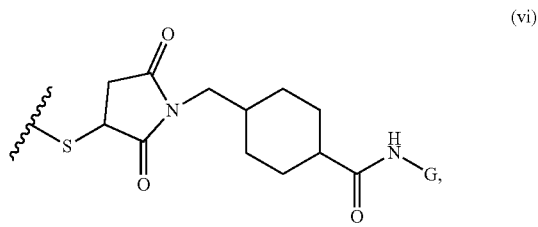

where R$^{29}$ is C$_1$-C$_6$ alkyl, (OCH$_2$CH$_2$)$_{1-50}$, C$_1$-C$_6$ alkyl-(OCH$_2$CH$_2$)$_{1-50}$, O, NH, or N(C$_1$-C$_6$ alkyl), and (viii) S-S-L2-G wherein L2 is (v)

[Chemical structure: succinimide-linked hexyl-succinimide-S-G]

[Chemical structure: amino acid-amide-PEG-amide-maleimide showing HN-CH(COOH)- connected via amide to -(CH2)2-O-(CH2CH2O)n-CH2CH2-NH-C(O)-(CH2)2-N(succinimide)-S attachment]

where n=1-35 and ===== designates a point of attachment of L2 to G, where G is an oligonucleotide, cationic peptide, polyamine, or polycation, the monomer of formula A2 is (vi)

[Chemical structure: S-succinimide-N-CH2-cyclohexyl-C(O)-NH-G]

[Chemical structure: methacrylate-O-(CH2CH2O)4-5]

(vii)

[Chemical structure: S-succinimide-N-CH2-R29-C(O)-G]

the monomer of formula A3 is absent or 2-(2-((tert-butoxycarbonyl)amino)ethoxy)ethyl methacrylate, the monomer of formula B1 is butyl methacrylate, the monomer of formula B2 is 2-propyl acrylic acid, the monomer of formula B3 is 2-(dimethylamino)ethyl methacrylate, and ∼∼∼ designates a point of attachment.

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), (viii) S-S-L2-G wherein L2 is Additional examples of block copolymers of Formula I include those where the monomer A1 is absent, the monomer of formula A2 is

[Chemical structure: amino acid-amide-PEG-amide-maleimide]

[Chemical structure: methacrylate-O-(CH2CH2O)4-5]

where n=1-35 and ===== designates a point of attachment of L2 to G, where G is an oligonucleotide, cationic peptide, polyamine, or polycation and ∼∼∼ designates a point of attachment.

In some such embodiments, the block copolymer of Formula I is a copolymer of formula VII as described hereinbelow.

the monomer of formula A3 is absent, the monomer of formula B1 is butyl methacrylate, the monomer of formula B2 is 2-propyl acrylic acid, the monomer of formula B3 is 2-(dimethylamino)ethyl methacrylate and the monomer of formula B4 is Other examples of block copolymers of Formula I include those where the monomer of A1 is absent, the monomer of formula A2 is selected from the group consisting of

[Chemical structure: methacrylate-O-CH2CH2-Q]

[Chemical structure: methacrylate-O-(CH2CH2O)7-9]

[Chemical structure: methacrylate-O-(CH2CH2O)17-19]

where Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, the monomer of A3 is absent, the monomer of formula B1 is butyl methacrylate, the monomer of formula B2 is 2-propyl acrylic acid, the monomer of formula B3 is 2-(dimethylamino)ethyl methacrylate and the monomer of formula B4 is

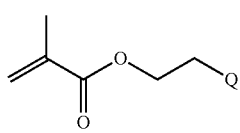

where Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is C$_1$-C$_6$ alkyl, (OCH$_2$CH$_2$)$_{1-50}$, C$_1$-C$_6$ alkyl-(OCH$_2$CH$_2$)$_{1-50}$, or thioether,

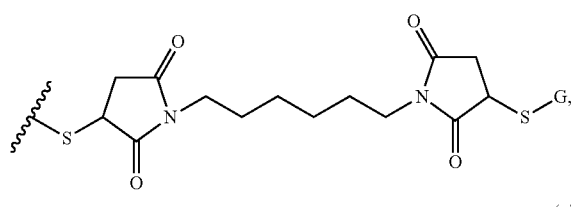

(vi)

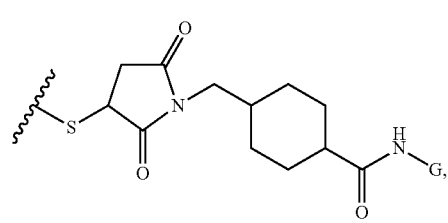

(vii)

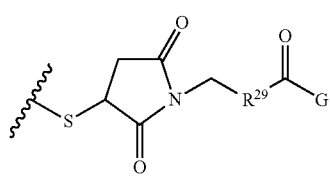

where R$^{29}$ is C$_1$-C$_6$ alkyl, (OCH$_2$CH$_2$)$_{1-50}$, C$_1$-C$_6$ alkyl-(OCH$_2$CH$_2$)$_{1-50}$, O, NH, or N(C$_1$-C$_6$ alkyl), and
(viii) S-S-L2-G wherein L2 is

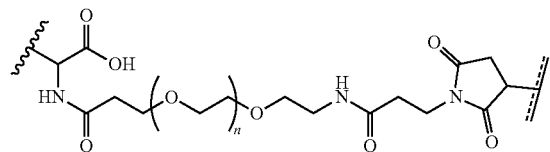

where n=1-35 and ===== designates a point of attachment of L2 to G, where G is an oligonucleotide, cationic peptide, polyamine, or polycation and ∿∿∿ designates a point of attachment. In some such embodiments as above, the block copolymer of Formula I is a copolymer of formula VII as described hereinbelow.

Additional examples of block copolymers of Formula I include those where the monomer of formula A1 is

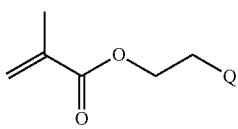

where Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is C$_1$-C$_6$ alkyl, (OCH$_2$CH$_2$)$_{1-50}$, C$_1$-C$_6$ alkyl-(OCH$_2$CH$_2$)$_{1-50}$, or thioether,

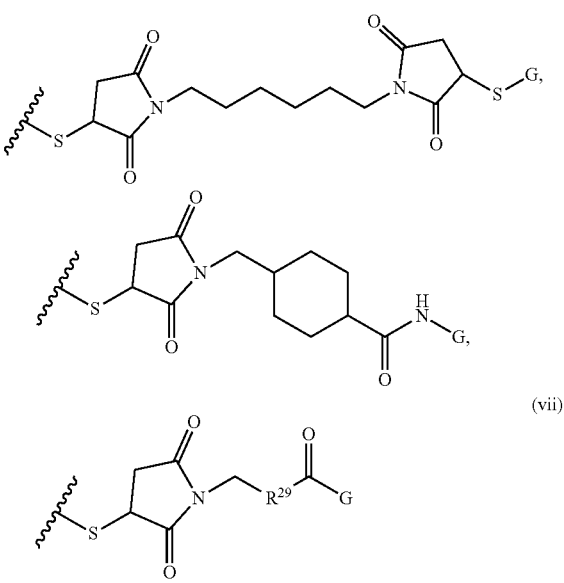

(vii)

where R$^{29}$ is C$_1$-C$_6$ alkyl, (OCH$_2$CH$_2$)$_{1-50}$, C$_1$-C$_6$ alkyl-(OCH$_2$CH$_2$)$_{1-50}$, O, NH, or N(C$_1$-C$_6$ alkyl), and
(viii) S-S-L2-G wherein L2 is

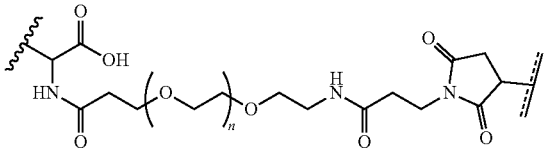

where n=1-35 and ===== designates a point of attachment of L2 to G,
where G is an oligonucleotide, cationic peptide, polyamine, or polycation;
the monomer of formula A2 is

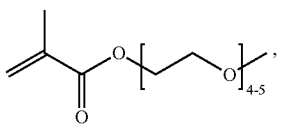

the monomer of formula A3 is absent or 2-(2-((tert-butoxycarbonyl)amino)ethoxy)ethyl methacrylate, the monomer of formula B1 is butyl methacrylate, the monomer of formula B2 is 2-propyl acrylic acid, the monomer of formula B3 is 2-(dimethylamino)ethyl methacrylate, and T-L-together are

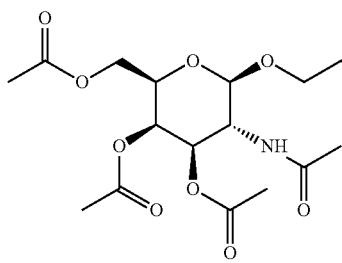
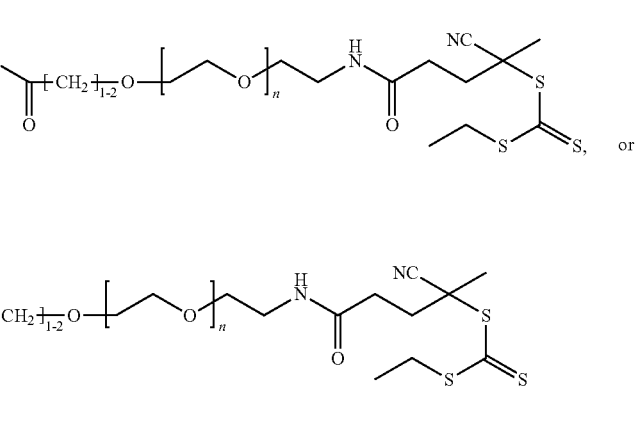

and ⌇⌇⌇ designates a point of attachment.

Additional examples of block copolymers of Formula I include those where the monomer of formula A1 is

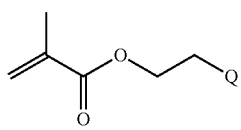

where Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, (v)

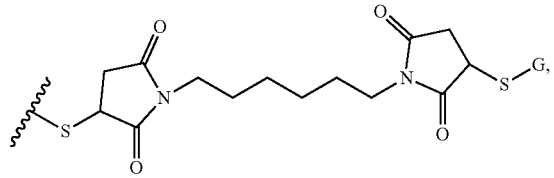

(vi)

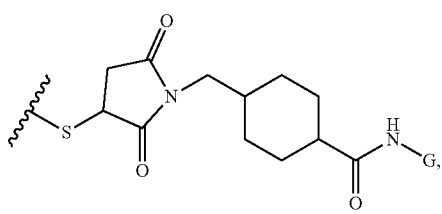

-continued (vii)

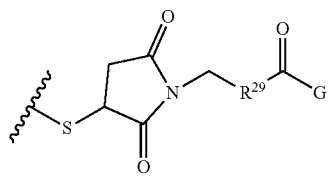

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

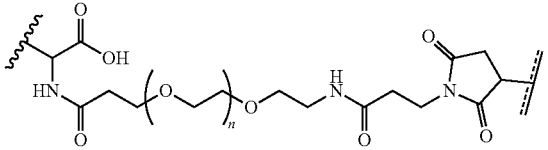

where n=1-35 and ≡≡≡ designates a point of attachment of L2 to G, where G is an oligonucleotide, cationic peptide, polyamine, or polycation;

the monomer of formula A2 is

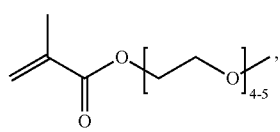

the monomer of formula A3 is absent or 2-(2-((tert-butoxycarbonyl)amino)ethoxy)ethyl methacrylate, the monomer of formula B1 is butyl methacrylate, the monomer of formula B2 is 2-propyl acrylic acid, the monomer of formula B3 is 2-(dimethylamino)ethyl methacrylate, and T1-L1-together are

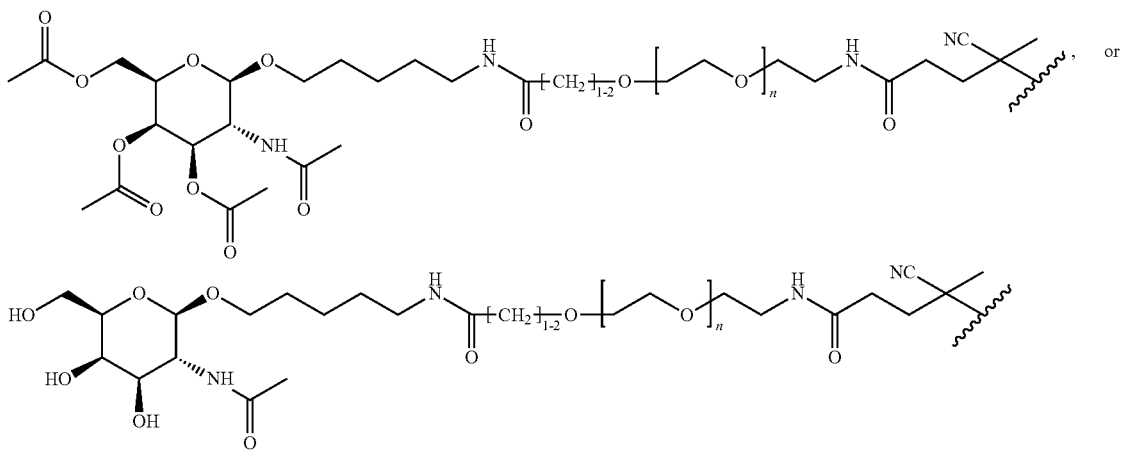

and ∼∼∼ designates a point of attachment.

Examples of block copolymers of Formula I include those where the monomer of formula A1 is

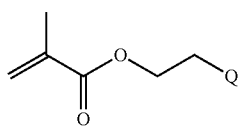

where Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is C$_1$-C$_6$ alkyl, (OCH$_2$CH$_2$)$_{1-50}$, C$_1$-C$_6$ alkyl-(OCH$_2$CH$_2$)$_{1-50}$, or thioether, (v)

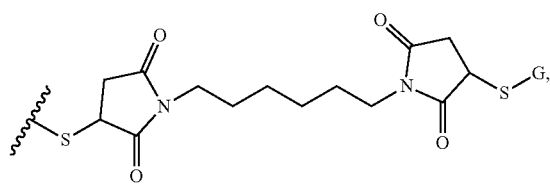

(vi)

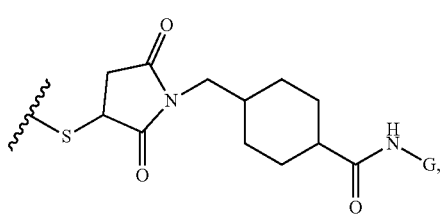

-continued (vii)

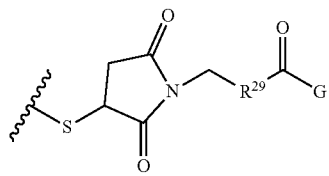

where R$^{29}$ is C$_1$-C$_6$ alkyl, (OCH$_2$CH$_2$)$_{1-50}$, C$_1$-C$_6$ alkyl-(OCH$_2$CH$_2$)$_{1-50}$, O, NH, or N(C$_1$-C$_6$ alkyl), and (viii) S-S-L2-G wherein L2 is

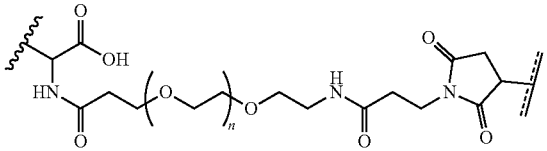

where n=1-35 and ----- designates a point of attachment of L2 to G, where G is an oligonucleotide, cationic peptide, polyamine, or polycation;

the monomer of formula A2 is

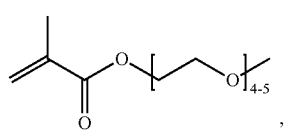

the monomer of formula A3 is absent or 2-(2-((tert-butoxycarbonyl)amino)ethoxy)ethyl methacrylate, the monomer of formula B1 is butyl methacrylate, the monomer of formula B2 is 2-propyl acrylic acid, the monomer of formula B3 is 2-(dimethylamino)ethyl methacrylate, x is 2-8 kDa, y is 3-8 kDa, and T1-L1-together are

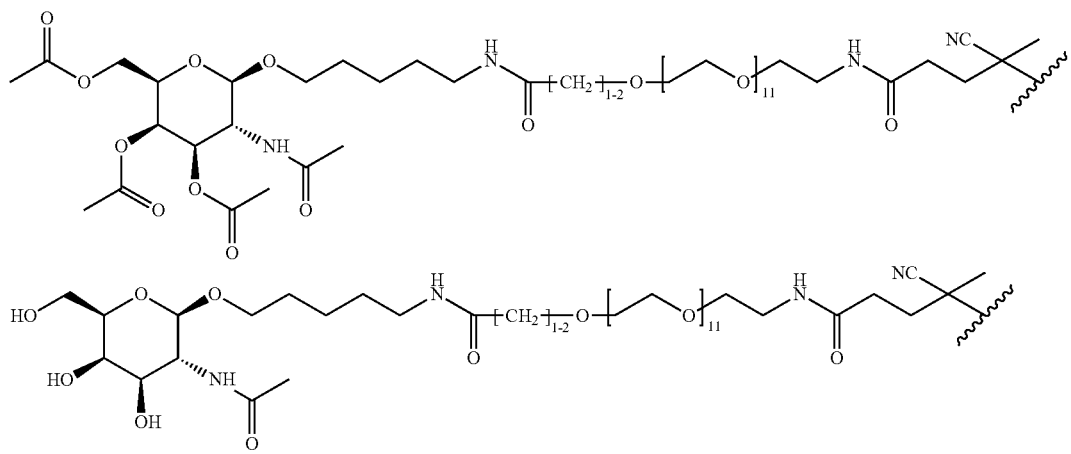

, or

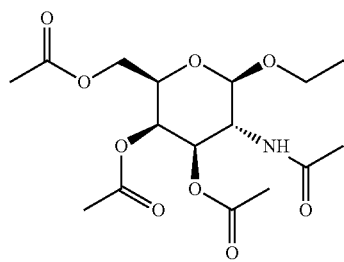

and ⌇⌇ designates a point of attachment.

Examples of block copolymers of Formula I include those where the monomer of formula A1 is

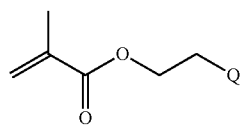

where Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether, (v)

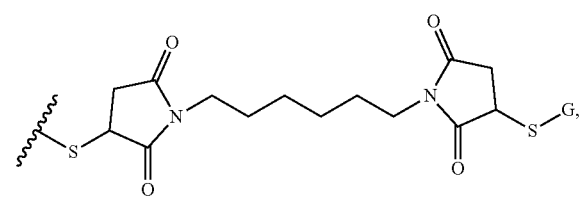

(vi)

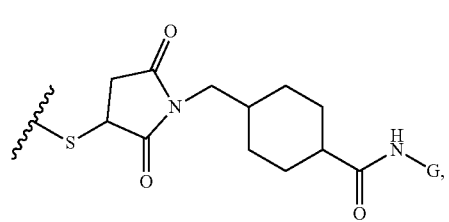

-continued (vii)

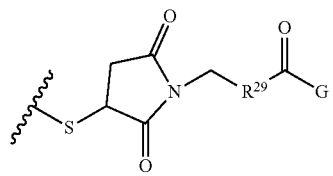

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

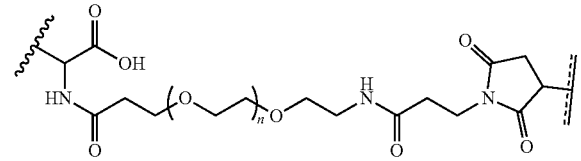

where n=1-35 and ═══ designates a point of attachment of L2 to G, wherein G is an oligonucleotide, cationic peptide, polyamine, or polycation;

the monomer of formula A2 is

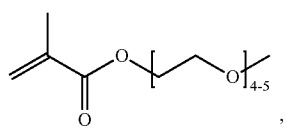

the monomer of formula A3 is absent or 2-(2-((tert-butoxy-carbonyl)amino)ethoxy)ethyl methacrylate, the monomer of formula B1 is butyl methacrylate, the monomer of formula B2 is 2-propyl acrylic acid, the monomer of formula B3 is 2-(dimethylamino)ethyl methacrylate, x is 2-8 kDa, y is 3-8 kDa, and T1-L1-together are

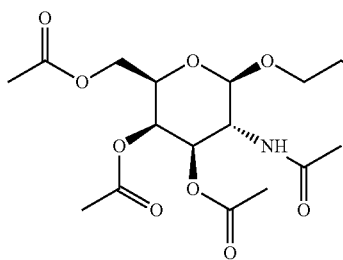

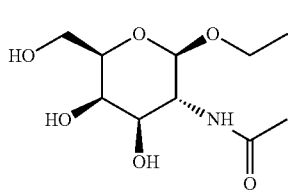

, or

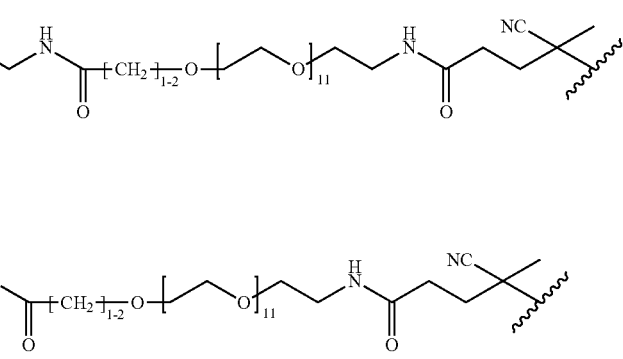

and ⁓ designates a point of attachment.

Examples of block copolymers of Formula I include those of formula III

T1-L1-[A1-A2]$_{x'}$-b-[B1-B2-B3]$_{y'}$Z    III where the monomer of formula A1 is

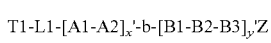

and is present in block A in an amount of 5-15 mole percent and wherein Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is C$_1$-C$_6$ alkyl, (OCH$_2$CH$_2$)$_{1-50}$, C$_1$-C$_6$alkyl-(OCH$_2$CH$_2$)$_{1-50}$, or thioether, (v)

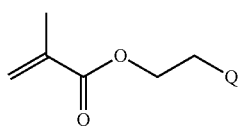

(vi)

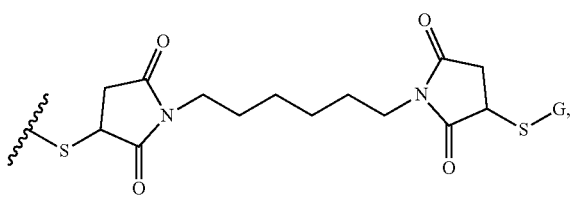

-continued (vii)

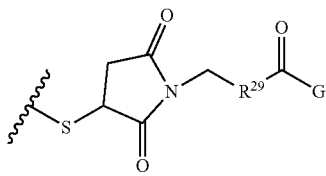

where R$^{29}$ is C$_1$-C$_6$ alkyl, (OCH$_2$CH$_2$)$_{1-50}$, C$_1$-C$_6$ alkyl-(OCH$_2$CH$_2$)$_{1-50}$, O, NH, or N(C$_1$-C$_6$ alkyl), and (viii) S-S-L2-G wherein L2 is

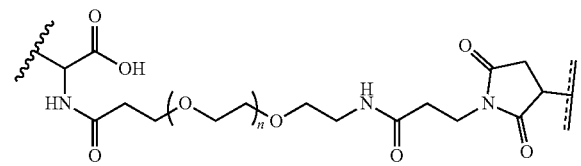

where n=1-35 and ===== designates a point of attachment of L2 to G, wherein G is an oligonucleotide, cationic peptide, polyamine, or polycation; monomer A2 is

and is present in block A in an amount of 85-95 mole percent; monomer B1 is butyl methacrylate and is present in block B in an amount of 53-58 mole percent; monomer B2 is 2-propyl acrylic acid and is present in block B in an amount of 10-15 mole percent; monomer B3 is 2-(dimethylamino)ethyl methacrylate and is present in block B in an amount of 30-35 mole percent; x' is 3-4 kDa; y' is 5-7 kDa; T1-L1-together are

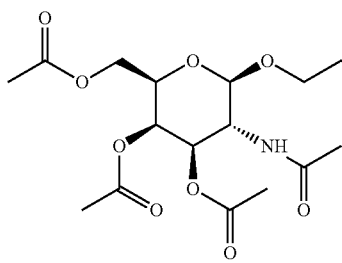
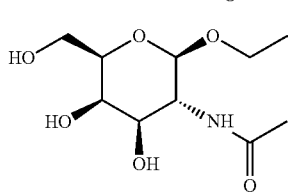

, or

;

Z is H, SH,

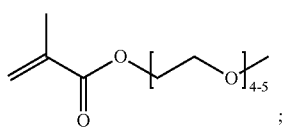, or wherein $R^{24}$ is S—($C_1$-$C_{12}$ alkyl), aryl, arylhalide, O—($C_1$-$C_{12}$ alkyl), $NR^{25}R^{26}$ wherein $R^{25}$ and $R^{26}$ are independently H, alkyl, aryl, or heteroaryl; and ⁓ designates a point of attachment.

In some embodiments of a copolymer of Formula III above, Q is not S-S-pyridyl and G is a cationic peptide, polyamine, or polycation. In some such variations, an mRNA molecule is complexed to the cationic peptide, polyamine, or polycation.

Examples of block copolymers of Formula I include those of formula IV

T1-L1-[A2]$_{x'}$-b-[B1-B2-B3-B4]$_{y'}$Z    IV wherein the monomer A2 is

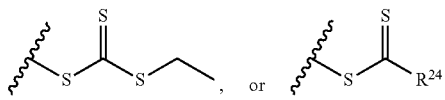
;

monomer B1 is butyl methacrylate and is present in block B in an amount of 45-60 mole percent; monomer B2 is 2-propyl acrylic acid and is present in block B in an amount of 3-15 mole percent; monomer B3 is 2-(dimethylamino) ethyl methacrylate and is present in block B in an amount of 25-40 mole percent; monomer of B4 is

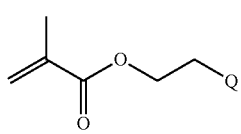

and is present in block B in an amount of 2-25 mole percent and wherein Q is selected from the group consisting of (i) S-S-pyridyl, (ii) S-S-G, (iii) (OCH$_2$CH$_2$)$_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, (OCH$_2$CH$_2$)$_{1-50}$, $C_1$-$C_6$ alkyl-(OCH$_2$CH$_2$)$_{1-50}$, or thioether,

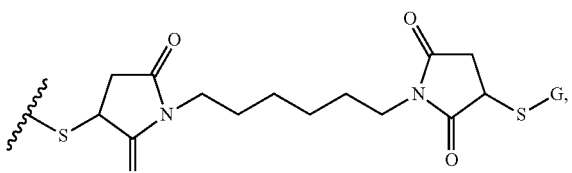
(vi)

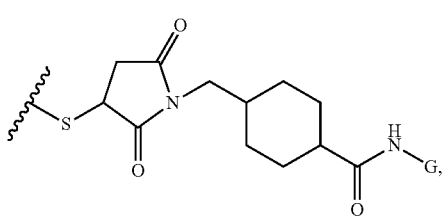
(vii)

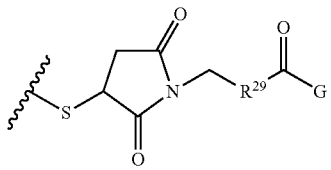

where $R^{29}$ is $C_1$-$C_6$ alkyl, (OCH$_2$CH$_2$)$_{1-50}$, $C_1$-$C_6$ alkyl-(OCH$_2$CH$_2$)$_{1-50}$, O, NH, or N($C_1$-$C_6$ alkyl), and
(viii) S-S-L2-G wherein L2 is

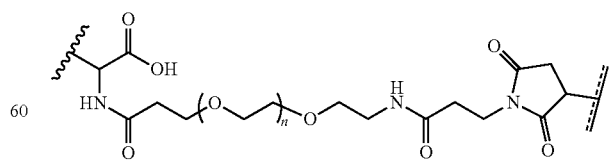

where n=1-35 and ═══ designates a point of attachment of L2 to G,
where G is an oligonucleotide, cationic peptide; x' is 3-4 kDa; y' is 5-7 kDa; T1-L1-together are

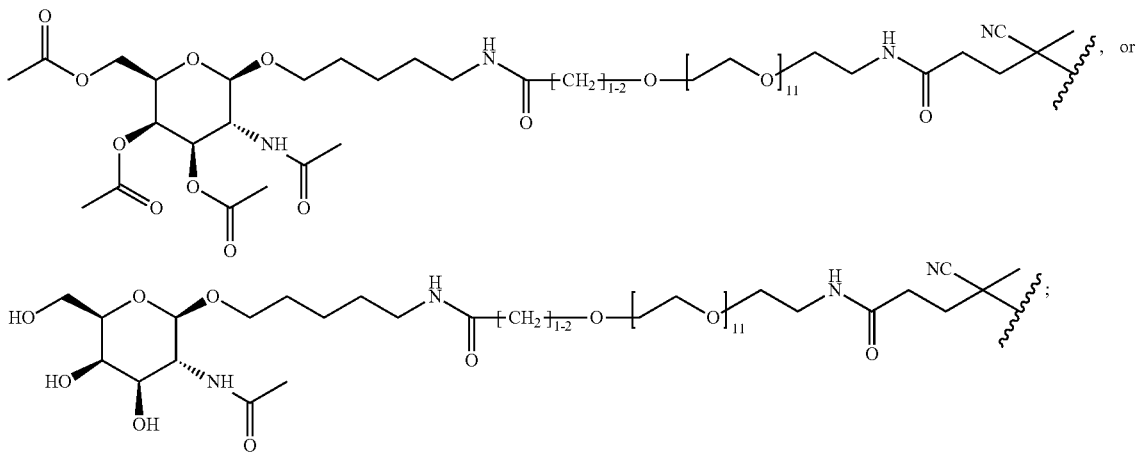

Z is H, SH,

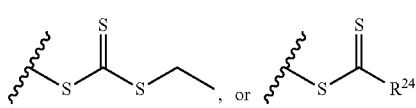, or 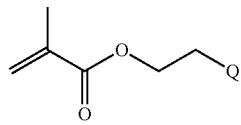

wherein $R^{24}$ is S—($C_1$-$C_{12}$ alkyl), aryl, arylhalide, O—($C_1$-$C_{12}$ alkyl), $NR^{25}R^{26}$ wherein $R^{25}$ and $R^{26}$ are independently H, alkyl, aryl, or heteroaryl; and ⌇ designates a point of attachment.

In some embodiments of a copolymer of Formula IV above, Q is not S-S-pyridyl and G is a cationic peptide, polyamine, or polycation. In some such variations, an mRNA molecule is complexed to the cationic peptide, polyamine, or polycation.

Additional examples of block copolymers of Formula I include those of formula VI T1-L1-[A2]x'-b-[B1-B2-B3-B4]y'Z   VI wherein the monomer A2 is selected from the group consisting of

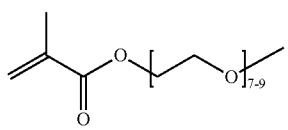

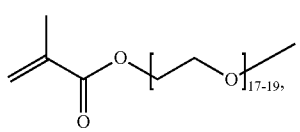

monomer B1 is butyl methacrylate and is present in block B in an amount of 45-60 mole percent; monomer B2 is 2-propyl acrylic acid and is present in block B in an amount of 3-15 mole percent; monomer B3 is 2-(dimethylamino) ethyl methacrylate and is present in block B in an amount of 25-40 mole percent; monomer of B4 is

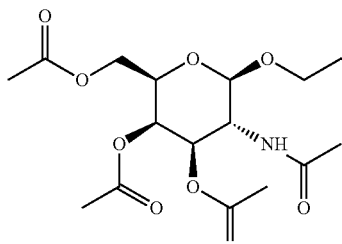

and is present in block B in an amount of 2-25 mole percent and wherein Q is selected from the group consisting of (i) S-S-pyridyl, (ii) S-S-G, (iii) $(OCH_2CH_2)_{1-120}$-S-S-G, (iv) V-L3-G where V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, $(OCH_2CH_2)_{1-50}$, $C_1$-$C_6$ alkyl-$(OCH_2CH_2)_{1-50}$, or thioether,

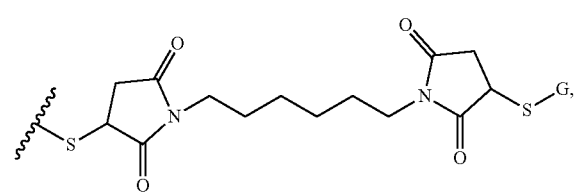

(vi)

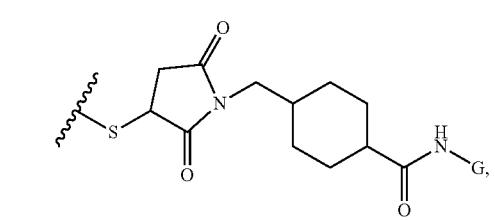

(vii)

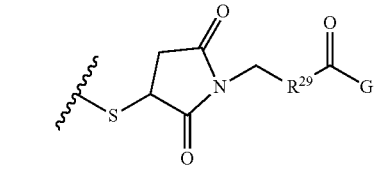

where $R^{29}$ is $C_1$-$C_6$ alkyl, $(OCH_2CH_2)_{1-50}$, $C_1$-$C_6$ alkyl-$(OCH_2CH_2)_{1-50}$, O, NH, or $N(C_1$-$C_6$ alkyl), and (viii) S-S-L2-G wherein L2 is

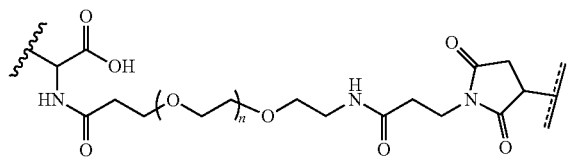

where n=1-35 and ----- designates a point of attachment of L2 to G,
where G is an oligonucleotide, cationic peptide, polyamine, or polycation;
x' is 3-10 kDa; y' is 3-7 kDa;
T1-L1-together are selected from the group consisting of In some embodiments of a copolymer of Formula VI above, x is 3-9 kDa; x is 3-8 kDa; x is 3-7 kDa; x is 3-6 kDa; x is 4-8 kDa; x is 4-7 kDa; x is 4-6 kDa; y is 3-6 kDa; y is 4-6 kDa; y is 4.5-5.5 kDa; y is 3-5 kDa; x is 3-9 kDa and y is 3-6 kDa; x is 3-9 kDa and y is 4-6 kDa; x is 3-9 kDa and y is 4.5-5.5 kDa; x is 3-9 kDa and y is 3-5 kDa; x is 3-8 kDa and y is 3-6 kDa; x is 3-8 kDa and y is 4-6 kDa; x is 3-8 kDa and y is 4.5-5.5 kDa; x is 3-8 kDa and y is 3-5 kDa; x is 3-7 kDa and y is 3-6 kDa; x is 3-7 kDa and y is 4-6 kDa; x is 3-7 kDa and y is 4.5-5.5 kDa; x is 3-7 kDa and y is 3-5 kDa; x is 3-6 kDa and y is 3-6 kDa; x is 3-6 kDa and y is 4-6 kDa; x is 3-6 kDa and y is 4.5-5.5 kDa; x is 3-6 kDa and y is 3-5 kDa; x is 4-7 kDa and y is 3-6 kDa; x is 4-7 kDa and y is 4-6 kDa; x is 4-7 kDa and y is 4.5-5.5 kDa; x is 4-7 kDa and y is 3-5 kDa; x is 4-6 kDa and y is 3-6 kDa; x is 4-6 kDa and y is 4-6 kDa; x is 4-6 kDa and y is 4.5-5.5 kDa; or x is 4-6 kDa and y is 3-5 kDa.

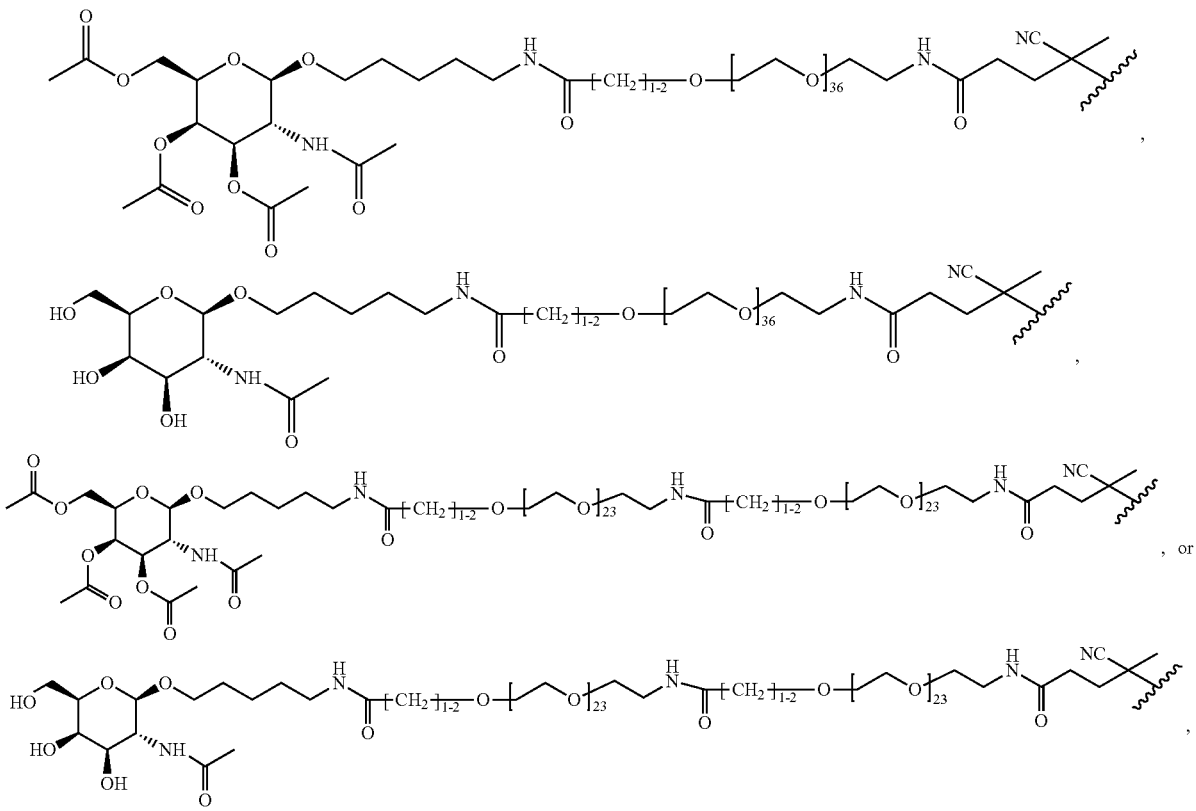

Z is H, SH,

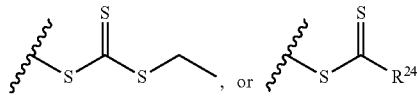

wherein $R^{24}$ is S-($C_1$-$C_{12}$ alkyl), aryl, arylhalide, O—($C_1$-$C_{12}$ alkyl), $NR^{25}R^{26}$ wherein $R^{25}$ and $R^{26}$ are independently H, alkyl, aryl, or heteroaryl; and ⌇⌇ designates a point of attachment.

In some embodiments of a copolymer of Formula VI above, Q is not S-S-pyridyl and G is a cationic peptide, polyamine, or polycation. In some such variations, an mRNA molecule is complexed to the cationic peptide, polyamine, or polycation.

Additional examples of block copolymers of Formula I include those of formula VII T1-L1-[A]x'-b-[B1-B2-B3-B4]y'Z          VII wherein
T1 is absent or a first targeting moiety;
L1 is absent or a linking moiety;
A is a first block that is a polymer formed from monomers comprising formula A2 or a random copolymer formed from monomers comprising formulae A2 and A3; A2, A4 and A5; A2 and A5; or A4 and A5;

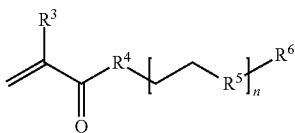
A2 wherein n is 1-120, $R^3$ is H or $C_1$-$C_6$ alkyl, $R^4$ is S, O, NH or N($C_1$-$C_6$ alkyl), $R^5$ is O or S and $R^6$ is H, $C_1$-$C_6$ alkyl, $C_1$-$C_6$ alkyl-$NH_2$, $C_1$-$C_6$ alkyl-NH($C_1$-$C_6$ alkyl), $C_1$-$C_6$ alkyl-N($C_1$-$C_6$ alkyl)$_2$;

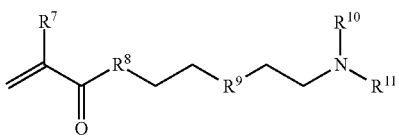
A3 wherein $R^7$ and $R^{10}$ are independently H or $C_1$-$C_6$ alkyl, $R^8$ is S, O, NH or N($C_1$-$C_6$ alkyl), and $R^9$ is O or S and $R^H$ is an amine protecting group;

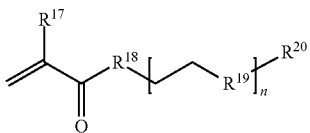
A4 wherein n is 1-230, $R^{17}$ is H or $C_1$-$C_6$ alkyl, $R^{18}$ is O, S, NH or N($C_1$-$C_6$ alkyl), $R^{19}$ is O or S, and $R^{29}$ is OH, NH, H, T2, or $C_1$-$C_6$ alkyl, where T2 is a second targeting moiety;

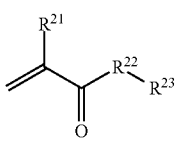
A5 wherein $R^{21}$ is H or $C_1$-$C_6$ alkyl, $R^{22}$ is O, NH or N($C_1$-$C_6$ alkyl), $R^{23}$ is H, aryl, arylhalide, alkyl, alkyl alcohol;

B is a second block that is a random copolymer formed from monomers comprising formulae B1, B2, B3 and B4 or B1, B2 and B3

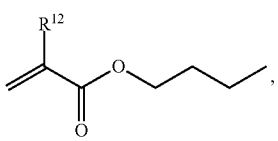
B1

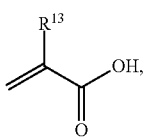
B2

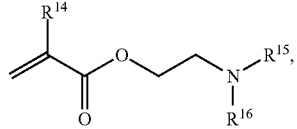
B3

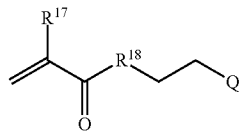
B4 wherein $R^{12}$, $R^{13}$, $R^{14}$, $R^{15}$, $R^{16}$ and $R^{17}$ are independently H or $C_1$-$C_6$ alkyl, $R^{18}$ is O, S, NH, N($C_1$-$C_6$ alkyl), or (OCH$_2$CH$_2$)$_{1-120}$, and Q is selected from the group consisting of (i) S-S-G, (ii) (OCH$_2$CH$_2$)$_{1-120}$-S-S-G, (iii) V-L3-G wherein V is an amide, ester, imine, oxime, thioester, product of a [3+2] cycloaddition, product of a [4+1] cycloaddition, carbonate, carbamate, urea, acetal, ketal, or hydrazone, and L3 is $C_1$-$C_6$ alkyl, (OCH$_2$CH$_2$)$_{1-50}$, $C_1$-$C_6$ alkyl-(OCH$_2$CH$_2$)$_{1-50}$, or thioether, (iv)

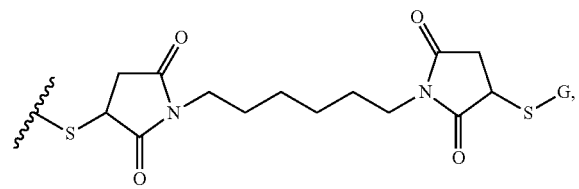

(v)

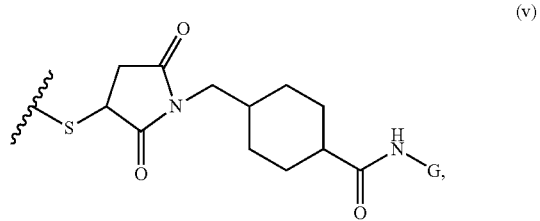

(vi)

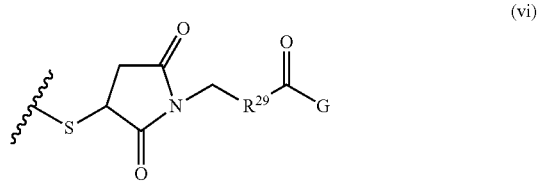

wherein $R^{29}$ is $C_1$-$C_6$ alkyl, (OCH$_2$CH$_2$)$_{1-50}$, $C_1$-$C_6$ alkyl-(OCH$_2$CH$_2$)$_{1-50}$, O, NH, or N($C_1$-$C_6$ alkyl), (vii) S-S-L2-G wherein L2 is

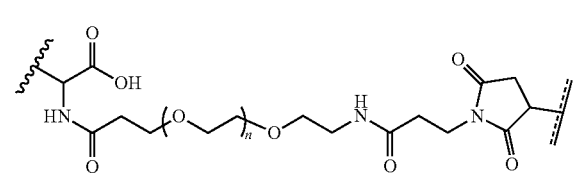

wherein n=1-35 and ----- designates a point of attachment of L2 to G, and (viii) S-S-pyridyl, wherein G is a cationic peptide, polyamine, or polycation; x is 2-20 kDa;

y is 2-20 kDa;
Z is H, SH, C(CH$_3$)$_2$CN,

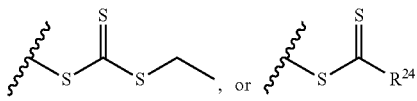

wherein R$^{24}$ is S—(C$_1$-C$_{12}$ alkyl), aryl, arylhalide, O—(C$_1$-C$_{12}$ alkyl), NR$^{25}$R$^{26}$ wherein R$^{25}$ and R$^{26}$ are independently H, alkyl, aryl, or heteroaryl;
the ratio of x to y is from 2:1 to 1:4; and
∼∼∼ designates a point of attachment.

In some embodiments of a block copolymer of Formula VII above, the monomer of formula A2 is

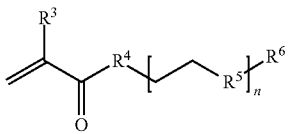

where n is 1-20, R$^3$ is H or C$_1$-C$_6$ alkyl, R$^4$ is S, O, NH or N(C$_1$-C$_6$ alkyl), R$^5$ is O or S and R$^6$ is H, C$_1$-C$_6$ alkyl, C$_1$-C$_6$ alkyl-NH$_2$, C$_1$-C$_6$ alkyl-NH(C$_1$-C$_6$ alkyl), C$_1$-C$_6$ alkyl-N(C$_1$-C$_6$ alkyl)$_2$.

In some embodiments of a copolymer of Formula VII above, Q is not S-S-pyridyl. In some such variations, an mRNA molecule is complexed to the cationic peptide, polyamine, or polycation.

In some embodiments of block copolymers of Formula VII as above, x is 2-15, 2-10 kDa, 3-10 kDa, 3-9 kDa, 3-8 kDa, 3-7 kDa, 3-6 kDa, 4-8 kDa, 4-7 kDa, or 4-6 kDa. In some embodiments, y is 2-10 kDa, 3-7 kDa, 3-6 kDa, 4-6 kDa, 4.5-5.5 kDa, or 3-5 kDa. In more particular variations, x is 2-15 kDa and y is 3-7 kDa; x is 2-15 kDa and y is 3-6 kDa; x is 2-15 kDa and y is 4-6 kDa; x is 2-15 kDa and y is 4.5-5.5 kDa; x is 2-15 kDa and y is 3-5 kDa; x is 2-10 kDa and y is 3-7 kDa; x is 2-10 kDa and y is 3-6 kDa; x is 2-10 kDa and y is 4-6 kDa; x is 2-10 kDa and y is 4.5-5.5 kDa; x is 2-10 and y is 3-5 kDa; x is 3-10 kDa and y is 3-7 kDa; x is 3-10 kDa and y is 3-6 kDa; x is 3-10 kDa and y is 4-6 kDa; x is 3-10 kDa and y is 4.5-5.5 kDa; x is 3-10 kDa and y is 3-5 kDa; x is 3-9 kDa and y is 3-7 kDa; x is 3-9 kDa and y is 3-6 kDa; x is 3-9 kDa and y is 4-6 kDa; x is 3-9 kDa and y is 4.5-5.5 kDa; x is 3-9 kDa and y is 3-5 kDa; x is 3-8 kDa and y is 3-7 kDa; x is 3-8 kDa and y is 3-6 kDa; x is 3-8 kDa and y is 4-6 kDa; x is 3-8 kDa and y is 4.5-5.5 kDa; x is 3-8 kDa and y is 3-5 kDa; x is 3-7 kDa and y is 3-7 kDa; x is 3-7 kDa and y is 3-6 kDa; x is 3-7 kDa and y is 4-6 kDa; x is 3-7 kDa and y is 4.5-5.5 kDa; x is 3-7 kDa and y is 3-5 kDa; x is 3-6 kDa and y is 3-7 kDa; x is 3-6 kDa and y is 3-6 kDa; x is 3-6 kDa and y is 4-6 kDa; x is 3-6 kDa and y is 4.5-5.5 kDa; x is 3-6 kDa and y is 3-5 kDa; x is 4-7 kDa and y is 3-7 kDa; x is 4-7 kDa and y is 3-6 kDa; x is 4-7 kDa and y is 4-6 kDa; x is 4-7 kDa and y is 4.5-5.5 kDa; x is 4-7 kDa and y is 3-5 kDa; x is 4-6 kDa and y is 3-7 kDa; x is 4-6 kDa and y is 3-6 kDa; x is 4-6 kDa and y is 4-6 kDa; x is 4-6 kDa and y is 4.5-5.5 kDa; x is 4-6 kDa and y is 3-5 kDa.

Examples of block copolymers of Formula I include

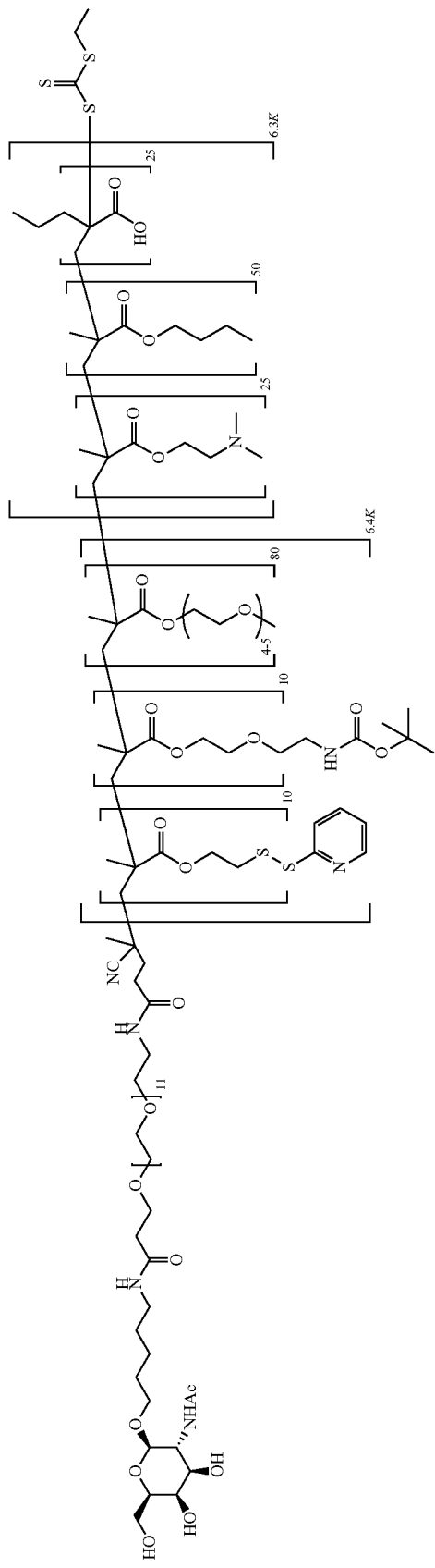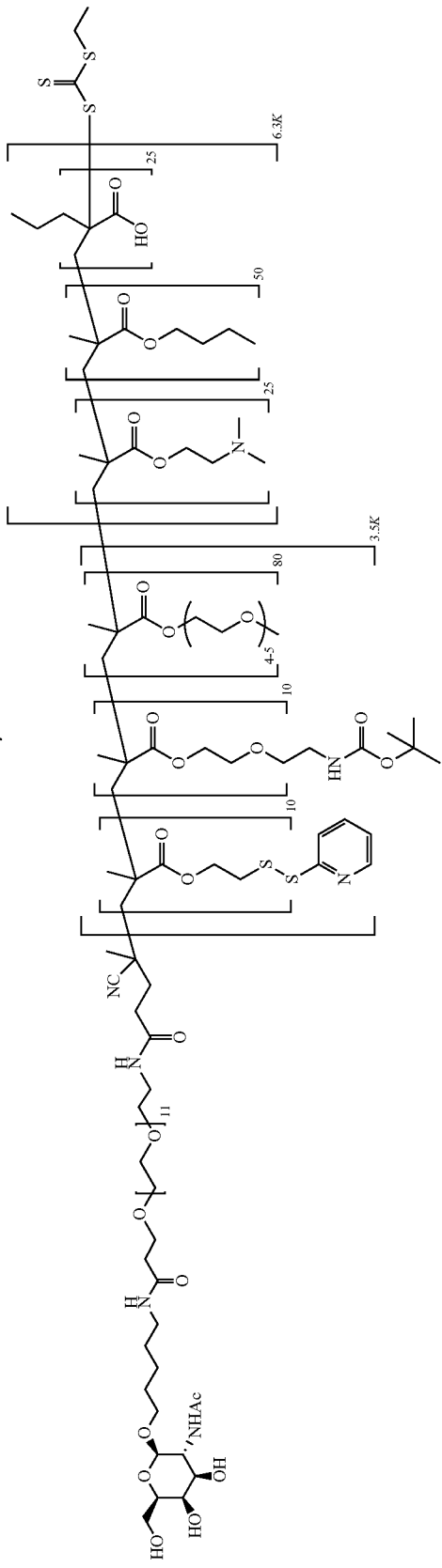

-continued
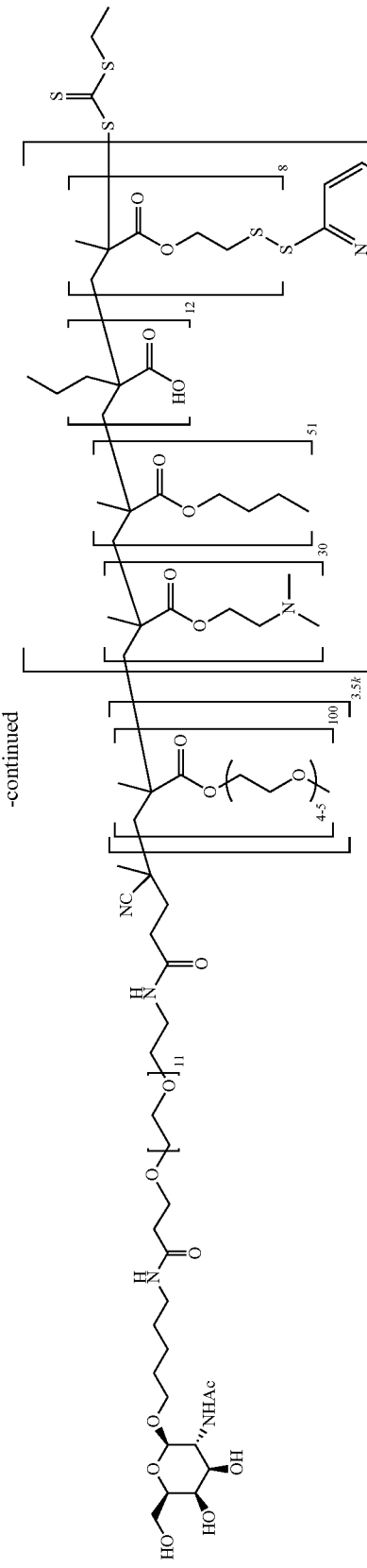
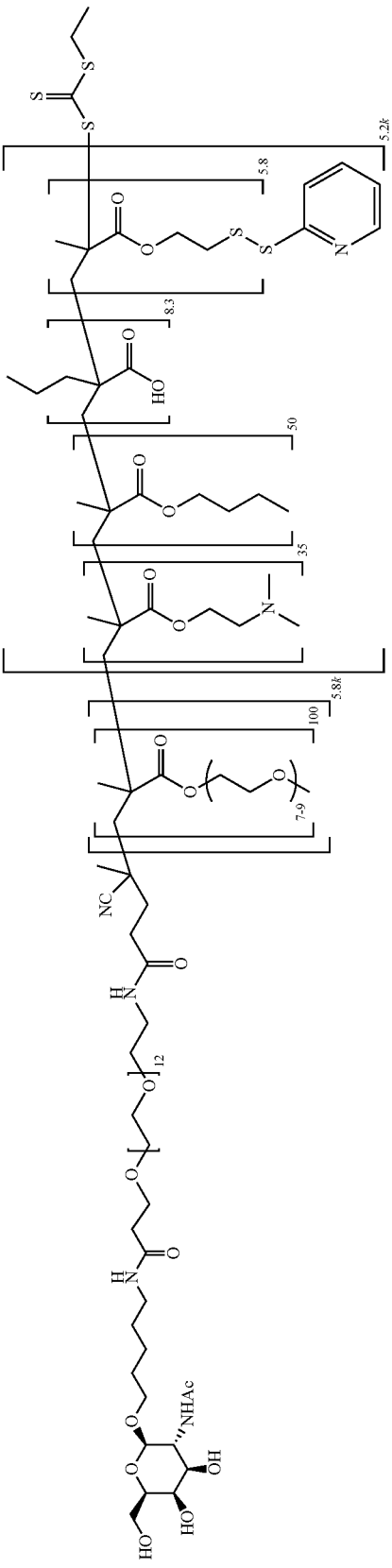

-continued
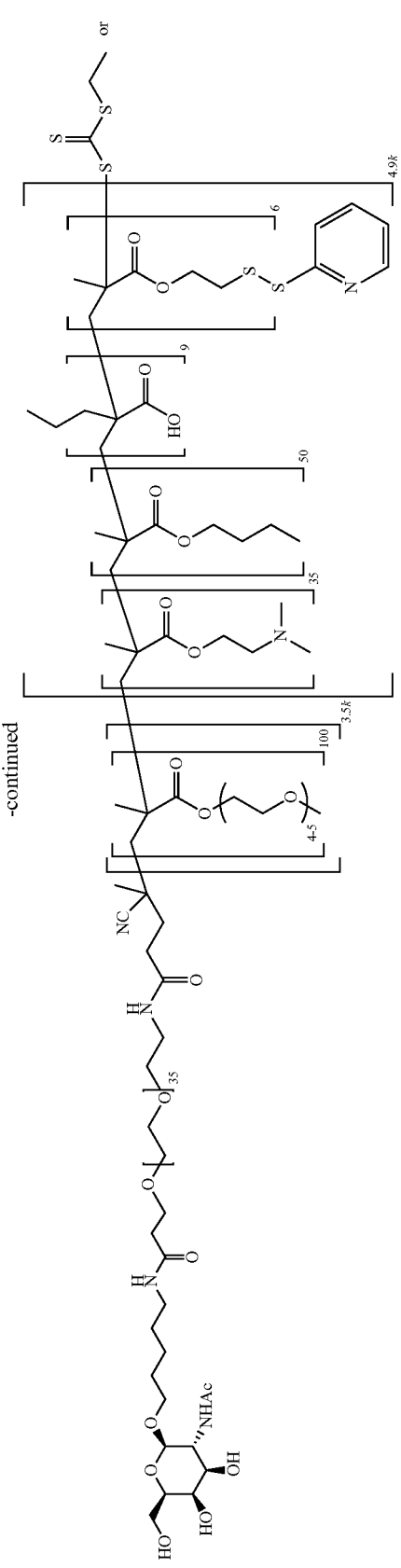
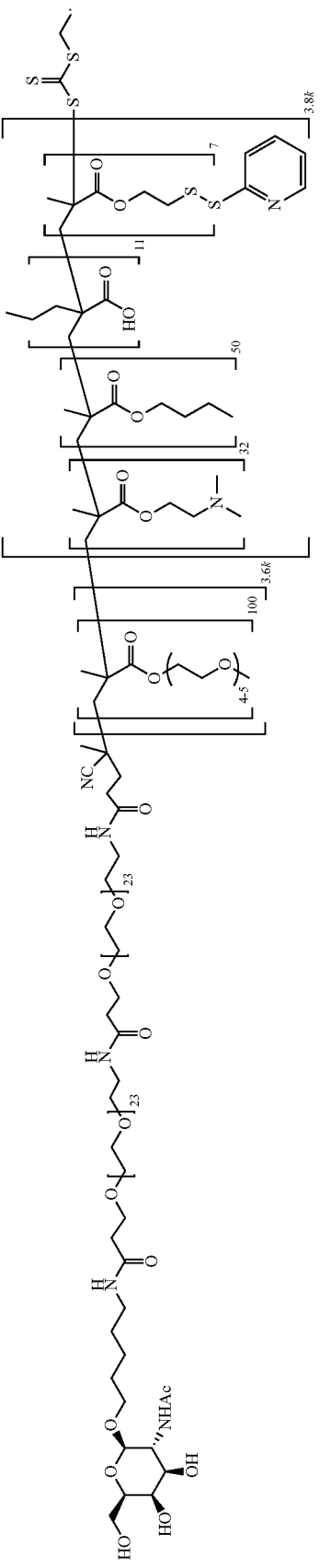

In some embodiments, a block copolymer of Formula I is selected from

NAG-PEG$_{12}$-[PEGMA (300, 100%)]$_{3.45k}$-b-[BMA$_{47.5\%}$-PAA$_{9.2\%}$-DMAEMA$_{35.8\%}$-PDSMA$_{7.5\%}$]$_{6.6k}$;

NAG-PEG$_{12}$-[PEGMA500 (100%)]$_{5.8k}$-b-[DMAEMA$_{35\%}$-BMA$_{50\%}$-PAA$_{8\%}$-PDSMA$_{6\%}$]$_{5.2k}$;

NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$;

NAG-PEG$_{24}$-amido-PEG$_{24}$-[PEGMA300,100%]$_{3.6k}$-b-[BMA$_{50\%}$-PAA$_{11\%}$-DMAEMA$_{32\%}$-PDSMA$_{7\%}$]$_{13.8k}$;

NAG-C5-PEG$_{24}$-amido-PEG$_{24}$-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

NAG-C5-PEG5k-Ph-aldehyde(oxime)NO-PEG$_{11}$-[PEGMA (300, 100%)]$_{3.8k}$-b-[DMAEMA$_{32\%}$-BMA-$_{47\%}$-PAA$_{14\%}$-PDSMA$_{7\%}$]$_{4.0k}$;

ECT-[PEGMA (300, 58%)-NAG-C5-PEG$_{36}$ (42%)]$_{19.9k}$-b-[DMAEMA$_{31\%}$-BMA$_{49\%}$-PAA$_{12\%}$-PDSMA$_{8\%}$]$_{5.03k}$;

NAG-PEG$_{12}$-[PEGMA (300, 73%)-NAG-C5-PEG$_{36}$ (18%)-TFPMA$_{5\%}$]$_{11k}$-b-[DMAEMA$_{36\%}$-BMA$_{46\%}$-PAA$_{10\%}$-PDSMA$_{7\%}$]$_{5.33k}$;

NAG-C5-PEG10k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

NAG-C5-PEG20k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

NAG-C5-PEG24-amido-PEG$_{24}$-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG5k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG10k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG20k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG24-amido-PEG$_{24}$-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-C5-PEG5k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-C5-PEG10k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-C5-PEG20k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-PEG$_{36}$-[PEGMA (500, 100%)]$_{6.19k}$-b-[DMAEMA$_{31.6\%}$-BMA$_{48.4\%}$-PAA$_{13.1\%}$-PDSMA$_{6.8\%}$]$_{4.3k}$;

NAG-PEG$_{36}$-[PEGMA (500, 100%)]$_{6.19k}$-b-[DMAEMA$_{30.8\%}$-BMA$_{50.8\%}$-PAA$_{11.6\%}$-PDSMA$_{6.8\%}$]$_{3.5k}$;

NAG-PEG$_{48}$-[PEGMA (300, 100%)]$_{3.8k}$-b-[BMA$_{49.3\%}$-PAA$_{9\%}$-DMAEMA$_{31.4\%}$-PDSMA$_{9\%}$]$_{6.3k}$;

NAG-PEG$_{12}$-[PEGMA(500, 100%)]$_{5.8k}$-b-[DMAEMA$_{35\%}$-BMA$_{50\%}$-PAA$_{8\%}$-PDSMA$_{6\%}$]$_{5.2k}$;

NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$;

Tri-NAG-PEG$_{12}$-[PEGMA(300, 80%)-PDSMA$_{10\%}$-BPAM$_{10\%}$]$_{6.1k}$-[BMA$_{50\%}$-PAA$_{25\%}$-DMAEMA$_{25\%}$]$_{4.9k}$;

Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{3.2k}$; and Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{4.2k}$.

Any one of the above block copolymers may be conjugated to a cationic peptide, polyamine, or polycation. For example, a cationic peptide comprising a cysteine residue (e.g., a cationic peptide having the sequence -Cys-(Lys)$_{10}$-OH (SEQ ID NO:101) or -Cys-(Lys)$_{10}$-NH$_2$ (SEQ ID NO:103) may be conjugated to the PDSMA monomer through the cysteine thiol to form a disulfide bridge.

As previously discussed herein, transfection agents used in the art today, such as peptides, polymers, and lipids of a cationic nature as well as nano- and microparticles for example, may achieve high transfection efficiencies in vitro, achieving similar extents of transfection without toxicity is difficult in vivo in greatly limits their use as delivery systems for nucleic acid-based drugs, particularly RNA based therapeutics such as siRNA and mRNA therapeutics. The block copolymers of Formula I as described herein include, e.g., various block sizes, mole percentages of monomers, and linkers that surprisingly provide for efficient modulation of a target gene, for example decreased or inhibited expression of a target gene or increased expression of a target gene, while limiting toxicity in vivo. For example, in certain embodiments, block copolymers of Formula I as described herein, where the block copolymer includes a cationic peptide, polyamine, or polycation and is ionically complexed via the cationic peptide, polyamine, or polycation with an mRNA encoding a protein of interest, provide for an increase in the amount of the encoded protein in a target tissue in vivo. The role and influence of block size, block ratio, mole percentage of monomers, linker length, and various combinations of these elements on the ability of copolymers as described herein to modulate expression of a target gene and limit in vivo toxicity is surprising and described in more detail in this specification and demonstrated in the examples contained herein.

In particular embodiments of block copolymers of Formula I comprising a cationic peptide, variation of certain parameters was found to influence the delivery of mRNA complexed with the copolymer. Such parameters may also be varied in a block copolymer of Formula I comprising a polyamine or polycation to similarly influence the delivery of mRNA. For example, increasing the length of the linking moiety L (e.g., increasing the length of an α-end PEG, such as, for example, increasing m w, x, y, and/or z in a linking moiety of the formula

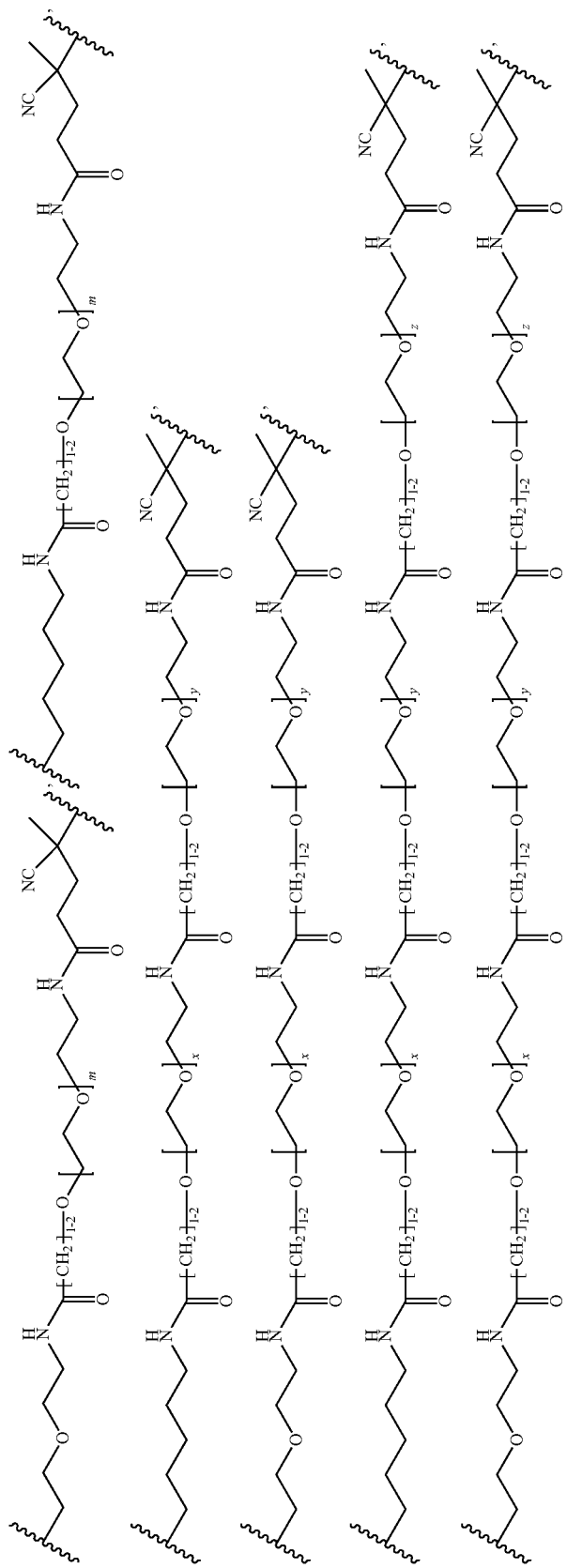

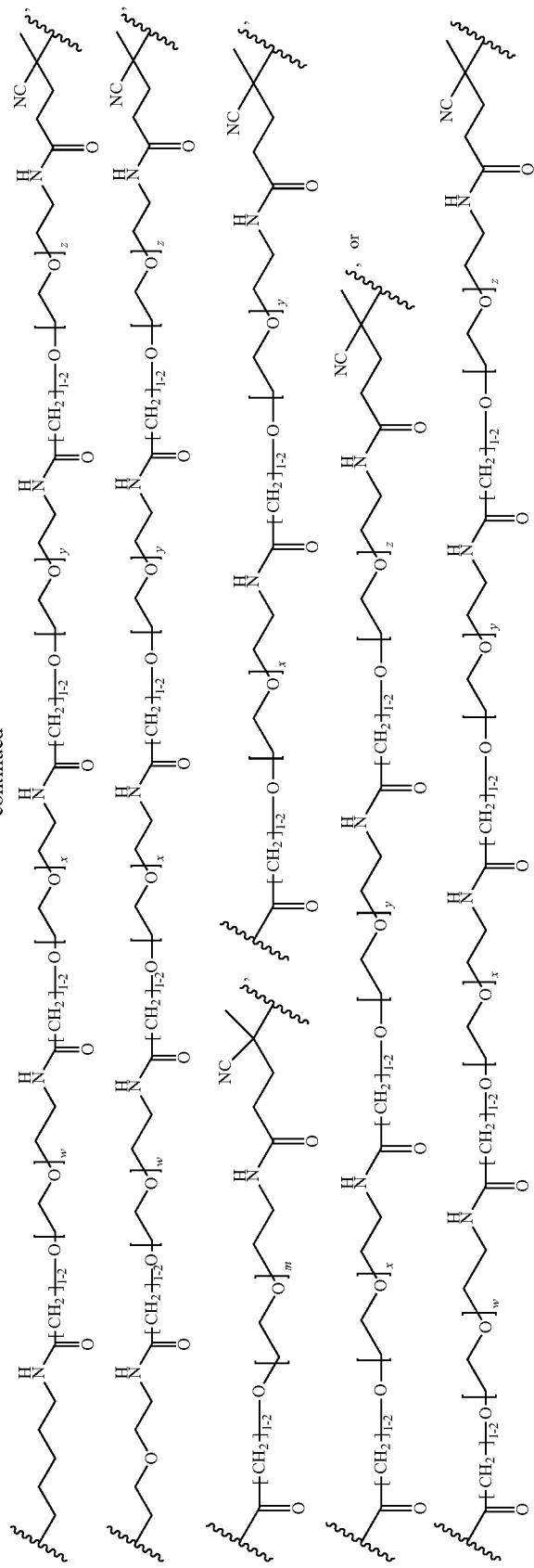

where each of m, w, x, y, and z is independently 1-100 or 10-460) can result in increased mRNA delivery to a target tissue. Without being bound to any particular theory, longer linking moieties may enable better presentation of a targeting moiety (e.g., T1), resulting in greater targeting of copolymer/mRNA particles to a molecular target present on the surface of cells within the target tissue. For example, where T1 includes an N-acetylgalactosamine (NAG) residue, increasing the length of the linking moiety may enable better presentation of NAG, resulting in greater targeting of particles to the asialoglycoprotein receptor (ASPGR) on hepatocytes. Further, increasing the size of block A (e.g., increasing the length of PEG in monomer A2) can result in increased expression of the mRNA. Again without being bound to any particular theory, increasing the size of block A appears to increase mRNA and particle stability. (See Example 27, showing longer blood circulation at 30 minutes post-dose.) In addition, reducing the size of block B may result in improved activity. For example, in some variations of a copolymer of Formula I, the size of block B is 3-5 kDa. Further, in specific variations where B1 is butyl methacrylate (BMA), B2 is 2-propyl acrylic acid (PAA), and B3 is 2-(dimethylamino)ethyl methacrylate (DMAEMA), a 3:2 ratio of BMA to DMAEMA with a small fraction (e.g., 4-15% mole percent) of PAA appears to enhance mRNA expression.

In other variations of block copolymers of Formula I comprising a cationic peptide, polyamine, or polycation, increasing the amount of a targeting moiety on the polymer can improve delivery of mRNA to a target tissue. Increasing the amount of a targeting moiety can be achieved, for example, by incorporating monomer A4 (comprising a targeting moiety T2) into block A of the polymer. Increasing the amount of a targeting moiety may alternatively, or additionally, include increasing the valency of the targeting moiety so as to increase, e.g., the avidity of the targeting moiety for its specific binding partner on the surface of a cell. In specific embodiments, (i) an N-acetylgalactosamine (NAG) sugar residue is incorporated into monomer A4 of block A to increase the amount of NAG on the polymer (such as on a polymer also comprising NAG as T1 on the α end) and/or (ii) a moiety comprising multiple NAG sugar residues (e.g., three NAG residues) is used at the α end of the polymer to increase avidity for the asialoglycoprotein receptor (ASPGR) on hepatocytes.

In some variations of a block copolymer of Formula I (e.g., a block copolymer of Formula VII), L1 is a polymer having a molecular weight of from 0.5 kDa to 6 kDa and comprising at least 10 ethylene oxide units. For example, in certain embodiments, L1 has a molecular weight of from 2 kDa to 3 kDa and comprises at least 36 ethylene oxide units (e.g., L1 can have a weight of 2.2 kDa and have 48 ethylene oxide units, such as a structure having the formula

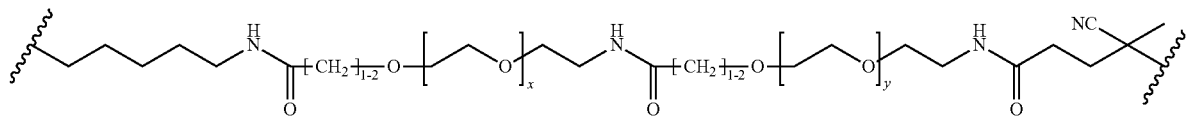

wherein x and y are each 24 and ∿ designates a point of attachment). In other embodiments, L1 has a molecular weight of from 3 kDa to 6 kDa and comprises at least 48 ethylene oxide units. In some such embodiments as above, the monomer of formula A2 is

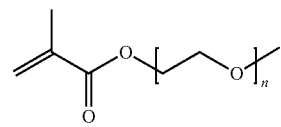

wherein n is 4 or 5 (PEGMA$_{300}$), n is 7-9 (PEGMA$_{500}$), or n is 17-19 (PEGMA$_{1000}$). In any such embodiments as above, T1 may specifically bind to the asialoglycoprotein receptor. For example, in some embodiments, T1 comprises one or more N-acetyl galactoseamine (NAG) moieties. In some such embodiments, T1 is a tri-NAG structure having three NAG moieties, such as, e.g., a structure having the formula

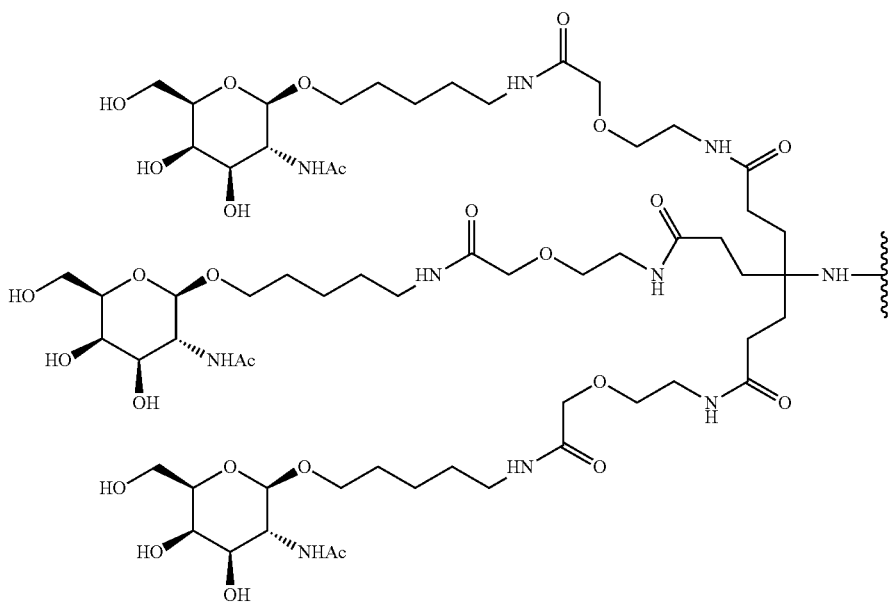 [SMILES: *NC(CCC(=O)NCCOCC(=O)NCCCCCO[C@@H]1O[C@H](CO)[C@H](O)[C@H](O)[C@H]1NC(C)=O)(CCC(=O)NCCOCC(=O)NCCCCCO[C@@H]1O[C@H](CO)[C@H](O)[C@H](O)[C@H]1NC(C)=O)CCC(=O)NCCOCC(=O)NCCCCCO[C@@H]1O[C@H](CO)[C@H](O)[C@H](O)[C@H]1NC(C)=O]

where ⌇⌇⌇ designates a point of attachment.

Examples of block copolymers of Formula I include those where monomer A1 is present in block A in an amount of 3-15 or 5-20 mole percent. Other examples of block copolymers of Formula I include those where monomer A1 is present in block A in an amount of 5-15 mole percent. Additional examples of block copolymers of Formula I include those where monomer A1 is present in block A in an amount of 3-10 or 5-10 mole percent. Additional examples of block copolymers of Formula I include those where monomer A1 is present in block A in an amount of 10-15 mole percent. Additional examples of block copolymers of Formula I include those where monomer A1 is absent. As used herein when describing the amount of a given monomer in terms of its "mole percent," the mole percent of a given monomer is the number of moles of a given monomer in the mixture of monomers that make up the particular block in which the monomer is present as a percentage of the total number of moles of monomers in that particular block.

Examples of block copolymers of Formula I include those where monomer A2 is present in block A in an amount of 10-30, 30-50, 50-70, 70-90, or 70-100 mole percent. Other examples of polymers of Formula I include those where monomer A2 is present in block A in an amount of 70-85 mole percent. Other examples of polymers of Formula I include those where monomer A2 is present in block A in an amount of 75-80 mole percent. Additional examples of polymers of Formula I include those where monomer A2 is present in block A in an amount of 85-95 mole percent. Additional example of polymer of Formula I include those where monomer A2 is present in block A in an amount of 100 mole percent. In some such embodiments as above, the block copolymer of Formula I is a copolymer of formula VII.

Examples of block copolymers of Formula I include those where monomer A3 is present in block A in an amount of 5-20 mole percent. Other examples of block copolymers of Formula I include those where monomer A3 is present in block A in an amount of 10-15 mole percent. Additional examples of Polymers of Formula I include those where monomer A3 is absent. In some such embodiments as above, the block copolymer of Formula I is a copolymer of formula VII.

Examples of block copolymers of Formula I include those where monomer A4 is present in block A in an amount of 10-50 or 50-95 mole percent. Other examples of block copolymers of Formula I include those where monomer A4 is present in block A in an amount of 10-30 mole percent. Additional examples of block copolymers of Formula I include those where monomer A4 is absent. In some such embodiments as above, the block copolymer of Formula I is a copolymer of formula VII.

Examples of block copolymers of Formula I include those where monomer A5 is present in block A in an amount of 0.1-30 mole percent. Other examples of block copolymers of Formula I include those where monomer A5 is present in block A in an amount of 1-20 mole percent. Additional examples of block copolymers of Formula I include those where monomer A5 is absent. In some such embodiments as above, the block copolymer of Formula I is a copolymer of formula VII.

Block copolymers of Formula I possessing the desired gene modulation activity and minimal in vivo toxicity include those where monomer A1 is present in block A in an amount of 5-20 mole percent, monomer A2 is present in block A in an amount of 70-90 mole percent, and monomer A3 is present in block A in an amount of 5-20 mole percent.

Block copolymers of Formula I possessing the desired gene modulation activity and minimal in vivo toxicity also include those where monomer A1 is present in block A in an amount of 5-15 mole percent, monomer A2 is present in block A in an amount of 70-85 mole percent, and monomer A3 is present in block A in an amount of 10-15 mole percent.

Additional block copolymers of Formula I possessing the desired gene modulation activity and minimal in vivo toxicity also include those where monomer A1 is present in block A in an amount of 5-10 mole percent, monomer A2 is present in block A in an amount of 75-80 mole percent, and monomer A3 is present in block A in an amount of 10-15 mole percent.

A particular example of a block copolymer of Formula I is that where monomer A1 is present in block A in an amount of 5-15 mole percent, monomer A2 is present in block A in an amount of 85-95 mole percent, and monomer A3 is absent.

Examples of block copolymers of Formula I include those where monomer B1 is present in block B in an amount of 35-65 or 50-60 mole percent. Other examples of block copolymers of Formula I include those where monomer B1 is present in block B in an amount of 45-60, 48-58 or 53-58 mole percent. Additional examples of block copolymers of Formula I include those where monomer B1 is present in block B in an amount of 45-55 or 50-55 mole percent. Further examples of block copolymers of Formula I include those where monomer B1 is present in block B in an amount of 50 mole percent. In some such embodiments as above, the block copolymer of Formula I is a copolymer of formula VII.

Examples of block copolymers of Formula I include those where monomer B2 is present in block B in an amount of 3-15, 5-20 or 10-30 mole percent. Other examples of block copolymers of Formula I include those where monomer B2 is present in block B in an amount of 10-25 mole percent. Other examples of block copolymers of Formula I include those where monomer B2 is present in block B in an amount of 3-12, 5-15, or 10-15 mole percent. Additional examples of block copolymers of Formula I include those where monomer B2 is present in block B in an amount of 21-28 mole percent. Further examples of block copolymers of Formula I include those monomer B2 is present in block B in an amount of 25 mole percent. Still further examples of block copolymers of Formula I include those where monomer B2 is present in block B in an amount of 6-12 or 7-10 mole percent. In some such embodiments as above, the block copolymer of Formula I is a copolymer of formula VII.

Examples of block copolymers of Formula I include those where monomer B3 is present in block B in an amount of 15-35 or 25-40 mole percent. Other examples of block copolymers of Formula I include those where monomer B3 is present in block B in an amount of 25-35 mole percent. Other examples of block copolymers of Formula I include those where monomer B3 is present in block B in an amount of 30-35 or 30-38 mole percent. Additional examples of block copolymers of Formula I include those where monomer B3 is present in block B in an amount of 21-28 mole percent. Further examples of block copolymers of Formula I include those where monomer B3 is present in block B in an amount of 25 mole percent. Still further examples of copolymers of Formula I include those where monomer B3 is present in block B in an amount of 32-38 or 33-37 mole percent. In some such embodiments as above, the block copolymer of Formula I is a copolymer of formula VII.

Examples of block copolymers of Formula I include those where monomer B4 is present in block B in an amount of 2-25 or 3-15 mole percent. Other examples of block copolymers of Formula I include those where monomer B4 is present in block B in an amount of 5-15 mole percent. Other examples of block copolymers of Formula I include those where monomer B4 is present in block B in an amount of 5-10 mole percent. Yet other examples of block copolymers of Formula I include those where monomer B4 is present in block B in an amount of 3-10 or 4-8 mole percent. Additional examples of block copolymers of Formula I include those monomer B4 is absent. In some such embodiments as above where B4 is present, the block copolymer of Formula I is a copolymer of formula VII.

Additional block copolymers of Formula I include those where monomer B1 is present in block B in an amount of 35-65 mole percent, monomer B2 is present in block B in an amount of 10-30 mole percent, and monomer B3 is present in block B in an amount of 15-35 mole percent.

Additional block copolymers of Formula I include those where monomer B1 is present in block B in an amount of 50-60 mole percent, monomer B2 is present in block B in an amount of 10-25 mole percent, and monomer B3 is present in block B in an amount of 25-35 mole percent.

Additional block copolymers of Formula I include those where monomer B1 is present in block B in an amount of 53-58 mole percent, monomer B2 is present in block B in an amount of 10-15 mole percent, and monomer B3 is present in block B in an amount of 30-35 mole percent.

Additional block copolymers of Formula I include those where monomer B1 is present in block B in an amount of 35-65 mole percent, monomer B2 is present in block B in an amount of 10-30 mole percent, monomer B3 is present in block B in an amount of 15-35 mole percent and monomer B4 is present in block B in an amount of 5-20 mole percent. In some such embodiments as above, the block copolymer of Formula I is a copolymer of formula VII.

Additional block copolymers of Formula I include those where monomer B1 is present in block B in an amount of 50-60 mole percent, monomer B2 is present in block B in an amount of 10-25 mole percent, monomer B3 is present in block B in an amount of 25-35 mole percent and monomer B4 is present in block B in an amount of 5-15 mole percent. In some such embodiments as above, the block copolymer of Formula I is a copolymer of formula VII.

Additional block copolymers of Formula I include those where monomer B1 is present in block B in an amount of 53-58 mole percent, monomer B2 is present in block B in an amount of 10-15 mole percent, monomer B3 is present in block B in an amount of 30-35 mole percent and monomer B4 is present in block B in an amount of 5-10 mole percent. In some such embodiments as above, the block copolymer of Formula I is a copolymer of formula VII.

Additional block copolymers of Formula I include those where monomer B1 is present in block B in an amount of 45-60 mole percent, monomer B2 is present in block B in an amount of 3-15 mole percent, monomer B3 is present in block B in an amount of 25-40 mole percent and monomer B4 is present in block B in an amount of 2-25 mole percent. In some such embodiments, B2 is present in block B in an amount of 3-12 or 5-15 percent. In some such embodiments as above, the block copolymer of Formula I is a copolymer of formula VII.

Additional block copolymers of Formula I include those where monomer B1 is present in block B in an amount of 48-58 mole percent, monomer B2 is present in block B in an amount of 5-15 mole percent, monomer B3 is present in block B in an amount of 28-35 mole percent and monomer B4 is present in block B in an amount of 5-10 mole percent. In some such embodiments, B2 is present in block B in an amount of 5-10 percent. In some such embodiments as above, the block copolymer of Formula I is a copolymer of formula VII.

Additional block copolymers of Formula I include those where monomer B1 is present in block B in an amount of 45-55 mole percent, monomer B2 is present in block B in an amount of 3-12 mole percent, monomer B3 is present in block B in an amount of 32-38 mole percent and monomer B4 is present in block B in an amount of 3-10 mole percent. In some such embodiments, B2 is present in block B in an amount of 3-6 or 6-12 mole percent. In some such embodiments as above, the block copolymer of Formula I is a copolymer of formula VII.

Additional block copolymers of Formula I include those where monomer A1 is present in block A in an amount of 5-20 mole percent, monomer A2 is present in block A in an amount of 70-90 mole percent, monomer A3 is present in block A in an amount of 5-20 mole percent, monomer B1 is present in block B in an amount of 35-65 mole percent, monomer B2 is present in block B in an amount of 10-30 mole percent, and monomer B3 is present in block B in an amount of 15-35 mole percent.

Additional block copolymers of Formula I include those where monomer A1 is present in block A in an amount of 5-15 mole percent, monomer A2 is present in block A in an amount of 70-85 mole percent, monomer A3 is present in block A in an amount of 10-15 mole percent, monomer B1 is present in block B in an amount of 50-60 mole percent, monomer B2 is present in block B in an amount of 10-25 mole percent, and monomer B3 is present in block B in an amount of 25-35 mole percent.

Additional block copolymers of Formula I include those where monomer A1 is present in block A in an amount of 5-10 mole percent, monomer A2 is present in block A in an amount of 75-80 mole percent, monomer A3 is present in block A in an amount of 10-15 mole percent, monomer B1 is present in block B in an amount of 53-58 mole percent, monomer B2 is present in block B in an amount of 10-15 mole percent, and monomer B3 is present in block B in an amount of 30-35 mole percent.

Additional block copolymers of Formula I include those where monomer A1 is present in block A in an amount of 5-15 mole percent, monomer A2 is present in block A in an amount of 85-95 mole percent, monomer A3 is absent, monomer B1 is present in block B in an amount of 53-58 mole percent, monomer B2 is present in block B in an amount of 10-15 mole percent, and monomer B3 is present in block B in an amount of 30-35 mole percent.

Examples of block copolymers of Formula I include those where x is 2-10 kDa or 3-8 kDa. Other examples of block copolymers of Formula I include those where x is 5-7 kDa or 8-15 kDa. Additional examples of block copolymers of Formula I include those where x is 3-5 kDa. Still other examples of block copolymers of Formula I include those where x is 3-15 kDa, 3-10 kDa, 3-9 kDa, 3-7 kDa, 3-6 kDa, 4-8 kDa, 4-7 kDa, or 4-6 kDa. In some such embodiments as above, the block copolymer of Formula I is a copolymer of formula VII.

Examples of block copolymers of Formula I include those where y is 2-10 kDa or 3-7 kDa. Other examples of block copolymers of Formula I include those where y is 5-7 kDa. Additional examples of block copolymers of Formula I include those where y is 3-6 kDa, 4-6 kDa, or 4.5-5.5 kDa. In some such embodiments as above, the block copolymer of Formula I is a copolymer of formula VII.

Examples of block copolymers of Formula I include those where the ratio of x to y is from 0.25:1 to 2:1; from 0.25:1 to 1.75:1; from 0.25:1 to 1.5:1; from 0.25:1 to 1.25:1; from 0.5:1 to 1.25:1; from 0.6 to 1.25:1; from 0.7:1 to 1.25:1; from 0.5:1 to 1.3:1; from 0.6 to 1.3:1; or from 0.7:1 to 1.3:1. Additional examples of block copolymers of Formula I include those where the ratio of x to y is from 0.6:1 to 0.8:1; from 0.65:1 to 0.75:1; from 0.7:1 to 0.75:1; from 1:1 to 1.3:1; or from 1:1 to 1:1.25:1. Another example of copolymers of Formula I include those where the ration of x to y is from 1:1 to 1:3. Yet other examples of block copolymers of Formula I include those where the ratio of x to y is 1:1 or 0.7:1. In some such embodiments as above, the block copolymer of Formula I is a copolymer of formula VII.

Examples of block copolymers of Formula I include those where Z is a trithiocarbonate moiety such as

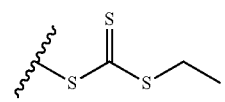

for example. Additional examples of block copolymers of Formula I include those where Z is a moiety derived from the cleavage or derivatization of a trithiocarbonate moiety such as a sulfhydryl moiety for example.

Additional examples of block copolymers of Formula I include those where the oligonucleotide of Q in monomer A1 or B4 (i.e., where G is present and is an oligonucleotide) is an siRNA, an antisense oligonucleotide, a dicer substrate, mRNA, a miRNA, an aiRNA or an shRNA. Additional examples of block copolymers of Formula I include those where the oligonucleotide of Q in monomer A1 is an siRNA or mRNA. Further examples of block copolymers of Formula I include those where the oligonucleotide is an siRNA that inhibits expression of the beta-catenin or MET gene. C-Met, also referred to as MET or MNNG HOS transforming gene, is a proto-oncogene implicated in a variety of cancers, including liver cancer, lung cancer, breast cancer, thyroid cancer, gastric cancer, ovarian cancer, pancreatic cancer, head and neck cancer, renal cancer and colorectal cancer, as well as sarcomas, hematologic malignancies, melanoma and central nervous system tumors. C-Met encodes the hepatocyte growth factor receptor (HGFR) protein, which can give rise to invasive growth when activated by its ligand, hepatocyte growth factor (HGF). Beta catenin, also referred to as CTNNB1, has been implicated in a number of cancers, including basal cell carcinoma, colorectal cancer, pilomatrixoma, medullablastoma, and ovarian cancer, as well as adenomatous polyposis of the colon. The gene encoding beta catenin may act as an oncogene in some cases. For example, an increase in beta catenin has been observed in people with basal cell carcinoma and can increase proliferation in related tumors. In addition, mutations in the gene encoding beta catenin have been observed in various cancers.

Specific examples of oligonucleotides include siRNA oligonucleotides that inhibit expression of the MET gene include those in Table 1.

TABLE 1

Synthesized MET dsRNAs.

| SEQ ID NO | Sense strand sequence (5'-3') | SEQ ID NO | Antisense strand sequence (5'-3') |
|---|---|---|---|
| 1 | acGfaCfaAfaUfgUfgUfgCfgAfuCfdTsdT | 27 | GfAfuCfgCfaCfaCfaUfuUfgUfcGfudTsdT |
| 2 | gcGfcGfuUfgAfcUfuAfuUfcAfuGfdTsdT | 28 | CfAfuGfaAfuAfaGfuCfaAfcGfcGfcdTsdT |
| 3 | gcGfcCfgUfgAfuGfaAfuAfuCfgAfdTsdT | 29 | UfCfgAfuAfuUfcAfuCfaCfgGfcGfcdTsdT |

TABLE 1-continued

Synthesized MET dsRNAs.

| SEQ ID NO | Sense strand sequence (5'-3') | SEQ ID NO | Antisense strand sequence (5'-3') |
|---|---|---|---|
| 4 | ucGfcCfgAfaAfuAfcGfgUfcCfuAfdTsdT | 30 | UfAfgGfaCfcGfuAfuUfuCfgGfcGfadTsdT |
| 5 | gcCfgAfaAfuAfcGfgUfcCfuAfuGfdTsdT | 31 | CfAfuAfgGfaCfcGfuAfuUfuCfgGfcdTsdT |
| 6 | guAfaGfuGfcCfcGfaAfgUfgUfaAfdTsdT | 32 | UfUfaCfaCfuUfcGfgGfcAfcUfuAfcdTsdT |
| 7 | guGfcAfgUfaUfcCfuCfuGfaCfaGfdTsdT | 33 | CfUfgUfcAfgAfgGfaUfaCfuGfcAfcdTsdT |
| 8 | cuGfgUfgUfcCfcGfgAfuAfuCfaGfdTsdT | 34 | CfUfgAfuAfuCfcGfgGfaCfaCfcAfgdTsdT |
| 9 | ucUfaGfuUfgUfcGfaCfaCfcUfaCfdTsdT | 35 | GfUfaGfgUfgUfcGfaCfaAfcUfaGfadTsdT |
| 10 | auGfgCfuCfuAfgUfuGfuCfgAfcAfdTsdT | 36 | UfGfuCfgAfcAfaCfuAfgAfgCfcAfudTsdT |
| 11 | auUfuCfgCfcGfaAfaUfaCfgGfuCfdTsdT | 37 | GfAfcCfgUfaUfuUfcGfgCfgAfaAfudTsdT |
| 12 | ggCfuCfuAfgUfuGfuCfgAfcAfcCfdTsdT | 38 | GfGfuGfuCfgAfcAfaCfuAfgAfgCfcdTsdT |
| 13 | aaCfuGfgUfgUfcCfcGfgAfuAfuCfdTsdT | 39 | GfAfuAfuCfcGfgGfaCfaCfcAfgUfudTsdT |
| 14 | guCfaAfuUfcAfgCfgAfaGfuCfcUfdTsdT | 40 | AfGfgAfcUfuCfgCfuGfaAfuUfgAfcdTsdT |
| 15 | cuCfuAfgUfuGfuCfgAfcAfcCfuAfdTsdT | 41 | UfAfgGfuGfuCfgAfcAfaCfuAfgAfgdTsdT |
| 16 | gcGfaUfcGfgAfgGfaAfuGfcCfuGfdTsdT | 42 | CfAfgGfcAfuUfcCfuCfcGfaUfcGfcdTsdT |
| 17 | aaAfuAfcGfgUfcCfuAfuGfcGfuGfdTsdT | 43 | CfAfgCfcAfuAfgGfaCfcGfuAfuUfudTsdT |
| 18 | uuUfaCfuUfcUfuGfaCfgGfuCfcAfdTsdT | 44 | UfGfgAfcCfgUfcAfaGfaAfgUfaAfadTsdT |
| 19 | ucAfuGfgGfuCfaAfuUfcAfgCfgAfdTsdT | 45 | UfCfgCfuGfaAfuUfgAfcCfcAfuGfadTsdT |
| 20 | ugUfgCfgAfuCfgGfaGfgAfaUfgCfdTsdT | 46 | GfCfaUfuCfcUfcCfgAfuCfgCfaCfadTsdT |
| 21 | gcGfcGfcCfgUfgAfuGfaAfuAfuCfdTsdT | 47 | GfAfuAfuUfcAfuCfaCfgGfcGfcGfcdTsdT |
| 22 | uuUfcGfcCfgAfaAfuAfcGfgUfcCfdTsdT | 48 | GfGfaCfcGfuAfuUfuCfgGfcGfaAfadTsdT |
| 23 | ugGfuUfuCfuCfgAfuCfaGfgAfcCfdTsdT | 49 | GfGfuCfcUfgAfuCfgAfgAfaAfcCfadTsdT |
| 24 | uuAfuGfcAfcGfgUfcCfcCfaAfuGfdTsdT | 50 | CfAfuUfgGfgGfaCfcGfuGfcAfuAfadTsdT |
| 25 | cgAfaAfuAfcGfgUfcCfuAfuGfgCfdTsdT | 51 | GfCfcAfuAfgGfaCfcGfuAfuUfuCfgdTsdT |
| 26 | ugGfuGfcCfaCfgAfcAfaAfuGfuGfdTsdT | 52 | CfAfcAfuUfuGfuCfgUfgGfcAfcCfadTsdT |

In Table 1, letters in capitals represent RNA nucleotides, lower case letters "c", "g", "a" and "u" represent 2'-O-methyl-modified nucleotides, "s" represents phosphorothioate and "dT" represents deoxythymidine residues. Upper case letters A, C, G, U followed by "f" indicate 2'-fluoro nucleotides.

In Table 1, a dsRNA pair is shown within a row. For example, the SEQ ID NO:1 sense strand and the SEQ ID NO:27 antisense strand form a dsRNA, the SEQ ID NO:2 sense strand and the SEQ ID NO:28 antisense strand form a dsRNA, SEQ ID NO:3 sense strand and the SEQ ID NO:29 antisense strand form a dsRNA, and so on.

Specific examples of oligonucleotides include siRNA oligonucleotides that inhibit expression of the beta-catenin gene include those in Table 2.

The dsRNAs synthesized are presented in Table 2 below.

TABLE 2

Synthesized beta-catenin dsRNAs.

| SEQ ID NO | Sense strand sequence (5'-3') | SEQ ID NO | Antisense strand sequence (5'-3') |
|---|---|---|---|
| 53 | caGfgGfgUfcCfuCfuGfuGfaAfcUfdTsdT | 77 | AfGfuUfcAfcAfgAfgGfaCfcCfcUfgdTsdT |
| 54 | ugCfuCfuUfcGfuCfaUfcUfgAfcCfdTsdT | 78 | GfGfuCfaGfaUfgAfcGfaAfgAfgCfadTsdT |
| 55 | gcUfcUfuCfgUfcAfuCfuGfaCfcAfdTsdT | 79 | UfGfgUfcAfgAfuGfaCfgAfaGfaGfcdTsdT |
| 56 | ggAfgCfuAfaAfaUfgGfcAfgUfgCfdTsdT | 80 | GfCfaCfuGfcCfaUfuUfuAfgCfuCfcdTsdT |

TABLE 2-continued

Synthesized beta-catenin dsRNAs.

| SEQ ID NO | Sense strand sequence (5'-3') | SEQ ID NO | Antisense strand sequence (5'-3') |
|---|---|---|---|
| 57 | ccUfgUfgCfaGfcUfgGfaAfuUfcUfdTsdT | 81 | AfGfaAfuUfcCfaGfcUfgCfaCfaGfgdTsdT |
| 58 | agAfgUfaGfcUfgCfaGfgGfgUfcCfdTsdT | 82 | GfGfaCfcCfcUfgCfaGfcUfaCfuCfudTsdT |
| 59 | cuGfaCfuAfuCfcAfgUfuGfaUfgGfdTsdT | 83 | CfCfaUfcAfaCfuGfgAfuAfgUfcAfgdTsdT |
| 60 | ccAfuUfcCfaUfuGfuUfuGfuGfcAfdTsdT | 84 | UfGfcAfcAfaAfcAfaUfgGfaAfuGfgdTsdT |
| 61 | auAfcCfaUfuCfcAfuUfgUfuUfgUfdTsdT | 85 | AfCfaAfaCfaAfuGfgAfaUfgGfuAfudTsdT |
| 62 | gcAfgGfgGfuCfcUfcUfgUfgAfaCfdTsdT | 86 | GfUfuCfaCfaGfaGfgAfcCfcCfuGfcdTsdT |
| 63 | ccAfgGfaCfcUfcAfuGfgAfuGfgGfdTsdT | 87 | CfCfcAfuCfcAfuGfaGfgUfcCfuGfgdTsdT |
| 64 | uaCfcAfuUfcCfaUfuGfuUfuGfuGfdTsdT | 88 | CfAfcAfaAfcAfaUfgGfaAfuGfgUfadTsdT |
| 65 | ugUfgAfaCfuUfgCfuCfaGfgAfcAfdTsdT | 89 | UfGfuCfcUfgAfgCfaAfgUfuCfaCfadTsdT |
| 66 | ugGfaUfaUfcGfcCfaGfgAfuGfaUfdTsdT | 90 | AfUfcAfuCfcUfgGfcGfaUfaUfcCfadTsdT |
| 67 | ugAfcUfaUfcCfaGfuUfgAfuGfgGfdTsdT | 91 | CfCfcAfuCfaAfcUfgGfaUfaGfuCfadTsdT |
| 68 | acCfaUfgCfaGfaAfuAfcAfaAfuGfdTsdT | 92 | CfAfuUfuGfuAfuUfcUfgCfaUfgGfudTsdT |
| 69 | acUfgUfuGfgAfuUfgAfuUfcGfaAfdTsdT | 93 | UfUfcGfaAfuCfaAfuCfcAfaCfaGfudTsdT |
| 70 | cuAfuCfcAfgUfuGfaUfgGfgCfuGfdTsdT | 94 | CfAfgCfcCfaUfcAfaCfuGfgAfuAfgdTsdT |
| 71 | gaCfuAfuCfcAfgUfuGfaUfgGfgCfdTsdT | 95 | GfCfcCfaUfcAfaCfuGfgAfuAfgUfcdTsdT |
| 72 | gcUfgAfcUfaUfcCfaGfuUfgAfuGfdTsdT | 96 | CfAfuCfaAfcUfgGfaUfaGfuCfaGfcdTsdT |
| 73 | aaUfaCfcAfuUfcCfaUfuGfuUfuGfdTsdT | 97 | CfAfaAfcAfaUfgGfaAfuGfgUfaUfudTsdT |
| 74 | acCfcUfgGfuGfcUfgAfcUfaUfcCfdTsdT | 98 | GfGfaUfaGfuCfaGfcAfcCfaGfgGfudTsdT |
| 75 | ugCfuUfuAfuUfcUfcCfcAfuUfgAfdTsdT | 99 | UfCfaAfuGfgGfaGfaAfuAfaAfgCfadTsdT |
| 76 | agGfaGfcUfaAfaAfuGfgCfaGfuGfdTsdT | 100 | CfAfcUfgCfcAfuUfuUfaGfcUfcCfudTsdT |

In Table 2, letters in capitals represent RNA nucleotides, lower case letters "c", "g", "a" and "u" represent 2'-O-methyl-modified nucleotides, "s" represents phosphorothioate and "dT" represents deoxythymidine residues. Upper case letters A, C, G, U followed by "f" indicate 2'-fluoro nucleotides.

In Table 2, a dsRNA pair is shown within a row. For example, the SEQ ID NO:53 sense strand and the SEQ ID NO:77 antisense strand form a dsRNA, the SEQ ID NO:54 sense strand and the SEQ ID NO:78 antisense strand form a dsRNA, SEQ ID NO:55 sense strand and the SEQ ID NO:79 antisense strand form a dsRNA, and so on.

Further examples of block copolymers of Formula I include those where the oligonucleotide is an siRNA that inhibits expression of the MET gene where the sense strand consists of a nucleotide sequence of SEQ ID NO:1 and the antisense region consists of a nucleotide sequence of SEQ ID NO:27.

Further examples of block copolymers of Formula I include those where the oligonucleotide is an siRNA that inhibits expression of the beta-catenin gene where the sense strand consists of a nucleotide sequence of SEQ ID NO:54 and the antisense region consists of a nucleotide sequence of SEQ ID NO:78.

Additional examples of block copolymers of Formula I include those that include a cationic peptide such as those amino acid polymers comprising 2-100 amino acid monomers whose overall charge is positive. Additional examples of block copolymers of Formula I include those where the cationic peptide in monomer A1 or B4 is a peptide that includes 5-30 lysine or arginine residues or a combination thereof. Additional examples of cationic peptides include a polylysine or polyarginine peptide. Additional examples of cationic peptides include a polylysine or polyarginine of 5-30 residues. Cationic peptides may include a cysteine residue, typically at the amino or carboxyl terminus; such peptides are particularly suitable for linkage to an A1 or B4 monomer using the cysteine thiol to form a disulfide bridge. Examples of cysteine-containing cationic peptides include -Cys-(Lys)$_{10}$-OH (SEQ ID NO:101), -Cys-(Arg)$_{10}$-OH (SEQ ID NO:102), -Cys-(Lys)$_{10}$-NH$_2$ (SEQ ID NO:103), -Cys-(Arg)$_{10}$-NH$_2$ (SEQ ID NO:104), H$_2$N-(Lys)$_{10}$-Cys-OH (SEQ ID NO:105), H$_2$N-(Arg)$_{10}$-Cys-OH (SEQ ID NO:106), H$_2$N-(Lys)$_{10}$-Cys-NH$_2$ (SEQ ID NO:115), and H$_2$N-(Arg)$_{10}$-Cys-NH$_2$ (SEQ ID NO:116). Peptides useful in practicing certain embodiments of the present invention can be prepared using standard peptide synthesis methodologies known to those of skill in the art. Alternatively, peptides useful in practicing certain embodiments of the present invention including those of SEQ ID NO:103, for example, can be purchased from American Peptide Company of San Diego, Calif. Yet another example of a cationic peptide includes -Cys-(Lys)₁₀-OH (SEQ ID NO:101) and -Cys-(Lys)₁₀-NH₂ (SEQ ID NO:103). In some such embodiments as above where B4 is present and A1 is absent, the block copolymer of Formula I is a copolymer of formula VII.

In particular embodiments of a block copolymer of Formula I including a cationic peptide, polyamine, or polycation as above, the copolymer is selected from the group consisting of:

(a) a block copolymer of Formula I, wherein G is present (i.e., Q is not S-S-pyridyl) and G is a cationic peptide, polyamine, or polycation;

(b) a block copolymer of Formula I as in (a) above, wherein x is 2-15 kDa, and y is 3-6 kDa, 3-7 kDa, 4-6 kDa, or 3-5 kDa;

(c) a block copolymer of Formula I as in (a) above, wherein A2 has the formula A2a, where n is 3-20 or 7-20;

(d) a block copolymer of Formula I as in (a) above, wherein A2 has the formula A2a, where n is 7-9 or 17-19;

(e) a block copolymer of Formula I as in (b) above, wherein A2 has the formula A2a, where n is 3-20 or 7-20;

(f) a block copolymer of Formula I as in (b) above, wherein A2 has the formula A2a, where n is 7-9 or 17-19;

(g) a block copolymer of Formula I as in (a) above, wherein A1 and A3 are absent, B4 is present, A2 has the formula A2a, where n is 3-20 or 7-20, B1 is butyl methacrylate, B2 is 2-propyl acrylic acid, B3 is 2-(dimethylamino)ethyl methacrylate, and B4 is

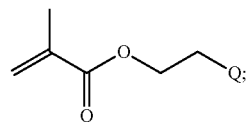

(h) a block copolymer of Formula I as in (g) above, wherein x is 2-15 kDa and y is 3-6 kDa, 3-7 kDa, 4-6 kDa, or 3-5 kDa;

(i) a block copolymer of Formula I as in (a) above, wherein A1 and A3 are absent, B4 is present, and T1 is

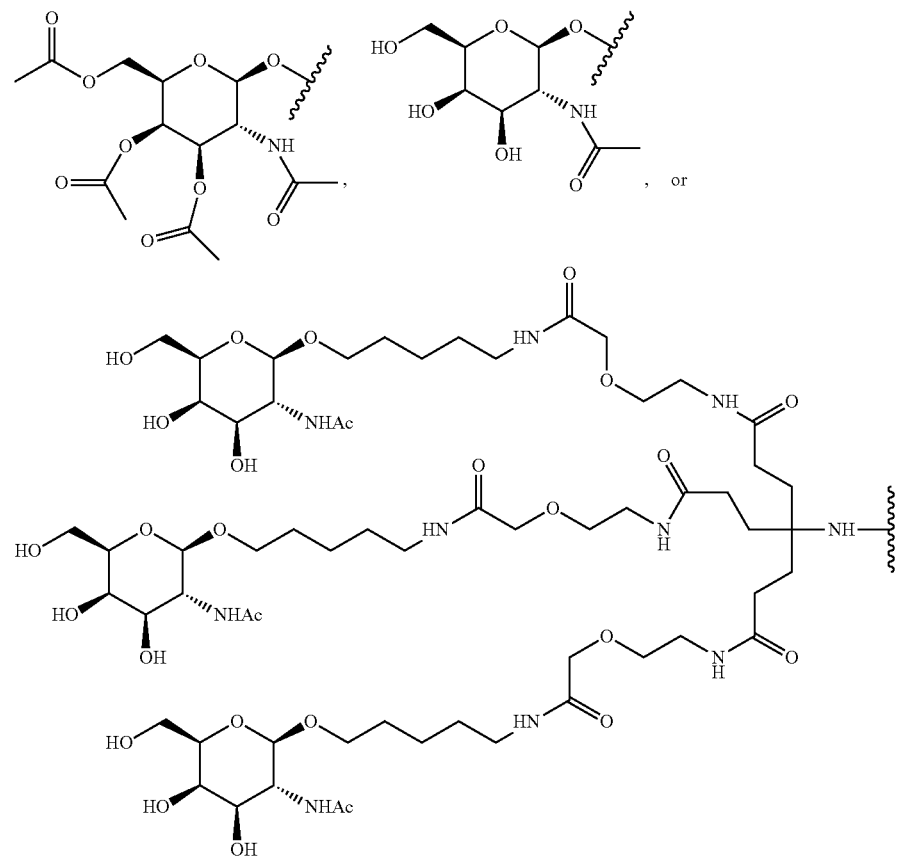

where ～ designates a point of attachment;

(j) a block copolymer of Formula I as in (i) above, wherein x is 2-15 kDa, y is 3-6 kDa, 3-7 kDa, or 4-6 kDa, and A2 has the formula A2a, where n is 3-20 or 7-20;

(k) a block copolymer of Formula I as in (j) above, wherein B1 is butyl methacrylate, B2 is 2-propyl acrylic acid, B3 is 2-(dimethylamino)ethyl methacrylate, B4 is

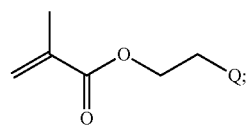

(l) a block copolymer of Formula I as in (a) above, wherein L1 is

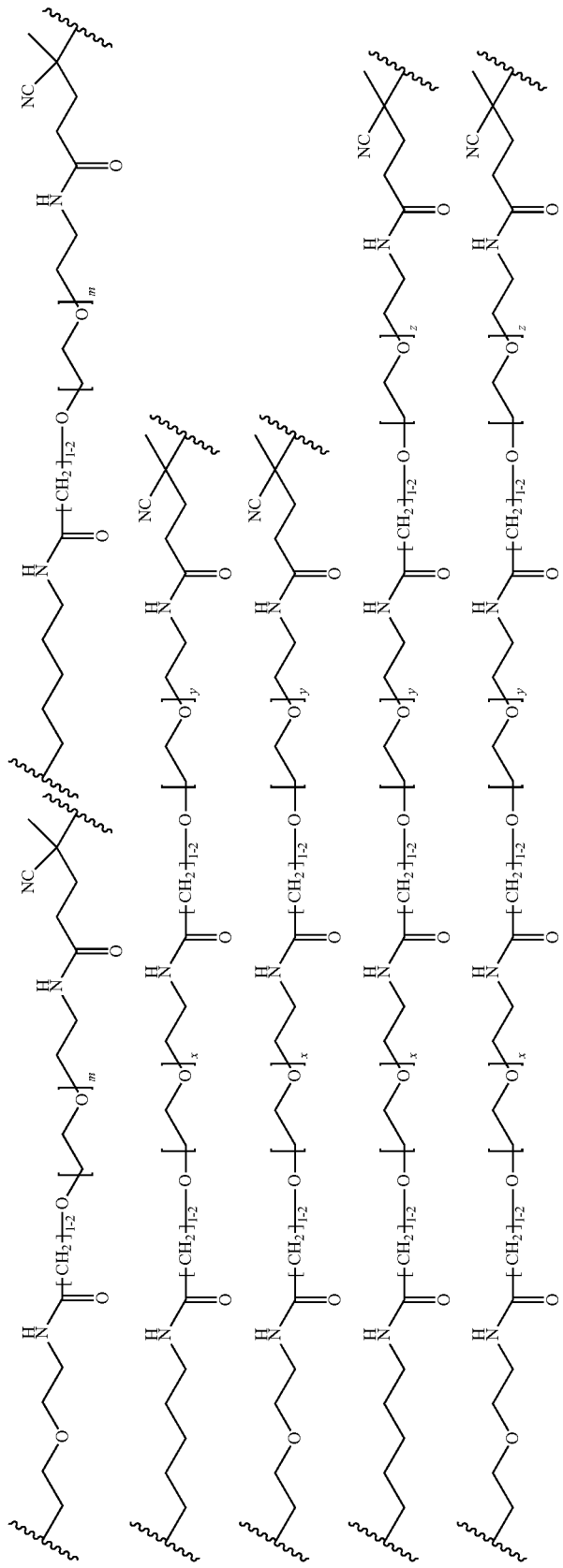

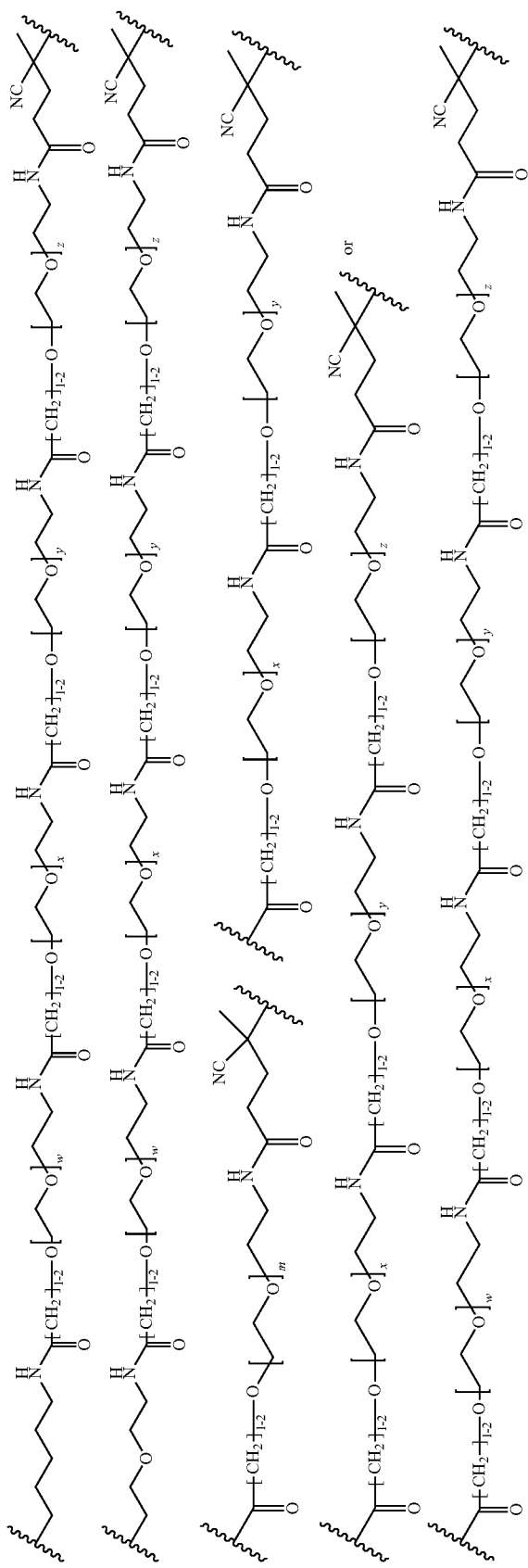

where m is 20-60 or 60-250, each of w, x, y, and z is independently 10-48, and ~~~ designates a point of attachment;

(m) a block copolymer of Formula I as in (1) above, wherein x is 2-15 kDa, y is 3-6 kDa, 3-7 kDa, 4-6 kDa, or 3-5 kDa, and A2 has the formula A2a, where n is 3-20 or 7-20;

(n) a block copolymer of Formula I as in (m) above, wherein A1 and A3 are absent, B4 is present, B1 is butyl methacrylate, B2 is 2-propyl acrylic acid, B3 is 2-(dimethylamino)ethyl methacrylate, and B4 is

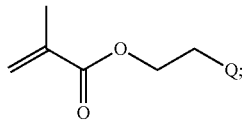

(o) a block copolymer of Formula I as in (a) above, wherein T1 is

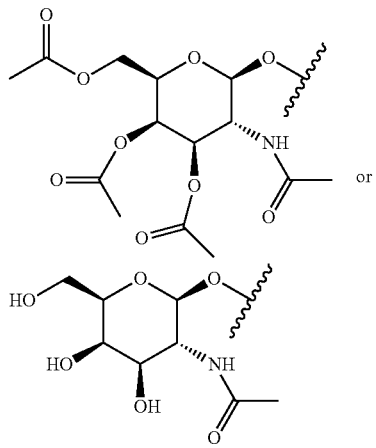

where ~~~ designates a point of attachment, and L1 is

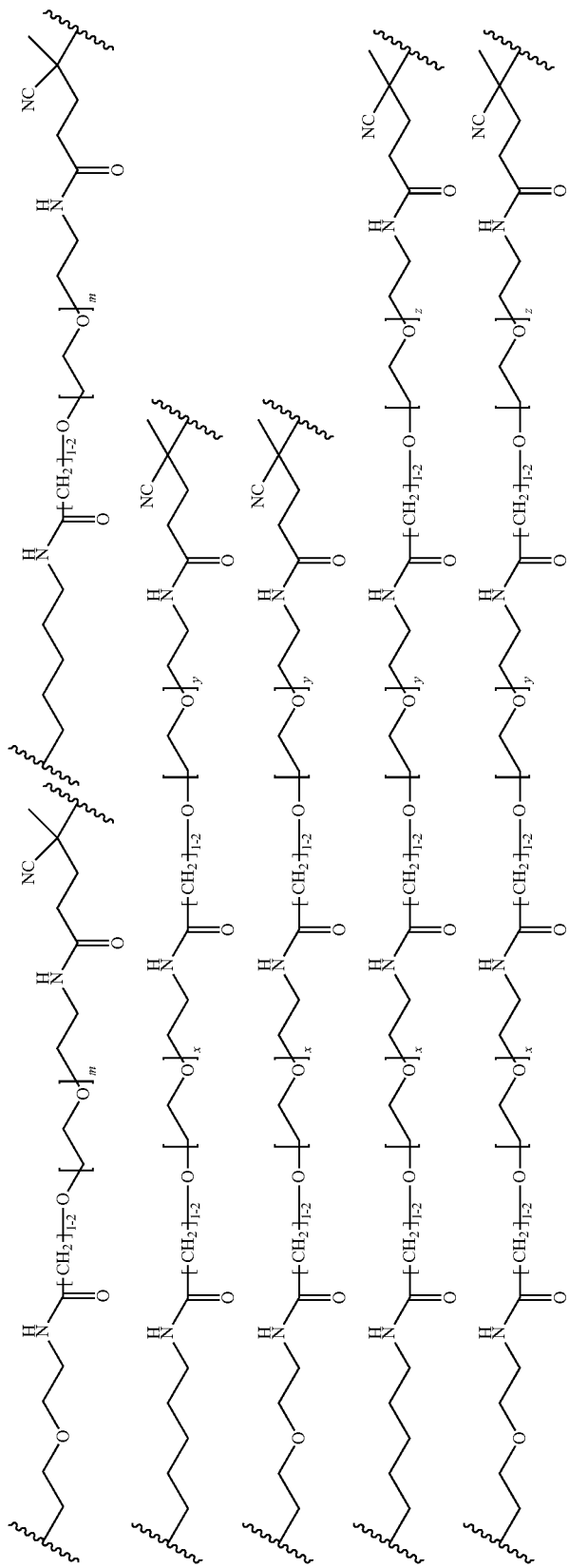

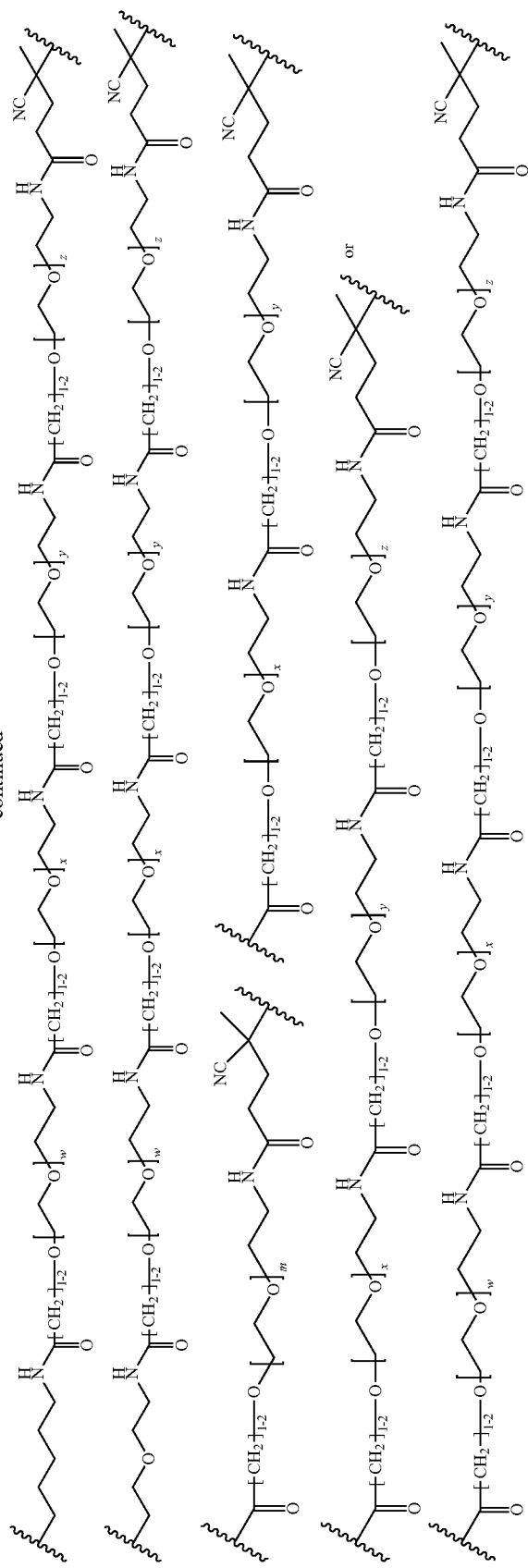

where m is 20-60 or 60-250, each of w, x, y, and z is independently 10-48, and ∼∼ designates a point of attachment;

(p) a block copolymer of Formula I as in (o) above, wherein x is 2-15 kDa, y is 3-6 kDa, 3-7 kDa, 4-6 kDa, or 3-5 kDa, and A2 has the formula A2a, where n is 3-20 or 7-20;

(q) a block copolymer of Formula I as in (p) above, wherein A1 and A3 are absent, B4 is present, B1 is butyl methacrylate, B2 is 2-propyl acrylic acid, B3 is 2-(dimethylamino)ethyl methacrylate, and B4 is

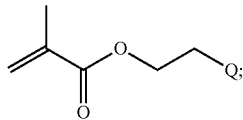

(r) a block copolymer of Formula VI, wherein G is present (i.e., Q is not S-S-pyridyl) and G is a cationic peptide, polyamine, or polycation;

(s) a block copolymer of Formula VII, wherein G is present (i.e., Q is not S-S-pyridyl);

(t) a block copolymer of Formula I, wherein A2 has the formula A2a, where n is 7-9 or 17-19, and wherein L1 is a polymer having a molecular weight of from 2 kDa to 3 kDa and comprising at least 36 ethylene oxide units, or a polymer having a molecular weight of from 3 kDa to 6 kDa and comprising at least 48 ethylene oxide units;

(u) a block copolymer as in any one of (a), (b), (c), (d), (e), (f), (g), (h), (l), (m), (n), (r), and (s) above, wherein T1 is a tri-NAG structure having three NAG moieties;

(v) a block copolymer as in any one of (a), (b), (c), (d), (e), (f), (j), (l), (m), (o), and (p) above, wherein A1 and A3 are absent and B4 is present;

(w) a block copolymer as in any one of (a), (b), (c), (d), (e), (f), (g), (h), (i), (j), (k), (l), (m), (n), (o), (p), (q), (r), (s), (t), (u), and (v) wherein A4 and A5 are absent;

(x) block copolymer as in any one of (a), (b), (c), (d), (e), (f), (g), (h), (i), (j), (k), (l), (m), (n), (o), (p), (q), (t), (u), (v), and (w), wherein the block copolymer is a copolymer of Formula VII;

(y) a block copolymer as in any one of (a), (b), (c), (d), (e), (f), (g), (h), (i), (j), (k), (l), (m), (n), (o), (p), (q), (r), (s), (t), (u), (v), (w), and (x) above, wherein G is the cationic peptide;

(z) a block copolymer of Formula VII wherein the copolymer is a cationic peptide conjugate of a polymer selected from the group consisting of:

NAG-PEG$_{12}$-[PEGMA (300, 100%)]$_{3.45k}$-b-[BMA$_{47.5\%}$-PAA$_{9.2\%}$-DMAEMA$_{35.8\%}$-PDSMA$_{7.5\%}$]$_{6.6k}$;

NAG-PEG$_{12}$-[PEGMA500 (100%)]$_{5.8k}$-b-[DMAEMA$_{35\%}$-BMA$_{50\%}$-PAA$_{8\%}$-PDSMA$_{6\%}$]$_{5.2k}$;

NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$;

NAG-PEG$_{24}$-amido-PEG$_{24}$-[PEGMA300,100%]$_{3.6k}$-b-[BMA$_{50\%}$-PAA$_{11\%}$-DMAEMA$_{32\%}$-PDSMA$_{7\%}$]$_{3.8k}$;

NAG-C5-PEG$_{24}$-amido-PEG$_{24}$-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

NAG-C5-PEG5k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

ECT-[PEGMA (300, 58%)-NAG-C5-PEG$_{36}$ (42%)]$_{19.9k}$-b-[DMAEMA$_{31\%}$-BMA$_{49\%}$-PAA$_{12\%}$-PDSMA$_{8\%}$]$_{5.03k}$;

NAG-PEG$_{12}$-[PEGMA (300, 73%)-NAG-C5-PEG$_{36}$ (18%)-TFPMA$_{5\%}$]$_{11k}$-b-[DMAEMA$_{36\%}$-BMA$_{46\%}$-PAA$_{10\%}$-PDSMA$_{7\%}$]$_{5.33k}$;

NAG-C5-PEG10k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

NAG-C5-PEG20k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;

NAG-C5-PEG24-amido-PEG$_{24}$-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG5k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG10k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG20k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;

NAG-C5-PEG24-amido-PEG$_{24}$-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-C5-PEG5k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-C5-PEG10k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-C5-PEG20k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;

NAG-PEG$_{36}$-[PEGMA (500, 100%)]$_{6.19k}$-b-[DMAEMA$_{31.6\%}$-BMA$_{48.4\%}$-PAA$_{13.1\%}$-PDSMA$_{6.8\%}$]$_{4.3k}$;

NAG-PEG$_{36}$-[PEGMA (500, 100%)]$_{6.19k}$-b-[DMAEMA$_{30.8\%}$-BMA$_{50.8\%}$-PAA$_{11.6\%}$-PDSMA$_{6.8\%}$]$_{3.5k}$;

NAG-PEG$_{48}$-[PEGMA (300, 100%)]$_{3.8k}$-b-[BMA$_{49.3\%}$-PAA$_{9\%}$-DMAEMA$_{31.4\%}$-PDSMA$_{9\%}$]$_{6.3k}$;

NAG-PEG$_{12}$-[PEGMA(500, 100%)]$_{5.8k}$-b-[DMAEMA$_{35\%}$-BMA$_{50\%}$-PAA$_{8\%}$-PDSMA$_{6\%}$]$_{5.2k}$;

NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$;

Tri-NAG-PEG$_{12}$-[PEGMA(300, 80%)-PDSMA$_{10\%}$-BPAM$_{10\%}$]$_{6.1k}$-[BMA$_{50\%}$-PAA$_{25\%}$-DMAEMA$_{25\%}$]$_{4.9k}$;

Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{3.2k}$; and Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{4.2k}$.

wherein the cationic peptide has the sequence -Cys-(Lys)$_{10}$-OH (SEQ ID NO:101) or -Cys-(Lys)$_{10}$-NH$_2$ (SEQ ID NO:103) and is conjugated to the PDSMA monomer through the cysteine thiol to form a disulfide bridge.

The copolymers as described herein are effective transfection agents and therefore therapeutic agents due to their ability to deliver a therapeutic oligonucleotide intercellularly where they can modulate expression of a target gene. By modulate, inhibit, down-regulate, or knockdown gene expression, it is meant that the expression of the gene, as measured by the level of RNA transcribed from the gene, or the level of polypeptide, protein or protein subunit translated from the RNA, is different from that observed in the absence of the copolymers described herein. For example, the level of RNA transcribed from the gene, or the level of polypeptide, protein or protein subunit translated from the RNA, is less than that observed in the presence of a control inactive nucleic acid, a nucleic acid with scrambled sequence or with inactivating mismatches, or observed in the absence of the copolymers described herein when gene expression is modulated, down-regulated or knocked down. Alternatively the level of a polypeptide, protein or protein subunit in a cell is greater than that observed in the absence of the copolymers described herein.

The copolymers and formulations described herein effectively transport oligonucleotides, such as mRNA, into cells both in vitro and in vivo. Without being bound to any particular theory, the transport of oligonucleotides by the copolymers described herein typically occurs via association of the copolymer with the cell membrane and subsequent uptake by the endosomes and eventual disruption of the endosomal membrane and release of the oligonucleotide, oligonucleotide and copolymer or copolymer to the cytosol. In the endosomes, the copolymers, and therefore oligonucleotides, are separated from the cytosol. As gene expression and mRNA translation occurs in the cytosol, the oligonucleotides have to exit the endosome and enter the cytosol for effective modulation of the target gene or effective translation of a transported mRNA. If the oligonucleotides do not exit the endosome and enter the cytosol, either the endosome matures into or fuses with a lysosome leading to degradation of its content, or the endosome fuses with the cell membrane leading to a return of its content into the extracellular medium. Therefore, without being bound to any particular theory, the copolymers as described herein are effective in delivering oligonucleotides intracellularly and thereby modulating a target gene or expressing a transported mRNA due to their ability to escape from endosomes. The copolymers as described herein may thus be described as "membrane destabilizing polymers" or "membrane disruptive polymers." Membrane destabilizing polymers or membrane disruptive polymers can directly or indirectly elicit a change, such as a permeability change for example, in a cellular membrane structure, such as an endosomal membrane for example, so as to permit an agent, for example an oligonucleotide or copolymer or both, to pass through such membrane structure. A membrane disruptive polymer can directly or indirectly elicit lysis of a cellular vesicle or otherwise disrupt a cellular membrane for example as observed for a substantial fraction of a population of cellular membranes. Generally, membrane destabilizing or membrane disruptive properties of polymers can be assessed by various means. In one non-limiting approach, a change in a cellular membrane structure can be observed by assessment in assays that measure, directly or indirectly, release of an agent from cellular membranes, such as an endosomal membrane for example, by determining the presence or absence of such agent, or an activity of such agent, in an environment external to such membrane. Another non-limiting approach involves measuring red blood cell lysis, such as hemolysis for example, as a surrogate assay for a cellular membrane of interest. (See, e.g., International PCT Publications WO 99/34831 and WO 2009/140427.) Such assays may be done at a single pH value or over a range of pH values.

The copolymers and formulations as described herein are useful in methods for the intracellular delivery of biologically active oligonucleotides, such as an RNA including siRNA and mRNA for example, to target cells, including target cells in vitro, ex vivo, and in vivo. In some embodiments, a method of delivering a biologically active oligonucleotide, such as an RNA for example, to a target cell includes (a) contacting a block copolymer of Formula I, where G is present and is an oligonucleotide, such as an RNA for example, with a cell where the copolymer is introduced into an endosomal membrane within the cell through endocytosis; and (b) destabilizing the endosomal membrane, whereby the oligonucelotide is delivered to the cytosol of the cell. In other embodiments, a method of delivering a biologically active oligonucleotide to a target cell includes (a) contacting a block copolymer of Formula I, where G is present and is a cationic peptide, polyamine, or polycation, and where the copolymer is formulated into a composition comprising the oligonucleotide, with a cell where the copolymer is introduced into an endosomal membrane within the cell through endocytosis; and (b) destabilizing the endosomal membrane, whereby the oligonucleotide is delivered to the cytosol of the cell. In other embodiments, a method of delivering a biologically active mRNA to a target cell includes (a) contacting a block copolymer of Formula I, where G is present and is a cationic peptide, polyamine, or polycation, and where the copolymer is formulated into a composition comprising the mRNA, with a cell where the copolymer is introduced into an endosomal membrane within the cell through endocytosis; and (b) destabilizing the endosomal membrane, whereby the mRNA is delivered to the cytosol of the cell.

Examples of methods for the intracellular delivery of a biologically active oligonucleotide to a target cell include those where the cell is in a mammalian animal, including, for example, a human, rodent, murine, bovine, canine, feline, sheep, equine, and simian mammal.

Examples of methods for the intracellular delivery of a biologically active oligonucleotide to a target cell include those where the oligonucleotide is an siRNA, an antisense oligonucleotide, a locked nucleic acid, a dicer substrate, mRNA, a miRNA, an aiRNA or an shRNA. Additional examples of methods for the intracellular delivery of a biologically active oligonucleotide to a target cell include those where the oligonucleotide is an siRNA or mRNA.

An example of a method for the intracellular delivery of a biologically active oligonucleotide to a target cell includes those where the oligonucleotide is an mRNA encoding a functional erythropoietin, a-galactosidase, LDL receptor, Factor VII, Factor VIII, Factor IX, alpha-L-iduronidase, iduronate sitlfatase, heparin-N-sulfatase, alpha-N-acetylglucosaminidase, galactose 6-suitatase, β-galactosidase, lysosomal acid lipase, ornithine transcarbamylase, alpha-1-antitrypsin or aryisulfatase-A polypeptide.

Copolymers and formulations as described herein are useful in treating a disease or condition associated with defective gene expression and/or activity in a subject, such as a mammal for example. Methods of treatment include administering to a mammal in need of treatment of a disease or condition associated with defective gene expression and/or activity a therapeutically effective amount of a block copolymer of Formula I including an oligonucleotide that is homologous to and can silence, for example by cleavage, a gene or that specifies the amino acid sequence of a protein and is translated during protein synthesis.

In certain embodiments, the disease or condition associated with defective gene expression is a disease characterized by a deficiency in a functional polypeptide (also referred to herein as a "disease associated with a protein deficiency"). A copolymer of the present disclosure, where the copolymer includes a cationic peptide, polyamine, or polycation, may be formulated into a composition comprising a messenger RNA (mRNA) molecule encoding a protein corresponding to a genetic defect that results in a deficiency of the protein. For treatment of the disease associated with the protein deficiency, the copolymer/mRNA formulation is administered to a subject (e.g., mammal such as, for example, a mouse, non-human primate, or human) for delivery of the mRNA to an appropriate target tissue, where the mRNA is translated during protein synthesis and the encoded protein is produced in an amount sufficient to treat the disease.

An example of a method of treating a disease or condition associated with defective gene expression and/or activity in a subject, such as a mammal for example, includes administering to a mammal in need thereof a therapeutically effective amount of a block copolymer of Formula I, wherein Q is S-S-oligonucleotide,

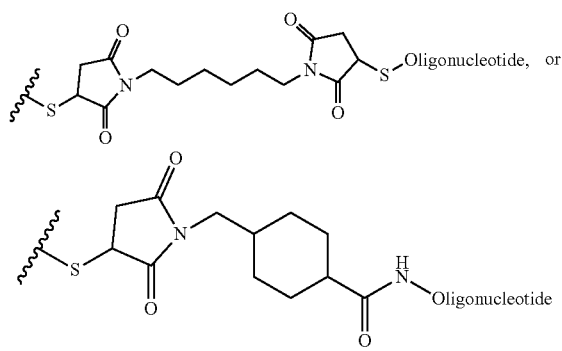

and ⌇⌇⌇ designates a point of attachment.

An additional example of a method of treating a disease or condition associated with defective gene expression includes a method for increasing the amount of a protein in a cell by contacting the cell with the pharmaceutical composition comprising (a) a block copolymer of Formula I wherein G is present and is a cationic peptide, polyamine, or polycation, (b) an mRNA molecule and (c) a pharmaceutically acceptable diluent or carrier. In one example the cell in the above described method is in vitro. In another example the cell in the above described method is in vivo.

A further example of a method for treating a disease or condition associated with defective gene expression includes a method of treating a subject having a deficiency in a functional polypeptide comprising administering to the subject a pharmaceutical composition comprising a block copolymer of Formula I, wherein G is present and is a cationic peptide, polyamine, or polycation, and at least one mRNA molecule at least a portion of which encodes the functional polypeptide where following administration the expression of the functional polypeptide is greater than before administration. In some embodiments, the mRNA encodes a functional erythropoietin, alpha-galactosidase A, LDL receptor, Factor VII, Factor VIII, Factor IX, alpha-L-iduronidase, iduronate-2-sulfatase, heparan-N-sulfatase, alpha-N-acetylglucosaminidase, galactose 6-sulfatase, acid β-galactosidase, lysosomal acid lipase, ornithine transcarbamylase, alpha-1-antitrypsin, arylsulfatase A, arylsulfatase B, acid ceramidase, acid α-L-fucosidsase, acid β-glucosidase (also known as glucocerebrosidase), galactocerebrosidase, acid α-mannosidase, acid β-mannosidase, N-acetylgalactosamine-6-sulfate sulfatase, acid sphingomyelinase, acid α-glucosidase, β-hexosaminidase B, acetyl-CoA:α-glucosaminide N-acetyltransferase, N-acetylglucosamine-6-sulfate sulfatase, alpha-N-acetylgalactosaminidase, sialidase, β-glucuronidase, or β-hexosaminidase A. In other embodiments, the mRNA encodes a functional Retinoblastoma protein (pRb), p53 tumor-suppressor protein, Phosphatase and tensin homolog (PTEN), Von Hippel-Lindau tumor suppressor (pVHL), Adenomatous polyposis coli (APC), FAS receptor (FasR), Suppression of tumorigenicity 5 (ST5), YPEL3, Suppressor of tumorigenicity protein 7 (ST7), or Suppressor of tumorigenicity 14 protein (ST14). In yet other embodiments, the mRNA encodes a functional Galactose-1-phosphate uridylyltransferase, Galactokinase, UDP-galactose 4-epimerase, Transthyretin, complement regulatory protein (e.g., factor H, factor I, or membrane cofactor protein), phenylalanine hydroxylase (PAH), homogentisate 1,2-dioxygenase, Porphobilinogen deaminase, hypoxanthine-guanine phosphoribosyltransferase (HGPRT), argininosuccinate lyase (ASL), or P-type ATPase protein, FIC-1.

In an exemplary method for increasing the amount of a protein in a cell by contacting the cell with the pharmaceutical composition comprising (a) a block copolymer of Formula I wherein G is present and is a cationic peptide, polyamine, or polycation, (b) an mRNA molecule and (c) a pharmaceutically acceptable diluent or carrier, the mRNA molecule codes for ornithine transcarbamylase or alpha-1-antitrypsin. In some such embodiments, the block copolymer of Formula I is a copolymer of formula VII In particular embodiments of a composition or method for increasing the amount of a protein in a cell, an mRNA encoding the protein of interest is formulated into a composition comprising a copolymer selected from the group consisting of:

(a) a block copolymer of Formula I, wherein G is present (i.e., Q is not S-S-pyridyl) and G is a cationic peptide, polyamine, or polycation;

(b) a block copolymer of Formula I as in (a) above, wherein x is 2-15 kDa, and y is 3-6 kDa, 3-7 kDa, 4-6 kDa, or 3-5 kDa;

(c) a block copolymer of Formula I as in (a) above, wherein A2 has the formula A2a, where n is 3-20 or 7-20;

(d) a block copolymer of Formula I as in (a) above, wherein A2 has the formula A2a, where n is 7-9 or 17-19;

(e) a block copolymer of Formula I as in (b) above, wherein A2 has the formula A2a, where n is 3-20 or 7-20;

(f) a block copolymer of Formula I as in (b) above, wherein A2 has the formula A2a, where n is 7-9 or 17-19;

(g) a block copolymer of Formula I as in (a) above, wherein A1 and A3 are absent, B4 is present, A2 has the formula A2a, where n is 3-20 or 7-20, B1 is butyl methacrylate, B2 is 2-propyl acrylic acid, B3 is 2-(dimethylamino)ethyl methacrylate, and B4 is

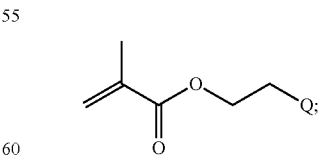

(h) a block copolymer of Formula I as in (g) above, wherein x is 2-15 kDa and y is 3-6 kDa, 3-7 kDa, 4-6 kDa, or 3-5 kDa;

(i) a block copolymer of Formula I as in (a) above, wherein A1 and A3 are absent, B4 is present, and T1 is

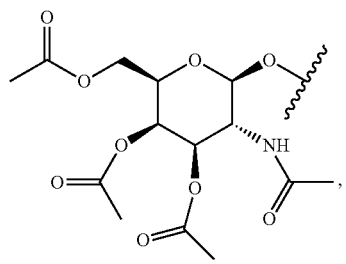 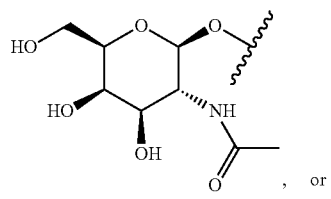, or
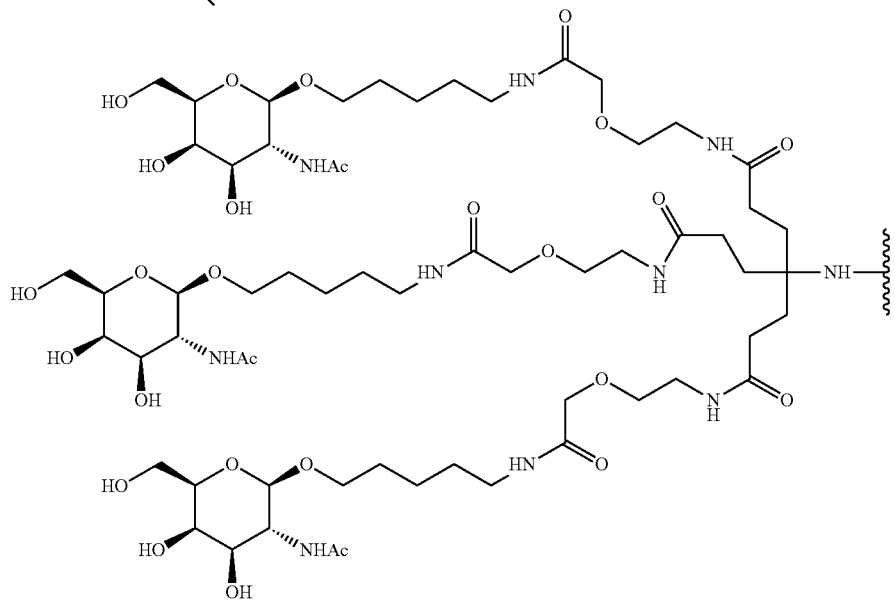
where ⁓ designates a point of attachment;
(j) a block copolymer of Formula I as in (i) above, wherein x is 2-15 kDa, y is 3-6 kDa, 3-7 kDa, 4-6 kDa, or 3-5 kDa, and A2 has the formula A2a, where n is 3-20 or 7-20;
(k) a block copolymer of Formula I as in (j) above, wherein B1 is butyl methacrylate, B2 is 2-propyl acrylic acid, B3 is 2-(dimethylamino)ethyl methacrylate, B4 is
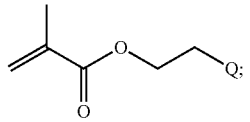
(l) a block copolymer of Formula I as in (a) above, wherein L1 is

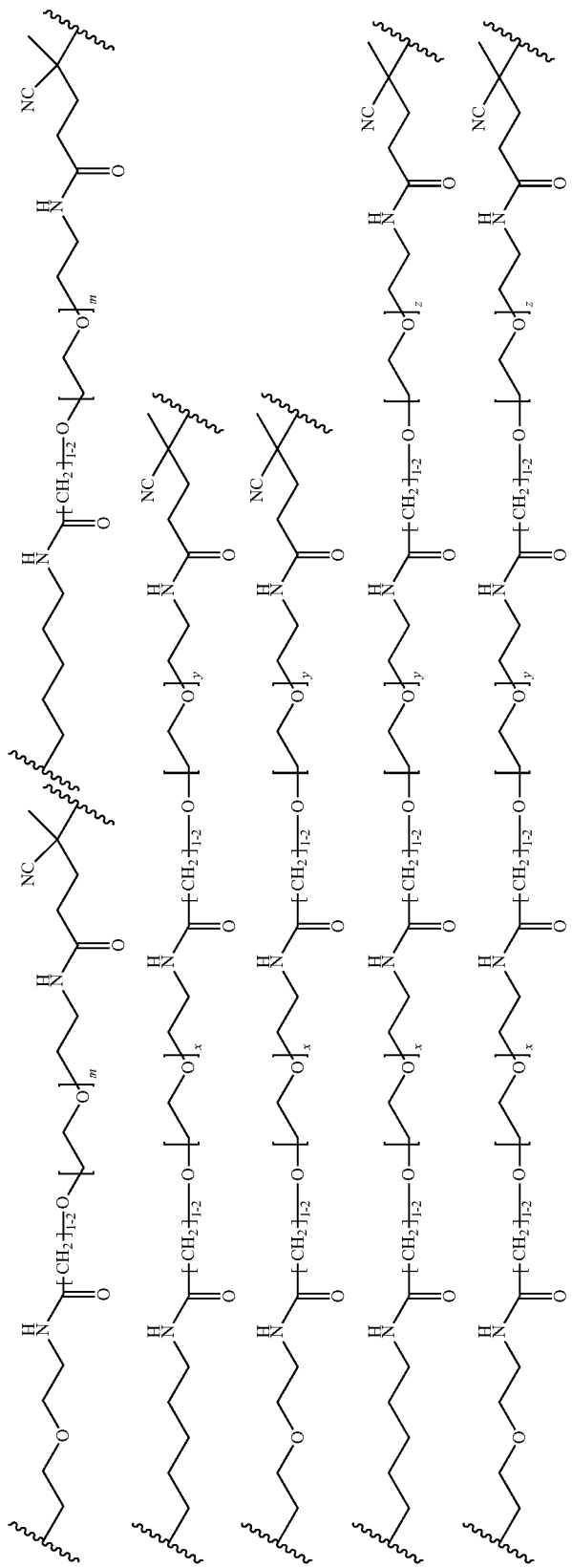

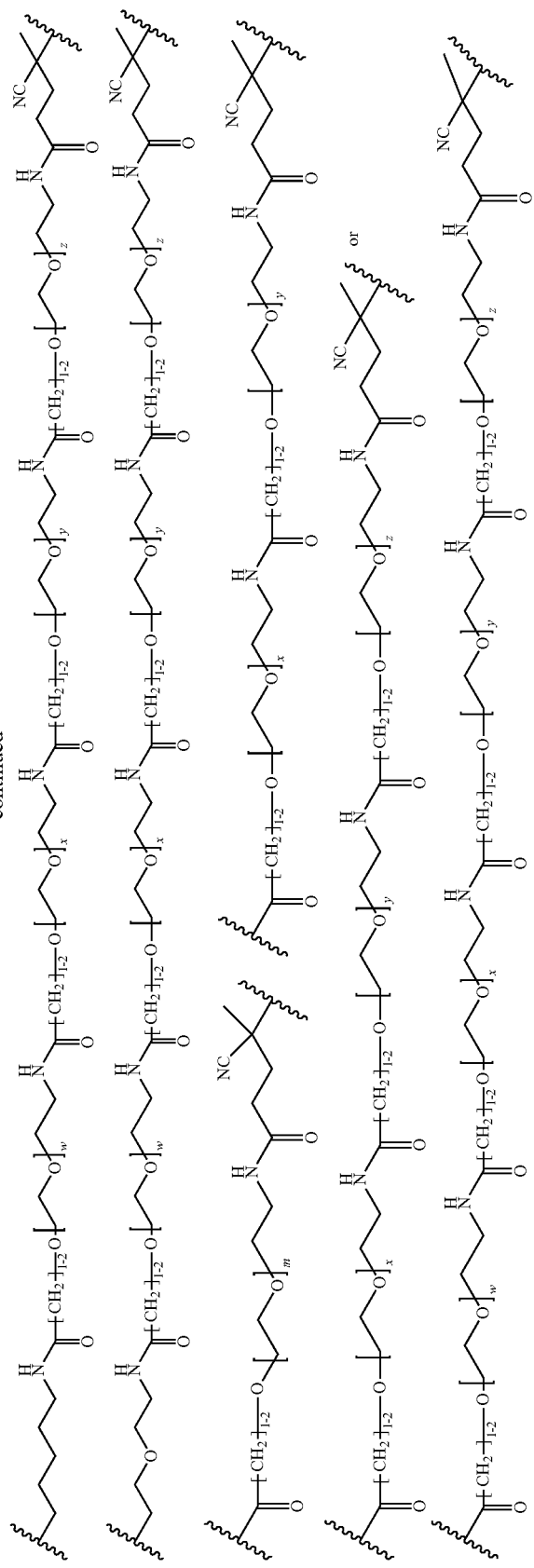

where m is 20-60 or 60-250, each of w, x, y, and z is independently 10-48, and ⌇ designates a point of attachment;

(m) a block copolymer of Formula I as in (1) above, wherein x is 2-15 kDa, y is 3-6 kDa, 3-7 kDa, 4-6 kDa, or 3-5 kDa, and A2 has the formula A2a, where n is 3-20 or 7-20;

(n) a block copolymer of Formula I as in (m) above, wherein A1 and A3 are absent, B4 is present, B1 is butyl methacrylate, B2 is 2-propyl acrylic acid, B3 is 2-(dimethylamino)ethyl methacrylate, and B4 is

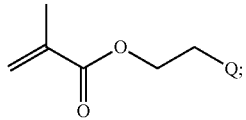

(o) a block copolymer of Formula I as in (a) above, wherein T1 is

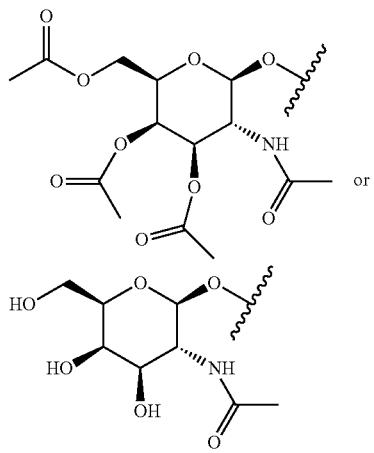

where ⌇ designates a point of attachment, and L1 is

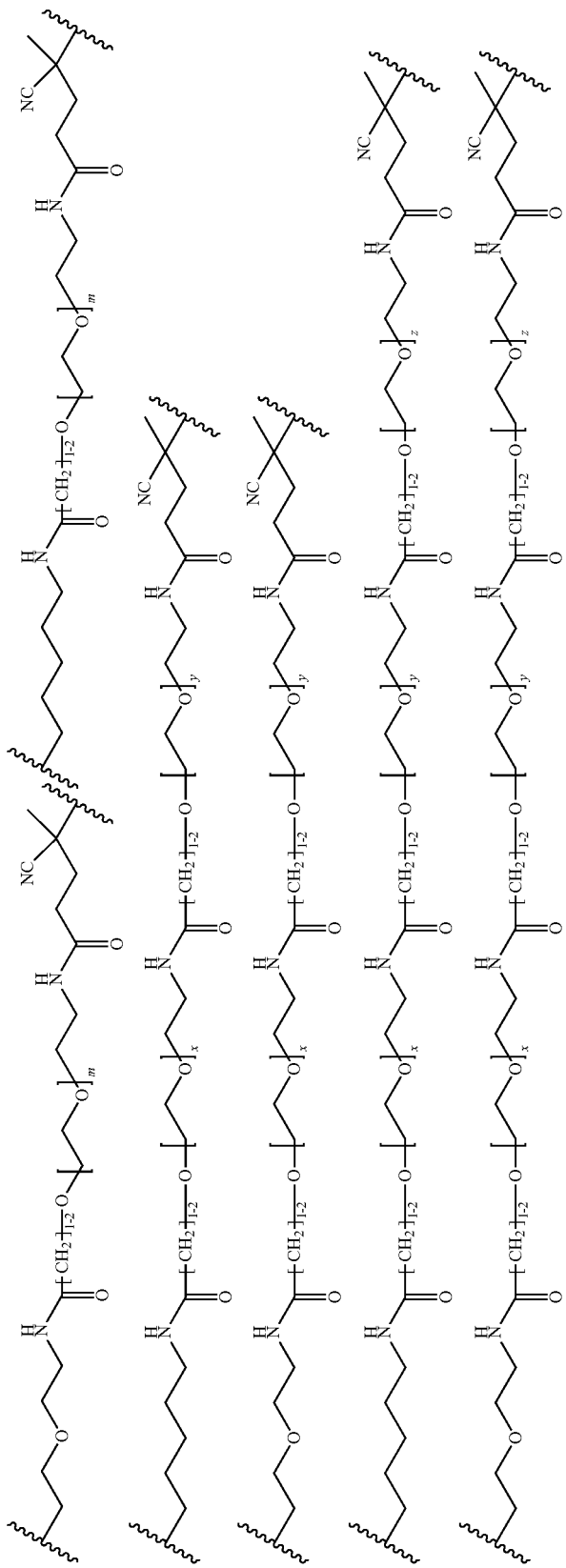

-continued
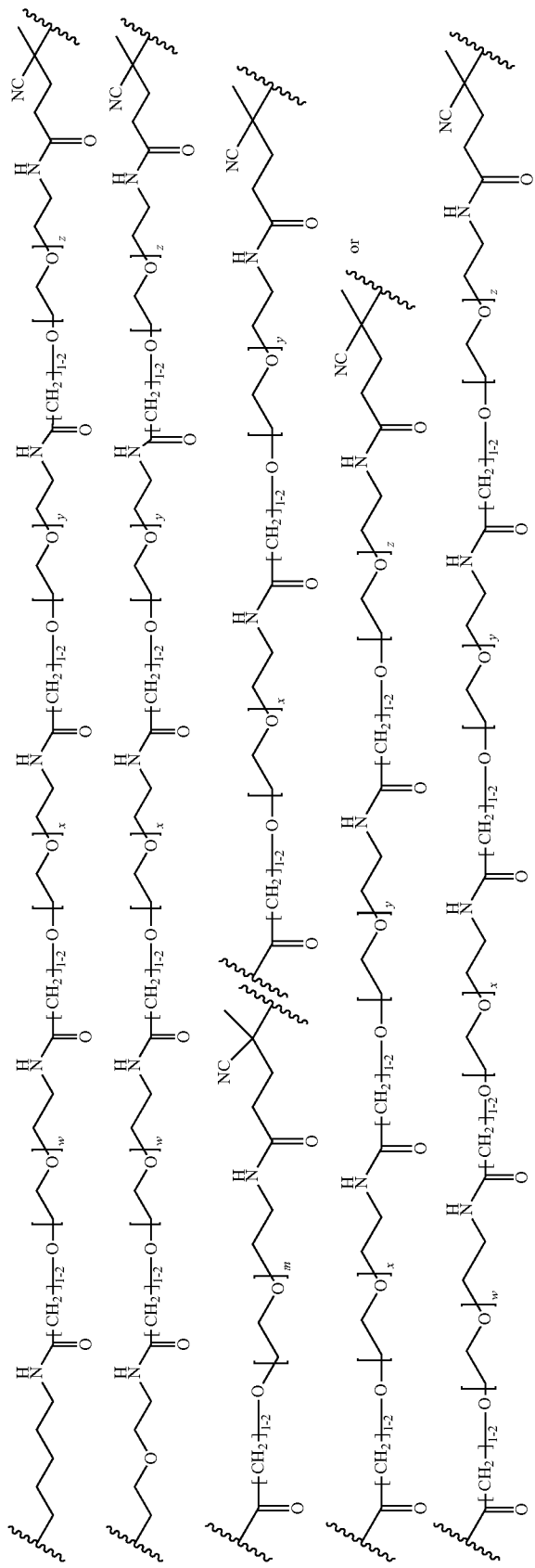

where m is 20-60 or 60-250, each of w, x, y, and z is independently 10-48, and ⌇⌇⌇ designates a point of attachment;
(p) a block copolymer of Formula I as in (o) above, wherein x is 2-15 kDa, y is 3-6 kDa, 3-7 kDa, 4-6 kDa, or 3-5 kDa, and A2 has the formula A2a, where n is 3-20 or 7-20;
(q) a block copolymer of Formula I as in (p) above, wherein A1 and A3 are absent, B4 is present, B1 is butyl methacrylate, B2 is 2-propyl acrylic acid, B3 is 2-(dimethylamino)ethyl methacrylate, and B4 is

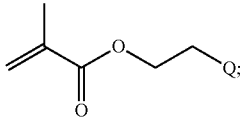

(r) a block copolymer of Formula VI, wherein G is present (i.e., Q is not S-S-pyridyl) and G is a cationic peptide, polyamine, or polycation;
(s) a block copolymer of Formula VII, wherein G is present (i.e., Q is not S-S-pyridyl);
(t) a block copolymer of Formula I, wherein A2 has the formula A2a, where n is 7-9 or 17-19, and wherein L1 is a polymer having a molecular weight of from 2 kDa to 3 kDa and comprising at least 36 ethylene oxide units, or a polymer having a molecular weight of from 3 kDa to 6 kDa and comprising at least 48 ethylene oxide units;
(u) a block copolymer as in any one of (a), (b), (c), (d), (e), (f), (g), (h), (l), (m), (n), (r), and (s) above, wherein T1 is a tri-NAG structure having three NAG moieties;
(v) a block copolymer as in any one of (a), (b), (c), (d), (e), (f), (j), (l), (m), (o), and (p) above, wherein A1 and A3 are absent and B4 is present;
(w) a block copolymer as in any one of (a), (b), (c), (d), (e), (f), (g), (h), (i), (j), (k), (l), (m), (n), (o), (p), (q), (r), (s), (t), (u), and (v) wherein A4 and A5 are absent;
(x) block copolymer as in any one of (a), (b), (c), (d), (e), (f), (g), (h), (i), (j), (k), (l), (m), (n), (o), (p), (q), (t), (u), (v), and (w) wherein the block copolymer is a copolymer of Formula VII;
(w) a block copolymer as in any one of (a), (b), (c), (d), (e), (f), (g), (h), (i), (j), (k), (l), (m), (n), (o), (p), (q), (r), (s), (t), (u), (v), (w), and (x) above, wherein G is the cationic peptide;
(x) a block copolymer of Formula VII wherein the copolymer is a cationic peptide conjugate of a polymer selected from the group consisting of:
NAG-PEG$_{12}$-[PEGMA (300, 100%)]$_{3.45k}$-b-[BMA$_{47.5\%}$-PAA$_{9.2\%}$-DMAEMA$_{35.8\%}$-PDSMA$_{7.5\%}$]$_{6.6k}$;
NAG-PEG$_{12}$-[PEGMA500 (100%)]$_{5.8k}$-b-[DMAEMA$_{35\%}$-BMA$_{50\%}$-PAA$_{8\%}$-PDSMA$_{6\%}$]$_{5.2k}$;
NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$;
NAG-PEG$_{24}$-amido-PEG$_{24}$-[PEGMA300,100%]$_{3.6k}$-b-[BMA$_{50\%}$-PAA$_{11\%}$-DMAEMA$_{32\%}$-PDSMA$_{7\%}$]$_{3.8k}$;
NAG-C5-PEG$_{24}$-amido-PEG$_{24}$-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;
NAG-C5-PEG5k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;
ECT-[PEGMA (300, 58%)-NAG-C5-PEG$_{36}$ (42%)]$_{19.9k}$-b-[DMAEMA$_{31\%}$-BMA$_{49\%}$-PAA$_{12\%}$-PDSMA$_{8\%}$]$_{5.03k}$;
NAG-PEG$_{12}$-[PEGMA (300, 73%)-NAG-C5-PEG$_{36}$ (18%)-TFPMA$_{5\%}$]$_{11k}$-b-[DMAEMA$_{36\%}$-BMA$_{46\%}$-PAA$_{10\%}$-PDSMA$_{7\%}$]$_{5.33k}$;
NAG-C5-PEG10k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;
NAG-C5-PEG20k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$;
NAG-C5-PEG24-amido-PEG$_{24}$-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;
NAG-C5-PEG5k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;
NAG-C5-PEG10k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;
NAG-C5-PEG20k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$;
NAG-C5-PEG24-amido-PEG$_{24}$-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;
NAG-C5-PEG5k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;
NAG-C5-PEG10k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;
NAG-C5-PEG20k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$;
NAG-PEG$_{36}$-[PEGMA (500, 100%)]$_{6.19k}$-b-[DMAEMA$_{31.6\%}$-BMA$_{48.4\%}$-PAA$_{13.1\%}$-PDSMA$_{6.8\%}$]$_{4.3k}$;
NAG-PEG$_{36}$-[PEGMA (500, 100%)]$_{6.19k}$-b-[DMAEMA$_{30.8\%}$-BMA$_{50.8\%}$-PAA$_{11.6\%}$-PDSMA$_{6.8\%}$]$_{3.5k}$;
NAG-PEG$_{48}$-[PEGMA (300, 100%)]$_{3.8k}$-b-[BMA$_{49.3\%}$-PAA$_{9\%}$-DMAEMA$_{31.4\%}$-PDSMA$_{9\%}$]$_{6.3k}$;
NAG-PEG$_{12}$-[PEGMA(500, 100%)]$_{5.8k}$-b-[DMAEMA$_{35\%}$-BMA$_{50\%}$-PAA$_{8\%}$-PDSMA$_{6\%}$]$_{5.2k}$;
NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$;
Tri-NAG-PEG$_{12}$-[PEGMA(300, 80%)-PDSMA$_{10\%}$-BPAM$_{10\%}$]$_{6.1k}$-[BMA$_{50\%}$-PAA$_{25\%}$-DMAEMA$_{25\%}$]$_{4.9k}$;
Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{3.2k}$; and
Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{4.2k}$.
wherein the cationic peptide has the sequence -Cys-(Lys)$_{10}$-OH (SEQ ID NO:101) or -Cys-(Lys)$_{10}$-NH$_2$ (SEQ ID NO:103) and is conjugated to the PDSMA monomer through the cysteine thiol to form a disulfide bridge.

To formulate an mRNA into a composition comprising a copolymer of the present disclosure, where the copolymer comprises a cationic peptide, polyamine, or polycation, the copolymer may be solubilized in an aqueous/isotonic buffer at about normal physiological pH (e.g., pH 7.4). Particularly suitable concentrations of solubilized polymer range from 1 mg/mL to 50 mg/mL. The mRNA may be prepared using a standard in vitro transcription reaction according to well-known procedures. The mRNA solution is typically diluted in an an aqueous/isotonic buffer at about normal physiological pH (e.g., pH 7.4) at a concentration from 0.01 mg/mL to 1 mg/mL. The polymer and mRNA stock solutions are then mixed together at, e.g., an N:P ratio (nitrogen to phosphorous ratio between the cationic peptide, polyamine, or polycation and the mRNA) ranging from 0.5 to 40. After an incubation time, the formulation may be used for delivery of the mRNA into target cells (e.g., the formulation may be contacted with cells in vitro or administered to a subject, such as mice, in vivo).

In certain embodiments of a composition or method for increasing the amount of a protein in a cell, the protein is ornithine transcarbamylase (OTC). In such embodiments, an mRNA encoding an OTC protein is formulated into a composition comprising a copolymer of the present disclosure such as, for example, a copolymer as set forth in any one of (a)-(z) above. In particular variations, the mRNA molecule encodes an OTC protein comprising an amino acid sequence having at least 90% or at least 95% sequence identity with residues 35-354 of SEQ ID NO:107 (e.g., at least 96%, at least 97%, at least 98%, at least 99%, at least 99.5%, or 100% sequence identity with residues 35-354 of SEQ ID NO:107). To direct an encoded OTC protein to the mitochondria of the cell, an mRNA molecule encoding the OTC protein includes a sequence encoding a mitochondrial targeting signal peptide (also referred to herein as a "mitochondrial leader sequence"). The mitochondrial leader sequence may be that of a native OTC protein (e.g., residues 1-34 of SEQ ID NO:107 (a native human mitochondrial leader sequence) or residues 1-34 of SEQ ID NO:108 (a native mouse mitochondrial leader sequence)), or may be derived from another protein comprising a mitochondrial targeting signal peptide, or synthesized de novo. An engineered cleavage site may be included at the junction between the mitochondrial leader sequence and the remainder of the polypeptide to optimize proteolytic processing in the cell. The mitochondrial leader sequence is operably linked to the mRNA sequence encoding the mature OTC protein, i.e., the two sequences are joined in the correct reading frame and positioned to direct the newly synthesized polypeptide to the mitochondria of a cell. Mitochondrial leader sequences are commonly positioned at the amino terminus of the protein. In specific variations, the encoded OTC protein with a mitochondrial leader sequence has an amino acid sequence as set forth in SEQ ID NO:107 or SEQ ID NO:108. Suitable mRNA sequences encoding an OTC protein of SEQ ID NO:107, and which may be formulated into a composition comprising a copolymer of the present disclosure, may comprise sequences as shown in SEQ ID NO:112 or SEQ ID NO:114 (coding sequence (CDS) for each corresponding to residues 48-1112). Suitable mRNA sequences encoding an OTC protein of SEQ ID NO:108, and which may be formulated into a composition comprising a copolymer of the present disclosure, may comprise a sequence as shown in SEQ ID NO:113 (coding sequence (CDS) corresponding to residues 48-1112). An OTC-encoding mRNA for formulation with a copolymer of the present disclosure typically further includes a poly(A) at its 3' end (e.g., a polyA tail of about 120 adenine residues), which may be added to a construct using well-known genetic engineering techniques (e.g., via PCR). Exemplary DNA sequences that may be used for insertion into an appropriate DNA vector for production and preparation of mRNA constructs of SEQ ID NOs. 112-114 are shown in SEQ ID NOs. 109-111, respectively. Exemplary OTC amino acid sequences and encoding nucleotide sequences are shown in Table 3.

TABLE 3

Ornithine Transcarbamylase (OTC) Amino Acid and Encoding Nucleotide Sequences

| SEQ ID NO: | Sequence | Description/Notes |
|---|---|---|
| 107 | MLFNLRILLNNAAFRNGHNFMVRNFRCGQPLQNKVQLKGRDL LTLKNFTGEEIKYMLWLSADLKFRIKQKGEYLPLLQGKSLGM IFEKRSTRTRLSTETGFALLGGHPCFLTTQDIHLGVNESLTD TARVLSSMADAVLARVYKQSDLDTLAKEASIPIINGLSDLYH PIQILADYLTLQEHYSSLKGLTLSWIGDGNNILHSIMMSAAK FGMHLQAATPKGYEPDASVTKLAEQYAKENGTKLLLTNDPLE AAHGGNVLITDTWISMGQEEEKKKRLQAFQGYQVTMKTAKVA ASDWTFLHCLPRKPEEVDDEVFYSPRSLVFPEAENRKWTIMA VMVSLLTDYSPQLQKPKF | Human ornithine transcarbamylase amino acid sequence with native (human) mitochondrial leader sequence (leader sequence underlined) |
| 108 | MLSNLRILLNNAALRKGHTSVVRHFWCGKPVQSQVQLKGRDL LTLKNFTGEEIKYMLWLSADLKFRIKQKGEYLPLLQGKSLGM IFEKRSTRTRLSTETGFALLGGHPCFLTTQDIHLGVNESLTD TARVLSSMADAVLARVYKQSDLDTLAKEASIPIINGLSDLYH PIQILADYLTLQEHYSSLKGLTLSWIGDGNNILHSIMMSAAK FGMHLQAATPKGYEPDASVTKLAEQYAKENGTKLLLTNDPLE AAHGGNVLITDTWISMGQEEEKKKRLQAFQGYQVTMKTAKVA ASDWTFLHCLPRKPEEVDDEVFYSPRSLVFPEAENRKWTIMA VMVSLLTDYSPQLQKPKF | cDNA encoding human ornithine transcarabmylase with mouse mitochondrial leader sequence (leader sequence underlined) |
| 109 | *TAATACGACTCACTATAGGG*AAATAAGAGAGAAAAGAAGAGT AAGAAGAAATATAAGAGCCACCATGCTGTTCAACCTCAGAAT CCTCCTCAATAACGCCGCCTTTAGAAACGGTCATAACTTCAT GGTCAGAAACTTTAGATGTGGTCAGCCTCTCCAGAACAAAGT GCAGCTCAAGGGGCGGGACCTGCTCACCCTGAAAAATTTCAC AGGCGAGGAAATCAAGTACATGCTCTGGCTGTCTGCCGATCT GAAGTTCAGGATCAAGCAGAAGGGCGAATATCTCCCACTGCT CCAGGGGAAAGTCTGGGTATGATCTTCGAAAAGCGGAGTAC TAGGACCAGACTGTCAACAGAGACTGGATTCGCTCTGCTCGG AGGACACCCATGCTTTCTGACCACACAGGACATTCATCTCGG TGTGAACGAGTCACTGACCGACACAGCTCGAGTCCTCAGCTC | cDNA encoding human ornithine transcarbamylase, codon optimized for expression in mouse (T7 promoter sequence underlined in italics; start codon |

TABLE 3-continued

Ornithine Transcarbamylase (OTC) Amino Acid and Encoding Nucleotide Sequences

| SEQ ID NO: | Sequence | Description/Notes |
|---|---|---|
| | CATGGCAGATGCCGTGCTGGCAAGGGTCTACAAACAGAGTGA<br>CCTCGATACCCTGGCTAAGGAAGCAAGCATCCCCATCATTAA<br>TGGACTCTCCGACCTGTATCACCCTATCCAGATTCTGGCCGA<br>TTACCTCACCCTGCAGGAGCATTATTCTAGTCTGAAAGGGCT<br>CACACTGAGCTGGATTGGCGACGGAAACAATATCCTGCACTC<br>CATTATGATGTCTGCCGCTAAGTTTGGCATGCATCTGCAGGC<br>AGCCACACCAAAAGGATACGAACCCGATGCTTCCGTGACTAA<br>GCTGGCCGAACAGTATGCTAAAGAGAACGGAACTAAGCTGCT<br>CCTGACCAATGACCCCCTGGAGGCTGCACACGGGGGTAACGT<br>CCTGATCACTGATACCTGGATTTCCATGGGCCAGGAGGAAGA<br>GAAGAAAAAGCGCCTGCAGGCATTCCAGGGATACCAGGTGAC<br>AATGAAAACTGCCAAGGTCGCCGCTTCTGATTGGACTTTTCT<br>CCATTGTCTGCCCCGAAAGCCTGAAGAGGTGGACGATGAGGT<br>CTTCTATTCACCTCGGAGCCTGGTGTTTCCAGAAGCCGAGAA<br>TCGCAAGTGGACAATCATGGCAGTGATGGTGTCCCTCCTCAC<br>AGACTATTCCCCACAGCTCCAGAAGCCCAAGTTTTGAGCGGC<br>CGCTTAATTAAGCTGCCTTCTGCGGGGCTTGCCTTCTGGCCA<br>TGCCCTTCTTCTCTCCCTTGCACCTGTACCTCTTGGTCTTTG<br>AATAAAGCCTGAGTAGGAAGTCTAGAGTTTAAACATTTAAAT<br>CT | underlined in bold) |
| 110 | *TAATACGACTCACTATAGGG*AAATAAGAGAGAAAAGAAGAGT<br>AAGAAGAAATATAAGAGCCACCATGCTCTCTAACCTCAGGAT<br>TCTGCTCAACAACGCTGCTCTGCGGAAAGGCCATACCTCTGT<br>CGTCAGGCACTTCTGGTGTGGGAAACCCGTGCAGAGCCAGGT<br>GCAGCTCAAGGGGCGGGACCTGCTCACCCTGAAAAATTTCAC<br>AGGCGAGGAAATCAAGTACATGCTCTGGCTGTCTGCCGATCT<br>GAAGTTCAGGATCAAGCAGAAGGGCGAATATCTCCCACTGCT<br>CCAGGGGAAAAGTCTGGGTATGATCTTCGAAAAGCGGAGTAC<br>TAGGACCAGACTGTCAACAGAGACTGGATTCGCTCTGCTCGG<br>AGGACACCCATGCTTTCTGACCACACAGGACATTCATCTCGG<br>TGTGAACGAGTCACTGACCGACACAGCTCGAGTCCTCAGCTC<br>CATGGCAGATGCCGTGCTGGCAAGGGTCTACAAACAGAGTGA<br>CCTCGATACCCTGGCTAAGGAAGCAAGCATCCCCATCATTAA<br>TGGACTCTCCGACCTGTATCACCCTATCCAGATTCTGGCCGA<br>TTACCTCACCCTGCAGGAGCATTATTCTAGTCTGAAAGGGCT<br>CACACTGAGCTGGATTGGCGACGGAAACAATATCCTGCACTC<br>CATTATGATGTCTGCCGCTAAGTTTGGCATGCATCTGCAGGC<br>AGCCACACCAAAAGGATACGAACCCGATGCTTCCGTGACTAA<br>GCTGGCCGAACAGTATGCTAAAGAGAACGGAACTAAGCTGCT<br>CCTGACCAATGACCCCCTGGAGGCTGCACACGGGGGTAACGT<br>CCTGATCACTGATACCTGGATTTCCATGGGCCAGGAGGAAGA<br>GAAGAAAAAGCGCCTGCAGGCATTCCAGGGATACCAGGTGAC<br>AATGAAAACTGCCAAGGTCGCCGCTTCTGATTGGACTTTTCT<br>CCATTGTCTGCCCCGAAAGCCTGAAGAGGTGGACGATGAGGT<br>CTTCTATTCACCTCGGAGCCTGGTGTTTCCAGAAGCCGAGAA<br>TCGCAAGTGGACAATCATGGCAGTGATGGTGTCCCTCCTCAC<br>AGACTATTCCCCACAGCTCCAGAAGCCCAAGTTTTGAGCGGC<br>CGCTTAATTAAGCTGCCTTCTGCGGGGCTTGCCTTCTGGCCA<br>TGCCCTTCTTCTCTCCCTTGCACCTGTACCTCTTGGTCTTTG<br>AATAAAGCCTGAGTAGGAAGTCTAGAGTTTAAACATTTAAAT<br>CT | cDNA encoding human ornithine transcarbamylase with mouse mitochondrial leader sequence, codon optimized for expression in mouse (T7 promoter sequence underlined in italics; start codon underlined in bold) |
| 111 | *TAATACGACTCACTATAGGG*AAATAAGAGAGAAAAGAAGAGT<br>AAGAAGAAATATAAGAGCCACCATGCTGTTTAACCTGAGGAT<br>TCTGCTGAACAACGCTGCTTTTCGGAACGGCCACAACTTTAT<br>GGTGCGGAACTTTCGGTGCGGACAGCCACTGCAGAACAAAGT<br>GCAGCTGAAGGGGAGGGACCTGCTGACCCTGAAAAATTTCAC<br>AGGAGAGGAAATCAAGTACATGCTGIGGCTGICTGCCGATCT<br>GAAGTTCCGGATCAAGCAGAAGGGCGAATATCTGCCACTGCT<br>GCAGGGCAAAAGICTGGGGATGATCTTCGAAAAGAGGAGTAC<br>TCGGACCAGACTGTCAACAGAGACTGGATTCGCTCTGCTGGG<br>AGGACACCCATGCTTTCTGACCACACAGGACATTCATCTGGG<br>CGTGAACGAGTCACTGACCGACACAGCTCGAGTCCTGAGCTC<br>CATGGCAGATGCCGTGCTGGCACGGGTCTACAAACAGAGCGA<br>CCTGGATACCCTGGCTAAGGAAGCAAGCATCCCCATCATTAA<br>TGGGCTGTCCGACCTGTATCACCCTATCCAGATTCTGGCCGA<br>TTACCTGACCCTGCAGGAGCATTATTCTAGTCTGAAAGGCCT<br>GACACTGAGCTGGATTGGGGACGAAACAATATCCTGCACTC<br>CATTATGATGTCTGCCGCTAAGTTTGGAATGCATCTGCAGGC<br>AGCCACACCAAAAGGCTACGAACCCGATGCCAGTGTGACTAA<br>GCTGGCCGAACAGTATGCTAAAGAGAACGGCACTAAGCTGCT<br>GCTGACCAATGACCCCTCTGGAGGCTGCACACGGAGGCAACGT<br>CCTGATCACTGATACCTGGATTTCCATGGGCCAGGAGGAAGA | cDNA encoding human ornithine transcarbamylase, codon optimized for expressionin human (T7 promoter sequence underlined in italics; start codon. underline in bold) |

TABLE 3-continued

Ornithine Transcarbamylase (OTC) Amino Acid and Encoding Nucleotide Sequences

| SEQ ID NO: | Sequence | Description/Notes |
|---|---|---|
| | GAAGAAAAAGCGCCTGCAGGCATTCCAGGGGTACCAGGTGAC AATGAAAACTGCCAAGGTCGCCGCTTCTGATTGGACTTTTCT GCATTGTCTGCCCCGAAAACCTGAAGAGGTGGACGATGAGGT CTTCTATTCACCTAGGAGCCTGGTGTTTCCAGAAGCCGAGAA TCGCAAGTGGACAATCATGGCTGTGATGGTGTCCCTGCTGAC TGATTATTCCCCCCAGCTGCAGAAACCTAAGTTCTGAGCGGC CGCTTAATTAAGCTGCCTTCTGCGGGGCTTGCCTTCTGGCCA TGCCCTTCTTCTCTCCCTTGCACCTGTACCTCTTGGTCTTTG AATAAAGCCTGAGTAGGAAGTCTAGAGTTTAAACATTTAAAT CT | |
| 112 | GGGAAAUAAGAGAGAAAAGAAGAGUAAGAAGAAAUAUAAGAG CCACCAUGCUGUUCAACCUCAGAAUCCUCCUCAUAACGCCG CCUUUAGAAACGGUCAUAACUUCAUGGUCAGAAACUUUAGAU GUGGUCAGCCUCUCCAGAACAAAGUGCAGCUCAAGGGGCGGG ACCUGCUCACCCUGAAAAAUUUCACAGGCGAGGAAAUCAAGU ACAUGCUCUGGCUGUCUGCCGAUCUGAAGUUCAGGAUCAAGC AGAAGGGCGAAUAUCUCCCACUGCUCCAGGGGAAAAGUCUGG GUAUGAUCUUCGAAAAGCGGAGUACUAGGACCAGACUGUCAA CAGAGACUGGAUUCGCUCUGCUCGGAGGACACCCAUGCUUUC UGACCACACAGGACAUUCAUCUCGGUGUGAACGAGUCACUGA CCGACACAGCUCGAGUCCUCAGCUCCAUGGCAGAUGCCGUGC UGGCAAGGGUCUACAAACAGAGUGACCUCGAUACCCUGGCUA AGGAAGCAAGCAUCCCCAUCAUUAAUGGACUCUCCGACCUGU AUCACCCUAUCCAGAUUCUGGCCGAUUACCUCACCCUGCAGG AGCAUUAUUCUAGUCUGAAAGGGCUCACACUGAGCUGGAUUG GCGACGGAAACAAUAUCCUGCACUCCAUUAUGAUGUCUGCCG CUAAGUUUGGCAUGCAUCUGCAGGCAGCCACACCAAAAGGAU ACGAACCCGAUGCUUCCGUGACUAAGCUGGCCGAACAGUAUG CUAAAGAGAACGGAACUAAGCUGCUCCUGACCAAUGACCCCC UGGAGGCUGCACACGGGGGUAACGUCCUGAUCACUGAUACCU GGAUUUCCAUGGGCCAGGAGGAAGAGAAGAAAAAGCGCCUGC AGGCAUUCCAGGGAUACCAGGUGACAAUGAAAACUGCCAAGG UCGCCGCUUCUGAUUGGACUUUUCUCCAUUGUCUGCCCCGAA AGCCUGAAGAGGUGGACGAUGAGGUCUUCUAUUCACCUCGGA GCCUGGUGUUUCCAGAAGCCGAGAAUCGCAAGUGGACAAUCA UGGCAGUGAUGGUGUCCCUCCUCACAGACUAUUCCCCACAGC UCCAGAAGCCCAAGUUUUGAGCGGCCGCUUAAUUAAGCUGCC UUCUGCGGGGCUUGCCUUCUGGCCAUGCCCUUCUUCUCUCCC UUGCACCUGUACCUCUUGGUCUUUGAAUAAAGCCUGAGUAGG AAG | mRNA encoding human ornithine transcarbamylase. codon optimized for expression in mouse (start codon underlined in bold) |
| 113 | GGGAAAUAAGAGAGAAAAGAAGAGUAAGAAGAAAUAUAAGAG CCACCAUGCUCUCUAACCUCAGGAUUCUGCUCAACAACGCUG CUCUGCGGAAAGGCCAUACCUCUGUCGUCAGGCACUUCUGGU GUGGGAAACCCGUGCAGAGCCAGGUGCAGCUCAAGGGGCGGG ACCUGCUCACCCUGAAAAAUUUCACAGGCGAGGAAAUCAAGU ACAUGCUCUGGCUGUCUGCCGAUCUGAAGUUCAGGAUCAAGC AGAAGGGCGAAUAUCUCCCACUGCUCCAGGGGAAAAGUCUGG GUAUGAUCUUCGAAAAGCGGAGUACUAGGACCAGACUGUCAA CAGAGACUGGAUUCGCUCUGCUCGGAGGACACCCAUGCUUUC UGACCACACAGGACAUUCAUCUCGGUGUGAACGAGUCACUGA CCGACACAGCUCGAGUCCUCAGCUCCAUGGCAGAUGCCGUGC UGGCAAGGGUCUACAAACAGAGUGACCUCGAUACCCUGGCUA AGGAAGCAAGCAUCCCCAUCAUUAAUGGACUCUCCGACCUGU AUCACCCUAUCCAGAUUCUGGCCGAUUACCUCACCCUGCAGG AGCAUUAUUCUAGUCUGAAAGGGCUCACACUGAGCUGGAUUG GCGACGGAAACAAUAUCCUGCACUCCAUUAUGAUGUCUGCCG CUAAGUUUGGCAUGCAUCUGCAGGCAGCCACACCAAAAGGAU ACGAACCCGAUGCUUCCGUGACUAAGCUGGCCGAACAGUAUG CUAAAGAGAACGGAACUAAGCUGCUCCUGACCAAUGACCCCC UGGAGGCUGCACACGGGGGUAACGUCCUGAUCACUGAUACCU GGAUUUCCAUGGGCCAGGAGGAAGAGAAGAAAAAGCGCCUGC AGGCAUUCCAGGGAUACCAGGUGACAAUGAAAACUGCCAAGG UCGCCGCUUCUGAUUGGACUUUUCUCCAUUGUCUGCCCCGAA AGCCUGAAGAGGUGGACGAUGAGGUCUUCUAUUCACCUCGGA GCCUGGUGUUUCCAGAAGCCGAGAAUCGCAAGUGGACAAUCA UGGCAGUGAUGGUGUCCCUCCUCACAGACUAUUCCCCACAGC UCCAGAAGCCCAAGUUUUGAGCGGCCGCUUAAUUAAGCUGCC UUCUGCGGGGCUUGCCUUCUGGCCAUGCCCUUCUUCUCUCCC UUGCACCUGUACCUCUUGGUCUUUGAAUAAAGCCUGAGUAGG AAG | mRNA encoding human ornithine transcarbamylase with mouse mitochondrial leader sequence, codon optimized for expression in mouse (start codon underlined in bold) |

TABLE 3-continued

Ornithine Transcarbamylase (OTC) Amino Acid and Encoding Nucleotide Sequences

| SEQ ID NO: | Sequence | Description/Notes |
|---|---|---|
| 114 | GGGAAAUAAGAGAGAAAAGAAGAGUAAGAAGAAAUAUAAGAG<br>CCACCAUGCUGUUUAACCUGAGGAUUCUGCUGAACAACGCUG<br>CUUUUCGGAACGGCCACAACUUUAUGGUGCGGAACUUUCGGU<br>GCGGACAGCCACUGCAGAACAAAGUGCAGCUGAAGGGGAGGG<br>ACCUGCUGACCCUGAAAAAUUUCACAGGAGAGGAAAUCAAGU<br>ACAUGCUGUGGCUGUCUGCCGAUCUGAAGUUCCGGAUCAAGC<br>AGAAGGGCGAAUAUCUGCCACUGCUGCAGGGCAAAAGUCUGG<br>GGAUGAUCUUCGAAAAGAGGAGUACUCGGACCAGACUGUCAA<br>CAGAGACUGGAUUCGCUCUGCUGGGAGGACACCCAUGCUUUC<br>UGACCACACAGGACAUUCAUCUGGGCGUGAACGAGUCACUGA<br>cCGACACAGCUCGAGUCCUGAGCUCCAUGGCAGAUGCCGUGC<br>UGGCACGGGUCUACAAACAGAGCGACCUGGAUACCCUGGCUA<br>AGGAAGCAAGCAUCCCCAUCAUUAAUGGGCUGUCCGACCUGU<br>AUCACCCUAUCCAGAUUCUGGCCGAUUACCUGACCCUGCAGG<br>AGCAUUAUUCUAGUCUGAAAGGCCUGACACUGAGCUGGAUUG<br>GGGACGGAAACAAUAUCCUGCACUCCAUUAUGAUGUCUGCCG<br>CUAAGUUUGGAAUGCAUCUGCAGGCAGCCACACCAAAAGGCU<br>ACGAACCCGAUGCCAGUGUGACUAAGCUGGCCGAACAGUAUG<br>CUAAAGAGAACGGCACUAAGCUGCUGCUGACCAAUGACCCUC<br>UGGAGGCUGCACACGGAGGCAACGUCCUGAUCACUGAUACCU<br>GGAUUUCCAUGGGCCAGGAGGAAGAGAAGAAAAAGCGCCUGC<br>AGGCAUUCCAGGGGUACCAGGUGACAAUGAAAACUGCCAAGG<br>UCGCCGCUUCUGAUUGGACUUUUCUGCAUUGUCUGCCCCGAA<br>AACCUGAAGAGGUGGACGAUGAGGUCUUCUAUUCACCUAGGA<br>GCCUGGUGUUUCCAGAAGCCGAGAAUCGCAAGUGGACAAUCA<br>UGGCUGUGAUGGUGUCCCUGCUGACUGAUUAUUCCCCCAGC<br>UGCAGAAACCUAAGUUCUGAGCGGCCGCUUAAUUAAGCUGCC<br>UUCUGCGGGCUUGCCUUCUGGCCAUGCCCUUCUUCUCUCCC<br>UUGCACCUGUACCUCUUGGUCUUUGAAUAAAGCCUGAGUAGG<br>AAG | mRNA encoding human ornithine transcarbamylase, codon optimized for expression in human (start codon underlined in bold) |

In other embodiments of a composition or method for increasing the amount of a protein in a cell, the protein is methylmalonyl CoA mutase (MUT), propionyl CoA carboxylase subunit A (PCCA), propionyl CoA carboxylase subunit B (PCCB), or a subunit of branched-chain ketoacid dehydrogenase (BCKDH). In such embodiments, an mRNA encoding a MUT, PCCA, PCCB, or BCKDH subunit protein is formulated into a composition comprising a copolymer of the present disclosure such as, for example, a copolymer as set forth in any one of (a)-(z) above. In particular variations, the mRNA molecule encodes a MUT protein comprising an amino acid sequence having at least 90% or at least 95% sequence identity with residues 33-750 of SEQ ID NO:117 (e.g., at least 96%, at least 97%, at least 98%, at least 99%, at least 99.5%, or 100% sequence identity with residues 33-750 of SEQ ID NO:117). In other variations, the mRNA molecule encodes a PCCA protein comprising an amino acid sequence having at least 90% or at least 95% sequence identity with residues 53-728 of SEQ ID NO:119 (e.g., at least 96%, at least 97%, at least 98%, at least 99%, at least 99.5%, or 100% sequence identity with residues 53-728 of SEQ ID NO:119). In other variations, the mRNA molecule encodes a PCCB protein comprising an amino acid sequence having at least 90% or at least 95% sequence identity with residues 29-539 of SEQ ID NO:121 (e.g., at least 96%, at least 97%, at least 98%, at least 99%, at least 99.5%, or 100% sequence identity with residues 29-539 of SEQ ID NO:121). To direct an encoded MUT, PCCA, PCCB, or BCKDH subunit protein to the mitochondria of the cell, an mRNA molecule encoding the protein includes a sequence encoding a mitochondrial leader sequence. The mitochondrial leader sequence may be that of a native protein (e.g., residues 1-32 of SEQ ID NO:117 (a native human MUT mitochondrial leader sequence), residues 1-52 of SEQ ID NO:119 (a native human PCCA mitochondrial leader sequence), or residues 1-28 of SEQ ID NO:121 (a native human PCCB mitochondrial leader sequence)), or may be derived from another protein comprising a mitochondrial targeting signal peptide, or synthesized de novo. An engineered cleavage site may be included at the junction between the mitochondrial leader sequence and the remainder of the polypeptide to optimize proteolytic processing in the cell. The mitochondrial leader sequence is operably linked to the mRNA sequence encoding the mature MUT, PCCA, PCCB, or BCKDH subunit protein, i.e., the two sequences are joined in the correct reading frame and positioned to direct the newly synthesized polypeptide to the mitochondria of a cell. In specific variations, the encoded MUT protein with a mitochondrial leader sequence has an amino acid sequence as set forth in SEQ ID NO:117, the encoded PCCA protein with a mitochondrial leader sequence has an amino acid sequence as set forth in SEQ ID NO:119, or the encoded PCCB protein with a mitochondrial leader sequence has an amino acid sequence as set forth in SEQ ID NO:121. A suitable mRNA sequence encoding a MUT protein of SEQ ID NO:117, and which may be formulated into a composition comprising a copolymer of the present disclosure, may comprise the sequence shown in SEQ ID NO:118 (coding sequence corresponding to residues 48-2297). A suitable mRNA sequence encoding a PCCA protein of SEQ ID NO:119, and which may be formulated into a composition comprising a copolymer of the present disclosure, may comprise the sequence shown in SEQ ID NO:120 (coding sequence corresponding to residues 48-2231). A suitable mRNA sequence encoding a PCCB protein of SEQ ID NO:121, and which may be formulated into a composition comprising a copolymer of the present disclosure, may comprise the sequence shown in SEQ ID NO:122 (coding sequence corresponding to residues 48-1664). A MUT-, PCCA-, PCCB-, or BCKDH- subunit-encoding mRNA for formulation with a copolymer of the present disclosure typically includes a poly(A) at its 3' end (e.g., a polyA tail of about 120 adenine residues). Exemplary MUT, PCCA, and PCCB amino acid sequences and encoding nucleotide sequences are shown in Table 4.

TABLE 4

MUT, PCCA, and PCCB Amino Acid and Encoding Nucleotide Sequences

| SEQ ID NO: | Sequence | Description/Notes |
|---|---|---|
| 117 | MLRAKNQLFLLSPHYLRQVKESSGSRLIQQRLLHQQQPLHPE WAALAKKQLKGKNPEDLIWHTPEGISIKPLYSKRDTMDLPEE LPGVKPFTRGPYPTMYTFRPWTIRQYAGFSTVEESNKFYKDN IKAGQQGLSVAFDLATHRGYDSDNPRVRGDVGMAGVAIDTVE DTKILFDGIPLEKMSVSMTMNGAVIPVLANFIVTGEEQGVPK EKLTGTIQNDILKEFMVRNTYIFPPEPSMKIIADIFEYTAKH MPKFNSISISGYHMQEAGADAILELAYTLADGLEYSRTGLQA GLTIDEFAPRLSFFWGIGMNFYMEIAKMRAGRRLWAHLIEKM FQPKNSKSLLLRAHCQTSGWSLTEQDPYNNIVRTAIEAMAAV FGGTQSLHTNSFDEALGLPTVKSARIARNTQIIIQEESGIPK VADPWGGSYMMECLTNDVYDAALKLINEIEEMGGMAKAVAEG IPKLRIEECAARRQARIDSGSEVIVGVNKYQLEKEDAVEVLA IDNTSVRNRQIEKLKKIKSSRDQALAERCLAALTECAASGDG NILALAVDASRARCTVGEITDALKKVFGEHKANDRMVSGAYR QEFGESKEITSAIKRVHKFMEREGRRPRLLVAKMGQDGHDRG AKVIATGFADLGFDVDIGPLFQTPREVAQQAVDADVHAVGIS TLAAGHKTLVPELIKELNSLGRPDILVMCGGVIPPQDYEFLF EVGVSNVFGPGTRIPKAAVQVLDDIEKCLEKKQQSV | Human methylmalonyl-coenzyme A mutase amino acid Sequence with native (human) mitochondrial leader sequence (leader sequence underlined) |
| 118 | GGGAAAUAAGAGAGAAAAGAAGAGUAAGAAGAAAUAUAAGAG CCACCAUGUUAAGAGCUAAGAAUCAGCUUUUUUUACUUUCAC CUCAUUACCUGAGGCAGGUAAAAGAAUCAUCAGGCUCCAGGC UCAUACAGCAACGACUUCUACACCAGCAACAGCCCCUUCACC CAGAAUGGGCUGCCCUGGCUAAAAAGCAGCUGAAAGGCAAAA ACCCAGAAGACCUAAUAUGGCACACCCCGGAAGGGAUCUCUA UAAAACCCUUGUAUUCCAAGAGAGAUACUAUGGACUUACCUG AAGAACUUCCAGGAGUGAAGCCAUUCACACGUGGACCAUAUC CUACCAUGUAUACCUUUAGGCCCUGGACCAUCCGCCAGUAUG CUGGUUUUAGUACUGUGGAAGAAAGCAAUAAGUUCUAUAAGG ACAACAUUAAGGCUGGUCAGCAGGGAUUAUCAGUUGCCUUUG AUCUGGCGACACAUCGUGGCUAUGAUUCAGACAACCCUCGAG UUCGUGGUGAUGUUGGAAUGGCUGGAGUUGCUAUUGACACUG UGGAAGAUACCAAAAUUCUUUUUGAUGGAAUUCCUUUAGAAA AAAUGUCAGUUUCCAUGACUAUGAAUGGAGCAGUUAUUCCAG UUCUUGCAAAUUUUAUAGUAACUGGAGAAGAACAAGGUGUAC CUAAAGAGAAGCUUACUGGUACCAUCCAAAAUGAUAUACUAA AGGAAUUUAUGGUUCGAAAUACAUACAUUUUUCCUCCAGAAC CAUCCAUGAAAAUUAUUGCUGACAUAUUUGAAUAUACAGCAA AGCACAUGCCAAAAUUUAAUUCAAUUUCAAUUAGUGGAUACC AUAUGCAGGAAGCAGGGGCUGAUGCCAUUCUGGAGCUGGCCU AUACUUUAGCAGAUGGAUUGGAGUACUCUAGAACUGGACUCC AGGCUGGCCUGACAAUUGAUGAAUUUGCACCAAGGUUGUCUU UCUUCUGGGGAAUUGGAAUGAAUUUCUAUAUGGAAAUAGCAA AGAUGAGAGCUGGUAGAAGACUCUGGGCUCACUUAAUAGAGA AAAUGUUUCAGCCUAAAAACUCAAAAUCUCUUCUUCUAAGAG CACACUGUCAGACAUCUGGAUGGUCACUUACUGAGCAGGAUC CCUACAAUAAUAUUGUCCGUACUGCAAUAGAAGCAAUGGCAG CAGUAUUUGGAGGGACUCAGUCUUUGCACACAAAUUCUUUUG AUGAAGCUUUGGGUUUGCCAACUGUGAAAAGUGCUCGAAUUG CCAGGAACACACAAAUCAUCAUUCAAGAAGAAUCUGGGAUUC CCAAAGUGGCUGAUCCUUGGGGAGGUUCUUACAUGAUGGAAU GUCUCACAAAUGAUGUUUAUGAUGCUGCUUUAAAGCUCAUUA AUGAAAUUGAAGAAAUGGGUGGAAUGGCCAAAGCUGUAGCUG AGGGGAUACCUAAACUUCGAAUUGAAGAAUGUGCUGCCCGAA GACAAGCUAGAAUAGAUUCUGGUUCUGAAGUAAUUGUUGGAG UAAAUAAGUACCAGUUGGAAAAAGAAGACGCUGUAGAAGUUC UGGCAAUUGAUAAUACUUCAGUGCGAAACAGGCAGAUUGAAA AACUUAAGAAGAUCAAAUCCAGCAGGGAUCAAGCUUUGGCUG AACGUUGUCUUGCUGCACUAACCGAAUGUGCUGCUAGCGGAG AUGGAAAUAUCCUGGCUCUUGCAGUGGAUGCAUCUCGGGCAA GAUGUACAGUGGGAGAAAUCACAGAUGCCCUGAAAAAGGUAU UUGGUGAACAUAAAGCGAAUGAUCGAAUGGUGAGUGGAGCAU AUCGCCAGGAAUUUGGAGAAAGUAAAGAGAUAACAUCUGCUA UCAAGAGGGUUCAUAAAUUCAUGGAACGUGAAGGUCGCAGAC CUCGUCUUCUUGUAGCAAAAAUGGGACAAGAUGGCCAUGACA GAGGAGCAAAAGUUAUUGCUACAGGAUUUGCUGAUCUUGGUU UUGAUGUGGACAUAGGCCCUCUUUUCCAGACUCCUCGUGAAG UGGCCCAGCAGGCUGUGGAUGCGGAUGUGCAUGCUGUGGGCA | mRNA encoding human methylmalonyl-coenzyme A mutase (start codon underlined in bold) |

TABLE 4-continued

MUT, PCCA, and PCCB Amino Acid and Encoding Nucleotide Sequences

| SEQ ID NO: | Sequence | Description/Notes |
|---|---|---|
| | UAAGCACCCUCGCUGCUGGUCAUAAAACCCUAGUUCCUGAAC UCAUCAAAGAACUUAACUCCCUUGGACGGCCAGAUAUUCUUG UCAUGUGUGGAGGGGUGAUACCACCUCAGGAUUAUGAAUUUC UGUUUGAAGUUGGUGUUUCCAAUGUAUUUGGUCCUGGGACUC GAAUUCCAAAGGCUGCCGUUCAGGUGCUUGAUGAUAUUGAGA AGUGUUUGGAAAAGAAGCAGCAAUCUGUAUAAGCGGCCGCUU AAUUAAGCUGCCUUCUGCGGGGCUUGCCUUCUGGCCAUGCCC UUCUUCUCUCCCUUGCACCUGUACCUCUUGGUCUUUGAAUAA AGCCUGAGUAGGAAG | |
| 119 | <u>MAGFWVGTAPLVAAGRRGRWPPQQLMLSAALRTLKHVLYYSR QCLMVSRNLG</u>SVGYDPNEKTFDKILVANRGEIACRVIRTCKK MGIKTVAIHSDVDASSVHVKMADEAVCVGPAPTSKSYLNMDA IMEAIKKTRAQAVHPGYGFLSENKEFARCLAAEDVVFIGPDT HAIQAMGDKIESKLLAKKAEVNTIPGFDGVVKDAEEAVRIAR EIGYPVMIKASAGGGGKGMRIAWDDEETRDGFRLSSQEAASS FGDDRLLIEKFIDNPRHIEIQVLGDKHGNALWLNERECSIQR RNQKVVEEAPSIFLDAETRRAMGEQAVALARAVKYSSAGTVE FLVDSKKNFYFLEMNTRLQVEHPVTECITGLDLVQEMIRVAK GYPLRHKQADIRINGWAVECRVYAEDPYKSFGLPSIGRLSQY QEPLHLPGVRVDSGIQPGSDISIYYDPMISKLITYGSDRTEA LKRMADALDNYVIRGVTHNIALLREVIINSRFVKGDISTKFL SDVYPDGFKGHMLTKSEKNQLLAIASSLFVAFQLRAQHFQEN SRMPVIKPDIANWELSVKLHDKVHTVVASNNGSVFSVEVDGS KLNVTSTWNLASPLLSVSVDGTQRTVQCLSREAGGNMSIQFL GTVYKVNILTRLAAELNKFMLEKVTEDTSSVLRSPMPGVVVA VSVKPGDAVAEGQEICVIEAMKMQNSMTAGKTGTVKSVHCQA GDTVGEGDLLVELE | Human propionyl CoA carboxylase, alpha polypeptide (PCCA) amino acid sequence with native (human) mitochondrial leader sequence (leader sequence underlined) |
| 120 | GGGAAAUAAGAGAGAAAAGAAGAGUAAGAAGAAAUAUAAGAG CCACCAUGGCGGGGUUCUGGGUCGGGACAGCACCGCUGGUCG CUGCCGGACGGCGUGGGCGGUGGCCGCCGCAGCAGCUGAUGC UGAGCGCGGCCUGCGACCCUGAAGCAUGCUCUGUACUAUU CAAGACAGUGCUUAAUGGUGUCCCGUAAUCUUGGUUCAGUGG GAUAUGAUCCAAUGAAAAAACUUUUGAUAAAAUUCUUGUUG CUAAUAGAGGAGAAAUUGCAUGUCGGGUUAUUAGAACUUGCA AGAAGAUGGGCAUUAAGACAGUUGCCAUCCACAGUGAUGUUG AUGCUAGUUCUGUUCAUGUGAAAAUGGCGGAUGAGGCUGUCU GUGUUGGCCCAGCUCCCACCAGUAAAAGCUACCUCAACAUGG AUGCCAUCAUGGAAGCCAUUAAGAAACCAGGGCCCAAGCUG UACAUCCAGGUUAUGGAUUCCUUUCAGAAAACAAAGAAUUUG CCAGAUGUUUGGCAGCAGAAGAUGUCGUUUUCAUUGGACCUG ACACACAUGCUAUUCAAGCCAUGGGCGACAAGAUUGAAAGCA AAUUAUUAGCUAAGAAAGCAGAGGUUAAUACAAUCCCUGGCU UUGAUGGAGUAGUCAAGGAUGCAGAAGAAGCUGUCAGAAUUG CAAGGGAAAUUGGCUACCCUGUCAUGAUCAAGGCCUCAGCAG GUGGUGGUGGGAAAGGCAUGCGCAUUGCUUGGGAUGAUGAAG AGACCAGGGAUGGUUUUAGAUUGUCAUCUCAAGAAGCUGCUU CUAGUUUUGGCGAUGAUAGACUACUAAUAGAAAAAUUUAUUG AUAAUCCUCGUCAUAUAGAAAUCCAGGUUCUAGGUGAUAAAC AUGGGAAUGCUUUAUGGCUUAAUGAAAGAGAGUGCUCAAUUC AGAGAAGAAAUCAGAAGGUGGUGGAGGAAGCACCAAGCAUUU UUUUGGAUGCGGAGACUCGAAGAGCGAUGGGAGAACAAGCUG UAGCUCUUGCCAGAGCAGUAAAAUAUUCCUCUGCUGGGACCG UGGAGUUCCUUGUGGACUCUAAGAAGAAUUUUUAUUUCUUGG AAAUGAAUACAAGACUCCAGGUUGAGCAUCCUGUCACAGAAU GCAUUACUGGCCUGGACCUAGUCCAGGAAAUGAUCCGUGUUG CUAAGGGCUACCCUCUCAGGCACAAACAAGCUGAUAUUCGCA UCAACGGCUGGGCAGUUGAAUGUCGGGUUUAUGCUGAGGACC CCUACAAGUCUUUUGGGUUACCAUCUAUUGGAGAUUGUCUC AGUACCAAGAACCGUUACAUCUACCUGGUGUCCGAGUGGACA GUGGCAUCCAACCAGGAAGUGAUAUUAGCAUUUAUUAUGAUC CUAUGAUUUCAAAACUAAUCACAUAUGGCUCUGAUAGAACUG AGGCACUGAAGAGAAUGGCAGAUGCACUGGAUAACUAUGUUA UUCGAGGUGUUACACAUAAUAUUGCAUUACUUCGAGAGGUGA UAAUCAACUCACGCUUUGUAAAAGGAGACAUCAGCACUAAAU UUCUCUCCGAUGUGUAUCCUGAUGGCUUCAAAGGACACAUGC UAACCAAGAGUGAAAGAACCAGUUAUUGGCAAUAGCAUCAU CAUUGUUUGUGGCAUUCCAGUUAAGAGCACAACAUUUUCAAG AAAAUUCAAGAAUGCCUGUUAUUAAACCAGACAUAGCCAACU GGGAGCUCUCAGUAAAAUUGCAUGAUAAAGUUCAUACCGUAG UAGCAUCAACAAUGGGUCAGUGUUCUCGGUGGAAGUUGAUG GGUCGAAACUAAAUGUGACCAGCACGUGGAACCUGGCUUCGC CCUUAUUGUCUGUCAGCGUUGAUGGCACUCAGAGGACUGUCC AGUGUCUUUCUCGAGAAGCAGGUGGAAACAUGAGCAUUCAGU | mRNA encoding human propionyl CoA carboxylase, alpha polypeptide (pCCA) (start codon underlined in bold) |

TABLE 4-continued

MUT, PCCA, and PCCB Amino Acid and Encoding Nucleotide Sequences

| SEQ ID NO: | Sequence | Description/Notes |
|---|---|---|
|  | UUCUUGGUACAGUGUACAAGGUGAAUAUCUUAACCAGACUUG<br>CCGCAGAAUUGAACAAAUUUAUGCUGGAAAAAGUGACUGAGG<br>ACACAAGCAGUGUUCUGCGUUCCCCGAUGCCCGGAGUGGUGG<br>UGGCCGUCUCUGUCAAGCCUGGAGACGCGGUAGCAGAAGGUC<br>AAGAAAUUUGUGUGAUUGAAGCCAUGAAAAUGCAGAAUAGUA<br>UGACAGCUGGGAAAACUGGCACGGUGAAAUCUGUGCACUGUC<br>AAGCUGGAGACACAGUUGGAGAAGGGGAUCUGCUCGUGGAGC<br>UGGAAUGAGCGGCCGCUUAAUUAAGCUGCCUUCUGCGGGGCU<br>UGCCUUCUGGCCAUGCCCUUCUUCUCUCCCUUGCACCGUAC<br>CUCUUGGUCUUUGAAUAAAGCCUGAGUAGGAAG |  |
| 121 | MAAALRVAAVGARLSVLASGLRAAVRSLCSQATSVNERIENK<br>RRTALLGGGQRRIDAQHKRGKLTARERISLLLDPGSFVESDM<br>FVEHRCADFGMAADKNKFPGDSVVTGRGRINGRLVYVFSQDF<br>TVFGGSLSGAHAQKICKIMDQAITVGAPVIGLNDSGGARIQE<br>GVESLAGYADIFLRNVTASGVIPQISLIMGPCAGGAVYSPAL<br>TDFTFMVKDTSYLFITGPDVVKSVTNEDVTQEELGGAKTHTT<br>MSGVAHRAFENDVDALCNLRDFFNYLPLSSQDPAPVRECHDP<br>SDRLVPELDTIVPLESTKAYNMVDIIHSVVDEREFFEIMPNY<br>AKNIIVGFARMNGRTVGIVGNQPKVASGCLDINSSVKGARFV<br>RFCDAFNIPLITFVDVPGFLPGTAQEYGGIIRHGAKLLYAFA<br>EATVPKVTVITRKAYGGAYDVMSSKHLCGDTNYAWPTAEIAV<br>MGAKGAVEIIFKGHENVEAAQAEYIEKFANPFPAAVRGFVDD<br>IIQPSSTRARICCDLDVLASKKVQRPWRKHANIPL | Human propionyl CoA carboxylase, beta polypeptide (PCCB) amino acid sequence with native (human) mitochondrial leader sequence (leader sequence underlined) |
| 122 | GGGAAAUAAGAGAGAAAAGAAGAGUAAGAAGAAAUAUAAGAG<br>CCACCAUGGCGGCGGCAUUACGGGUGGCGGCGGUCGGGGCAA<br>GGCUCAGCGUUCUGGCGAGCGGUCUCCGCGCCGCGGUCCGCA<br>GCCUUUGCAGCCAGGCCACCUCUGUUAACGAACGCAUCGAAA<br>ACAAGCGCCGGACCGCGCUGCUGGGAGGGGGCCAACGCCGUA<br>UUGACGCGCAGCACAAGCGAGGAAAGCUAACAGCCAGGGAGA<br>GGAUCAGUCUCUUGCUGGACCCUGGCAGCUUUGUUGAGAGCG<br>ACAUGUUUGUGGAACACAGAUGUGCAGAUUUUGGAAUGGCUG<br>CUGAUAAGAAUAAGUUUCCUGGAGACAGCGUGGUCACUGGAC<br>GAGGCCGAAUCAAUGGAAGAUUGGUUUAUGUCUUCAGUCAGG<br>AUUUUACAGUUUUUGGAGGCAGUCUGUCAGGAGCACAUGCCC<br>AAAAGAUCUGCAAAAUCAUGGACCAGGCCAUAACGGUGGGGG<br>CUCCAGUGAUUGGGCUGAAUGACUCUGGGGGAGCACGGAUCC<br>AAGAAGGAGUGGAGUCUUUGGCUGGCUAUGCAGACAUCUUUC<br>UGAGGAAUGUUACGGCAUCCGGAGUCAUCCCUCAGAUUUCUC<br>UGAUCAUGGGCCCAUGUGCUGGUGGGGCCGUCUACUCCCCAG<br>CCCUAACAGACUUCACGUUCAUGGUAAAGGACACCUCCUACC<br>UGUUCAUCACUGGCCCUGAUGUUGUGAAGUCUGUCACCAAUG<br>AGGAUGUUACCCAGGAGGAGCUCGGUGGUGCCAAGACCCACA<br>CCACCAUGUCAGGUGUGGCCCACAGAGCUUUUGAAAAUGAUG<br>UUGAUGCCUUGUGUAAUCUCCGGGAUUUCUUCAACUACCUGC<br>CCCUGAGCAGUCAGGACCCGGCUCCCGUCCGUGAGUGCCACG<br>AUCCCAGUGACCGUCUGGUUCCUGAGCUUGACACAAUUGUCC<br>CUUUGGAAUCAACCAAAGCCUACAACAUGGUGGACAUCAUAC<br>ACUCUGUUGUUGAUGAGCGUGAAUUUUUUGAGAUCAUGCCCA<br>AUUAUGCCAAGAACAUCAUUGUUGGUUUUGCAAGAAUGAAUG<br>GGAGGACUGUUGGAAUUGUUGGCAACCAACCUAAGGUGGCCU<br>CAGGAUGCUUGGAUAUUAAUUCAUCUGUGAAAGGGGCUCGUU<br>UUGUCAGAUUCUGUGAUGCAUUCAAUAUUCCACUCAUCACUU<br>UUGUUGAUGUCCCUGGCUUUCUACCUGGCACAGCACAGGAAU<br>ACGGGGGCAUCAUCCGGCAUGGUGCCAAGCUUCUCUACGCAU<br>UUGCUGAGGCAACUGUACCCAAAGUCACAGUCAUCACCAGGA<br>AGGCCUAUGGAGGUGCCUAUGAUGUCAUGAGCUCUAAGCACC<br>UUUGUGGUGAUACCAACUAUGCCUGGCCCACCGCAGAGAUUG<br>CAGUCAUGGGAGCAAAGGGCGCUGUGGAGAUCAUCUUCAAAG<br>GGCAUGAGAAUGUGGAAGCUGCUCAGGCAGAGUACAUCGAGA<br>AGUUUGCCAACCCUUUCCCUGCAGCAGUGCGAGGGUUUGUGG<br>AUGACAUCAUCCAACCUUCUUCCACACGUGCCCGAAUCUGCU<br>GUGACCUGGAUGUCUUGGCCAGCAAGAAGGUACAACGUCCUU<br>GGAGAAAACAUGCAAAUAUUCCAUUGUAAGCGGCCGCUUAAU<br>UAAGCUGCCUUCUGCGGGGCUUGCCUUCUGGCCAUGCCCUUC<br>UUCUCUCCCUUGCACCGUACCUCUUGGUCUUUGAAUAAAGC<br>CUGAGUAGGAAG | mRNA encoding human propionyl CoA carboxylase, beta polypeptide (PCCB) (start codon underlined in bold) |

Examples of a disease or condition associated with defective gene expression and/or activity in a subject treatable by the methods disclosed herein include liver cancer, hepatitis, hypercholesterolemia, liver fibrosis or haemochromatosis.

Another example of a disease or condition associated with defective gene expression and/or activity in a subject treatable by the methods disclosed herein includes hepatocellular carcinoma.

Additional examples of a disease or condition associated with defective gene expression and/or activity in a subject treatable by the methods disclosed herein include breast, ovaries, pancreas, endometrium, lungs, kidneys, colon, brain, or myeloid cells of hematopoietic origin.

A further example of a disease or condition associated with defective gene expression and/or activity in a subject treatable by the methods disclosed herein includes glioblastoma.

Further examples of a disease or condition associated with defective gene expression and/or activity in a subject treatable by the methods disclosed herein include ornithine transcarbamylase deficiency (OTCD), alpha-1-antitrypsin deficiency (A1ATD), cystic fibrosis (CF) and hyperoxaluria.

Further examples of a disease or condition associated with defective gene expression and/or activity in a subject treatable by the methods disclosed herein include protein deficiency diseases associated with single-gene metabolic defects in the liver. Exemplary protein deficiency diseases of the liver include diseases associated with urea cycle defects (e.g., ornithine transcarbamylase (OTC) deficiency and carbamoyl phosphate synthetase I (CPS1) deficiency); tyrosinemia type 1 (fumarylacetoacetase (FAH) enzyme deficiency); primary hyper-oxaluria type 1 (alanine:glyoxylate-aminotransferase (AGT) deficiency); organic acidemia (e.g., methylmalonic acidemia (MMA; deficiency in, for example, methylmalonyl CoA mutase), propionic acidemia (PA; propionyl CoA carboxylase (PCC) deficiency), and maple syrup urine disease (MSUD; branched-chain ketoacid dehydrogenase (BCKDH) deficiency)); Wilson's Disease (deficiency in copper-transporting ATPase, Atp7B); Crigler-Najjar Syndrome Type 1 (bilirubin uridinediphosphate glucuronyltransferase (BGT) enzyme deficiency); hemochromatosis (hepcidin deficiency); glycogen storage disease (GSD) type 1a (glucose-6-phosphatase (G6Pase) deficiency); glycogen storage disease (GSD) type 1b (glucose 6-phosphate translocase deficiency); lysosomal storage diseases (LSDs; deficiencies in lysosomal enzymes) such as, e.g., Gaucher's Disease types 1, 2, and 3 (lysosomal glucocerebrosidase (GB) deficiency), Niemann-Pick Disease Type C (mutation in either the NPC1 or NPC2 gene), and Niemann-Pick Disease Types A and B (acid sphingomyelinase (ASM) deficiency); alpha-1 antitrypsin (A1AT) deficiency; hemophilia B (Factor IX deficiency); galactosemia types 1, 2, and 3 (galactose-1-phosphate uridylyltransferase, galactokinase, and UDP-galactose 4-epimerase deficiencies, respectively); transthyretin-related hereditary amyloidosis (TTR-familial amyloid polyneuropathy; transthyretin deficiency); atypical haemolytic uremic syndrome-1 (deficiencies in complement regulatory proteins, e.g., factor H, factor I, or membrane cofactor protein); phenylketonuria (phenylalanine hydroxylase (PAH) deficiency); alcaptonuria (homogentisate 1,2-dioxygenase deficiency); acute intermittent porphyria (porphobilinogen deaminase deficiency); Lesch-Nyhan syndrome (hypoxanthine-guanine phosphoribosyltransferase (HGPRT) deficiency; argininosuccinic aciduria (argininosuccinate lyase (ASL) deficiency); and progressive familial intrahepatic cholestasis (PFIC) (P-type ATPase protein, FIC-1 deficiency). Additional examples of protein deficiency diseases that are lysosomal storage diseases (LSDs) include Fabry disease (alpha-galactosidase A deficiency); Farber disease (acid ceramidase deficiency); fucosidosis (acid α-L-fucosidsase deficiency); GM1 gangliosidosis (acid β-galactosidase deficiency); Hunter syndrome (mucopolysaccharidosis type II (MPS II); iduronate-2-sulfatase deficiency); Hurler-Scheie, Hurler, and Scheie syndromes (mucopolysaccharidosis type I (MPS I); alpha-L-iduronidase deficiency); Krabbe disease (galactocerebrosidase deficiency); α-mannosidosis (acid α-mannosidase deficiency); β-mannosidosis (acid β-mannosidase deficiency); Maroteaux-Lamy syndrome (mucopolysaccharidosis type VI (MPS VI); arylsulfatase B deficiency); metachromatic leukodystrophy (arylsulfatase A deficiency); Morquio syndrome type A (mucopolysaccharidosis type IVA (MPS IVA); N-acetylgalactosamine-6-sulfate sulfatase deficiency); Morquio syndrome type B (mucopolysaccharidosis type IVB (MPS IVB); acid β-galactosidase deficiency); Pompe disease (acid α-glucosidase deficiency); Sandhoff disease (β-hexosaminidase B deficiency); Sanfilippo syndrome type A (mucopolysaccharidosis type IIIA (MPS IIIA); heparan-N-sulfatase deficiency); Sanfilippo syndrome type B (mucopolysaccharidosis type IIIB (MPS IIIB); alpha-N-acetylglucosaminidase deficiency); Sanfilippo syndrome type C (mucopolysaccharidosis type IIIC (MPS IIIC); acetyl-CoA:α-glucosaminide N-acetyltransferase deficiency); Sanfilippo syndrome type D (mucopolysaccharidosis type IIID (MPS IIID); N-acetylglucosamine-6-sulfate sulfatase deficiency); Schindler/Kanzaki disease (alpha-N-acetylgalactosaminidase deficiency); sialidosis (sialidase deficiency); Sly syndrome (mucopolysaccharidosis type VII (MPS VII); β-glucuronidase deficiency); and Tay-Sachs disease (β-hexosaminidase A deficiency).

In particular variations, a composition comprising (i) a polymer of Formula I wherein G is present and is a cationic peptide, polyamine, or polycation (e.g., a copolymer of formula VII) and (ii) an mRNA encoding an ornithine transcarbamylase (OTC) protein is used in a method to treat ornithine transcarbamylase deficiency (OTCD). OTCD is a urea cycle disorder that can trigger hyperammonemia, a life-threatening illness that leads to brain damage, coma or even death. This is due to deficiency in the activity of OTC, a key enzyme in the urea cycle, which primarily takes place in the liver and is responsible for removal of excess nitrogen in the body. Ammonium nitrogen is produced from protein intake as well as protein breakdown in the body. In the liver, this ammonium nitrogen is converted into urea by enzymes in the urea cycle. Urea is non-toxic and cleared easily through the kidneys in urine, normally. However when the OTC enzyme is deficient, ammonia levels rise in blood and cause severe brain damage. Patients with severe OTC deficiency are most often identified 2-3 days after birth where the patient has significantly elevated blood ammonia levels and ends up in a coma. Patients with milder OTC deficiency can have crises during times of stress resulting in elevated ammonia levels that can also lead to coma. Current therapies include ammonia scavenger drugs (Buphenyl, Ravicti) for use in patients with hyperammonemia.

The OTC gene is X-linked. The disease is present in males with one mutant allele and in females either homozygous or heterozygous with mutant alleles. Male patients are typically those with the severest OTC deficiency found right after birth. In addition to elevation in blood ammonia levels, urinary orotic acid levels are also elevated. In patients with severe OTC deficiency, OTC enzyme activity is <20% of normal levels. In patients with milder OTC deficiency, OTC enzyme activity is up to 30% of normal levels.

A method for treating OTCD with a composition comprising an OTC-encoding mRNA and a copolymer of the present disclosure generally includes administering to a subject having OTCD a therapeutically effective amount of the composition, whereby the OTC-encoding mRNA is delivered to liver cells and translated during protein synthesis to produce the OTC protein. The OTC-encoding mRNA may be an mRNA as set forth above with respect to a composition or method for increasing OTC protein in a cell. In particular variations, the copolymer is a copolymer as set forth in any one of (a)-(z) above with respect to a composition or method for increasing OTC protein in a cell.

The efficacy of a copolymer/mRNA composition for treating a disease can be evaluated in vivo in animal models of disease. Particularly suitable animal models for evaluating efficacy of a copolymer/mRNA composition for treatment of OTCD includes known mouse models having deficiencies of the OTC enzyme in the liver. One such mouse model, OTC$^{spf-ash}$ (sparse fur and abnormal skin and hair) mice, contain an R129H mutation resulting in reduced levels of OTC protein and have only 5-10% of the normal level of enzyme activity in liver (see Hodges et al., *PNAS* 86:4142-4146, 1989). Another model, OTC$^{spf}$ mice, contain an H117N mutation which results in reduced levels of enzyme activity to 5-10% of normal levels (see Rosenberg et al., *Science* 222:426-428, 1983). Both of these mouse models have elevated urine orotic acid levels compared to their wild-type littermate mice. A third model for OTC deficiency is inducing hyperammonemia in OTC$^{spf}$ or OTC$^{spf-ash}$ mice (Cunningham et al., *Mol Ther* 19(5): 854-859, 2011). These mice are treated with OTC siRNA or AAV2/8 vector/OTC shRNA to knockdown residual endogenous OTC expression and activity. Plasma ammonia levels are elevated and mice die approximately 2-14 days.

In additional variations, a composition comprising (i) a polymer of Formula I wherein G is present and is a cationic peptide, polyamine, or polycation (e.g., a copolymer of formula VII) and (ii) an mRNA encoding an enzyme deficient in an organic acidemia, or a subunit of the enzyme, is used to treat the organic acidemia. Organic acidemia (also known as aciduria) (OA) is a group of disorders characterized by the excretion of non-amino organic acids in the urine. Most organic acidemias result from dysfunction of a specific step in amino acid catabolism, usually the result of deficient enzyme activity. The majority of organic acid disorders are caused by abnormal amino acid catabolism of branched-chain amino acids or lysine. They include propionic acidemia (PA), methylmalonic acidemia (MMA), maple syrup urine disease (MSUD), and others. These organic acidemias are inherited in an autosomal recessive manner. A neonate affected with an OA is usually well at birth and for the first few days of life. The usual clinical presentation is that of toxic encephalopathy and includes vomiting, poor feeding, neurologic symptoms such as seizures and abnormal tone, and lethargy progressing to coma. Outcome can be improved by diagnosis and treatment in the first ten days of life. In the older child or adolescent, variant forms of the OAs can present as loss of intellectual function, ataxia or other focal neurologic signs, Reye syndrome, recurrent ketoacidosis, or psychiatric symptoms.

Clinical laboratory findings indicate that organic acidemias include acidosis, ketosis, hyperammonemia, abnormal liver function, hypoglycemia, and neutropenia. First-line diagnosis in the organic acidemias is urine organic acid analysis using gas chromatography with mass spectrometry (GC/MS). The urinary organic acid profile is nearly always abnormal in the face of acute illness. Confirmatory testing involves assay of the activity of the deficient enzyme in lymphocytes or cultured fibroblasts and/or molecular genetic testing. Characteristics of the three primary disorders are summarized in Table 5.

TABLE 5

Metabolic Findings in Organic Acidemias Caused by Abnormal Amino Acid Catabolism

| Disorder | Amino Acid Pathway(s) Affected | Enzyme | Diagnostic Analytes by GC/MS and Quantitative Amino Acid Analysis |
|---|---|---|---|
| Propionic acidemia (PA) | Isoleucine, valine, methionine, threonine | Propionyl CoA carboxylase (PCC) (composed of three PCCA subunits and three PCCB subunits) | Propionic acid, 3-OH propionic acid, methyl citric acid, propionyl glycine in urine<br>Propionyl carnitine, increased glycine in blood |
| Methylmalonic acidemia (MMA) | Isoleucine, valine, methionine, threonine | Methylmalonyl CoA mutase (MUT) | Methylmalonic acid in blood and urine<br>Propionic acid, 3-OH propionic acid, methyl citrate in urine<br>Acyl carnitines, increased glycine in blood |
| Maple syrup urine disease (MSUD) | Leucine, isoleucine, valine | Branched-chain ketoacid dehydrogenase (BCKDH) (composed of four different subunits) | Branched-chain ketoacids and hydroxyacids in urine<br>Alloisoleucine in plasma |

Once the detection of specific analytes narrows the diagnostic possibilities, the activity of the deficient enzyme is assayed in lymphocytes or cultured fibroblasts as a confirmatory test. For many pathways, no single enzyme assay can establish the diagnosis. For others, tests such as complementation studies need to be done.

The goal of therapy is to restore biochemical and physiologic homeostasis. Neonates require emergency diagnosis and treatment depending on the specific biochemical lesion, the position of the metabolic block, and the effects of the toxic compounds. Treatment strategies include: (1) dietary restriction of the precursor amino acids and (2) use of adjunctive compounds to (a) dispose of toxic metabolites or (b) increase activity of deficient enzymes. Liver transplantation has been successful in a small number of affected individuals. Even with current clinical management approaches, individuals with organic acidemias have a greater risk of infection and a higher incidence of pancreatitis, which can be fatal.

Enzyme replacement therapy via specific mRNA delivery to the liver offers the most effective treatment of the organic acidemias. In certain embodiments of a method for treating an organic acidemia, a composition comprising (i) a polymer of Formula I wherein G is present and is cationic peptide and (ii) an mRNA encoding a methylmalonyl CoA mutase (MUT) is used to treat methylmalonic acidemia MMA. In other embodiments, a composition comprising (i) a polymer of Formula I wherein G is present and is cationic peptide and (ii) an mRNA encoding a PCC subunit (PCCA or PCCB) is used to treat propionic acidemia (PA). In yet other embodiments, a composition comprising (i) a polymer of Formula I wherein G is present and is cationic peptide and (ii) an mRNA encoding a BCKDH subunit is used to treat maple syrup urine disease (MSUD). A method for treating MMA, PA, or MSUD with a composition comprising an Mut, Pcca/b, or BCKDH subunit mRNA and a copolymer of the present disclosure generally includes administering to a subject having an organic acidemia of the specified type a therapeutically effective amount of the composition, whereby the Mut, Pcca/b, or BCKDH subunit mRNA is delivered to liver cells and translated during protein synthesis to produce the respective protein. A Mut or Pcca/b mRNA may be an mRNA as set forth above with respect to a composition or method for increasing the respective protein in a cell. In particular variations, the copolymer is a copolymer as set forth in any one of (a)-(z) above with respect to a composition or method for increasing MUT, PCC, or BCKDH protein.

The efficacy of a copolymer/mRNA composition for treating an organic acidemia disease can be evaluated in vivo in animal models of disease. For example, particularly suitable animal models for evaluating efficacy of a copolymer/mRNA composition for treatment of MMA and PA are as follows. Mut$^{-/-}$ neonatal mice with a severe form of MMA, which normally die within the first 21 days of life, have been successfully treated with hepatocyte-directed delivery of the methylmalonyl-CoA mutase (Mut) gene. Following an intrahepatic injection of adeno-associated virus expressing the murine Mut gene, Mut$^{-/-}$ mice were rescued and lived beyond 1 year of age (Carrillo-Carrasco et al., Hum. Gene Ther. 21:1147-1154, 2010). Another MMA disease model where mice survive into adulthood is Mut$^{-/-}$ mice with Mut cDNA expressed under the control of an insulated, muscle-specific promoter; Mut$^{-/-}$; Tg$^{INS-MCK-Mut}$ (Manoli et al., 2011, SIMD Abstract). These mice have elevated plasma methylmalonic acid levels and decreased oxidative capacity as measured by a $^{13}$C propionate oxidation/breathe assay. A mouse model of PA (Pcca$^{-/-}$ mice) succumbs to death 24-36 h after birth and is associated with fatal ketoacidosis (Miyazaki et al., J. Biol. Chem. 276: 35995-35999, 2001). Pcca gene transfer that provides a postnatal PCC activity of 10-20% in the liver of a transgenic mouse strain attenuates the fatal ketoacidosis in newborn mice (Miyazaki et al., 2001, supra). Recently, an intrahepatic adeno-associated virus mediated gene transfer for human Pcca was tested in neonatal Pcca$^{-/-}$ mice (Chandler et al., Hum. Gene Ther. 22:477-481, 2010). The authors found a sustained therapeutic effect as demonstrated in a survival rate of approximately 64% and reduction of disease-related metabolites (Chandler et al., 2010, supra). Another mouse disease model of PA is a hypomorphic model where Pcca$^{-/-}$ mice express a transgene bearing an A138T mutant of the PCCA protein. These mice have 2% of wild-type PCC activity, survive to adulthood and have elevations in disease-related metabolites (Guenzel et al., Mol. Ther. 21:1316-1323, 2013). Treatment of these mice with adeno-virus or AAV vector expressing human PCCA cDNA resulted in increased PCC enzyme activity and correction of disease marker levels (Guenzel et al., 2013, supra). Taken together, in murine models of MMA and PA gene transfer approaches rescue neonatal mice or restore enzyme activity and correct disease metabolite levels in adult disease models thereby permitting evaluation of mRNA delivery for restoration of the defective enzymes.

In certain embodiments, copolymers of the present invention are also useful in the preparation of a medicament for the treatment of a disease or condition associated with defective gene expression and/or activity in a subject.

In certain embodiments, copolymers of the present invention are also useful in the preparation of a medicament for the treatment of a disease or condition associated with deficiency in a functional polypeptide.

In any of the above described methods of treating a disease or condition associated with defective gene expression and/or activity, the gene is, but is not limited to, a growth factor or growth factor receptor gene, an gene encoding an enzyme (for example, a phosphatase or a kinase, e.g., a protein tyrosine, serine, or threonine kinase), an adaptor protein gene, a gene encoding a G protein superfamily molecule, or a gene encoding a transcription factor.

Examples of suitable gene targets useful in the methods of treating a disease or condition associated with defective gene expression and/or activity as described herein include the following genes or genes encoding the following proteins MEX3, MMP2, ApoB, ERBB2, Vascular Endothelial Growth Factor (VEGF), Vascular Endothelial Growth Factor Receptor (VEGFR), Platelet Derived Growth Factor Receptor (PDGF), ABL, KITT, FMS-like tyrosine kinase 3 (FLT3), Cav-1, Epidermal Growth Factor Receptor (EGFR), H-Ras, K-Ras, N-Ras, Bcl-2, Survivin, FAK, STAT-3, HER-3, Beta-Catenin, ornithine transcarbamylase, alpha-1-antitrypsin, and Src.

Other examples of suitable gene targets useful in the methods of treating a disease or condition associated with defective gene expression and/or activity as described herein include tumor suppressors, where loss of function of the mutated gene can be corrected by delivery of mRNA encoding the functional protein to treat cancer. Suitable tumor suppressor targets include Retinoblastoma protein (pRb), p53 tumor-suppressor protein, Phosphatase and tensin homolog (PTEN), Von Hippel-Lindau tumor suppressor (pVHL), Adenomatous polyposis coli (APC), FAS receptor (FasR), Suppression of tumorigenicity 5 (ST5), YPEL3, Suppressor of tumorigenicity protein 7 (ST7), and Suppressor of tumorigenicity 14 protein (ST14).

Copolymers as described herein can be formulated into pharmaceutical compositions. In certain embodiments, the present invention provides for pharmaceutical compositions which comprise, as active ingredient, a block copolymer of Formula I, Formula III, Formula IV, Formula VI, or Formula VII. Typically, pharmaceutical compositions of the present invention include a block copolymer of Formula I, Formula III, Formula IV, Formula VI, or Formula VII and pharmaceutically acceptable carriers, diluents and/or excipients.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The block copolymers of Formula I and pharmaceutical compositions prepared from them can be administered in a wide variety of routes of administration such as parenteral, oral, topical, rectal, inhalation and the like. Formulations will vary according to the route of administration selected. Examples are oral and parenteral dosage forms. Thus, the block copolymers of Formula I and pharmaceutical compositions prepared from them can be administered by injection, that is, intravenously, intramuscularly, intracutaneously, subcutaneously, intraduodenally, or intraperitoneally. Also, the block copolymers of Formula I and pharmaceutical compositions prepared from them can be administered by inhalation, for example, intranasally. Additionally, the compounds of the present disclosure can be administered transdermally. The following dosage forms may comprise as the active component, a block copolymer of Formula I or as active component complexed to it such as an oligonucleotide—for example mRNA.

For preparing pharmaceutical compositions from block copolymers of Formula I, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

The pharmaceutical composition is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of polymer in a unit dose preparation may be varied or adjusted, for example from about 0.1 mg/kg to about 200 mg/kg, preferably from about 0.5 mg/kg to about 100 mg/kg, with the associated oligonucleotide (e.g., mRNA) varied or adjusted from about 0.001 mg/kg to about 10 mg/kg, preferably from about 0.1 mg/kg to about 5 mg/kg, according to the particular application and the potency of the active component.

The pharmaceutical compositions disclosed herein can, if desired, also contain other compatible therapeutic agents. For example, copolymers as described herein can be formulated into pharmaceutical compositions that include a second active ingredient such as a chemotherapeutic agent. Chemotherapeutic agents can also be coadministered with the presently described copolymers. Such coadministration could include sequential administration.

In therapeutic use as agents for the treatment of disease, the polymers utilized in the pharmaceutical methods of this invention can be administered at an initial dosage of about 0.01 mg to about 200 mg/kg daily, with the associated oligonucleotide (e.g., mRNA) at an initial dose of about 0.001 mg to about 10 mg/kg daily. A daily polymer dose range of about 0.01 mg to about 100 mg/kg, about 0.1 mg to about 100 mg/kg, or about 0.1 mg to about 50 mg/kg is preferred. An oligonucleotide (e.g. mRNA), formulated with the polymer, may be administered at a daily dose of, for example, about 0.001 mg to about 5 mg/kg, about 0.01 mg to about 5 mg/kg, about 0.1 mg to about 5 mg/kg, about 0.01 mg to about 10 mg/kg, or about 0.1 mg to about 10 mg/kg. The dosages, however, may be varied depending upon the requirements of the patient, the severity of the condition being treated, and the compound being employed.

Determination of the proper dosage for a particular situation is within the skill of the art. Determination of a therapeutically effective dosage is typically based on animal model studies followed up by human clinical trials and is guided by determining effective dosages and administration protocols that significantly reduce the occurrence or severity of the subject disease or condition in model subjects. Effective doses of the compositions of the present disclosure vary depending upon many different factors, including means of administration, target site, physiological state of the patient, whether the patient is human or an animal, other medications administered, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by beneficial effects of administering a composition. Generally, treatment is initiated with smaller dosages which are less than the optimum dose of the compound. Thereafter, the dosage is increased by small increments until the optimum effect under the circumstances is reached. Effective dosages can be achieved by single or multiple administrations, including, e.g., multiple administrations per day or daily, weekly, bi-weekly, or monthly adminitrations. For example, a total daily dosage may be divided and administered in portions during the day, if desired. In certain variations, a regimen consists of an initial administration followed by multiple, subsequent administrations at semi-weekly, weekly, or bi-weekly intervals. Another regimen consists of an initial administration followed by multiple, subsequent administrations at monthly or bi-monthly intervals. Alternatively, administrations can be on an irregular basis as indicated by monitoring of clinical symptoms and/or physiological correlates of the disease or condition.

Examples of pharmaceutical compositions of the present invention include those comprising a block copolymer of Formula I and a pharmaceutically acceptable diluent or carrier, wherein Q is S-S-oligonucleotide,

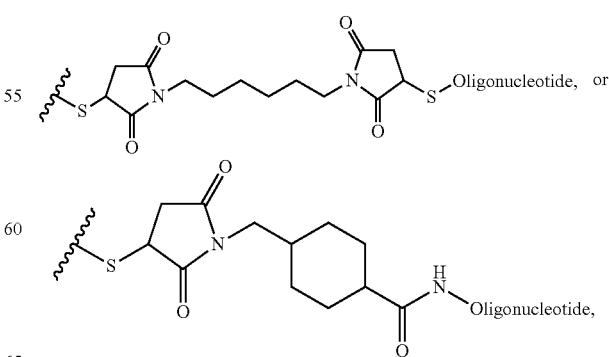

and  designates a point of attachment.

Another example of a pharmaceutical composition of the present invention includes a pharmaceutical composition comprising (a) a block copolymer of Formula I wherein G is present and is a cationic peptide, polyamine, or polycation, (b) an mRNA molecule and (c) a pharmaceutically acceptable diluent or carrier. In some such embodiments, the block copolymer of Formula I is a copolymer of formula VII.

Additional examples of pharmaceutical compositions of the present invention includes pharmaceutical compositions comprising (a) a block copolymer of Formula I wherein G is present and is a cationic peptide, polyamine, or polycation, (b) an mRNA molecule and (c) a pharmaceutically acceptable diluent or carrier, where the mRNA molecule is complexed to the cationic peptide, polyamine, or polycation. In some such embodiments, the block copolymer of Formula I is a copolymer of formula VII.

Additional examples of pharmaceutical compositions of the present invention includes pharmaceutical compositions comprising (a) a block copolymer of Formula I wherein G is present and is cationic peptide, (b) an mRNA molecule and (c) a pharmaceutically acceptable diluent or carrier, where the mRNA molecule is complexed to the cationic peptide and the nitrogen to phosphorous ratio between the cationic peptide and mRNA is between 100:1 and 1:1. Other examples include pharmaceutical compositions where the nitrogen to phosphorous ratio between the cationic peptide and mRNA is between 50:1 and 1:1. Other examples include pharmaceutical compositions where the nitrogen to phosphorous ratio between the cationic peptide and mRNA is between 20:1 and 1:1. Other examples include pharmaceutical compositions where the nitrogen to phosphorous ratio between the cationic peptide and mRNA is between 30:1 and 10:1. Other examples include pharmaceutical compositions where the nitrogen to phosphorous ratio between the cationic peptide and mRNA is between 25:1 and 15:1. In some such embodiments as above, the block copolymer of Formula I is a copolymer of formula VII.

Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Bronsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) ("Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001)).

In certain embodiments, Reversible Addition-Fragmentation chain Transfer or RAFT is used in synthesizing ethylenic backbone polymers of this invention. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In most instances, this cycle of addition to the C=S bond followed by fragmentation of the ensuing radical continues until all monomer has been consumed or the reaction is quenched. Generally, the low concentration of active radicals at any particular time limits normal termination reactions.

In some embodiments, polymers of the present invention have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, the polymers (e.g., membrane destabilizing polymers) provided herein have a polydispersity index (PDI) of less than 2.0, or less than 1.8, or less than 1.6, or less than 1.5, or less than 1.4, or less than 1.3, or less than 1.2. In some embodiments, the polymer is a block copolymer (e.g., membrane destabilizing block copolymers) comprising a hydrophilic block and a hydrophobic block and having a polydispersity index (PDI) of less than 2.0, or less than 1.8, or less than 1.6, or less than 1.5, or less than 1.4, or less than 1.3, or less than 1.2.

Polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

The copolymers of this invention can be made by processes which include processes analogous to those known in the chemical arts, particularly in light of the description contained herein. Certain processes for the manufacture of the copolymers of this invention are provided as further features of the invention and are illustrated by the following examples and as described in the experimental section.

An example of a process for the preparation of a block copolymer of Formula I includes
a) contacting a compound of Structure Va, Vb, Vc, or Vd

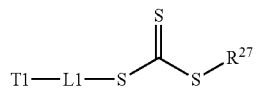
Va where $R^{27}$=$C_1$-$C_{12}$ alkyl,

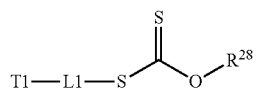
Vb where $R^{28}$=$C_1$-$C_{12}$ alkyl,

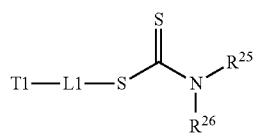
Vc where $R^{25}$ and $R^{26}$ are independently H, alkyl, aryl, or heteroaryl,

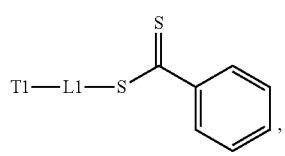
Vd where T1 is absent or a first targeting moiety and L1 is absent or a linking moiety; with one or more monomers selected from monomers of the formulae A1, A2 and A3

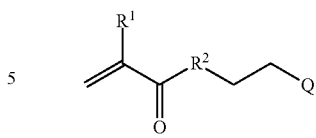
A1 where $R^1$ is H or $C_1$-$C_6$ alkyl, $R^2$ is O, NH or N($C_1$-$C_6$ alkyl), Q is —$SR^{20}$ or S-S-pyridyl, and $R^{20}$ is a thiol-protecting group;

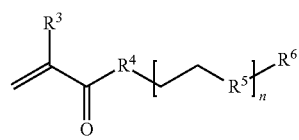
A2 where n is 1-120, $R^3$ is H or $C_1$-$C_6$ alkyl, $R^4$ is S, O, NH or N($C_1$-$C_6$ alkyl), $R^5$ is O or S and $R^6$ is H or $C_1$-$C_6$ alkyl;

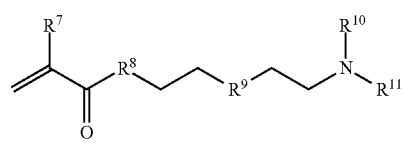
A3 where $R^7$ and $R^{10}$ are independently H or $C_1$-$C_6$ alkyl, $R^8$ is S, O, NH or N($C_1$-$C_6$ alkyl), and $R^9$ is O or S and $R^H$ is an amine protecting group; in the presence of a free radical;
b) contacting the product of step a) with monomers of formulae B1, B2 and B3

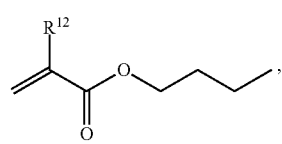
B1

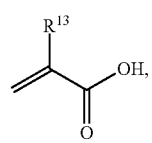
B2

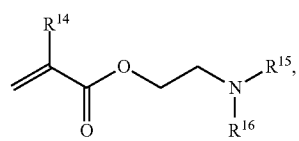
B3 where $R^{12}$, $R^{13}$, $R^{14}$, $R^{15}$ and $R^{16}$ are independently H or $C_1$-$C_6$ alkyl; in the presence of a free radical; and
c) deprotecting the product of step b) and contacting it with an oligonucleotide, cationic peptide, polyamine, or polycation comprising a thiol-reactive or amine-reactive group; or contacting the product of step b) with an oligonucleotide, cationic peptide, polyamine, or polycation comprising a thiol group. In some embodiments of a process as above, for the monomer of formula A2, n is 1-20.

In one example the synthetic process described above is carried out where compound Va is

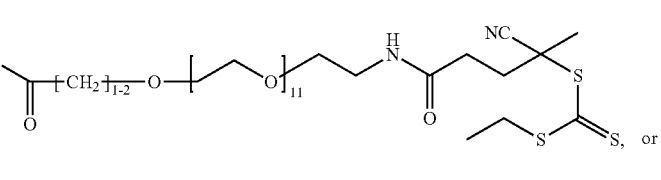

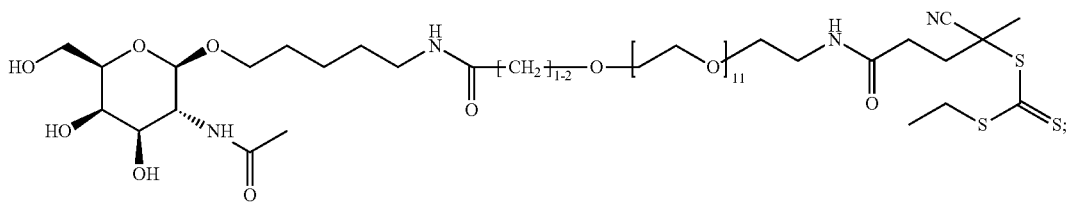

the monomer of formula A1 is

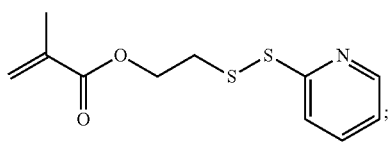 [SMILES: C=C(C)C(=O)OCCSSc1ccccn1]

the monomer of formula A2 is

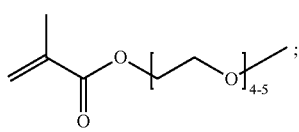

the monomer of formula A3 is

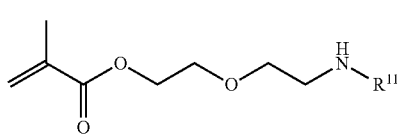

wherein $R^{11}$ is an amine protecting group; the monomer of formula B1 is butyl methacrylate; the monomer of formula B2 is 2-propyl acrylic acid; and the monomer of formula B3 is 2-(dimethylamino)ethyl methacrylate.

Another example of a process for the preparation of a block copolymer of Formula I includes a) contacting a compound of Structure Va, Vb, Vc, or Vd,

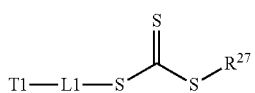

Va where $R^{27}=C_1$-$C_{12}$ alkyl,

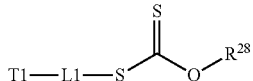

Vb where $R^{28}=C_1$-$C_{12}$ alkyl,

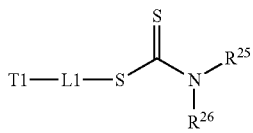

Vc where $R^{25}$ and $R^{26}$ are independently H, alkyl, aryl, or heteroaryl,

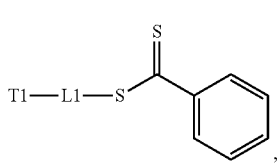

Vd where T1 is absent or a first targeting moiety and L1 is absent or a linking moiety; with one or more monomers selected from monomers of the formulae A2, A4 and A5,

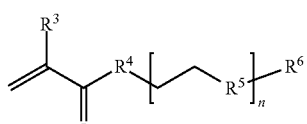

A2 where n is 1-120, $R^3$ is H or $C_1$-$C_6$ alkyl, $R^4$ is S, O, NH or N($C_1$-$C_6$ alkyl), $R^5$ is O or S and $R^6$ is H or $C_1$-$C_6$ alkyl;

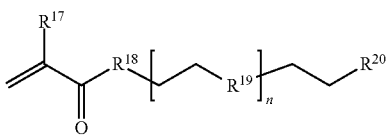
A4 where $R^{17}$ is H or $C_1$-$C_6$ alkyl, $R^{18}$ is O, S, NH or N($C_1$-$C_6$ alkyl), $R^{19}$ is O or N, $R^{20}$ is H, T2, or $C_1$-$C_6$ alkyl, where T2 is a second targeting moiety;

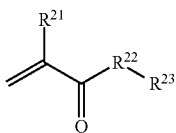
A5 where $R^{21}$ is H or $C_1$-$C_6$ alkyl, $R^{22}$ is O, NH or N($C_1$-$C_6$ alkyl), $R^{23}$ is H, aryl, arylhalide, alkyl, alkyl alcohol; in the presence of a free radical;
b) contacting the product of step a) with monomers of formulae B1, B2, B3, and B4,

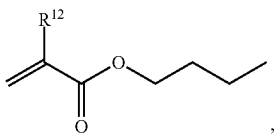
B1

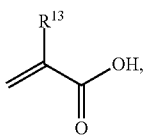
B2

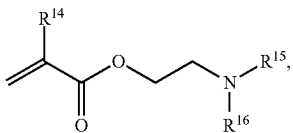
B3

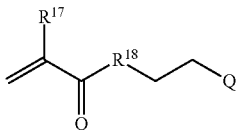
B4 where $R^{12}$, $R^{13}$, $R^{14}$, $R^{15}$, $R^{16}$ and $R^{17}$ are independently H or $C_1$-$C_6$ alkyl, $R^{18}$ is O, S, NH or N($C_1$-$C_6$ alkyl), and Q is —$SR^{20}$ or S-S-pyridyl, and $R^{20}$ is a thiol-protecting group; in the presence of a free radical; and
c) deprotecting the product of step b) and contacting it with an oligonucleotide, cationic peptide, polyamine, or polycation comprising a thiol-reactive or amine-reactive group; or contacting the product of step b) with an oligonucleotide, cationic peptide, polyamine, or polycation comprising a thiol group. In some embodiments of a process as above, for the monomer of formula A2, n is 1-20.

In one example the synthetic process described above is carried out where the monomer of formula A2 is

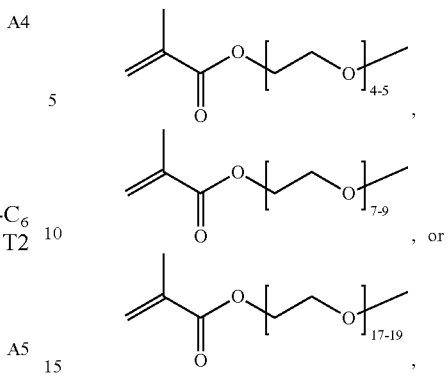

the monomer of formula B1 is butyl methacrylate; the monomer of formula B2 is 2-propyl acrylic acid; the monomer of formula B3 is 2-(dimethylamino)ethyl methacrylate; and the monomer of formula B4 is

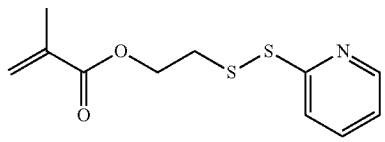

In some embodiments of a process as above for the preparation of a block copolymer of Formula I where the product of step b) is contacted with a cationic peptide, polyamine, or polycation comprising a thiol-reactive or amine-reactive group, or with a cationic peptide, polyamine, or polycation comprising a thiol group, the process further includes contacting the product of step c) with a polynucleotide (e.g., an mRNA) to form a complex comprising the block copolymer of Formula I and the polynucleotide. In particular variations of a method as above, $R^{25}$ and/or $R^{26}$ of Structure Vc is a heteroaryl having the structure

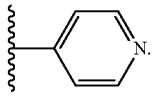 [SMILES: *c1ccncc1]

Tri-NAG structures can be constructed in a variety of ways. One such method starts with di-tert-butyl-4-amino-4 [2-(tertbutoxycarbonyl0ethyl]heptanedionate. Fmoc protection of the tertiary amine, followed by removal of the t-butyl esters results in a branched tri-carboxylic acid. The tri-carboxylic acid can be activated for an amidation reaction with trifluoroacetic acid pentafluorophenyl ester. The resulting tri-pentaluorophenyl ester can be reacted with (2-aminoethocy)-acetic acid to afford a chain extended tri-carboxylic acid. The tri-carboxylic acid can again be activated for an amidation reaction with trifluoroacetic acid pentafluorophenyl ester. The resulting tri-pentaluorophenyl ester can be reacted with NAc-Galactosamine-$C_5$—$NH_2$ (or the O-Ac protected sugar), to afford the tri-NAG derivative as the Fmoc protected amine. The resulting Fmoc protected amine can be deprotected to the teritiary amine. At this stage, the tri-NAG amine can be coupled to $HO_2C$-PEGx-ECT to make a tri-NAG-PEGx-ECT chain transfer agent in a similar manor to other chain transfer agents described herein. Alternatively, the tri-NAG amine can be acylated with a PEGx amino acid, wherein the amino functionality is protected, for example as the TFA amide. Following deprotection of the amine, the amine can be amidated with 4-formylbenzoic acid that is activated for the amidation reaction (for example as the NHS ester). The resulting tri-NAG-PEGx-Ph-aldehyde can then be added to a chain transfer agent or a polymer that has a hydroxylamine group to form an oxime. It is understood in the above reaction sequence that PEGx is meant to be PEG where x=2-460.

EXAMPLES

Throughout this description, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "PAA" (or the letter "P" as equivalent shorthand notation) represents 2-propylacrylic acid or monomeric residue derived therefrom; "PEGMA$_n$", wherein n=8-9 or 4-5, refers to the pegylated methacrylic monomer, $CH_3O(CH_2CH_2O)_n C(O)C(CH_3)CH_2$ or monomeric residue derived therefrom; "PDSMA" represents 2-(pyridin-2-yldisulfanyl)ethyl methacrylate or monomeric residue derived therefrom; "TFPMA" represents 2,3,5,6-tetrafluorphenyl methacrylate or monomeric residue derived therefrom; "PFPMA" represents pentafluorophenyl methacrylate or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art. Figures of polymers or macro CTAs in the following examples are not meant to describe any particular arrangement of the constitutional units within a particular block. "KDa" and "k" as used herein refer to molecular weight in kilodaltons.

Structures of the monomers used in the preparation of the polymers:

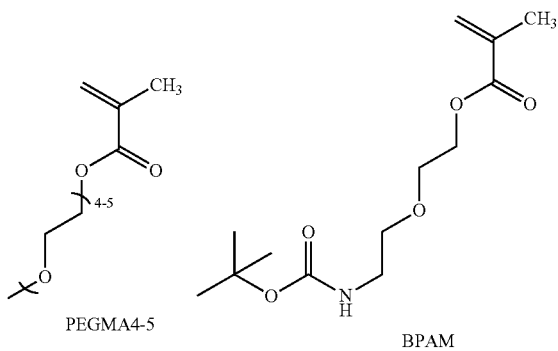

PEGMA4-5          BPAM

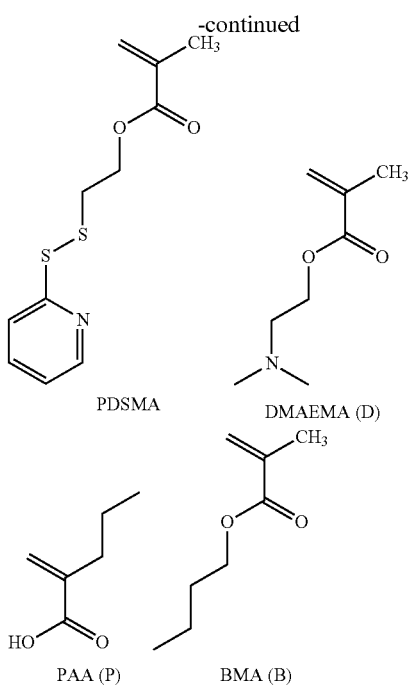

PDSMA             DMAEMA (D)

PAA (P)           BMA (B)

$^1$H NMR spectra of the monomers and polymers were recorded on Bruker AV301 or Varian 400 MHz in deuterated solvents as indicated in each experiment at 25° C. Mass spectra was acquired on Bruker Esquire Ion Trap instrument using the following settings: electro-spray ionization, capillary exit voltage of 100.0 V, scanning from 80.00 m/z to 2200.00 m/z, dry gas flow of 6.0 L/min. Mass spectroscopy was also conducted on an 6520 Accurate Mass Q-TOF LC/MS equipped with an Agilent 1290 Infinity UHPLC system with UV detector. Gel permeation chromatography (GPC) was used to determine molecular weights and polydispersities (PDI, $M_w/M_n$) of the copolymer samples in DMF using a Viscotek GPCmax VE2001 and refractometer VE3580 (Viscotek, Houston, Tex.). HPLC-grade dimethylformamide (DMF) containing 1.0 wt % LiBr was used as the mobile phase. UV/Vis spectroscopy was performed using a NanoDrop UV/Vis spectrometer (path length 0.1 cm). Particle sizes of the polymers and polymer-siRNA conjugate particles were measured by dynamic light scattering using a Malvern Zetasizer Nano ZS. HPLC analysis was performed on Shimadzu LD-20AB with the variable-wavelength UV detector with a C18 analytical reverse phase column (ES Industries Chromega Columns, Sonoma C18 catalog number 155B21-SMA-C18(2), 100 Å, 25.0 cm×4.6 mm, column heated to 30° C.). All reagents were from commercial sources, unless indicated otherwise, and the monomers were purified from traces of stabilizing agents prior to use in the polymerization reactions. Cyano-4-(ethylsulfanylthiocarbonyl) sulfanylpentanoic acid (ECT) was obtained from Omm Scientific. Azobisisobutyronitrile (AIBN) (Wako chemicals) was used as the radical initiator in all polymerization reactions, unless stated otherwise.

Example 1. Synthesis of PEG$_{0.6K}$-CTA (Compound 6)

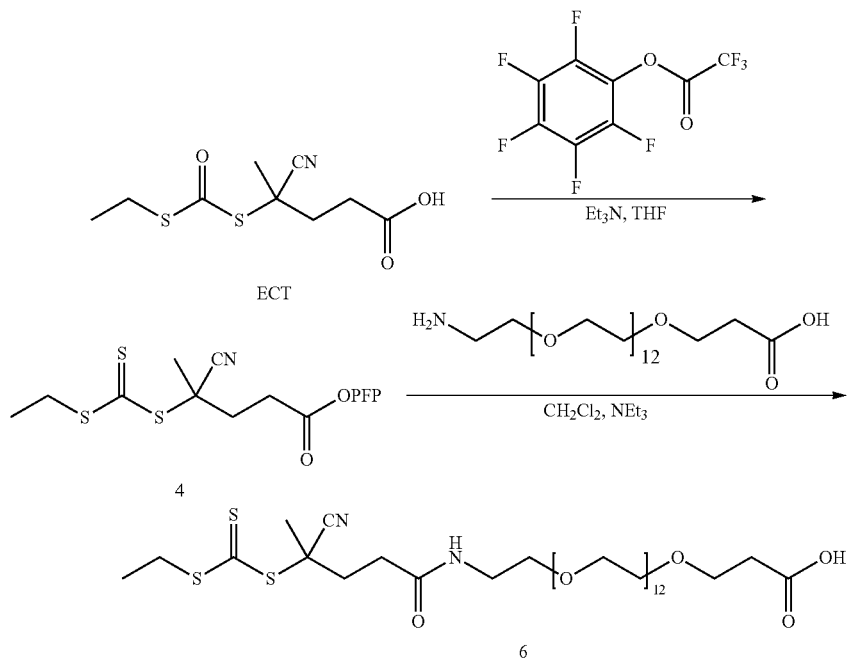

HOOC-PEG$_{0.6K}$-ECT (Compound 6). To a 100 mL one-neck round-bottom flask was added ECT (473 mg, 2.0 mmol, Omm Scientific) followed by anhydrous tetrahydrofuran (20 mL) and triethylamine (0.307 mL, 2.2 mmol). This mixture was stirred at 0° C. for 5 min before trifluoroacetic acid pentafluorophenyl ester (0.368 mL, 2.14 mmol) was added drop wise to the stirred reaction. The mixture was stirred at 0° C. for 5 min then warmed to room temperature.

After allowing to react for 20 min at room temperature, the reaction was diluted into EtOAc (100 mL) and extracted with saturated aqueous solution of NaHCO$_3$ (3×40 mL). The EtOAc layer was separated, dried over Na$_2$SO$_4$, filtered and then evaporated providing the crude PFP-ester 4 as yellow oil.

The crude ester 4 was dissolved in anhydrous CH$_2$Cl$_2$ (20 mL) and then cooled to 0° C. To the cooled stirred solution was added triethylamine (0.251 mL, 1.8 mmol) and Amino-dPEG12-acid (1.12 g, 1.8 mmol, Quanta Biodesign), and the mixture was warmed to room temperature. After stirring for 20 min at room temperature, the reaction mixture was evaporated using a rotary evaporator providing yellow oil. The yellow oil was dissolved in CH$_2$Cl$_2$ (approximately 2 mL) and the product was purified by flash chromatography (SiO$_2$, column size 5.0 cm ID×10.0 cm length; isocratic elution with 100% CH$_2$Cl$_2$ for 500 mL; then CH$_2$Cl$_2$/MeOH, 20:1 v/v for 500 mL; then CH$_2$Cl$_2$/MeOH, 10:1 v/v for 3.0 L). The product-containing fractions, as determined by TLC, were combined, and the solvent was removed by rotary evaporation providing 750 mg (48%) of the desired compound 6 as orange oil. $^1$H NMR (CD3OD): δ 1.35 (t, 3H, J=7.5 Hz, CH$_3$), 1.89 (s, 3H, CH$_3$), 2.38-2.57 (m, 6H), 3.32-3.41 (m, 4H), 3.50-3.75 (m, 48H).

Example 2. Synthesis of Nag(OAc4)C5N-PEG-$_{0.6K}$-CTA (Compound 8)

Step 1. Synthesis of Compound 3.

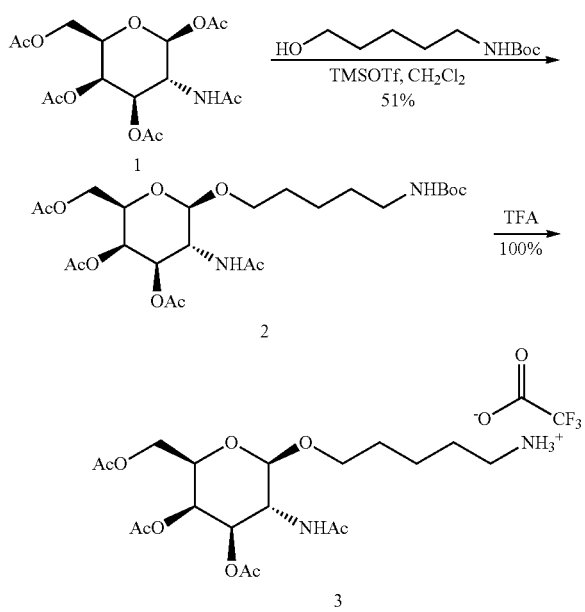

N-t-Boc-5-amino-1-pentanol. To a 1.0 L one-neck round-bottom flask containing a solution of 5-amino-1-pentanol (15.0 g, 145.4 mmol) in water (140 mL) and saturated aqueous NaHCO$_3$ (1.4 mL), a solution of di-tert-butyl dicarbonate (33.3 g, 152.7 mmol) in THF (280 mL) was added. The mixture was then stirred at room temperature overnight with the flask open to the atmosphere. The reaction mixture was diluted with saturated aqueous NaHCO$_3$ (90 mL) and extracted with EtOAc (400 mL). The organic layer was separated, dried over Na$_2$SO$_4$, filtered, and the solvent was evaporated providing 28.9 g (98%) of the final product as clear colorless oil. $^1$H NMR analysis showed the product was clean of impurities, and no further purification was attempted. Alternatively, N-t-Boc-5-amino-1-pentanol can be obtained from TCI America of Portland, Oreg.

Compound 2. Compound 2 was prepared by a procedure adopted from the literature (Westerlind, U. et al. *Glycoconj. J.* 2004, 21, 227-241). To a 500-mL one-neck round-bottom flask was added 2-acetamido-1,3,4,6-tetra-O-acetyl-2-deoxy-D-galactopyranose 1 (12.8 g, 32.8 mmol) followed by anhydrous CH$_2$Cl$_2$ (150 mL) and trimethylsilyl trifluoromethanesulfonate (14.3 mL, 79.2 mmol). This mixture was stirred at reflux overnight (ca. 18 h) under a flow of argon gas. The reaction mixture was cooled to 0° C. and treated with triethylamine (6.4 mL, 45.9 mmol) for 30 min before being warmed to room temperature, then washed with saturated aqueous NaHCO$_3$ (100 mL). The organic layer was separated and dried over Na$_2$SO$_4$, filtered and evaporated providing crude oxazoline intermediate. To the crude oxazoline product was added anhydrous CH$_2$Cl$_2$ (200 mL), N-t-Boc-5-amino-1-pentanol (10.0 g, 49.2 mmol) and 3 Å molecular sieves (18.0 g, dried at 150° C. for >24 h). This mixture was stirred at room temperature for 30 min under a blanket of argon gas. Trimethylsilyl trifluoromethanesulfonate (2.97 mL, 16.4 mmol) was added to the reaction mixture, and the solution was stirred at room temperature overnight. The solution was cooled to 0° C. and treated with triethylamine (3.2 mL, 23.07 mmol) for 30 min before being warmed to room temperature. After the reaction reached room temperature the mixture was filtered, and the mother liquor was evaporated providing the crude product as brown oil which was dissolved in anhydrous pyridine (100 mL) and treated with acetic anhydride (36 mL, 38.2 mmol). This mixture was stirred under an argon atmosphere at room temperature overnight, then evaporated under vacuum yielding a brown liquid, which was dissolved in CH$_2$Cl$_2$ (200 mL). The solution was vigorously stirred with a saturated aqueous NaHCO$_3$ solution (100 mL) and solid NaHCO$_3$ in an open flask at room temperature to quench remaining Ac$_2$O and the organic layer was separated. The aqueous layer was extracted with CH$_2$Cl$_2$ (1×200 mL) and all organic layers were combined. The organic layers were washed with saturated aqueous NaHCO$_3$ solution (1×100 mL), separated, dried over Na$_2$SO$_4$, filtered and evaporated providing the crude product as a brown oil which was then dissolved in CH$_2$Cl$_2$ (15 mL) and purified using column chromatography (SiO$_2$, column size 7.5 cm ID×16.0 cm length, EtOAc:Hexanes 1:3 v/v for 500 mL, EtOAc:Hexanes 4:1 v/v for 500 mL, 100% EtOAc for 1.0 L, 10% MeOH in EtOAc v/v for 3.0 L). Product-containing fractions were pooled and evaporated under vacuum to a white solid which was further purified by trituration with ether to yield the desired product as a white solid (5 g, 29%). ESI MS [M+H]$^+$ m/z 533.4.

Compound 3. To a 100 mL round bottom flask was added Compound 2 (3.14 g, 5.9 mmol) followed by trifluoroacetic acid (10 mL, TFA). The mixture was stirred until all of the carbohydrate was completely dissolved, then the TFA was evaporated under vacuum to yield light yellow oil. To the oily residue was added diethyl ether (10 mL), the mixture was sonicated for 2-5 min, and the supernatant was decanted. The trituration process was repeated (3×10 mL Et$_2$O), and the crude product was dried under vacuum to yield a white foam (3.2 g), which was used as described below.

Step 2.

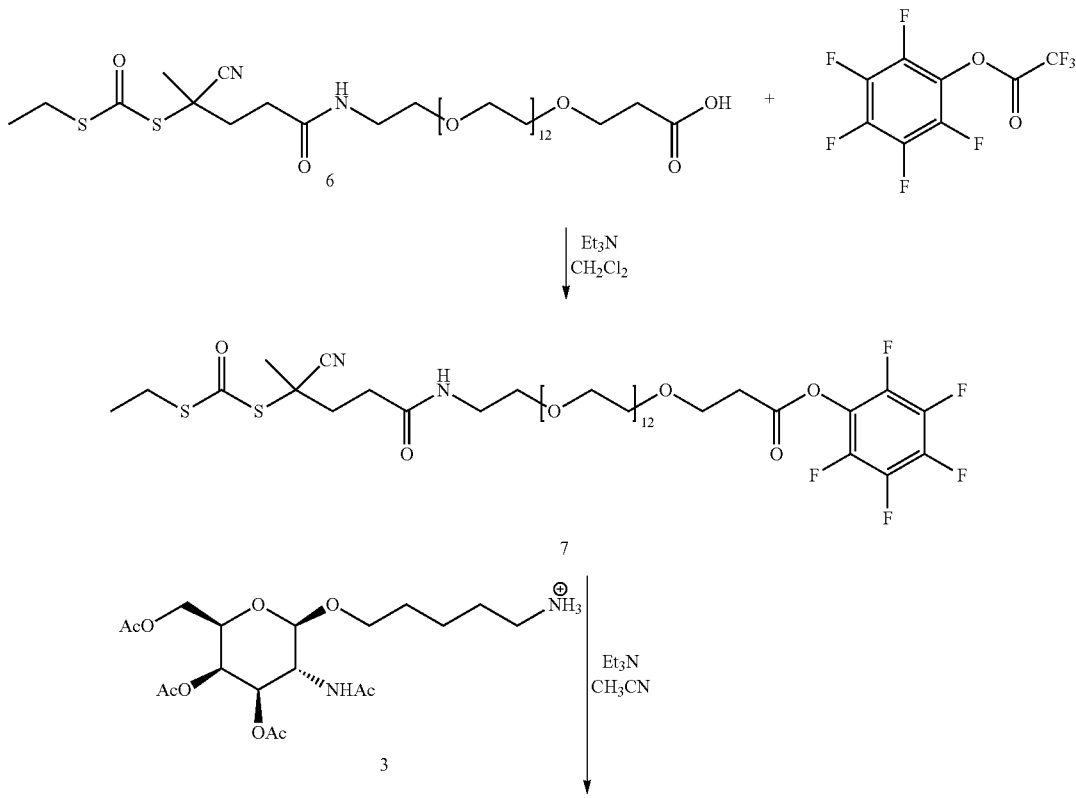

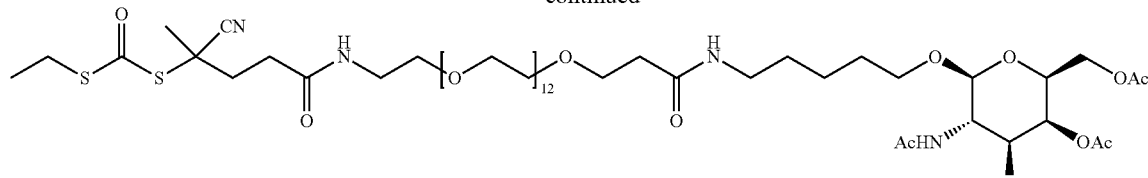

8

Compound 7. To a 250 mL one-neck round-bottom flask was added Compound 6 (3.37 g, 3.9 mmol, HPLC purified) followed by anhydrous $CH_2Cl_2$ (40.0 mL), and triethylamine (2.17 mL, 15.6 mmol). This solution was stirred at 0° C. under a low flow of argon gas for 5 min before trifluoroacetic acid pentafluorophenyl ester (737 µL, 4.29 mmol) as added dropwise to the reaction mixture. Then the mixture was warmed to room temperature and was stirred at room temperature for 30 min.

The reaction progress was followed by TLC ($SiO_2$, $CH_2Cl_2$ and MeOH, 9:1 v/v) by looking for the disappearance of the starting material ($R_f$=0.30) and the appearance of the PFP activated product ($R_f$=0.64). Once the starting material was consumed by TLC, the crude reaction was diluted with $CH_2Cl_2$ (300 mL) and the mixture was extracted using $NaHCO_3$ (3×50 mL). The organic layer was separated, dried over $Na_2SO_4$, filtered and evaporated providing 3.9 g (97%) of the final product as orange oil. All solvents and volatile reagents were thoroughly removed using high vacuum overnight before the crude product is carried on to the next synthetic step.

Compound 8. To a 100 mL one-neck round-bottom flask was added Compound 7 (3.6 g, 3.5 mmol) followed by anhydrous acetonitrile (7.5 mL) and triethylamine (1.46 mL, 10.5 mmol). The mixture was stirred under a flow of argon gas until all of the material was dissolved, then cooled to 0° C. with an ice bath. Deprotected amine 3 (1.81 g, 3.32 mmol) was dissolved in anhydrous acetonitrile (7.5 mL), and the resulting solution was added to the reaction mixture at 0° C. dropwise over 5 min. The reaction was allowed to warm to room temperature and was stirred at room temperature overnight. The solvents were evaporated using a rotary evaporator, and the crude product was dried under high vacuum. The reaction progress was followed by analytical HPLC by diluting the reaction mixture (5 µL) into $CH_3CN$ (695 µL) and 50 µL of the diluted mixture was analyzed by HPLC (10% $CH_3CN$ for 2 min, then linear gradient from 10% to 60% $CH_3CN$ over 20 min, total flow rate of 1.0 mL/min). The desired product had a retention time of 21.0 min.

The crude product was dissolved in MeOH (approximately 40 mL) and purified in 2-mL aliquots using preparative reverse phase HPLC (Phenomenex, Luna 5 C18(2), 100 Å, 25.0 cm×21.2 mm, equipped with a SecurityGuard PREP Cartridge, C18 15×21.2 mm ID, $CH_3CN/H2O$, 30% $CH_3CN$ for 5 min, then linear gradient from 30% to 53% $CH_3CN$ over 20 min, total flow rate of 20.0 mL/min,). The desired product eluted between 22.0 and 23.0 min. All the fractions containing the desired product were combined, and the solvent was completely removed using a rotary evaporator to yield 2.54 g (60%) of compound 8 after overnight drying under vacuum.

ESI MS: m/z 1277.6 ($[M+H]^{+1}$), 650.6 ($[M+Na+H]^{+2}$), 658.5 ($[M+K+H]^{+2}$), 661.7 ($[M+2Na]^{+2}$), 669.7 ($[M+Na+K]^{+2}$), 677.5 ($[M+2K]^{+2}$).

$^1$H NMR (CD3OD): δ 1.35 (t, 3H, J=7.5 Hz), 1.33-1.62 (m, 6H), 1.88 (s, 3H), 1.93 (s, 3H), 1.95 (s, 3H), 2.03 (s, 3H), 2.15 (s, 3H), 2.32-2.56 (m, 6H), 3.15-3.25 (m, 2H), 3.25-3.42 (m, 6H), 3.50-3.70 (m, 44H), 3.97-4.20 (m, 4H), 4.55 (d, 1H, J=8.4 Hz), 5.05 (dd, 1H, $J_1$=11.4 Hz, $J_2$=3.4 Hz), 5.33 (dd, 1H, $J_1$=3.4 Hz, $J_2$=0.9 Hz).

Example 3. Synthesis of Polymer NagC5N-PEG-$_{0.6}$-[PEGMA4-5$_{80}$-PDSMA$_{10}$-BPAM$_{10}$]$_{6.4}$-b-[D25-B$_{50}$-P25]$_{6.3}$ (P1)

Example 3.1. Synthesis of Macro-CTA C1

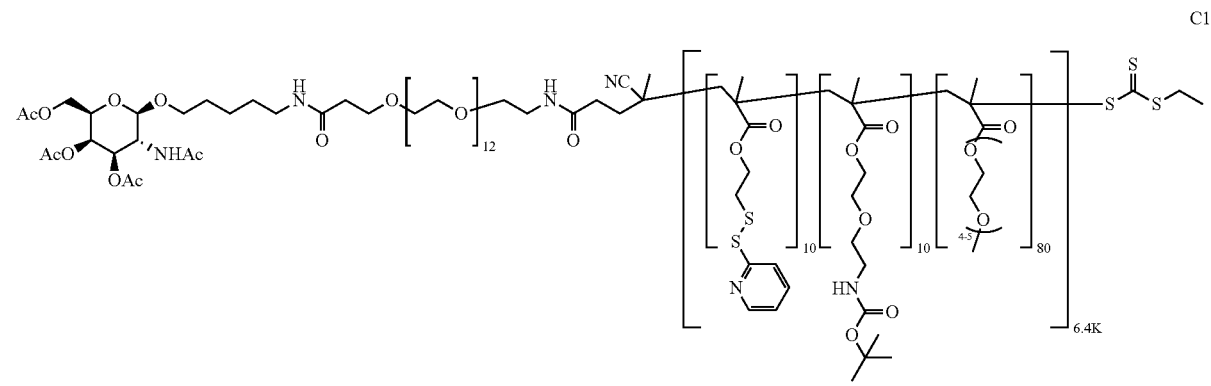

C1

PEGMA4-5 (0.675 g, 2.25 mmoles), PDSMA (0.072 g, 0.282 mmoles), BPAM (0.077 g, 0.282 mmoles), Nag(OAc4)C5N-PEG$_{0.6K}$-CTA (Compound 8) (0.090 g, 0.0704 mmoles; 1:40 CTA:Monomers), AIBN (0.578 mg, 0.00252 mmoles; CTA:AIBN 20:1) and DMF (1.65 g) were introduced under nitrogen in a sealed vial. The mixture was degassed by bubbling nitrogen for 30 minutes, and the reaction was allowed to proceed at 68° C. with rapid stirring for 2 hours. The reaction was stopped by placing the vial in ice and exposing the mixture to air. The polymer was purified by dialysis against methanol for 24 hours (Spectrum Labs, Spectra/Por Dialysis Membrane MWCO: 2000), followed by removal of solvents under vacuum. The resulting Macro-CTA was dried under vacuum for 6 hours. The structure and composition of the purified polymer were verified by $^1$H NMR, which also confirmed the absence of signals corresponding to vinyl groups of un-incorporated monomers. Purity of the polymer was confirmed by GPC analysis. $M_{n,GPC}$=7.7 kDa, dn/dc=0.05700, PDI=1.28.

Example 3.2. Synthesis of Polymer P1 rated monomers. GPC analysis: $M_n$=13.996 kDa, dn/dc=0.056505, PDI=1.26.

The acetyl groups were removed by treatment of the polymer with sodium methoxide (6 equivalents) in anhydrous methanol/chloroform under an atmosphere of argon at room temperature for 1.0 hour. The polymer was capped with 2,2'-dipyridyl disulfide (2 equivalents relative to pyridyl disulfide residues in the polymer) at room temperature for 1.0 hour under a flow of argon gas. After the capping the reaction was diluted with MeOH and filtered. The filtrate was transferred to a dialysis membrane with a 2000 g/mol molecular weight cut off (Spectrum Labs, Spectra/Por Dialysis Membrane MWCO: 2000) and dialyzed against

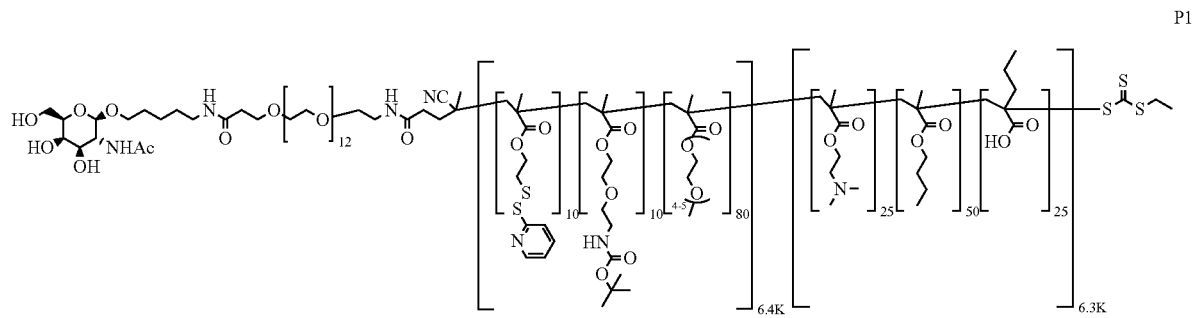

P1

BMA (0.246 g, 1.73 mmoles), PAA (0.099 g, 0.87 mmoles), DMAEMA (0.136 g, 0.87 mmoles), MacroCTA C1 (0.113 g, 0.0147 mmoles; 1:236 CTA:Monomers), AIBN (0.241 mg, 0.00147 mmoles; CTA:AIBN 10:1) and DMF (0.615 g) were introduced in a vial. The mixture was degassed by bubbling nitrogen into the mixture for 30 minutes, and then allowed to react for 10 hr at 67-68° C. The reaction was stopped by placing the vial in ice and exposing the mixture to air. The polymer was purified by dialysis from acetone/DMF 1:1 into hexane/ether 75/25 (three times). The resulting polymer was dried under vacuum for at least 8 hours. The structure and composition of the purified polymer were verified by $^1$H NMR, which also confirmed the absence of signals corresponding to vinyl groups from un-incorpo- MeOH over 24 hours followed by dialysis against water. The solvent was evaporated, and the polymer was dried under vacuum.

Example 4. Synthesis of Polymer NagC5N-PEG$_{0.6}$-[PEGMA4-5$_{80}$-PDSMA$_{10}$-BPAM$_{10}$]$_{7.2}$-b-[D$_{25}$-B$_{50}$-P$_{25}$]$_{6.1}$ (P2)

Example 4.1. Preparation of MacroCTA C2

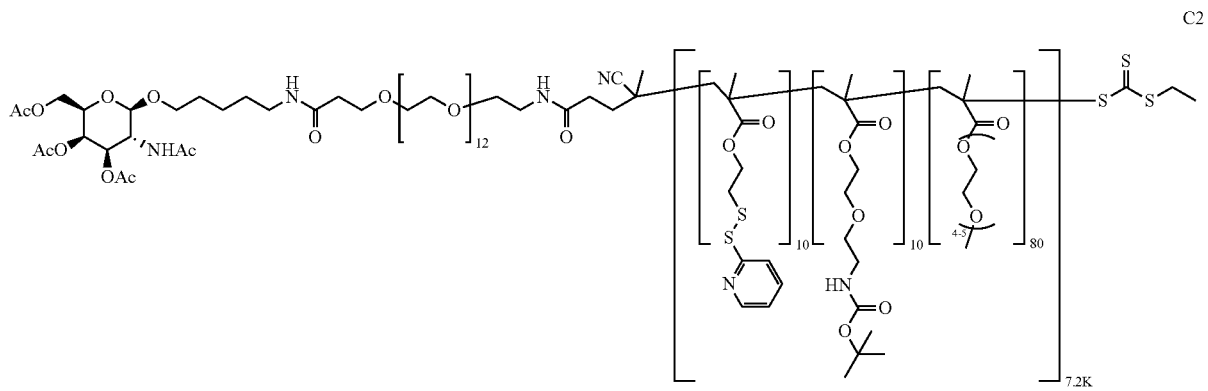

C2

MacroCTA C2 was prepared as described in Example 3.1 starting from PEGMA4-5 (8.083 g, 27.0 mmoles), PDSMA (0.860 g, 3.37 mmoles), BPAM (0.921 g, 3.37 mmoles), Nag(OAc4)C5N-PEG$_{0.6K}$-CTA (Compound 8) (1.076 g, 0.842 mmoles; 1:40 CTA:Monomers), AIBN (6.914 mg, 0.0421 mmoles; CTA:AIBN 20:1) and DMF (19.73 g). Polymerization time was 2 hr 55 min. GPC: $M_n$=8.500 kDa; PDI~1.23; dn/dc=0.5780

Example 4.2. Preparation of Polymer P2

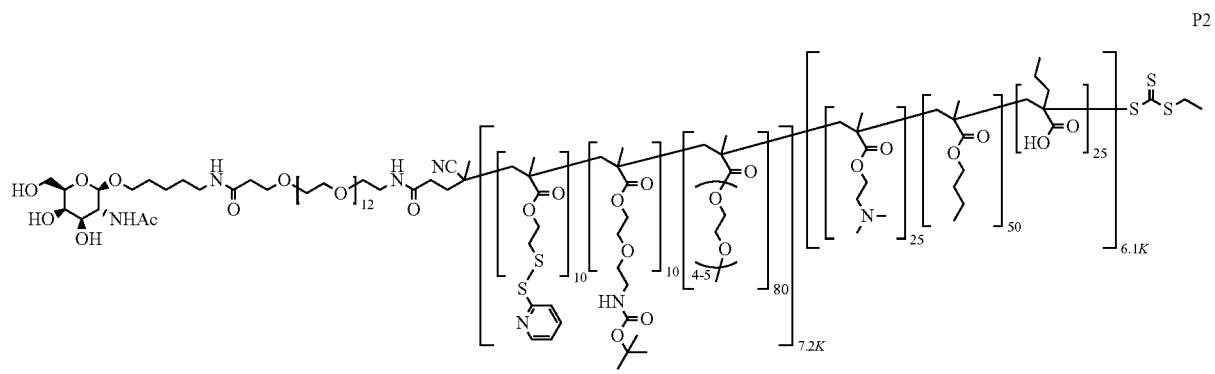

Extension of MacroCTA C2 by RAFT polymerization was carried out as described in Example 3.1 using BMA (0.553 g, 3.89 mmoles), PAA (0.226 g, 1.98 mmoles), DMAEMA (0.311 g, 1.98 mmoles), MacroCTA C2 (0.560 g, 0.0659 mmoles; 1:118 CTA:Monomers), AIBN (1.082 mg, 0.00659 mmoles; CTA:AIBN 10:1) and DMF (1.37 g+0.69 g). Polymerization was stopped after 5 hours, and the product was purified by dialysis from Acetone/DMF 1:1 into hexane/ether 75/25 (three times). GPC: dn/dc=0.053188; $M_n$=14.7 kDa; PDI=1.31. The acetyl groups were removed with NaOMe as described in Example 3.2.

Example 5. Synthesis of Polymer NagC5N-PEG$_{0.6}$-[PEGMA4-5$_{80}$-PDSMA$_{10}$-BPAM$_{10}$]$_{7.2}$-b-[D$_{25}$-B$_{50}$-P$_{25}$]$_{10.8}$ (P3)

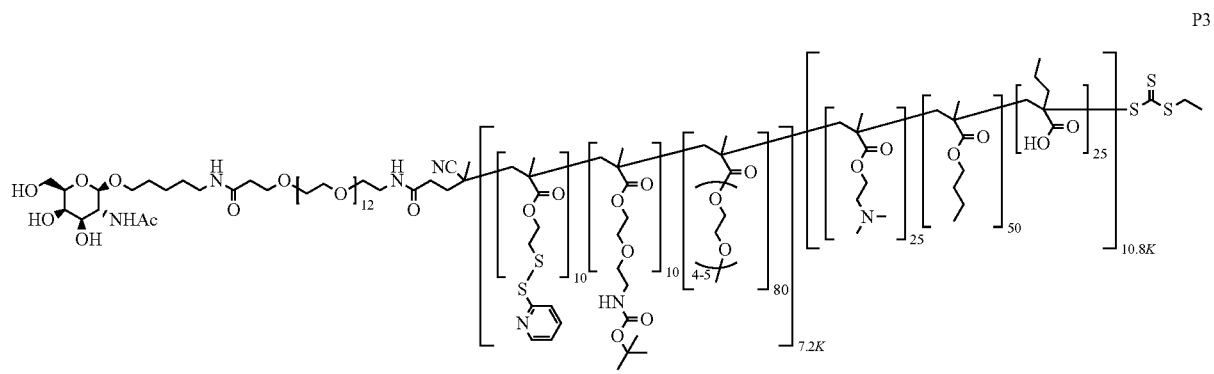

MacroCTA C2 (Example 4) was extended by RAFT polymerization as described in Example 3.2 using BMA (0.197 g, 1.39 mmoles), PAA (0.079 g, 0.69 mmoles), DMAEMA (0.109 g, 0.69 mmoles), Macro-CTA (0.100 g, 0.0118 mmoles; 1:236 CTA:Monomers), AIBN (0.193 mg, 0.00118 mmoles; CTA:AIBN 10:1) and DMF (0.492 g) for 4.5 hours, and the product was purified by dialysis from Acetone/DMF 1:1 into hexane/ether 75/25 (three times). GPC: dn/dc=0.053160; Mn=19.3 kDa; PDI=1.39. The acetyl groups were removed with NaOMe as described in Example 3.2.

Example 6. Synthesis of Polymer PEG-$_{0.6}$-[PEGMA4-5$_{80}$-PDSMA$_{10}$-BPAM$_{10}$]$_{6.7}$-b-[D$_{25}$-B$_{50}$-P$_{25}$]$_{6.2}$ (P4)

Example 6.1 Preparation of MacroCTA C4

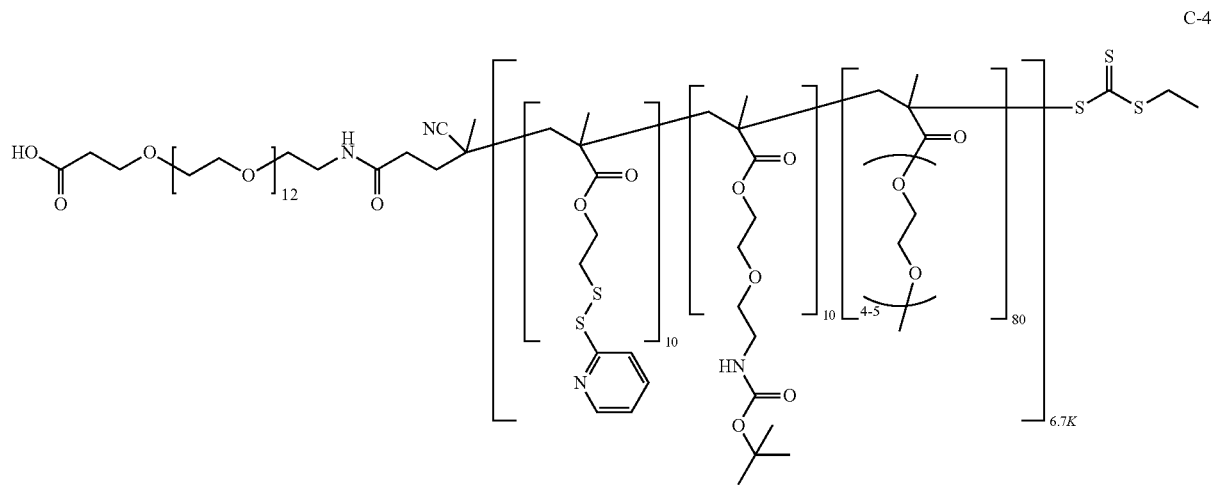

Macro-CTA C4 was prepared as described in Example 3 starting with PEGMA4-5 (5.128 g, 17.1 mmoles), PDSMA (0.546 g, 2.14 mmoles), BPAM (0.584 g, 2.14 mmoles), PEG$_{0.6K}$-CTA (Compound 6) (0.461 g, 0.534 mmoles; 1:40 CTA:Monomers), AIBN (4.385 mg, 0.0267 mmoles; CTA: AIBN 20:1) and DMF (12.52 g); reaction time was 1 hr 40 min. GPC: Mn=7.50 kDa; PDI~1.20; dn/dc=0.053910.

Example 6.2 Preparation of Polymer P4

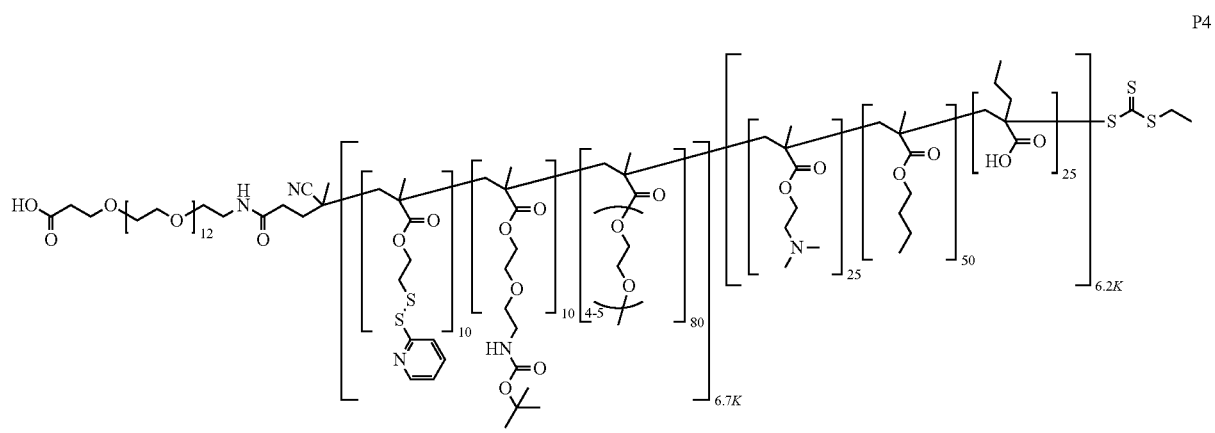

Synthesis and purification of Polymer P4 was carried out as described in Example 3.2 using BMA (1.656 g, 11.6 mmoles), PAA (0.676 g, 5.92 mmoles), DMAEMA (0.931 g, 5.92 mmoles), MacroCTA C4 (1.5 g, 0.197 mmoles; 1:118 CTA:Monomers), AIBN (3.241 mg, 0.0197 mmoles; CTA: AIBN 10:1) and DMF (4.16 g+2.08 g). GPC: dn/dc=0.050; $M_n$=13.8 kDa; PDI=1.1.

Example 7. Synthesis of Polymer NagC5N-PEG$_{0.6}$-[PEGMA4-5$_{80}$-PDSMA$_{10}$-BPAM$_{10}$]$_{6.6}$-b-[D$_{25}$-B$_{50}$-P$_{25}$]$_{114.7}$ (P5)

Example 7.1 Preparation of MacroCTA C5

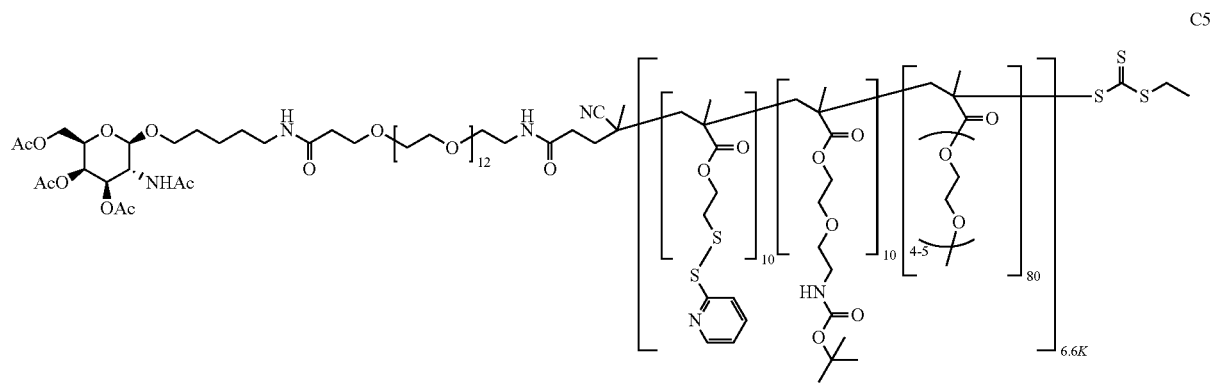

MacroCTA C5 was synthesized as described in Example 3.1 starting from PEGMA4-5 (0.5 g, 1.67 mmoles), PDSMA (0.053 g, 0.208 mmoles), BPAM (0.057 g, 0.208 mmoles), Nag(OAc4)C5N-PEG$_{0.6K}$-CTA (Compound 8) (0.0665 g, 0.0521 mmoles; 1:40 CTA:Monomers), AIBN (0.428 mg, 0.0026 mmoles; CTA:AIBN 20:1) and DMF (1.22 g). Polymerization time was 2 hr 30 min. GPC: Mn=7.85 kDa; PDI=1.18; dn/dc=0.066.

Example 7.2 Preparation of Polymer P5

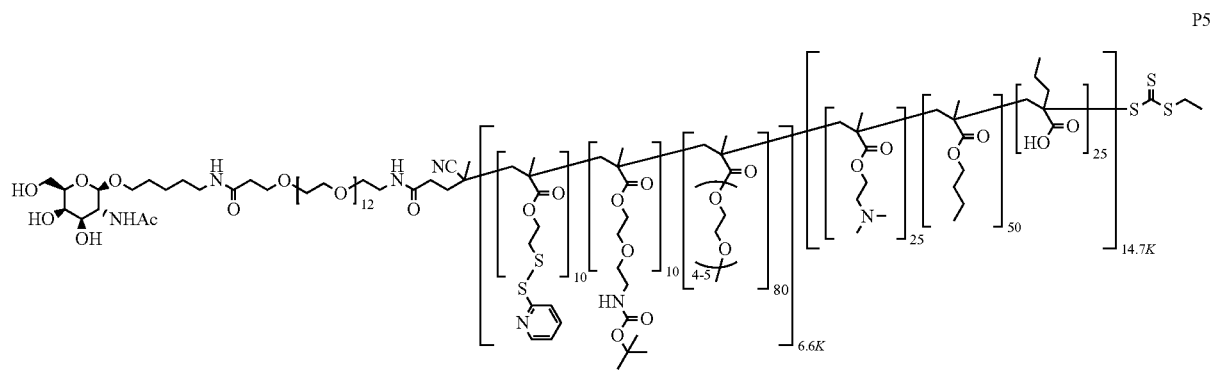

Synthesis and purification of Polymer P5 was carried out as described in Example 3.2 using BMA (0.62 g, 4.36 mmoles), PAA (0.249 g, 2.18 mmoles), DMAEMA (0.342 g, 2.18 mmoles), MacroCTA C5 (0.189 g, 0.0242 mmoles; 1:360 CTA:Monomers), AIBN (0.398 mg, 0.00242 mmoles; CTA:AIBN 10:1) and DMF (1.55 g). Polymerization was allowed to proceed for 10 hrs. GPC: dn/dc=0.063851; M$_n$=22.5 kDa; PDI=1.41. Deprotection was carried out as described in Example 3.2.

Example 8. Synthesis of Polymer NagC5N-PEG$_{0.6}$-[PEGMA4-5$_{80}$-PDSMA$_{10}$-BPAM$_{10}$]$_{3.5}$-b-[D$_{25}$-B$_{50}$-P$_{25}$]$_{16.3}$ (P6)

Example 8.1 Preparation of MacroCTA C6

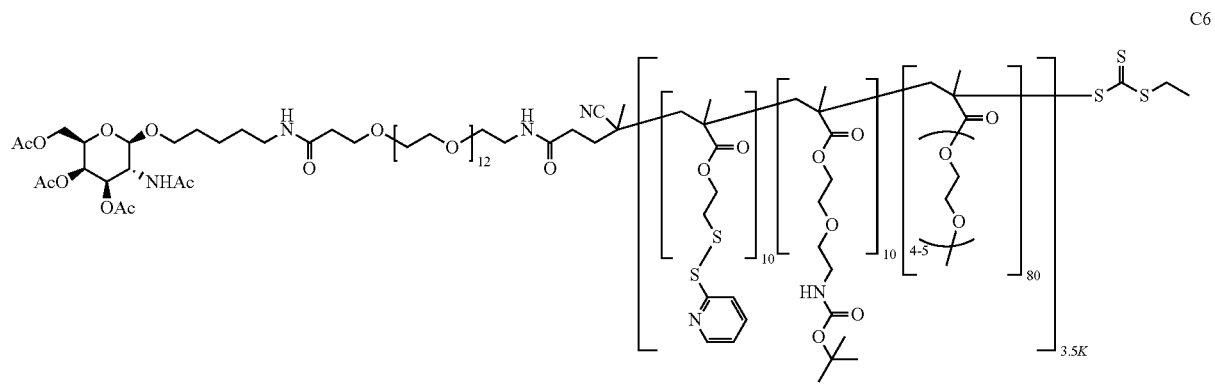

Macro-CTA C6 was synthesized as described in Example 3.1 starting from PEGMA4-5 (1.503 g, 5.00 mmoles), PDSMA (0.160 g, 0.626 mmoles), BPAM (0.171 g, 0.626 mmoles), Nag(OAc4)C5N-PEG$_{0.6K}$-CTA (Compound 8) (0.500 g, 0.391 mmoles; 1:40 CTA:Monomers), AIBN (3.213 mg, 0.0196 mmoles; CTA:AIBN 20:1) and DMF (3.668 g); reaction time was 1 hr 45 min. GPC: M$_n$=4.8 kDa; PDI=1.19; dn/dc=0.061481.

Example 8.2 Preparation of Polymer P6

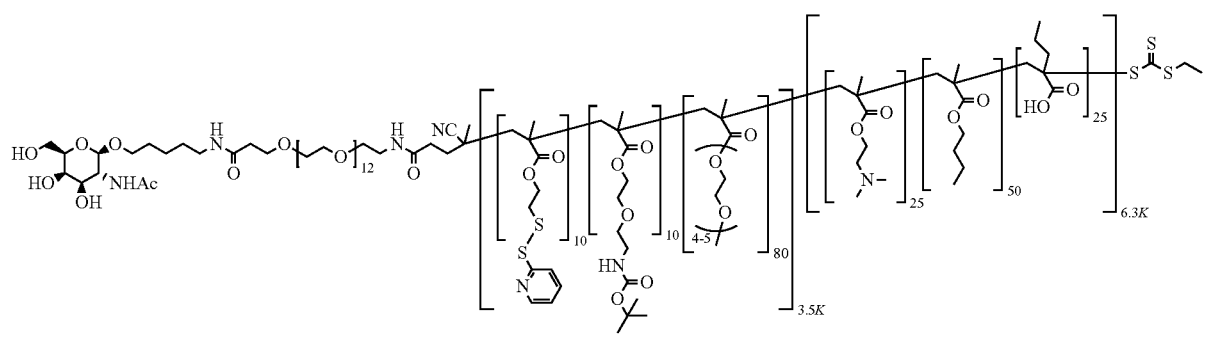

Synthesis and purification of Polymer P6 was carried out as described in Example 3.2 using BMA (0.218 g, 1.54 mmoles), PAA (0.089 g, 0.781 mmoles), DMAEMA (0.123 g, 0.781 mmoles), MacroCTA C6 (0.125 g, 0.0260 mmoles; 1:118 CTA:Monomers), AIBN (0.428 mg, 0.00260 mmoles; CTA:AIBN 10:1) and DMF (0.830 g). Polymerization was allowed to proceed for 4 hrs and 50 min. GPC: dn/dc=0.05812; M$_n$=11.1 kDa; PDI=1.38. Deprotection was carried out as described in Example 3.2.

Example 9. Synthesis of Polymer NagC5N-PEG$_{0.6}$-[PEGMA4-5$_{86}$-PDSMA$_{14}$]$_{3.82KDa}$-[BMA$_{45}$-PAA$_{15}$-DMAEMA$_{40}$]$_{5.98KDa}$ (P$^7$)

Example 9.1 Preparation of Nag(OH)C5N-PEG$_{0.6K}$-CTA (Compound 8a)

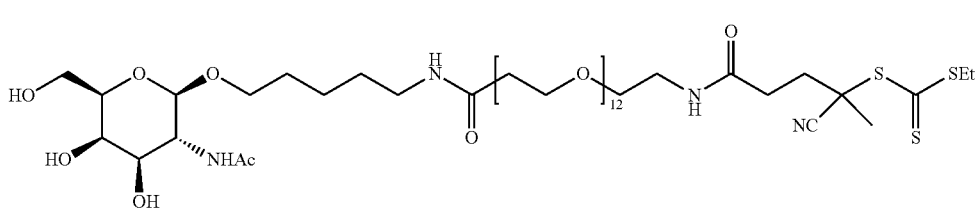

Compound 8a

Nag(OH)C5N-PEG$_{0.6}$K-CTA (Compound 8a) was prepared in a similar manner to the Nag(OAc4)C5N-PEG$_{0.6K}$-CTA in Example 2 (Compound 8) except that compound 3 in Example 2 is replaced by the unprotected sugar compound of compound 3a and the coupling reaction between compound 6 of Example 2 and compound 3 of Example 2 has been modified as shown below for compounds 6a and 3a.

Compound 3a is prepared as follows from compound 3b.

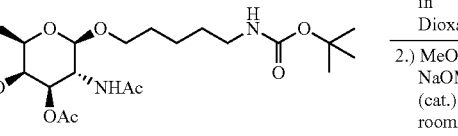

To a 250 mL one-neck round-bottom flask was added compound 3b (1.86 g, 3.5 mmol) followed by 4M HCl in dioxane (30 mL). This mixture was stirred and sonicated until all of the sugar was completely dissolved. Then the mixture was evaporated on a rotary evaporator providing an oily residue. To completely remove all HCl gas the compound was dissolved in dioxane (30 mL) and solvents removed by rotary evaporation. The solvent exchange process was preformed a total of 3 times to completely remove all HCl. Then the flask was put under high vacuum for >30 min providing a white foam solid. The crude compound was dissolved in anhydrous MeOH (25 mL) and treated with 0.5 M sodium methoxide solution in MeOH (5.80 g, 7.175 mL, 3.59 mmol, 1.025 eq, measured by weight to ensure accuracy of addition). The first equivalent of NaOMe is used to de-protonate the quaternary amine salt liberating the free amine. Only a slight excess of NaOMe beyond one equivalent (i.e., 0.025 eq, 0.09 mmol) is needed to facilitate the acetyl deprotection. Once NaOMe is added the mixture is then stirred under a flow of argon overnight at room temperature. Reaction progress was monitored by LCMS using Agilent Q-TOF Liquid Chromatography Mass Spectrometer by dissolving the product in MeOH at ca. 1.0 μg/mL. The LC used a C18 UPLC column (Agilent Eclipse Plus C18, catalog number 959757-902, 1.8 μm, 2.1 mm×50 mm, column at room temperature, CH$_3$CN/H$_2$O containing 0.1% formic acid, isocratic gradient at 5% CH$_3$CN for 1 min, then linear gradient from 5% to 90% CH$_3$CN over 4 min, total flow rate of 0.4 mL/min). The desired product elutes between 0.4-0.5 min using the above HPLC conditions while the crude intermediate product (i.e., Boc removed with acetyls still present) elutes between 2.0-2.2 min. Once the sugar was fully de-protected the catalytic NaOMe (0.09 mmol) is quenched by adding a slight excess of acetic acid (10 μL, 0.175 mmol) to the reaction mixture. Then all solvents are removed by evaporating on a rotary evaporator. This process yielded 1.1 g (100%) of the final product as a white solid. The final product was characterized using a 400 MHz 1H NMR with CD$_3$OD as solvent and all spectra were consistent with the desired product compound 3a.

Nag(OH)C5N-PEG$_{0.6}$K-CTA (Compound 8a) was prepared as follows. Compound 6a was prepared as in Example 2 (Compound 6).

Figure 2:
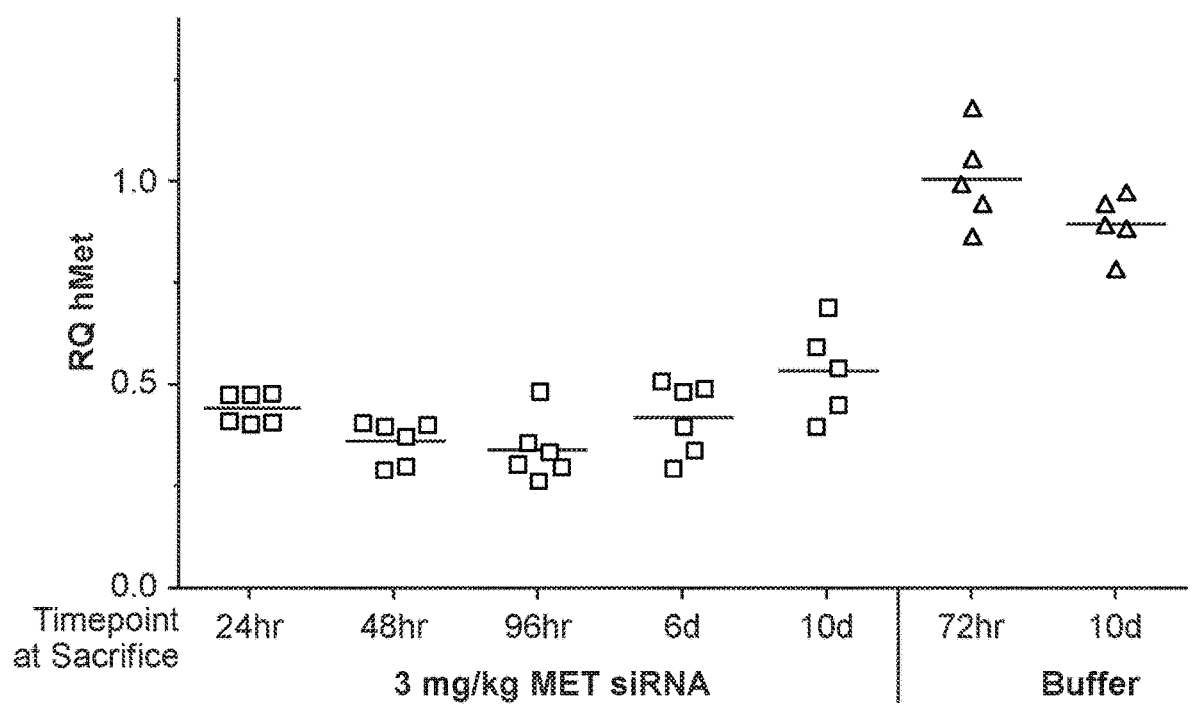
FIG. 2 is a graph demonstrating human MET mRNA knockdown relative to human β-catenin mRNA after MET siRNA (si034)/polymer dosing.

To a 250 mL one-neck round-bottom flask was added compound 6a (3.17 g, 3.68 mmol) followed by anhydrous acetonitrile (10 mL). In a separate flaks the compound 3a (1.07 g, 3.5 mmol) was dissolved in anhydrous DMF (10 mL). Once compound 3a was partially dissolved as a milky white suspension the solution was transferred to a 100 mL addition funnel. In another flask was added PyBOP (2.0 g, 3.85 mmol) and anhydrous DMF (10 mL). The PyBOP/DMF solution was taken up into a 20 mL syringe. Then all 3 solutions (compound 6a/CH$_3$CN, compound 3a/DMF, and PyBOB/DMF) were combined simultaneously and as fast as possible while the reaction solution was vigorously stirred. Once the additions were complete the reaction was treated with N,N-diisopropylethylamine (1.22 mL, 7.0 mmol) and the solution was stirred at room temperature under a flow of argon gas for 30 min. The reaction progress was determined using Agilent Q-TOF Liquid Chromatography Mass Spectrometer by dissolving the crude reaction (1.0 μL) into MeOH (1.0 mL) and injecting 1.0 μL (FIGS. 1-2). The LC used a C18 UPLC column (Agilent Eclipse Plus C18, catalog number 959757-902, 1.8 μm, 2.1 mm×50 mm, column at room temperature, CH$_3$CN/H$_2$O containing 0.1% formic acid, isocratic gradient at 5% CH$_3$CN for 1 min, then linear gradient from 5% to 90% CH$_3$CN over 4 min, total flow rate of 0.4 mL/min). The desired product elutes between 3.0-3.1 min using the above HPLC conditions. The sugar starting material (i.e., compound 3a) was not detected on the mass spec analysis after the reaction was stirred at room temperature for 30 min. Mass spec analysis confirms the presence of compound 8a [M+Na]$^{+1}$=1173.5207 m/z; [M+H]$^{+1}$=1151.5397 m/z).

After reacting for 30 min the crude reaction mixture of compound 8a was diluted by the addition of H$_2$O (25 mL)

and purified using C18 preparative reverse phase HPLC by Shimadzu (Phenomenex, Luna 5 C18(2), part number 00G-4252-P0-AX, 100 Å, 25.0 cm×21.2 mm, with a Security-Guard PREP Cartridge, C18 15×21.2 mm ID, part number AJ0-7839, $CH_3CN/H_2O$ with 0.01% TFA, isocratic gradient at 5% $CH_3CN$ for 5 min, then linear gradient from 5% to 50% $CH_3CN$ over 17 min, then 50% to 53% CH3CN over 3 min, total flow rate of 20.0 mL/min, column at room temperature). 2.0 mL of the crude compound dissolved in $DMF/H_2O$ (ca. 75 mg/mL) were injected each HPLC run. Using the HPLC purification conditions above the desired product compound 8a eluted between 21.5 and 22.5 min. All the fractions containing the desired product were combined and the water/CH3CN solvent was completely removed using a rotary evaporator then high vacuum overnight. The combined yield of the final product after HPLC purification and overnight high vacuum produced 3.05 g (76%) of the desired product as a bright orange solid. $^1H$ NMR analysis was consistent with the presence of the desired product compound 8a.

was 24.9627 g. To the resulting solution was added PEGMA (11.18 g, 37.2621 mmoles, filtered through aluminum oxide (activated, basic, Brockmann I) and PDSMA (1.1211 g, 4.1393 mmoles). The resulting solution was mixed and then transferred to a sealed 50 mL round bottom flask equipped with a magnetic stir bar. The resulting solution was de-oxygenated by bubbling nitrogen into the solution for 50 min on ice. The flask was moved to room temperature for 4 min and then placed in an oil bath pre-heated to 68° C. for 1 hour 42 minutes (stir speed was set at 350 rpm). The reaction was stopped by placing the vial in ice and exposing the mixture to air. The reaction solution was diluted with MeOH, transferred to dialysis membranes (Spectrum Labs, Spectrum Spectra/Por 6 Dialysis Membrane Tubing MWCO: 2000) and dialyzed against MeOH (6×4000 mL) for 6 days. Samples were taken for LC-MS, GPC and $^1H$ NMR analyses. After dialysis, the solvent was removed under reduced atmosphere followed by high vacuum to afford 2.45 g of polymer. LC-MS analysis indicated no

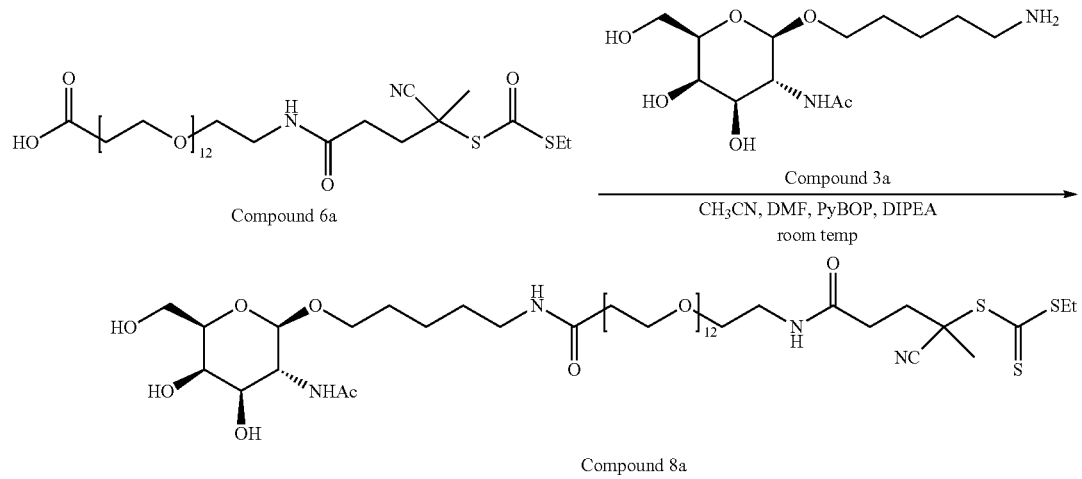

Example 9.2 Preparation of MacroCTA C7

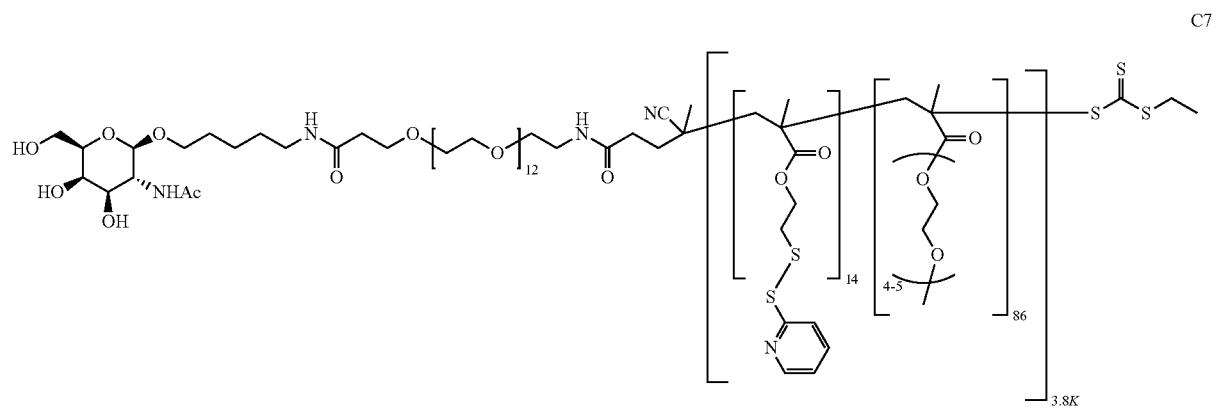

AIBN/DMF (21.93 g of 1.05603 mg/g ABIN in DMF) was added to Nag(OH)C5N-$PEG_{0.6K}$-CTA (synthesized as described in Example 9.1, compound 8a) (3.075 g; 2.6705 mmol) in a 40 ml reaction vessel and mixed to dissolve the CTA. DMF was then added until the total weight of DMF residual CTA peak. $^1H$ NMR, which also confirmed the absence of signals corresponding to vinyl groups of un-incorporated monomers. Purity of the polymer was confirmed by GPC analysis. $M_{n,GPC}$=4.97 KDa, PDI=1.12, dn/dc=0.06469, PDI=1.12. Alternatively, macro-CTA C7 can be synthesized as described in Example 3.1 starting from PEGMA4-5 and PDSMA quantities described above.

Example 9.3. Synthesis of Polymer P7

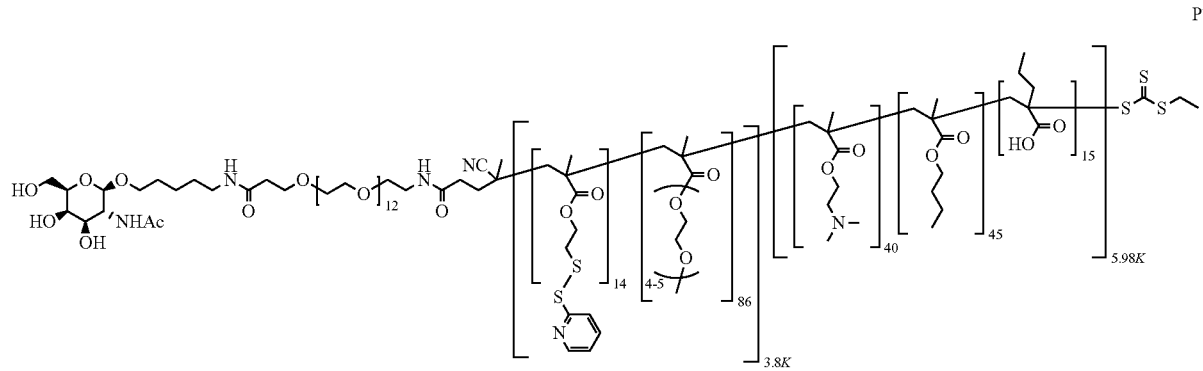

AIBN/DMF solution (7.0225 g; 1.10468 mg/g AIBN in DMF) was added to macro-CTA C7 (2.350 g) in a 40 mL reaction vessel; the sample was mixed to dissolve the macro-CTA. DMF was then added until the total weight of DMF was 15.05 g. BMA (3.967 g, filtered through aluminum oxide (activated, basic, Brockmann I), PAA (1.6217 g) and DMAEMA (2.237 g, filtered through aluminum oxide [activated, basic, Brockmann I]) were added to the resulting solution and the solution was mixed. The mixture was vortexed for several minutes to give a homogeneous stock solution and transferred to a sealed 50 mL round bottom flask equipped with a magnetic stir bar. The mixture was then cooled to 0° C. using an ice bath and maintained at 0° C. while degassed by vigorously bubbling nitrogen inside the solution for 55 minutes. The flask septa was placed into an oil bath pre-heated to 61° C. (stirring speed was 350) and allowed to stir for 4 hours 30 minutes. The reaction was stopped by placing the vial in ice and exposing the mixture to air. The reaction was then diluted with acetone (roughly the same volume of acetone as the DMF used in the reaction vial) and precipitated into a stirred mixture of ether/hexanes (1:3 v/v) in a 50 mL centrifuge tube once and then into a large beaker with 600 mL ether/hexanes (1:3 v/v). The polymer precipitate was isolated and dissolved with MeOH, transferred to three individual dialysis membranes (Spectrum Labs, Spectrum Spectra/Por 6 Dialysis Membrane Tubing MWCO: 2,000) and dialyzed against methanol (5×4000 mL) for 4 days. After the dialysis against methanol, it was dialyzed against nanopure water using the same membrane (×6, water changed every hour). When the dialysis was complete, the solution was transferred to tared vials and treated with liquid nitrogen before being lyophilized for 5 days to afford 3.46 g of the final product. The final product was analyzed by UV/vis, NMR, GPC and HPLC equipped with RI detector (for batch dn/dc). Analysis of the polymer by $^1$H-NMR indicated a polymer with no vinyl groups remaining and the presence of PDSMA. The NMR is consistent for proposed structure. GPC results: Mn=10.936 KDa, PDI=1.30, dn/dc=0.057867.

Example 10. Synthesis of Polymer NAG-PEG$_{0.6}$-[PEGMA$_{100}$]$_{3.5k}$-[BMA$_{49}$-PAA$_{10}$-DMAEMA$_{33}$-PDSMA$_8$]$_{7.1k}$ (P8)

Example 10.1 Preparation of MacroCTA C8

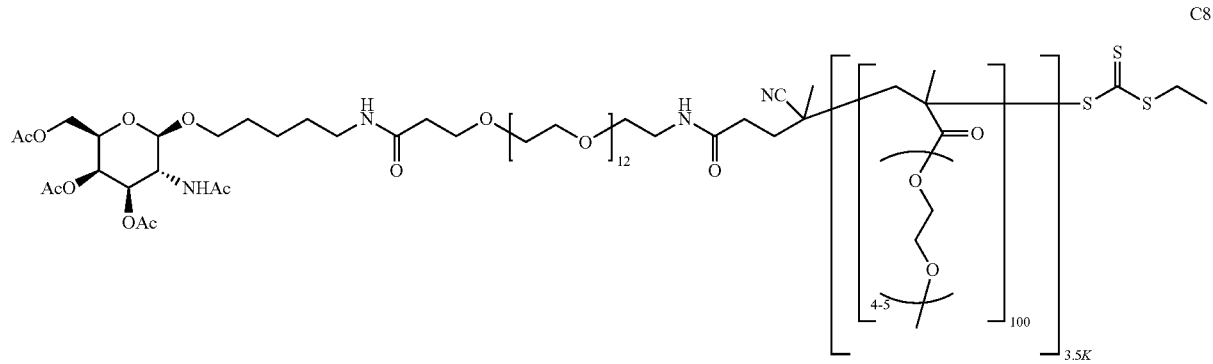

To a 20 mL reaction vial was added to Nag(OH)C5N-PEG$_{0.6K}$-CTA (synthesized as described in Example 9.1, compound 8a) (794.6 mg, 0.6922 mmol, CTA) followed by a solution of AIBN (5.0438 g solution dissolved in DMF at a concentration of 1.1268 mg/g, 5.68 mg AIBN, 0.03461 mmol, 2,2'-azobis(2-methylpropionitrile), compound recrystallized from MeOH) then an additional amount of DMF (432.2 mg) was added bringing the total amount of DMF used in this reaction to 5.4760 g. This solution was mixed and vortexed for several minutes until all of the CTA was completely dissolved. Once all the CTA was completely dissolved PEGMA (3219.3 mg, 10.730 mmol, poly(ethylene glycol) methyl ether methacrylate with average $M_n$=300 g/mol, inhibited with 100 ppm MEHQ and 300 ppm of BHT inhibitors, Aldrich part number 447935-500 mL, inhibitors removed by passing the neat monomer through a plug of $Al_2O_3$, was added to the reaction vial. This mixture was stirred for several minutes. The reaction vial was partially sealed and cooled to 0° C. using an ice bath while the mixture was degassed by vigorously bubbling nitrogen for 30 minutes with magnetic stirring of the reaction solution. Then the vial was completely sealed and placed into a heater block. The stirring speed was set at 300 rpm, the thermometer was set at 68° C. and was maintained at this temperature during the entire process. The reaction was left to stir at 68° C. for 1 hours and 47 minutes. After the reaction is complete it was quenched by opening the vial and then placing the reaction vial in ice exposing the mixture to air. The reaction vial was diluted with MeOH (10 mL) and transferred to a dialysis membrane with a 2000 g/mol molecular weight cut off (Spectrum Labs, Spectrum Spectra/Por 6 Dialysis Membrane Tubing MWCO: 2000) and dialyzed against MeOH (3×4000 mL) for 4 days. The dialysis solution was changed every day for 3 iterations total. The polymer in the dialysis bag was analyzed according to the following procedure: A small aliquot of the dialysis solution (ca. 500-1000 µL) was withdrawn from the dialysis tubing and placed into a tared vial. The solution was then evaporated using a rotary evaporator. Once the solvents are removed the vial was transferred to a high vacuum line and placed under high vacuum. The compound is dried for <15 min. Once the vial weight is constant then the compound was dissolved immediately in DMF with 1% weight LiBr solution. The final concentration of the polymer was approximately 8 mg/mL in DMF with 1% wt LiBr (DMF measured by weight then converted to volume). A 20 kDa polystyrene standard (Fluka, part number 81407-1G) dissolved in DMF with 1% wt LiBr at a concentration of roughly 3 mg/mL (DMF measured by weight then converted to volume) is then injected (100 µL) on the GPC followed by the polymer sample of interest (60, 80, 100, and 120 µL). Once the final GPC analysis is determined then the dialysis solution was transferred to a 40 mL reaction vial then the solvents were removed using a rotary evaporator. Then the material was place on a high vacuum line (pressure <0.5 torr) for >24 hours. This process provided 682.9 mg of the final product. The final product is then analyzed by NMR and GPC. The final product was stored at room temperature under high vacuum. The NMR is consistent for proposed structure. GPC results: Mn=4.600, dn/dc=0.053354.

Example 10.2. Synthesis of Polymer P8

To a 40 mL reaction vial was added macro-CTA C8 (682.1 mg, 0.148 mmol) followed by a solution of AIBN (2.2338 g solution dissolved in DMF at a concentration of 1.0927 mg/g, (2.44 mg AIBN, 0.0148 mmol, 2,2'-azobis(2-methylpropionitrile), compound recrystallized from MeOH) then an additional amount of DMF (2.6163 g) was added bringing the total amount of DMF used in this reaction to 4.8501 g. This solution was mixed and vortexed for several minutes until all of the CTA was completely dissolved. Once all the CTA was completely dissolved then BMA (1.1849 g, 8.314 mmoles, purified by passing the neat monomer through a plug of $Al_2O_3$, butyl methacrylate, d-0.894 g/mL), PAA (488.0 mg, 4.231 mmoles, unpurified 2-propylacrylic acid, d-0.951 g/mL), DMAEMA (661.8 mg, 4.231 mmoles, purified by passing the neat monomer through a plug of $Al_2O_3$, 2-(dimethylamino)ethyl methacrylate, d-0.933 g/mL), and PDSMA (227.0 mg, 0891 mmol). This mixture was mixed for several minutes. The reaction mixture was then transferred to a brand new 20 mL reaction vial containing a magnetic stir bar. The reaction vial was partially sealed and cooled to 0° C. using an ice bath while the mixture was degassed by vigorously bubbling nitrogen for 30 minutes with magnetic stirring of the reaction solution. The vial was then completely sealed and placed into a heater block. The stirring speed was set at 300, the thermometer was set at 62° C. The reaction was left to stir at 62° C. for 5 hours and 50 minutes. After the reaction is complete it was quenched by opening the vial and then placing the reaction vial in ice exposing the mixture to air. The reaction solution was then diluted with acetone (~5 mL, roughly the same volume of acetone as the DMF used in the reaction vial) and precipitated into a stirred mixture of $Et_2O$/hexanes (1000 mL, 1:4 v/v) in a glass beaker. After the polymer had settled to the bottom (ca. 15 min) the solvents were decanted off. The precipitated polymer dissolved in MeOH was transferred into dialysis membranes with a 2000 g/mol molecular weight cut off (Spectrum Labs, Spectrum Spectra/Por 6 Dialysis Membrane Tubing MWCO: 2000) and dialyzed against MeOH (3×4000 mL) for 3 days (72 h). The dialysis solution was changed every day for 3 iterations total. After 3 days (72 h) dialysis against MeOH the dialysis solution is changed to nanopure $H_2O$ and dialyzed against $H_2O$ (5×4000 mL) for 5 hr. The dialysis solution was changed roughly every hour for 5 iterations total. Upon completion of dialysis the solutions were transferred to tared vials and frozen solid using a bucket of dry ice. Then the material was placed into the lyophilizer for >4 days total drying time. This process provided 1.0325 g of the final product. The final product was then analyzed by NMR and GPC. Analysis of the polymer by $^1$H-NMR indicated a polymer with no vinyl groups remaining and the presence of PDSMA. The NMR is consistent for proposed structure. GPC results: Mn=11.7 kDa, dn/dc=0.058046. The final product was stored in glass

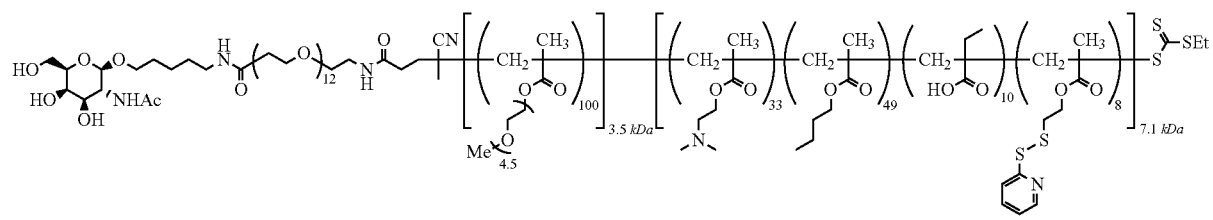

Example 11. Synthesis of H$_2$N-Cys-Lys$_{(10)}$-OH (SEQ ID NO:101)

The cysteine-terminated oligolysine, NH2-CKKKKKK-KKKK-COOH (H$_2$N-Cys-Lys$_{(10)}$-OH) (SEQ ID NO:101), H$_2$N-Cys-Arg$_{(10)}$-NH$_2$.  (SEQ ID NO: 104)

Example 12. Synthesis of Polymer NAG-PEG$_{0.6}$-[PEGMA$_{90}$-PDSMA$_{10}$]$_{5.3kDa}$-b-[BMA$_{55}$-PAA$_{10}$-DMAEMA$_{35}$]$_{6.7kDa}$ Conjugated to Poly-Lysine Peptide (P9)

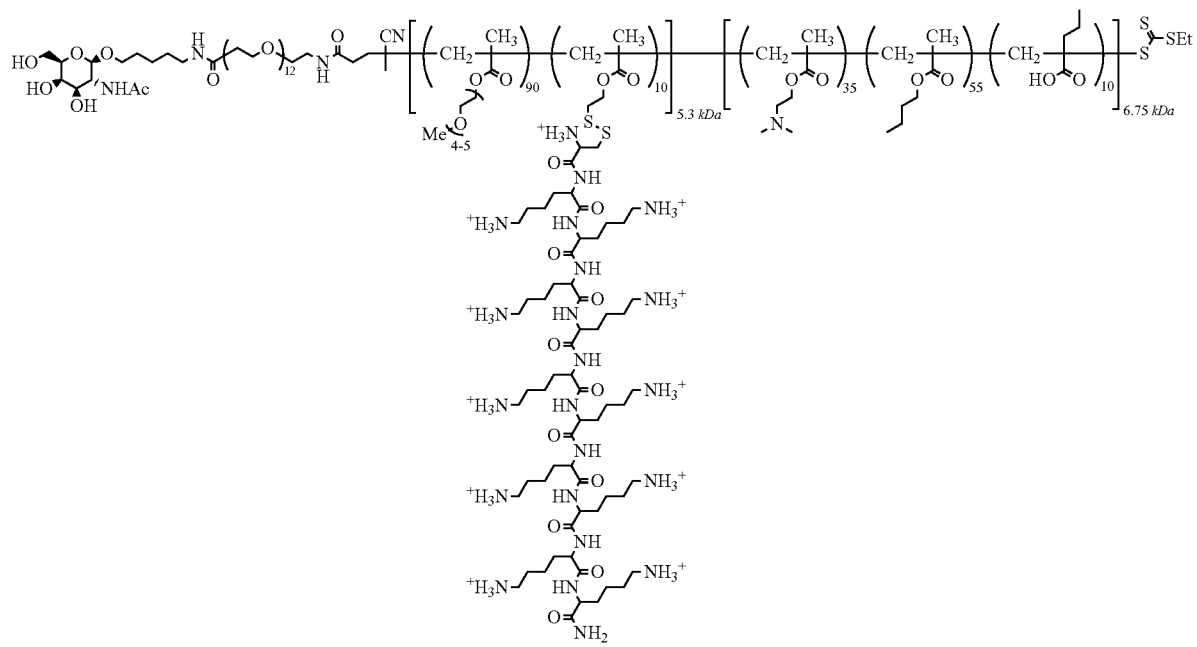

P9 was synthesized on a solid Wang support following standard Fmoc/tBu chemistry by manual synthesis. Fmoc-protected amino acids were activated using HBTU and DIPEA as coupling agents. Coupling was verified by a negative ninhydrin assay. Fmoc was removed from coupled residue with treatment by a 20% solution of piperidine in DMF. CK10 was cleaved from resin by treating the solid support with TFA/dimethoxybenzene/TIPS (95:5:2.5:2.5, v/v/v/v). Cleaved peptides were then precipitated in cold ether, dissolved in methanol and reprecipitated in cold ether. Peptides were purified by semi-preparative RP-HPLC using a Jupiter Luna C18 300A column 250×21.0 mm (Phenomenex, Torrance, Calif.). Fractions were pooled and re-analyzed by RP-HPLC and LC/MS and demonstrated a purity of greater than 95%.

The following additional peptides, prepared by automated synthesis, were purchased:

H$_2$N-Cys-Lys$_{(10)}$-NH$_2$  (SEQ ID NO: 103)

H$_2$N-Cys-Arg$_{(10)}$-OH  (SEQ ID NO: 102)

A stock solution of NAG-PEG$_{0.6}$[PEGMA$_{90}$-PDSMA$_{10}$]$_{5.3kDa}$-b-[BMA$_{55}$-PAA$_{10}$-DMAEMA$_{35}$]$_{6.75}$kDa (prepared as in Example 9.3 but with differing monomer incorporation rates) was prepared in MeOH at 300 mg/mL and briefly degassed with a moderate flow of argon for 2-3 min. Concurrently, a stock solution of poly-lysine peptide (prepared as described in Example 11) was prepared in MeOH at 50 mg/mL and briefly degassed with a moderate flow of argon for 2-3 min. The polymer solution containing NAG-PEG$_{0.6}$-[PEGMA$_{90}$-PDSMA$_{10}$]$_{5.3kDa}$-b-[BMA$_{55}$-PAA$_{10}$-DMAEMA$_{35}$]$_{6.75kDa}$ (440.0 µL, 132.0 mg polymer, 0.0116 mmol polymer, 0.0145 mmol PDS) was then transferred to a new 40 mL reaction vial. To the stirred vial containing NAG-PEG$_{0.6}$-[PEGMA$_{90}$-PDSMA$_{10}$]$_{5.3kDa}$-b-[BMA$_{55}$-PAA$_{10}$-DMAEMA$_{35}$]$_{6.75kDa}$ was rapidly added an aliquot of the peptide solution (706.0 µL, 35.3 mg peptide, 0.0139 mmol peptide). The mixture was covered with an atmosphere of argon, sealed, and then allowed to react for 25 min. Next, the reaction was opened and treated with N-maleoyl-β-alanine (16 µL of a stock solution prepared in MeOH at 50 mg/mL, 8.0 mg, 0.047 mmol) to cap any unreacted sulfhydryl groups. This capping procedure was allowed to stir at room temperature for another 25 min. Then the solution was diluted with MeOH (20 mL), transferred to a dialysis membrane (MWCO 3500) and dialyzed in MeOH (1×4000 mL) for 2 hours. The dialysis solution was changed and the product was dialized overnight in MeOH (1×4000 mL) for 16 hours. The next day the dialysis solution was change to 20 mM acetate buffer at pH 4.5, and dialyzed for 6 hours. Then the solution was replaced with nanopure water (1×4000 mL, no buffer) and left to dialyze overnight. The next day multiple changes of the nanopure H$_2$O dialysis solution were made (3×4000 mL) over a 4 hour period. The dialysis solution was changed roughly every hour for 3 iterations total to completely remove excess NaOAc salts. When the dialysis is complete the solution was transferred to tared vials and frozen solid using a bucket of dry ice. Then the material was placed into the lyophilizer for >4 days total drying time. This process provided 123 mg of the final product. The final product was then analyzed by NMR. NMR analysis of the conjugate showed that essentially all of the pyridyl disulfide (PDS) groups in the conjugation block were removed. This implies nearly complete substitution of the PDS groups for poly-Lysine peptide and a fully loaded polymer-peptide conjugate. The final product was stored in glass vials with rubber septum that were purged with argon and sealed. The vials were stored at −20° C.

Example 13. Synthesis of Polymer NAG-PEG$_{0.6}$-[PEGMA$_{100}$]$_{3.5k}$-[BMA$_{49}$-PAA$_{10}$-DMAEMA$_{33}$-PDSMA$_8$]$_{7.1k}$. Conjugated to Poly-Lysine Peptide (P10)

for 16 hrs. Following dialysis, the solution was transferred to a 20 ml vial, frozen with liquid nitrogen, and lyophilized for 3 days to afford 150 mg polymer as a white powder. The final product was then analyzed by NMR. NMR analysis of the conjugate showed that essentially all of the pyridyl disulfide (PDS) groups in the conjugation block were removed. This implies nearly complete substitution of the PDS groups for poly-Lysine peptide and a fully loaded polymer-peptide conjugate. Alternatively, the NAG-PEG$_{0.6}$-[PEGMA$_{100}$]$_{3.5k}$-[BMA$_{49}$-PAA$_{10}$-DMAEMA$_{33}$-PDSMA$_8$]$_{7.1k}$ poly-Lysine peptide conjugate of this Example 13 can be prepared using the methods previously described in Example 12.

Example 14. Determining Monomer Incorporation Within Individual Blocks of a Polymer During Polymer Synthesis The amount of a given monomer within a given polymer block, typically the polymer block to which the oligonucleotide or peptide is conjugated, of the polymers exemplified and claimed herein has been determined by the following procedure. Samples taken before and after the polymeriza-

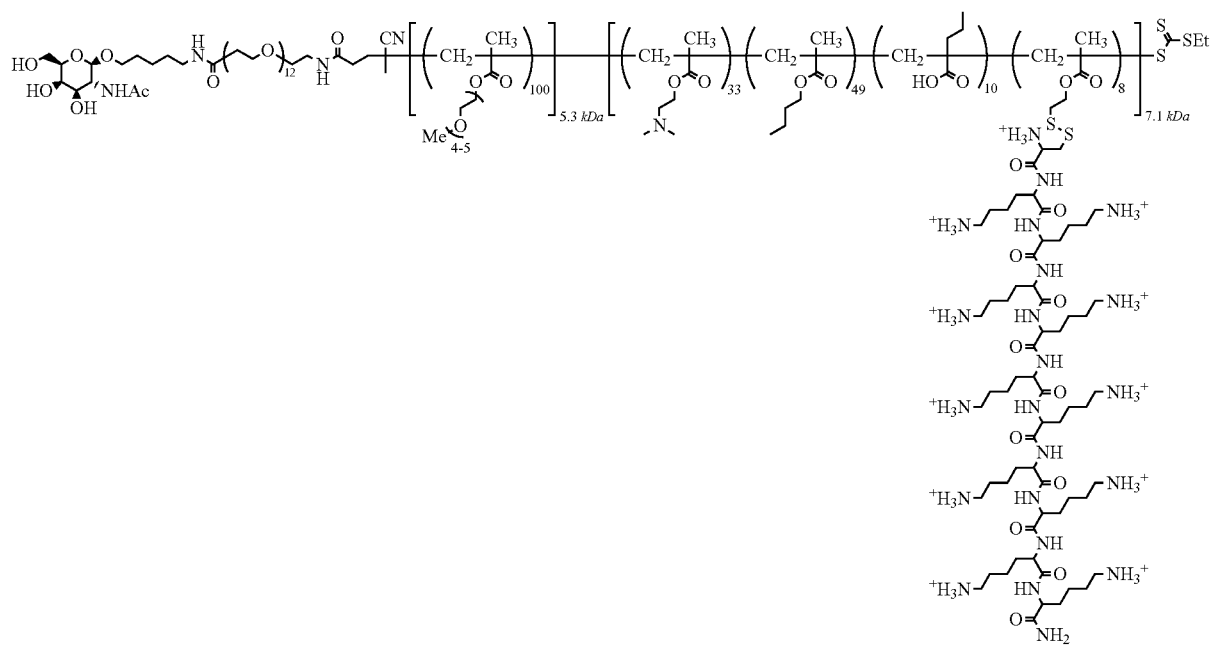

To a solution of NAG-PEG$_{0.6}$-[PEGMA$_{100}$]$_{3.5k}$-[BMA$_{49}$-PAA$_{10}$-DMAEMA$_{33}$-PDSMA$_8$]$_{7.1}$k (200 mg) in MeOH (665 µl) (prepared as described in Example 10.2) was added a solution of poly-Lysine peptide (H$_2$N-Cys-Lys(10)-OH (8 TFA) prepared as described in Example 11) (51.7 mg) in MeOH (665 µl). Based on polymer PDS content, the amount of peptide added represents 0.5 eq per PDS group. The resulting solution was stirred at ambient temperature for 25 min. The solution was diluted with MeOH (20 fold, 26.5 ml), and dialyzed against MeOH (MWCO 3500). MeOH was exchanged after 2 hrs and dialysis continued for an additional 16 hrs. The solution was further dialyzed against 20 mM acetate buffer with 1 mM EDTA, pH 4.0 for 6 hrs. The dialysis buffer was exchanged, and dialysis continued tion reaction (i.e., T$_0$ (time zero) and T$_f$(time final)) are analyzed by analytical HPLC to determine the extent of monomer consumption and/or monomer incorporation.

The initial monomer amounts in the polymerization reaction (time 0, T$_0$) are determined by sampling the polymerization reaction solution prior to nitrogen or argon purge. A (20 µL) sample of the reaction solution is withdrawn from the reaction solution and diluted into 180 µL of Methanol (MeOH). A portion of the resulting solution (10 µL) is further diluted into 590 µL MeOH, to afford a test sample with an overall dilution of 1:600 (from the polymerization reaction) for analysis by analytical HPLC.

Upon completion of the polymerization reaction a time final ($T_f$) sample is prepared analogous to the $T_0$ sample described above.

Analytical HPLC analysis of the $T_0$, and $T_f$ samples are performed using a C18 Phenomenex 5μ 100 Å 250×4.6 mm×5 micron (Part #00G-4252-E0) Luna column with guard column heated to 30° C. Three independent dilutions for each time point (i.e., $T_0$, and $T_f$) are prepared and analyzed for each time point. A 10 μl of sample is injected onto the column and eluted with the following gradient. Hold an isocratic eluent of 5% acetonitrile/water with 0.1% TFA for 2 minutes. Switch to a linear gradient from 5% to 95% acetonitrile over 25 minutes. Hold an isocratic eluent of 95% acetonitrile for 5 minutes. Return to 5% acetonitrile over 0.01 minutes. Hold the isocratic eluent of 5% acetonitrile/water with 0.1% TFA for 5 minutes.

The following methodology is used to calculate the % incorporation of a given monomer:

To calculate the % incorporation of a given monomer:
a. Calculate the consumption of individual monomers in the reaction (monomer % consumption):

=(1−($T_f$ monomer peak area/$T_0$ monomer peak area)× 100.

b. Calculate the molar fraction consumed of the individual monomers based on monomer input percent =(Monomer % conversion (calculated in step (a) above)×0.01)×monomer feed % c. Total monomer consumption in the polymerization reaction and overall percent conversion:
  i. Total monomer consumption=sum of molar fraction consumed for the individual monomers calculated in step (b) above.
  ii. Overall % conversion=Average of total monomer consumption (calculated in step (c)(i) above) from the 3 individual preparations×100.
d. Calculate the percent monomer incorporation for each monomer in the polymer
  i. =(Monomer molar fraction consumed (step (b) above)/total monomer consumed (step (c)(i) above)× 100.
  ii. Average percent monomer incorporation for the 3 independent preparations.

Example 15. Determining Monomer Incorporation Within Individual Blocks of a Polymer During Polymer Synthesis The amount of a given monomer within a given polymer block, typically the polymer block containing PAA, BMA and DMAEAMA, of the polymers exemplified and claimed herein has been determined by the following procedure. Samples taken before and after the polymerization reaction (i.e., $T_0$ (time zero) and $T_f$ (time final)) are analyzed by analytical HPLC to determine the extent of monomer consumption and/or monomer incorporation.

The initial monomer amounts in the polymerization reaction (time 0, $T_0$) are determined by sampling the polymerization reaction solution prior to nitrogen purge. A (20 μL) sample of the reaction solution is withdrawn and diluted into 180 μL of 1,1,1,3,3,3-hexafluoro-2-propanol (HFIP)/Methanol (MeOH)/Nano-pure water ($H_2O$) (2:1:1, v/v) containing 0.1% TFA. A portion of the resulting solution (10 μL) is further diluted into 590 μL of HFIP/MeOH/$H_2O$ (2:1:1, v/v) containing 0.1% TFA, to afford a test sample with an overall dilution of 1:600 (from the polymerization reaction) for analysis by analytical HPLC.

Upon completion of the polymerization reaction a time final ($T_f$) sample is prepared analogous to the $T_0$ sample described above. A (20 μL) sample of the reaction solution is withdrawn and diluted into 180 μL of 1,1,1,3,3,3-hexafluoro-2-propanol (HFIP)/Methanol (MeOH)/Nano-pure water ($H_2O$) (2:1:1, v/v) containing 0.1% TFA. A portion of the resulting solution (10 μL) is further diluted into 590 μL of HFIP/MeOH/$H_2O$ (2:1:1, v/v) containing 0.1% TFA, to afford a test sample with an overall dilution of 1:600 (from the polymerization reaction) for analysis by analytical HPLC.

Analytical HPLC analysis of the $T_0$, and $T_f$ samples are performed using a C18 Phenomenex 5μ 100 Å 250×4.6 mm×5 micron (Part #00G-4252-E0) Luna column with guard column heated to 30° C. Three independent dilutions for each time point (i.e., $T_0$, and $T_f$) are to be prepared and analyzed. A 10 μl of sample is injected onto the column and eluted with the following gradient. Hold an isocratic eluent of 5% acetonitrile/water with 0.1% TFA for 10 minutes. Switch to a linear gradient from 5% to 15% acetonitrile over 10 minutes. Switch to a linear gradient from 15% to 95% acetonitrile over 20 minutes. Hold an isocratic eluent of 95% eluent acetonitrile for 5 minutes. Return to 5% acetonitrile over 0.01 minutes. Hold the isocratic eluent of 5% acetonitrile/water with 0.1% TFA for 5 minutes.

The following methodology is used to calculate the % incorporation of a given monomer:
e. Calculate the consumption of individual monomers in the reaction (monomer % consumption):

=(1−($T_f$ monomer peak area/$T_0$ monomer peak area)× 100 f. Calculate the molar fraction consumed of the individual monomers based on monomer input percent =(Monomer % conversion (calculated in step 3.4a)× 0.01)×monomer feed % (DMAEMA=0.25, PAA=0.25,BMA=0.50)

g. Total monomer consumption in the polymerization reaction and overall percent conversion:
  iii. Total monomer consumption=sum of molar fraction consumed for the individual monomers calculated in (b).
  iv. Overall % conversion=Average of total monomer consumption (calculated in (c) (i) from the 3 individual preparations×100
h. Calculate the percent monomer incorporation for each monomer in the polymer
  i. =(Monomer molar fraction consumed (calculated in (b) above)/total monomer consumed (calculated in (c)(i)))×100
  ii. Average percent monomer incorporation for the 3 independent preparations.

Example 16. Conjugation of siRNA to Polymers and Knockdown Activity of the siRNA Polymeric Conjugates ApoB siRNA sequences and PCR primers were prepared as described in WO/2010/054266. Preparation of thiolated siRNA was as follows. To a 15 mL Falcon tube was added tris(2-carboxyethyl)phosphine hydrochloride (1.0 mg, 3.5 μmol, TCEP) followed by $NaHCO_3$ (1.2 mg, 14.0 μmol), $H_2O$ (500 μL) and ApoB-SSC$_6$OH duplex (5.0 mg, Agilent Technologies). This mixture was allowed to stand at room temperature. After 30 min, 5.0 M NaCl (20.0 μL) was added followed by cold (−20° C.) 100% EtOH (5.0 mL). The mixture was placed into a −80° C. freezer for 30 min to achieve complete RNA precipitation. The Falcon tube was then centrifuged to pellet the RNA. The mother liquor was removed and the remaining RNA pellet was triturated using cold (+4° C.) 70% EtOH (1×1.0 mL). The remaining RNA pellet was then dissolved in isotonic glucose (5.0 mL, 5.05 wt % glucose, 10 mM HEPES, pH 7.4) or other suitable buffer to give an aqueous RNA solution with RNA concentration at 0.7 µg/µL (by UV analysis).

Lyophilized polymer was dissolved in 100% EtOH to a stock concentration of 100 mg/ml. The polymer was then slowly diluted into isotonic glucose with 20 mM HEPES and gently mixed. Reduced siRNA was then added bringing each component to the desired final concentration. Conjugation took place overnight at room temperature before dosing. A separate conjugation reaction was run for each dose group. The conjugation reactions were analyzed by gel electrophoresis (20% polyacrylamide, 1×TBE gel from Invitrogen, 1×TBE buffer for ca. 1 h at 200 V, stained in 50 mL 1×TBE with 2.5 µL SYBR gold for 15 min). Aliquots of the 3.0 mL in vivo samples prepared above were withdrawn and a dilution series was prepared. For example, the sample (4.0 µL) was diluted with blue-dye loading buffer (6.0 µL) giving a sample with final RNA concentration of 0.04 µg/µL. Then 4 µL of this diluted sample was applied to the gel. Similarly, the sample (4.0 µL) was treated with DTT (1.0 µL, 1.0 M solution) for 10 minutes before being diluted further with 2.5% SDS (2.0 µL) and loading buffer (3.0 µL) giving a sample with final RNA concentration of 0.04 µg/µL. Then 4 µL of this reduced solution was also applied to the gel for analysis. Conjugation efficiencies were greater than 90%.

The knockdown activity of the resulting conjugated siRNA formulations was tested as described below.

Example 17. Knockdown Activity and Liver Toxicity siRNA Polymeric Conjugates Female Balb/C mice, age 8 weeks at dosing, or CD-1 mice, age 7 weeks at dosing, were housed in groups of 4-5 animals. Food, water, temperature and humidity are according to vivarium performance standards (SOPs) which are in accordance with the 1996 Guide for the Care and Use of Laboratory Animals (NRC), AAALAC-International, and Seattle Children's Research Institute Institutional Animal Care and Use Committee (IACUC). Animals were acclimated to the facility for at least 5 days prior to experimentation. A single dose of the formulated conjugate from Example 9 or control of 10 mL/kg, 0.2 mL per 20 g mouse was administered i.v. via tail vein on Day 0. Study endpoints (24 hr or 48 hr) included: Clinical Observations; quantification of ApoB mRNA in liver; and quantification of aspartate transaminase (AST) and alanine transaminase (ALT) at necropsy.

Blood was collected immediately prior to necropsy via retro-orbital sinus and placed into serum separator tube. Blood was processed to serum and samples were stored at 4° C. until sent to Phoenix Central Laboratories (Seattle, Wash.) for analysis of liver transaminases.

After blood samples were collected, animals were euthanized using $CO_2$ asphyxiation followed by cervical dislocation, and the abdomen was opened. Approximately 200 mg of liver tissue was excised from the left lateral lobe and placed in sterile 24-well cell culture plates containing 2 mL of RNAlater (Applied Biosystems) solution. Using scissors treated with RNaseZap (Ambion), the tissue was chopped into small pieces to allow penetration of RNAlater solution into tissue. Samples were stored at 4° C. until processed for total RNA isolation.

Dosing solutions were analyzed by dynamic light scattering (Malvern, UK) to determine particle size.

ApoB mRNA was measured using quantitative PCR by SYBR green chemistry as described in Applied Biosystems tutorial Essentials of qPCR. In brief, approximately 50 mg liver tissue was transferred from RNAlater into TRI Reagent in individual sterile homogenization tubes. The tissue was then homogenized and the RNA fraction was extracted. Total RNA was isolated using the MagMax-96 for Microarrays Total RNA Isolation Kit (Applied Biosystems). RNA samples were diluted to 30 ng/ml for cDNA synthesis. 10 µl of RNA was subjected to random primed reverse transcription using the High Capacity cDNA Reverse Transcription Kit (Applied Biosystems) and diluted 1:5 in nuclease free water for use in the qPCR reactions.

For determining relative expression, RNA from each Vehicle sample was pooled into one sample for cDNA synthesis which is referred to as the Pool sample. The Pool sample was run on each PCR plate to serve as the reference sample for relative expression. Primer sets specific to ApoB as well as two internal normalizing genes (Calnexin and HPRT) were run in triplicate for each sample on the same PCR plate. StepOne™ software (Applied Biosystems) was used to calculate the relative quantity of the target gene ApoB normalized to the two internal normalizer genes and then relative to the POOL sample using the comparative $C_T$ ($\Delta\Delta C_T$) method. Each Vehicle sample was assayed in addition to the Pool Sample to show that the Pool Sample was representative of the individual Vehicle control samples.

Quantification of serum ALT and AST levels was done at Phoenix Central Laboratories (Everett, Wash.). Body weights were collected for each animal prior to dosing and prior to necropsy. The percent weight change was then calculated. Descriptive statistics (average and standard deviation [SD]) were determined for each group and dose level for ApoB relative gene expression (RQ), ALT and AST levels, and body weight.

Results of the experiments are summarized in the Tables 6 and 7.

TABLE 6

Liver transaminases (AST and ALT), relative gene expression (RQ), and % knockdown for ApoB mRNA in the liver of Balb/c 24 Hours after administration of polymer-siRNA conjugates or vehicle; SD = standard deviation.

| Polymer | Polymer Dose (mg/kg) | SiRNA Amount (mg/kg) | AST (U/L) Average | AST (U/L) ± SD | ALT (U/L) Average | ALT (U/L) ± SD | RQ | RQ ± SD | % KD |
|---|---|---|---|---|---|---|---|---|---|
| P1 | 150 | 7.5 | 386 | 328 | 242 | 248 | 0.0464 | 0.0154 | 95 |
|  | 125 | 6.3 | 151 | 43 | 106 | 46 | 0.1008 | 0.0431 | 90 |
|  | 100 | 5.0 | 130 | 34 | 69 | 26 | 0.3064 | 0.0979 | 69 |
|  | 75 | 3.8 | 163 | 71 | 51 | 7 | 0.5629 | 0.1092 | 44 |

TABLE 6-continued

Liver transaminases (AST and ALT), relative gene expression (RQ), and % knockdown for ApoB mRNA in the liver of Balb/c 24 Hours after administration of polymer-siRNA conjugates or vehicle; SD = standard deviation.

| Polymer | Polymer Dose (mg/kg) | SiRNA Amount (mg/kg) | AST (U/L) Average | AST (U/L) ± SD | ALT (U/L) Average | ALT (U/L) ± SD | RQ | RQ ± SD | % KD |
|---|---|---|---|---|---|---|---|---|---|
|    | 50  | 2.5 | 114   | 54    | 33    | 23    | 0.9450 | 0.1470 | 5   |
|    | 25  | 1.3 | 103   | 14    | 42    | 3     | 0.9441 | 0.1062 | 6   |
| P2 | 150 | 7.4 | 165   | 74    | 93    | 40    | 0.0767 | 0.0453 | 92  |
|    | 125 | 6.2 | 126   | 18    | 69    | 29    | 0.1683 | 0.1014 | 83  |
|    | 100 | 4.9 | 116   | 38    | 64    | 20    | 0.1634 | 0.0856 | 84  |
|    | 75  | 3.7 | 130   | 44    | 52    | 16    | 0.2438 | 0.1326 | 76  |
|    | 50  | 2.5 | 108   | 30    | 60    | 19    | 0.7364 | 0.0839 | 26  |
|    | 25  | 1.2 | 92    | 13    | 42    | 4     | 0.8461 | 0.1782 | 15  |
| P3 | 150 | 5.6 | 7398  | 7374  | 6734  | 5937  | 0.0034 | 0.0033 | 100 |
|    | 125 | 4.7 | 967   | 1067  | 1102  | 1357  | 0.0182 | 0.0127 | 98  |
|    | 100 | 3.8 | 244   | 137   | 330   | 321   | 0.0382 | 0.0208 | 96  |
|    | 75  | 2.8 | 282   | 174   | 276   | 214   | 0.0336 | 0.0270 | 97  |
|    | 50  | 1.9 | 104   | 29    | 58    | 11    | 0.1720 | 0.0630 | 83  |
|    | 25  | 0.9 | 98    | 44    | 38    | 5     | 0.7454 | 0.1703 | 25  |
| P5 | 150 | 4.8 | 50634 | 11596 | 47918 | 9205  | 0.1472 | 0.0536 | 85  |
|    | 125 | 4.0 | 42285 | 12158 | 37118 | 11460 | 0.0212 | 0.0191 | 98  |
|    | 100 | 3.2 | 13574 | 10505 | 11712 | 8202  | 0.0047 | 0.0037 | 99  |
|    | 75  | 2.4 | 772   | 279   | 1313  | 426   | 0.0254 | 0.0053 | 91  |
|    | 50  | 1.6 | 261   | 136   | 540   | 351   | 0.0775 | 0.0342 | 92  |
|    | 25  | 0.8 | 114   | 65    | 145   | 236   | 0.3482 | 0.0192 | 65  |
|    | 15  | 0.5 | 82    | 11    | 31    | 12    | 0.6133 | 0.0687 | 39  |
| Vehicle | n/a | n/a | 104 | 40 | 42 | 14 | 0.9645 | 0.1079 | 0 |

TABLE 7

Liver transaminases (AST and ALT), relative gene expression (RQ), and % knockdown (% KD) for ApoB mRNA in the liver of CD-1 mice at 48 Hours after administration of polymer-siRNA conjugates or vehicle; SD = standard deviation.

| Polymer | Polymer Dose (mg/kg) | SiRNA Amount (mg/kg) | AST (U/L) Average | AST (U/L) ± SD | ALT (U/L) Average | ALT (U/L) ± SD | RQ | RQ ± SD | % KD |
|---|---|---|---|---|---|---|---|---|---|
| P1 | 125 | 3.0  | 130  | 48    | 53   | 38    | 0.3047 | 0.2201 | 70 |
|    | 42  | 1.0  | 100  | 41    | 60   | 64    | 0.5208 | 0.1078 | 48 |
|    | 19  | 0.3  | 138  | 56    | 46   | 26    | 0.9544 | 0.1055 | 5  |
| P4 | 150 | 3.6  | 128  | 48    | 42   | 18    | 0.8884 | 0.2323 | 11 |
|    | 125 | 3.0  | 148  | 122   | 48   | 25    | 0.9012 | 0.0822 | 0  |
|    | 100 | 2.4  | 220  | 104   | 81   | 59    | 0.8260 | 0.1177 | 17 |
|    | 75  | 1.8  | 111  | 55    | 39   | 20    | 1.1688 | 0.3112 | 0  |
|    | 42  | 1.0  | 254  | 168   | 82   | 51    | 1.1727 | 0.2261 | 0  |
| P5* | 75 | 2.4  | 5641 | 10866 | 8022 | 15793 | 0.1258 | 0.0746 | 87 |
|    | 50  | 1.6  | 219  | 259   | 189  | 314   | 0.3962 | 0.1617 | 60 |
|    | 25  | 0.8  | 114  | 35    | 46   | 21    | 0.6324 | 0.1369 | 37 |
| P6 | 125 | 5.0  | 156  | 95    | 146  | 129   | 0.0348 | 0.0050 | 97 |
|    | 75  | 2.45 | 87   | 28    | 93   | 64    | 0.0444 | 0.0075 | 96 |
|    | 50  | 1.6  | 67   | 13    | 42   | 10    | 0.1599 | 0.0511 | 84 |
|    | 30  | 4.0  | 64   | 10    | 32   | 10    | 0.2618 | 0.1397 | 74 |
|    | 20  | 2.45 | 196  | 202   | 47   | 12    | 0.4100 | 0.1579 | 59 |
|    | 10  | 1.6  | 79   | 32    | 35   | 16    | 0.7279 | 0.1815 | 27 |
| Vehicle | n/a | n/a | 72 | 17 | 33 | 4 | 1.0185 | 0.0616 | 0 |

*Experiment stopped at 24 Hours due to observed toxicity.

Example 18. Formulation of Block Copolymers of the Invention and mRNA Complexes

A The polymers P7 of Example 9, P9 of Example 12 or P10 of Example 13 were solubilized at 100 mg/mL in 200 proof ethanol and then diluted to 20 mg/mL in 20 mM HEPES buffer at pH 7.4 containing 5% glucose (HEPES buffer). The individual polymer stock solutions were kept at −20° C. until used. The P7 and P9 stock solutions were mixed together at a 77% and 23% molar ratio prior to use. P10 and P7 were also mixed together but at a 30% and 70% molar ratio prior to use. Typically, for P9/P7 793 µL of P9 at 20 mg/mL in HEPES buffer was added to 207 µL of P7 in buffer for a final volume of 1 mL and a final polymer concentration of 20 mg/mL. Typically, for P10/P7 365 µL of P10 at 20 mg/mL in HEPES buffer was added to 635 µL of P7 in buffer for a final volume of 1 mL and a final polymer concentration of 20 mg/mL. The FLuc (firefly luciferase) mRNA stock solution at 2 mg/mL in 10 mM Tris-HCL (pH7.5) from TriLink Biotechnologies (San Diego, Calif., USA)(catalog number L-6107) was diluted to 0.2 mg/mL in HEPES buffer. The polymer mRNA formulation was assembled at a N/P ratio of 20 by adding 1 mL of the diluted polymer stock solution at 20 mg/mL to 1 mL of mRNA at 0.2 mg/mL in HEPES buffer under a mild vortex agitation. The formulation was kept at 4° C. overnight prior to in vivo dosing. The formulations were dosed intravenously at 1 mg/kg mRNA and 100 mg/kg of polymer.

The formulation particle size was measured by adding 10 µL of formulation to 90 µL of HEPES buffer into a disposable micro-cuvette and analyzed using the Malvern Instrument ZETASIZER NANO-ZS. The formulation zeta-potential at pH 7.4 was measured by adding 10 µL of formulation to 740 µL of HEPES buffer into a disposable 1 mL cuvette. The zeta dip cell was inserted into the 1 mL cuvette and the formulation was analyzed using the ZETASIZER NANO-ZS. The zeta-potential was also measured at pH 4 as described above by adding 10 µL of formulation to 740 µL of 20 mM acetate buffer pH 4 containing 5% glucose. The ability of the polymer formulation to compact the mRNA was measured in a 96 well plate using a SYBR Gold dye accessibility assay. Typically, 50 µL of the polymer formulation at 0.01 mg/mL mRNA was added to 150 µL of diluted SYBR Gold stock solution (1 µL of Stock SYBR Gold in 3 mL of HEPES buffer) and incubated for 15 minutes at room temperature with agitation (100 RPM). The fluorescence was read at an excitation wavelength of 495 nm and emission wavelength of 538 nm. The percent dye accessibility was calculated by dividing the fluorescence intensity of the formulated mRNA by the fluorescence intensity of the free mRNA×100.

Example 19. In Vivo Testing of Polymer-mRNA Formulations

Female CD-1 mice (6-8 weeks old) were used for in vivo testing of polymer-FLuc mRNA formulations. The formulations were dosed intravenously at 1 mg/kg of mRNA and 100 mg/kg of total polymer dose, with 3-5 mice injected per group. Mice injected with HEPES buffer alone and HEPES buffer containing unformulated FLuc mRNA at 1 mg/kg were used as controls. All mice were given a final volume of approximately 0.25 ml or 10 mL/kg based on individual body weights.

The in vivo expression of luciferase was evaluated by detecting luminescence in mice using the Xenogen IVIS Lumina II Imaging System (Caliper Life Sciences, now Perkin Elmer). The imaging was performed at 3 and 6 hours following dosing. 15 minutes prior to imaging, each mouse received 0.25 ml of D-luciferin (Perkin Elmer), a luciferase substrate, at 15 mg/ml (dissolved in 1×PBS) by intraperitoneal injection. A few minutes before imaging, mice were place in an isoflurane chamber to induce anesthesia (isoflurane concentration at ~3%). Subsequently, mice were moved into the IVIS imaging chamber, with the snout connected to an isoflurane-filled nose cone with the mouse's ventral side up. The luminescence images were acquired using Living Image software (Caliper Life Sciences) with the exposure time, binning and F/Stop remain the same throughout the study. Mice were put back to the cage as soon as the imaging was finished and they recovered within 1-3 minutes.

After the image acquisition was finished for all mice, the luminescence results were analyzed using Living Image software. Briefly, the color scale of each image was first adjusted to display specific luminescence signal and eliminate background signal. Then a region of interest (ROI) for the liver was defined using the ROI tools, and ROI measure button was clicked to show the photon flux data. Total flux (photons/sec) of the ROI on each animal was used to represent the intensity of luminescence. Total flux was averaged from all 5 mice for each formulation group for comparison.

Table 8 displays luminescence values in the liver for animals treated with either P9/P7+FLuc mRNA, P10/P7+FLuc mRNA, buffer, or unformulated mRNA. Data was acquired at 3 and 6 hours post dose. While neither of buffer or unformulated mRNA showed any activity, all mice receiving either of two polymer-mRNA formulations demonstrated strong luminescence signal in the liver.

TABLE 8

Luminescence results from individual animals at 3 and 6 hrs post dosing.

| Formulation | Animal ID | 3 hr Luminescence ||| 6 h Luminescence |||
| --- | --- | --- | --- | --- | --- | --- | --- |
| | | Total Flux (photons/sec) | Ave | SD | Total Flux (photons/sec) | Ave | SD |
| Buffer | 1 | 1.57E+05 | 1.28E+05 | 2.56E+04 | 1.25E+05 | 1.57E+05 | 3.04E+04 |
| | 2 | 1.08E+05 | | | 1.60E+05 | | |
| | 3 | 1.20E+05 | | | 1.86E+05 | | |
| Unformulated FLuc mRNA | 4 | 4.56E+04 | 1.11E+05 | 5.98E+04 | 1.77E+05 | 1.14E+05 | 7.43E+04 |
| | 5 | 1.63E+05 | | | 3.19E+04 | | |
| | 6 | 1.23E+05 | | | 1.34E+05 | | |
| PRX392/PRX367 + FLuc mRNA | 7 | 9.17E+07 | 5.11E+07 | 2.48E+07 | 7.38E+07 | 3.59E+07 | 2.58E+07 |
| | 8 | 5.27E+07 | | | 2.85E+07 | | |
| | 9 | 3.36E+07 | | | 3.42E+07 | | |
| | 10 | 2.89E+07 | | | 2.22E+06 | | |
| | 11 | 4.88E+07 | | | 4.09E+07 | | |
| PRX398/PRX367 + FLuc mRNA | 12 | 1.63E+08 | 7.18E+07 | 7.31E+07 | 1.02E+08 | 3.95E+07 | 4.32E+07 |
| | 13 | 1.68E+07 | | | 1.06E+07 | | |
| | 14 | 2.00E+07 | | | 1.06E+07 | | |
| | 15 | 1.92E+07 | | | 6.77E+06 | | |
| | 16 | 1.40E+08 | | | 6.73E+07 | | |

Example 20. In Vivo Testing of Knockdown Activity and Liver Toxicity of siRNA Polymer Formulations of Beta-Catenin and MET siRNA in a Hepatocellular Carcinoma (HCC) Mouse Model The gene knockdown response induced by β-catenin and MET siRNAs in a synthetic/transgenic HCC mouse model was evaluated following single doses of β-catenin, MET or a combination of β-catenin and MET siRNAs.

Female FVB mice (6-8 wk) received tail vein injections of human beta-catenin (ΔN90) & human MET DNA plasmids (10 μg each+0.8 μg of SB plasmid; 2 ml total volume) to induce HCC. At week 4, a single dose of beta-catenin siRNA (a dsRNA molecule where the sense strand is nucleotide sequence of SEQ ID NO:54 and the antisense region is nucleotide sequence of SEQ ID NO:78 which is also designated as si033), MET siRNA (a dsRNA molecule where the sense strand is nucleotide sequence of SEQ ID NO:1 and the antisense region is nucleotide sequence of SEQ ID NO:27 which is also designated as si034), a combination (si033+si034), or ITG buffer was given at week 4. The polymer was polymer P6. Animals were sacrificed 1, 2, 3, 4, 6, or 10 days after siRNA dosing. Liver/tumor tissue samples were collected for PCR and Western analyses using standard techniques known in the art. Serum samples were evaluated for serum chemistry including alanine aminotransferase (ALT).

Formulations for dosing were prepared by taking lyophilized polymer (polymer P6) and dissolving it in ITG to a stock concentration of 60 mg/ml. The polymer is then diluted in ITG to 7.5 mg/ml with 0.3 mg/ml reduced thiolated siRNA (either si033 or si034). The conjugation reaction is incubated at room temperature overnight. Formulations were stored in glass vials under argon at 4° C. throughout dosing. si033 and si034 were formulated with polymer P6 as described above. Animals were given IV injections of either 3.0 mg/kg formulated si033, 3.0 mg/kg formulated si034, or 1.5 mg/kg each of a combination of formulated si033 and si034 as described in Table 9. All animals were given a final dosing volume of approximately 0.25 ml or 10 mL/kg based on body weight.

Human β-catenin mRNA was knocked down relative to human MET mRNA through day 4 after β-catenin siRNA (si033)/polymer dosing as shown in FIG. 1.

Human MET mRNA was knocked down relative to β-catenin mRNA through day 10 after MET siRNA (si034)/polymer dosing as shown in FIG. 2.

Figure 3:
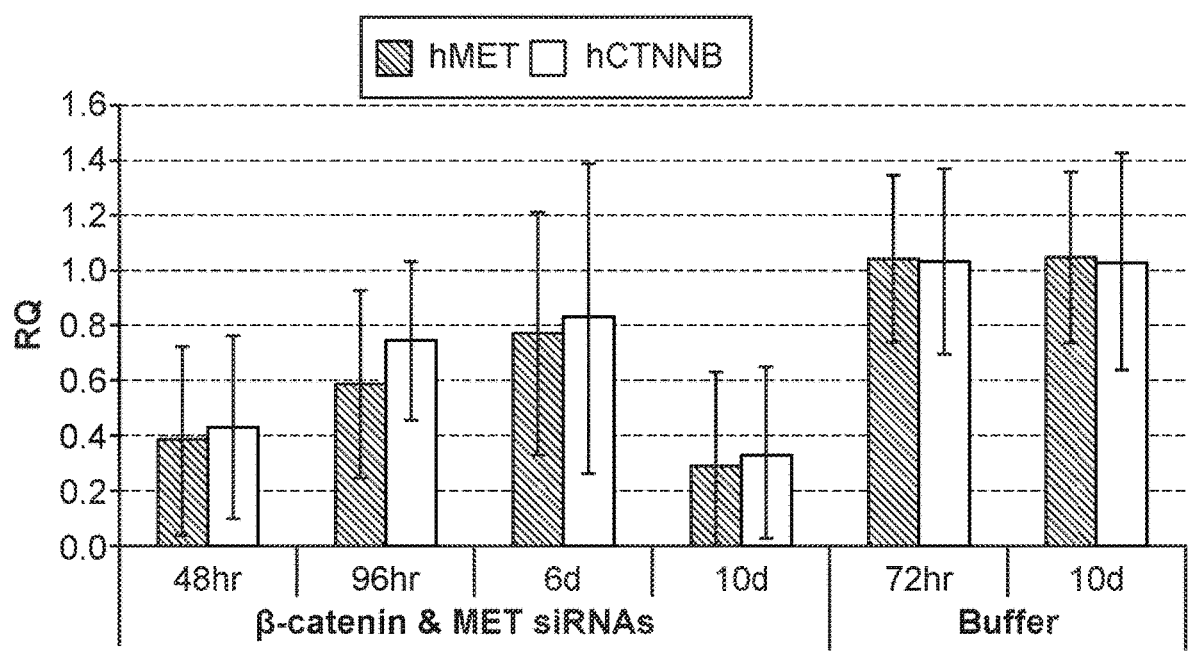
FIG. 3 is a graph demonstrating knockdown of human β-catenin mRNA and human MET mRNA upon the administration of a combination formulation of β-catenin and MET siRNAs with polymer.
Figure 4:
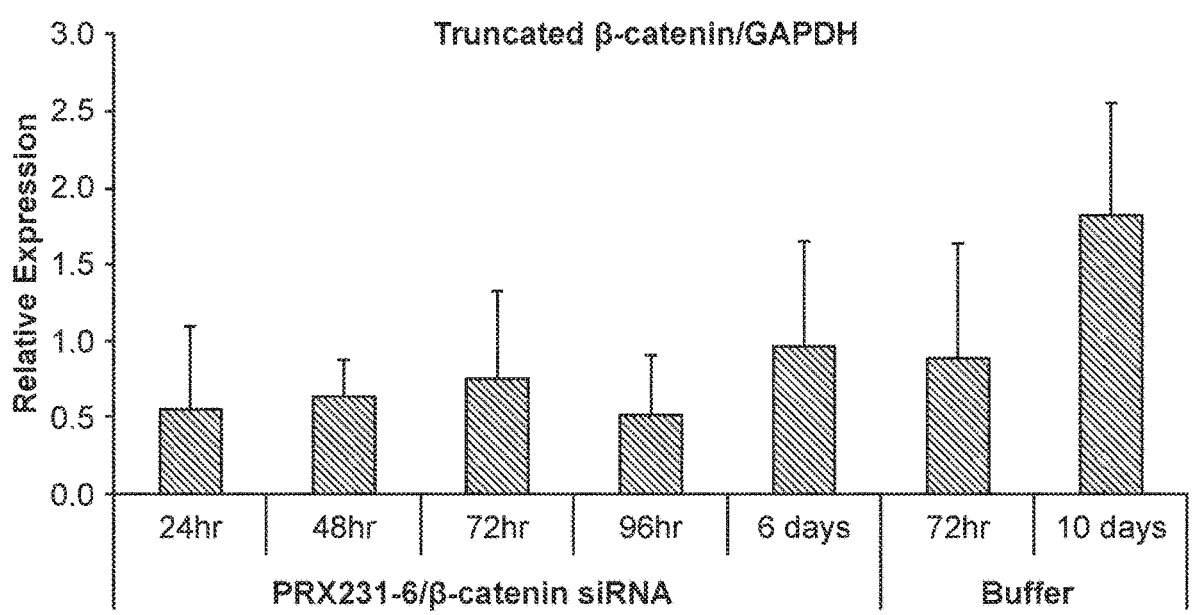
FIG. 4 is a graph demonstrating the knockdown of β-catenin protein by β-catenin siRNA following β-catenin siRNA (si033)/polymer treatment.
Figure 5:
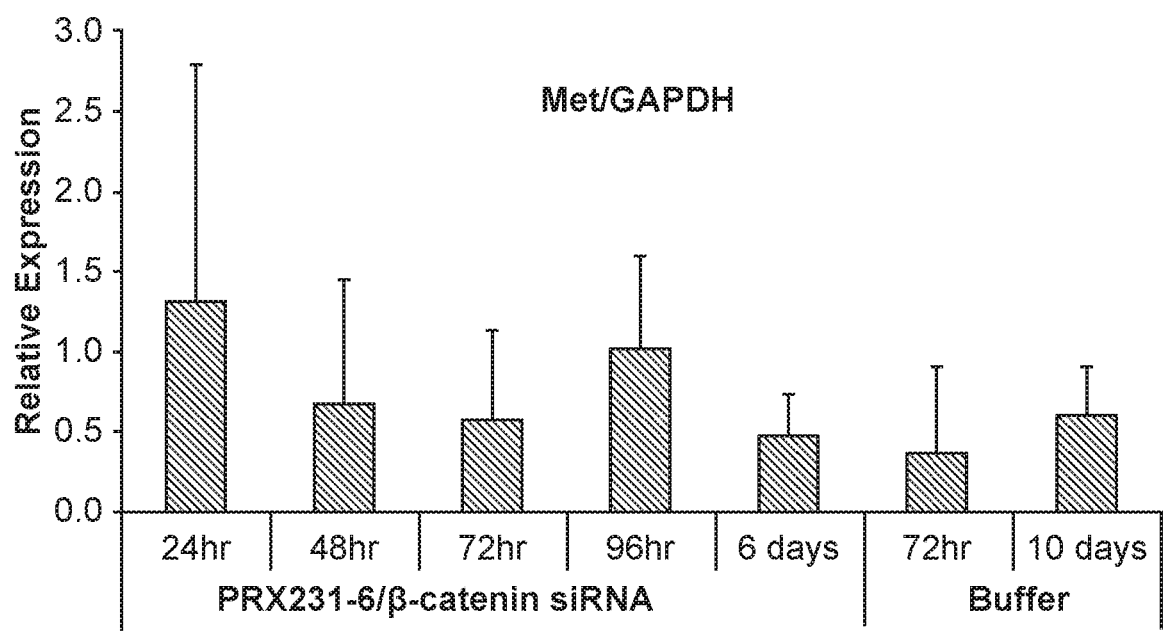
FIG. 5 is a graph demonstrating the knockdown of MET protein following β-catenin siRNA (si033)/polymer treatment.
Figure 6:
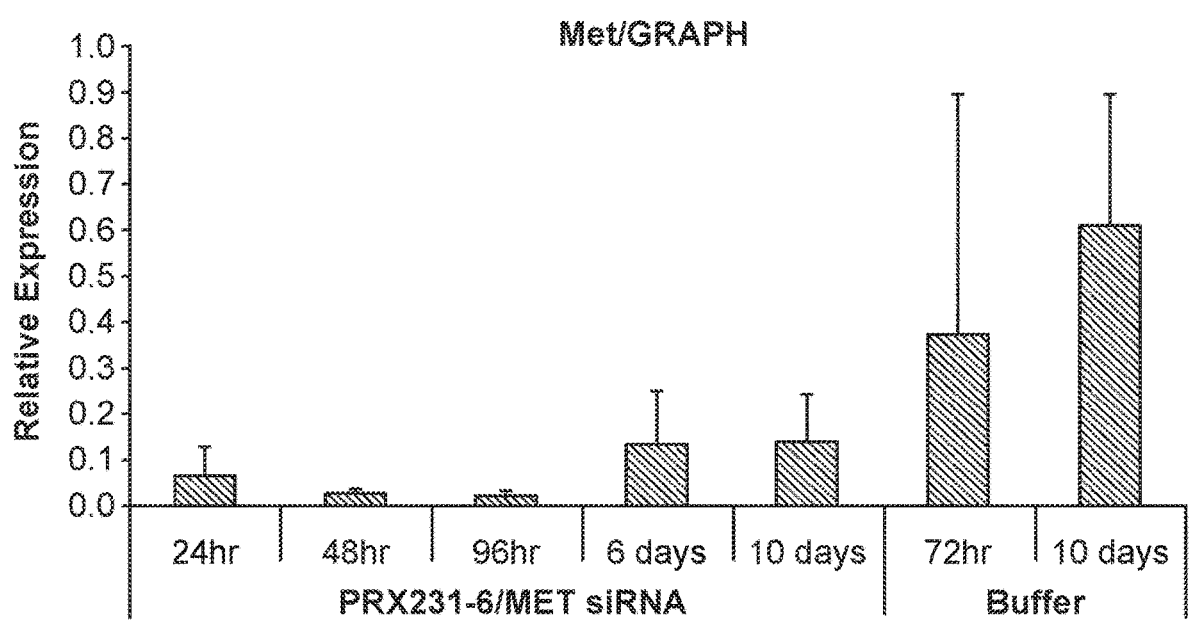
FIG. 6 is a graph demonstrating the knockdown of MET protein by MET siRNA following MET siRNA (si034)/polymer treatment.
Figure 7:
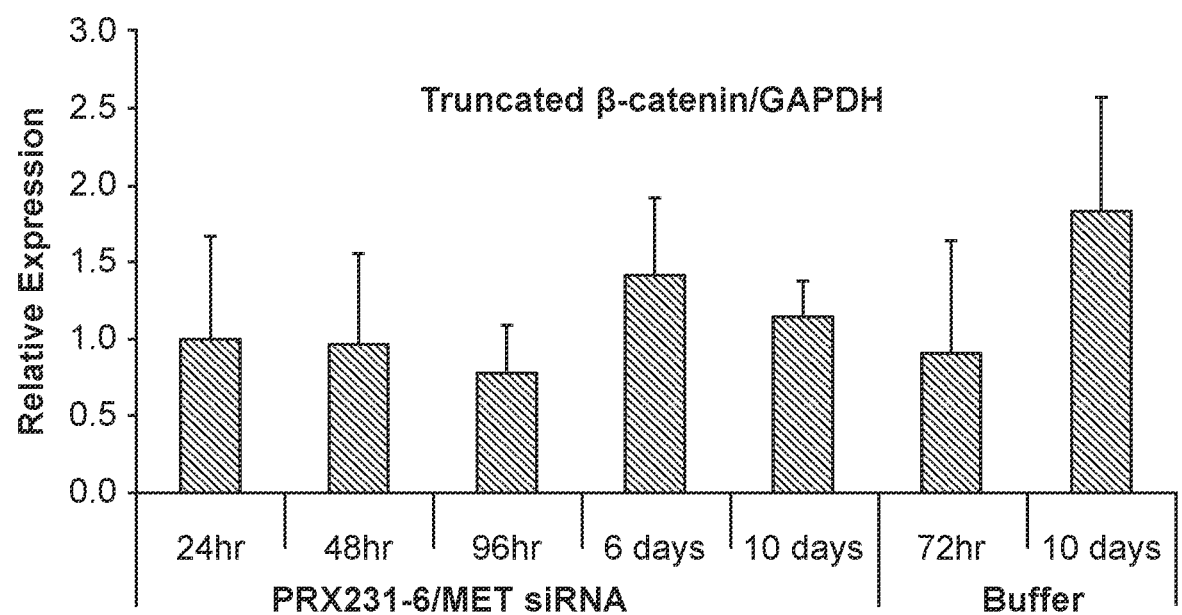
FIG. 7 is a graph demonstrating the knockdown of β-catenin protein by MET siRNA following MET siRNA (si034)/polymer treatment.

The combination treatment upon the administration of a combination formulation of si033 and si034 with polymer P6 showed variable mRNA KD as shown in FIG. 3.

β-catenin and Met expressions levels relative to GAPDH following β-catenin siRNA (si0333)/polymer treatment are shown in FIGS. 4 and 5 respectively β-catenin and Met expressions levels relative to GAPDH following Met siRNA (si034)/polymer P6 treatment are shown in FIGS. 6 and 7 respectively.

Figure 8:
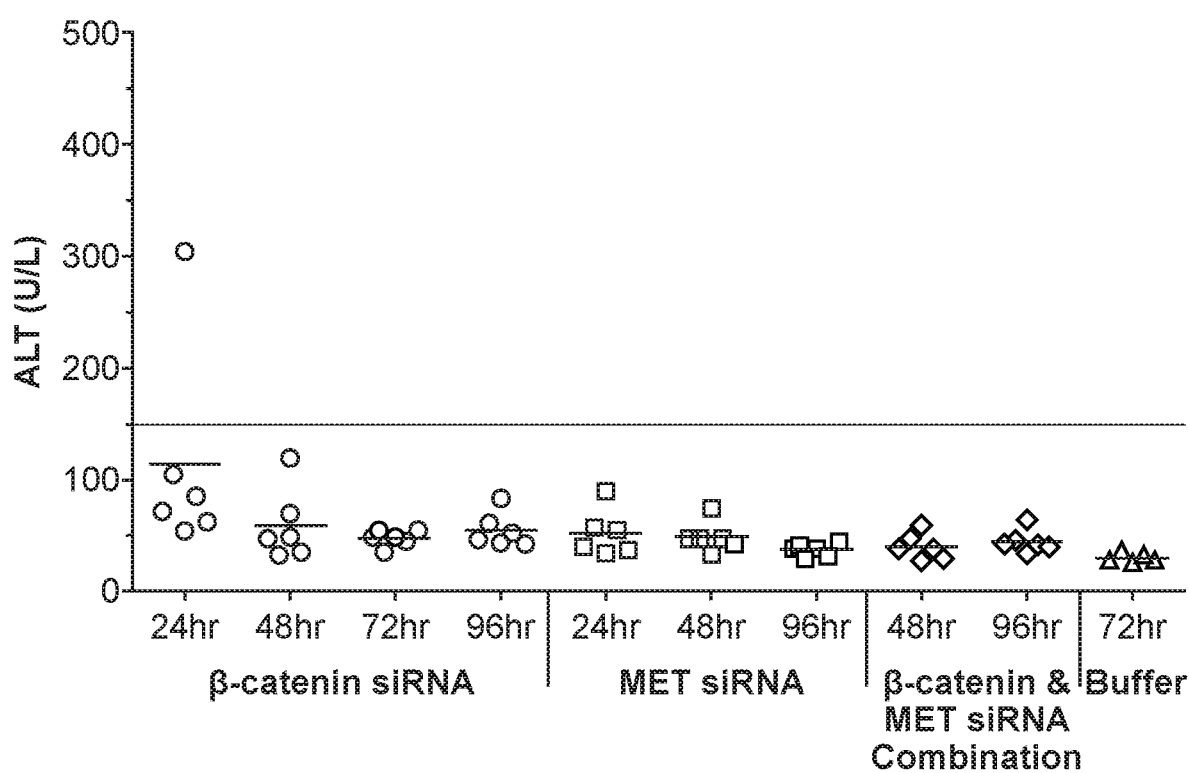
FIG. 8 is a graph demonstrating ALT levels through 96 hr post siRNA dosing of formulations of si033 (β-catenin siRNA) with polymer, si034 (MET siRNA) with polymer or a combination of si033 and si034 with polymer.
Figure 9:
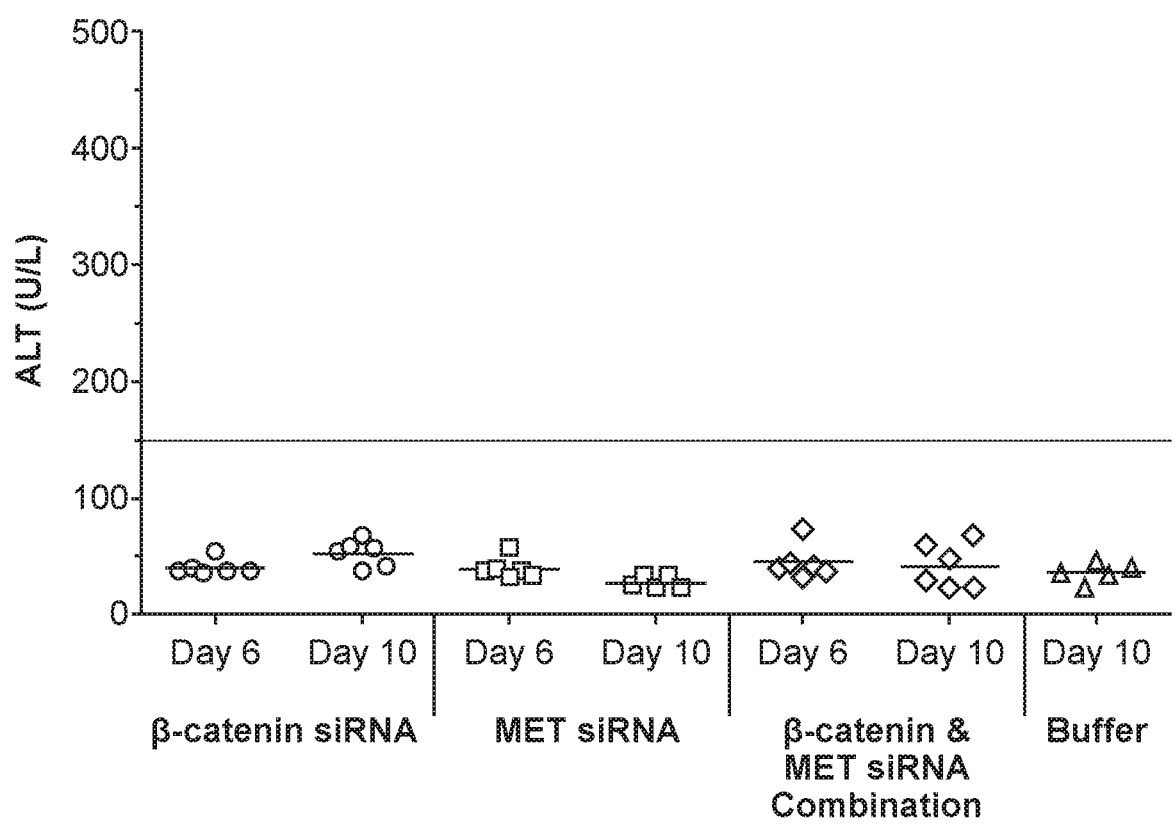
FIG. 9 is a graph demonstrating ALT levels 6 and 10 days post siRNA dosing of formulations of si033 (β-catenin siRNA) with polymer, si034 (MET siRNA) with polymer or a combination of si033 and si034 with polymer.
Figure 10A:
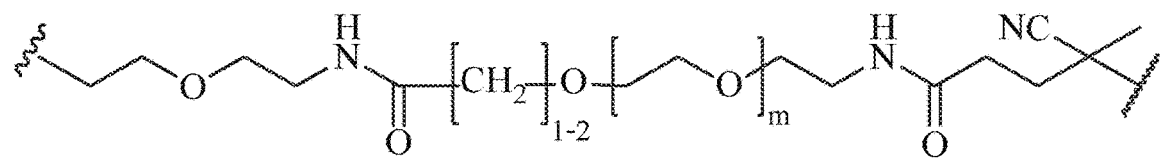
FIGS. 10A and 10B depict exemplary structures of linking moiety L1.
Figure 10A:
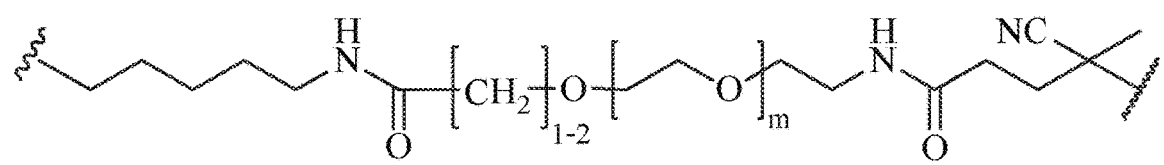
Figure 10A:
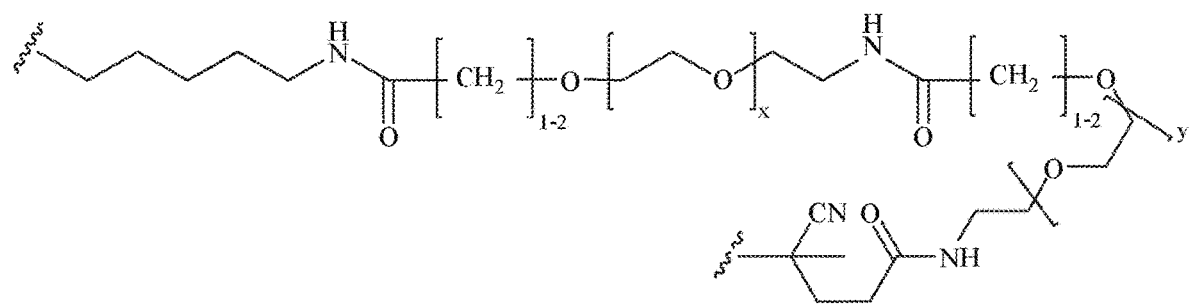
Figure 10A:
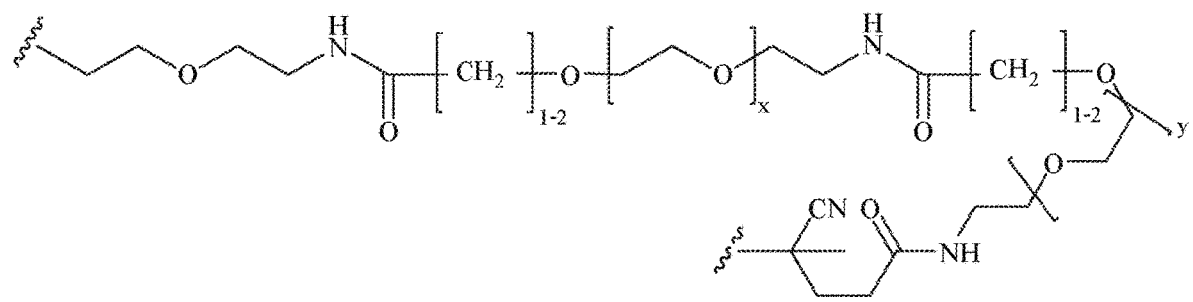
Figure 10A:
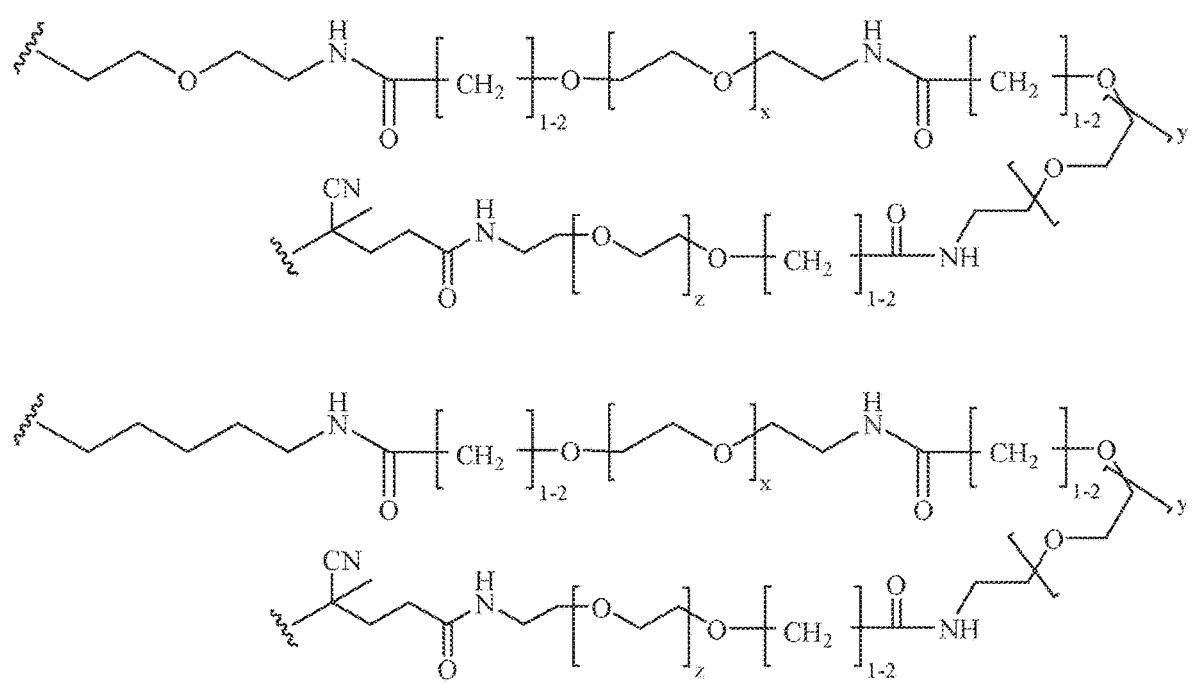
Figure 10B:
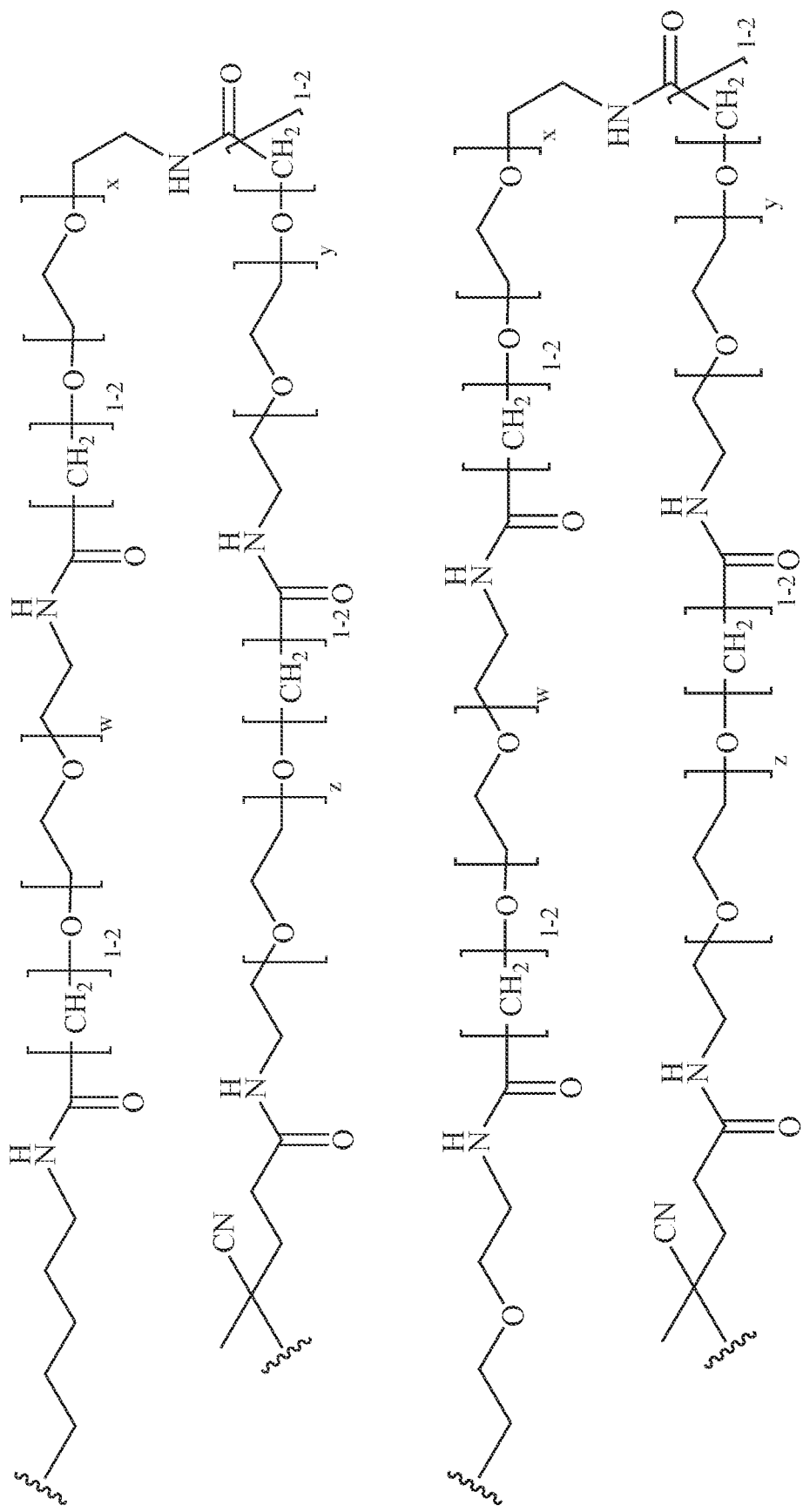
Figure 11A:
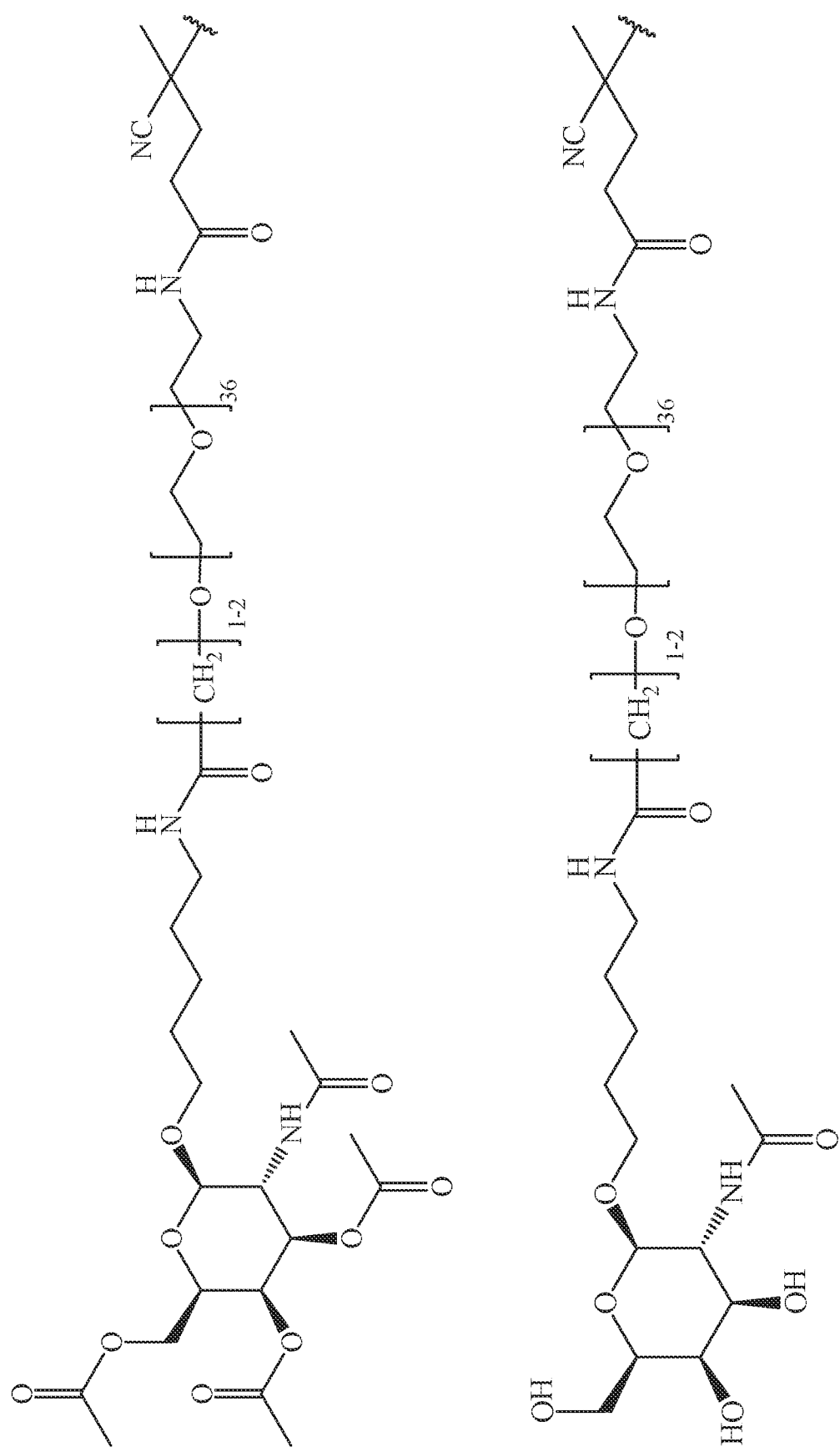
FIGS. 11A-11D depict exemplary structures of targeting moiety T1 linked to linking moiety L1 (T1-L1-together).
Figure 11A:
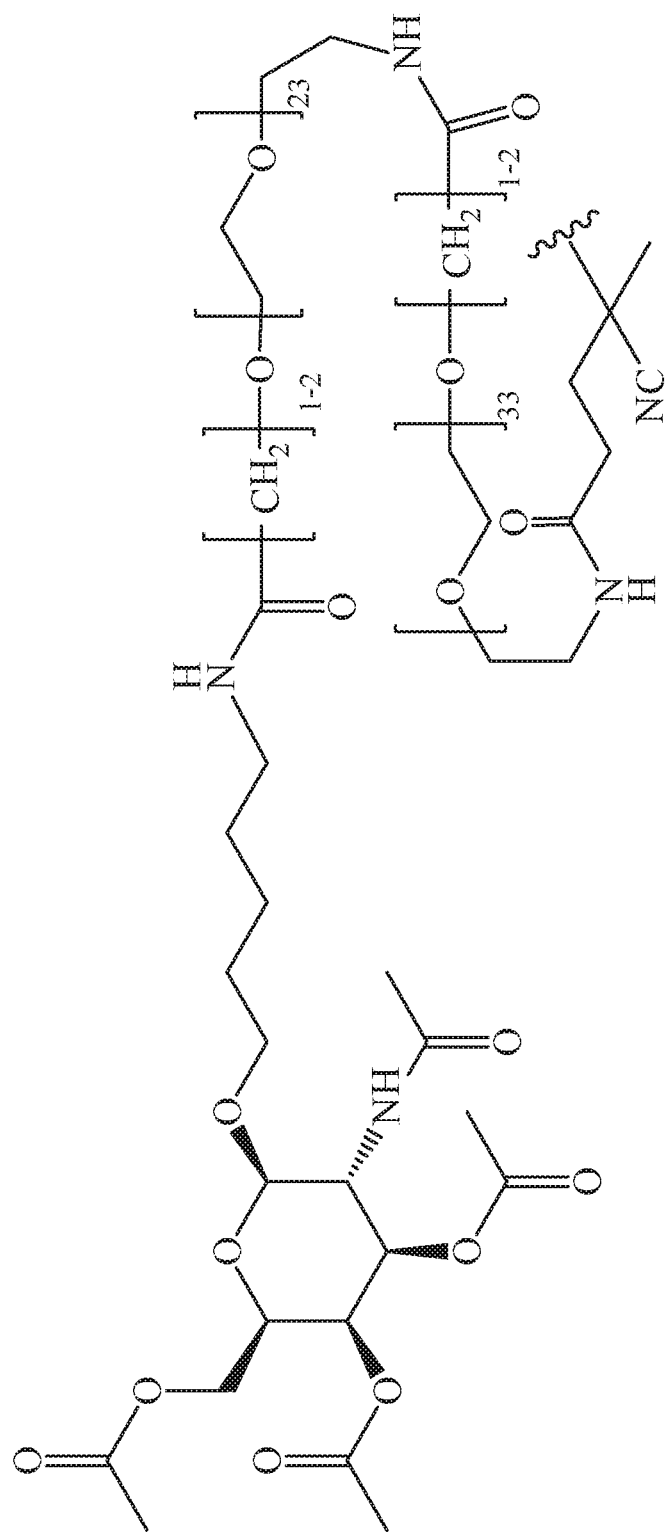
Figure 11B:
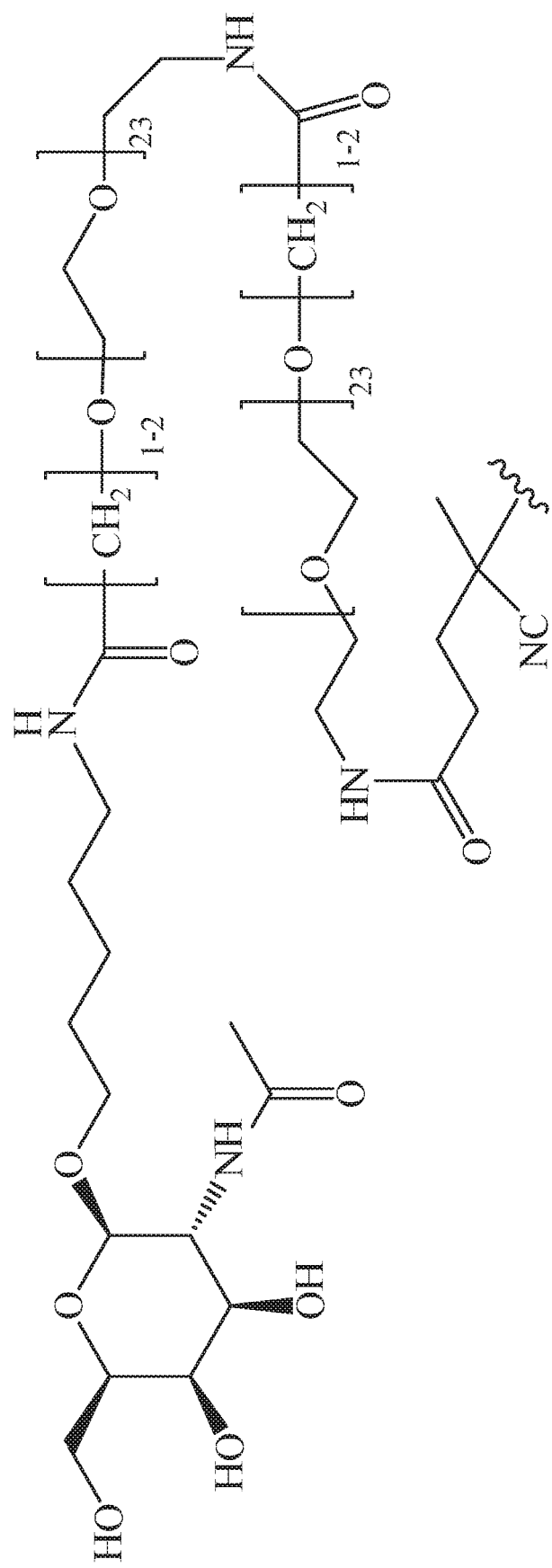
Figure 11B:
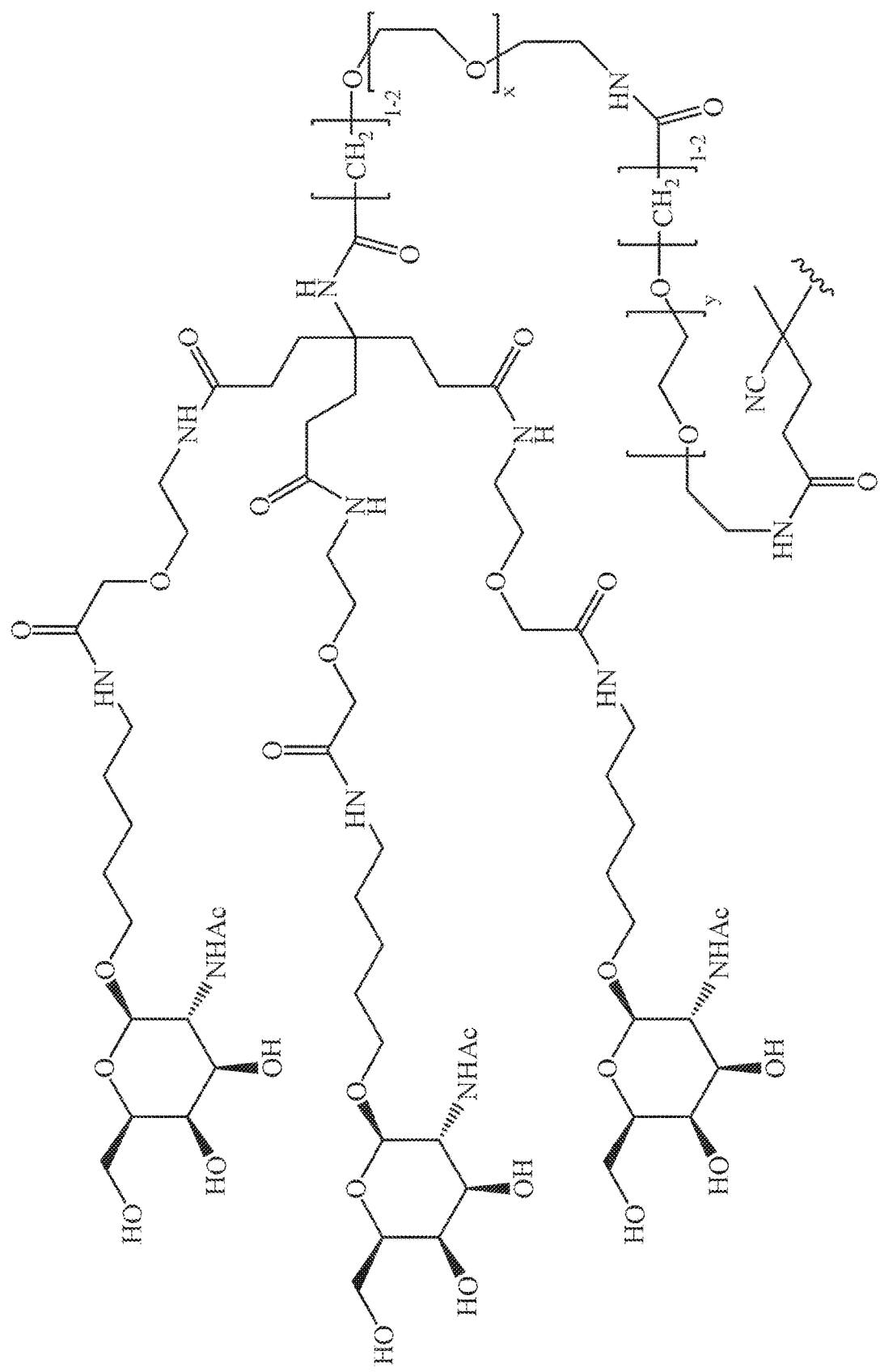
Figure 11C:
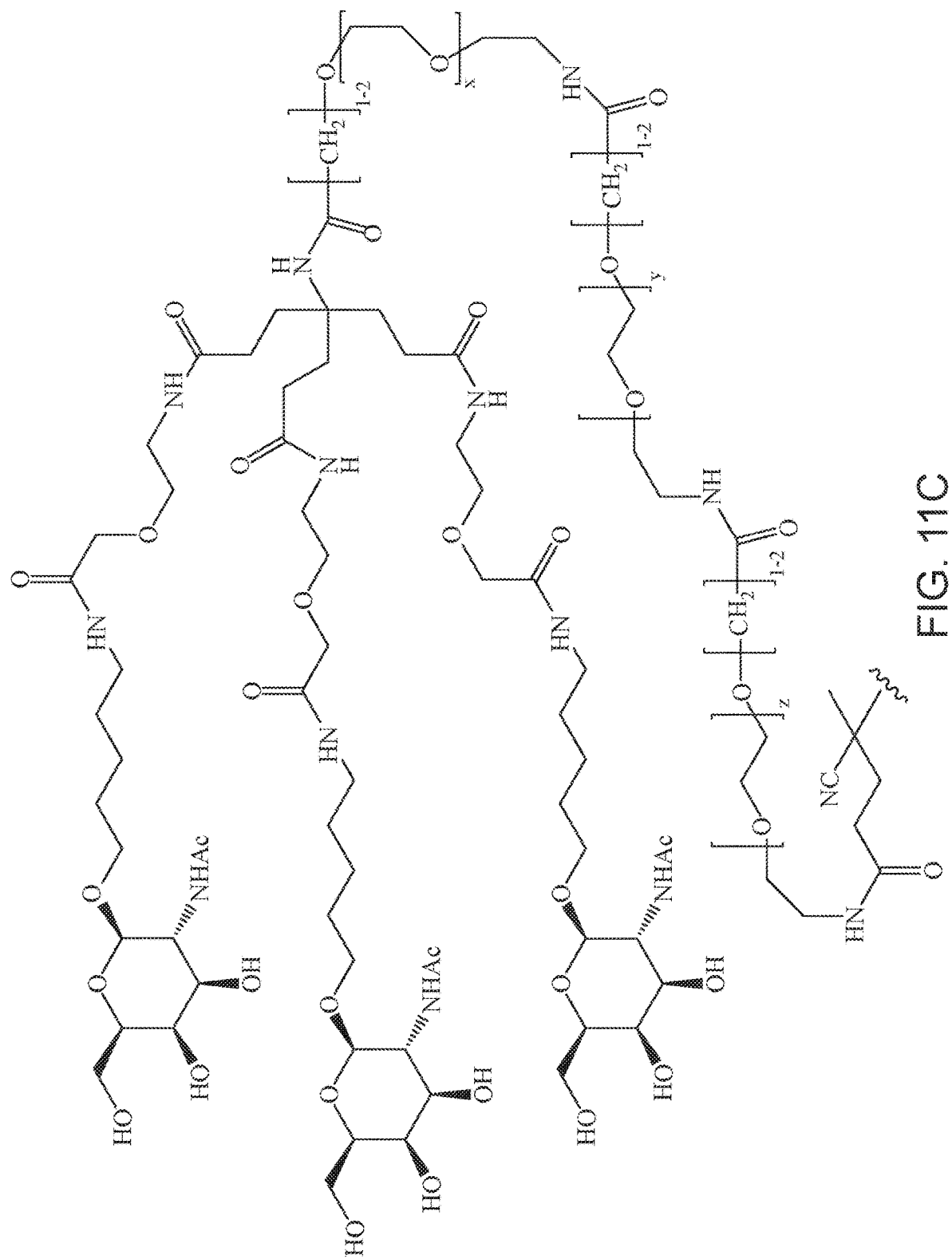
Figure 11C:
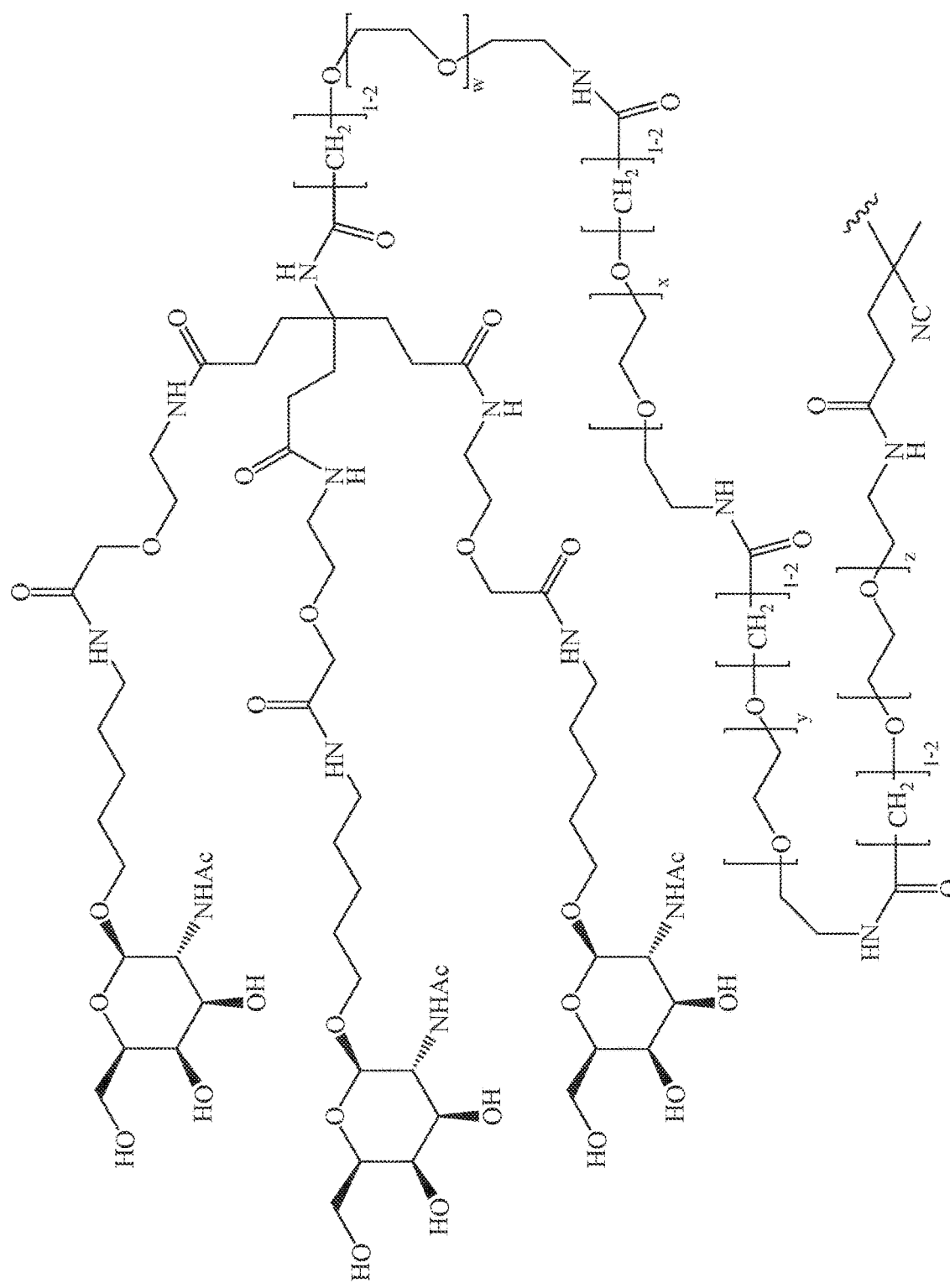
Figure 11D:
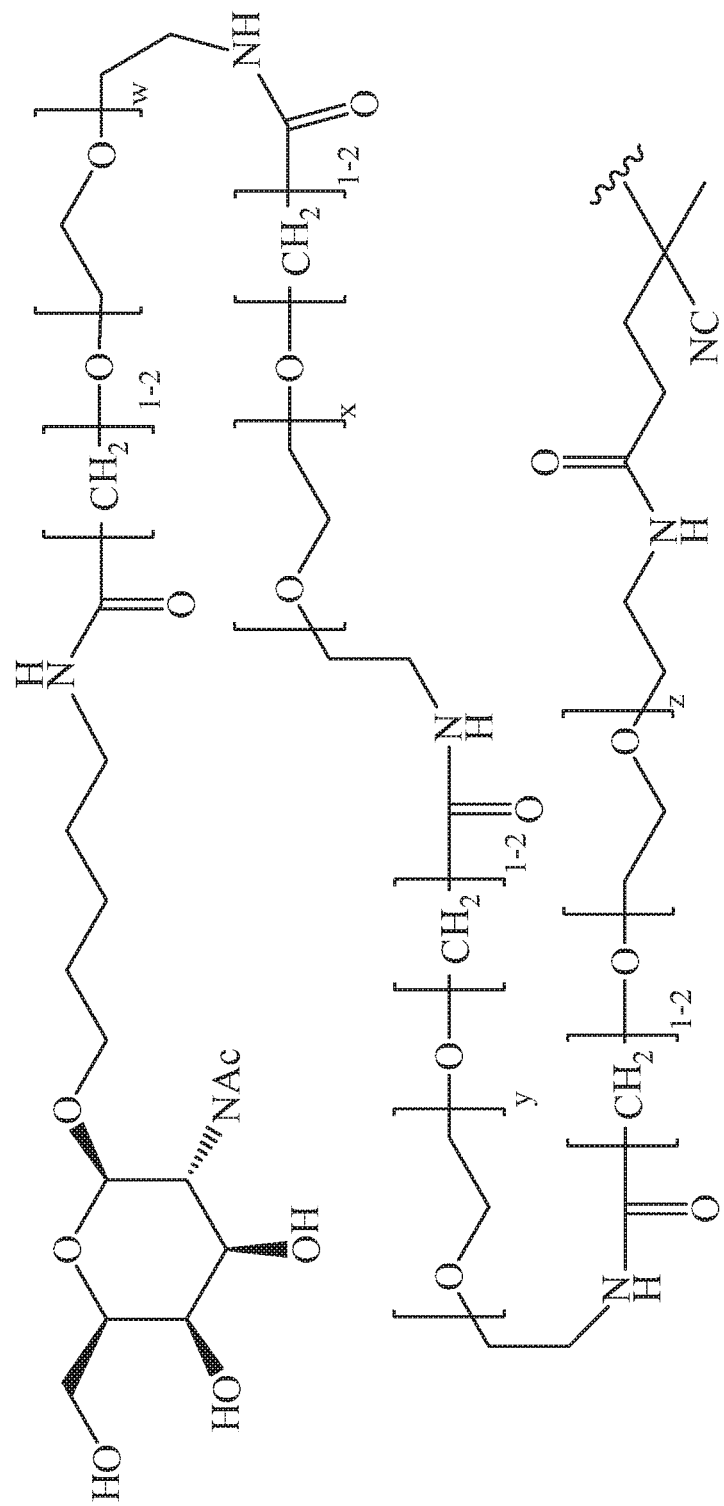
Figure 12A:
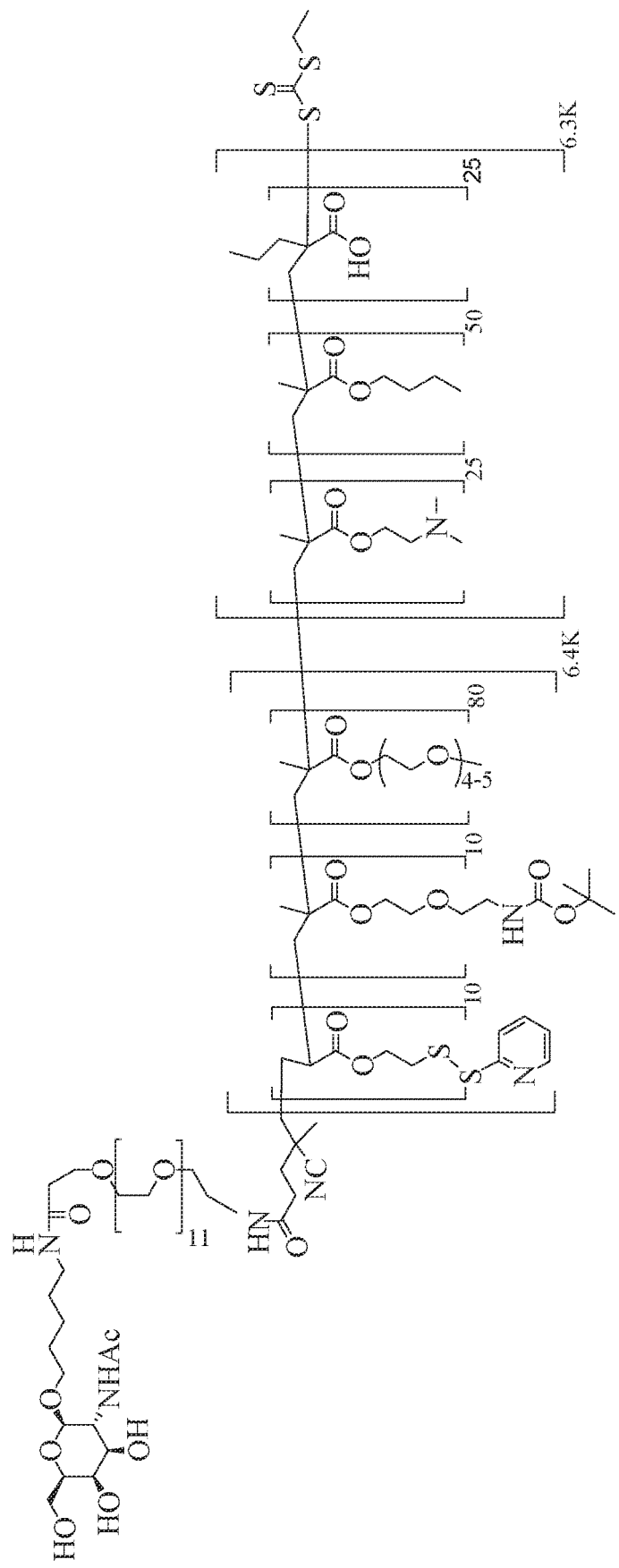
FIGS. 12A-12C depict exemplary block copolymers of Formula I.
Figure 12A:
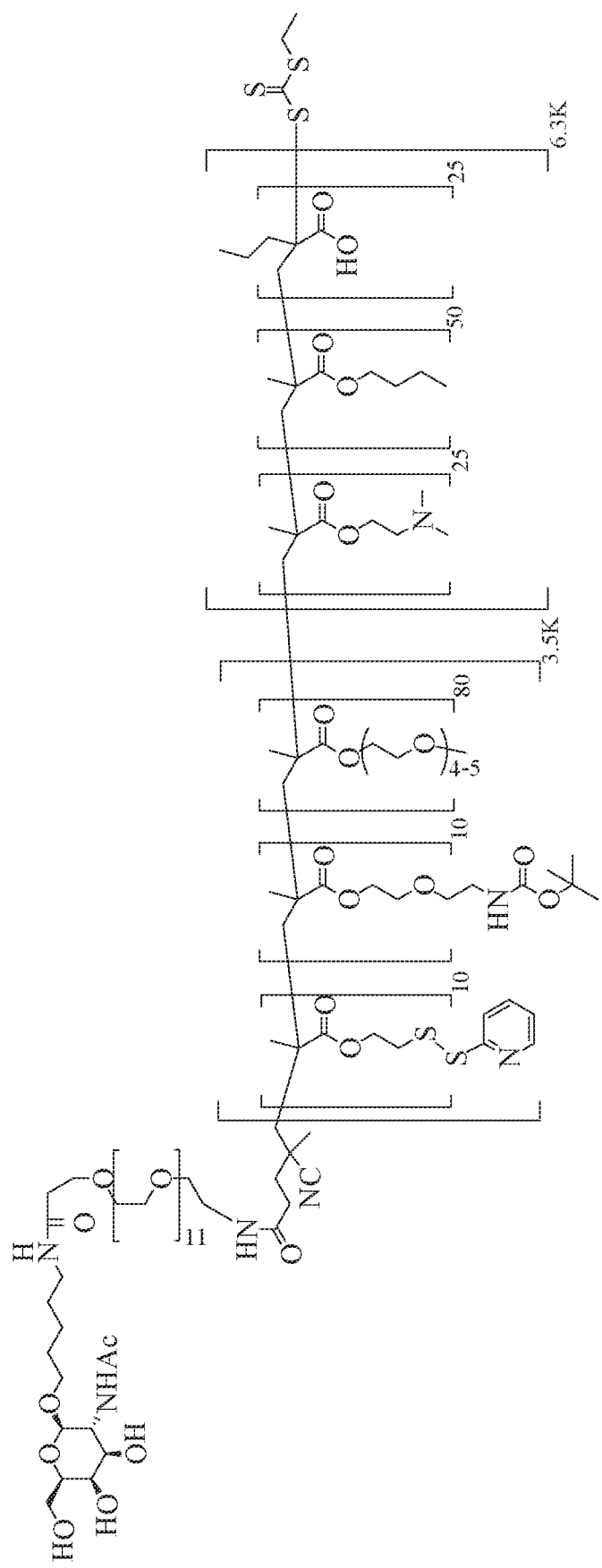
Figure 12B:
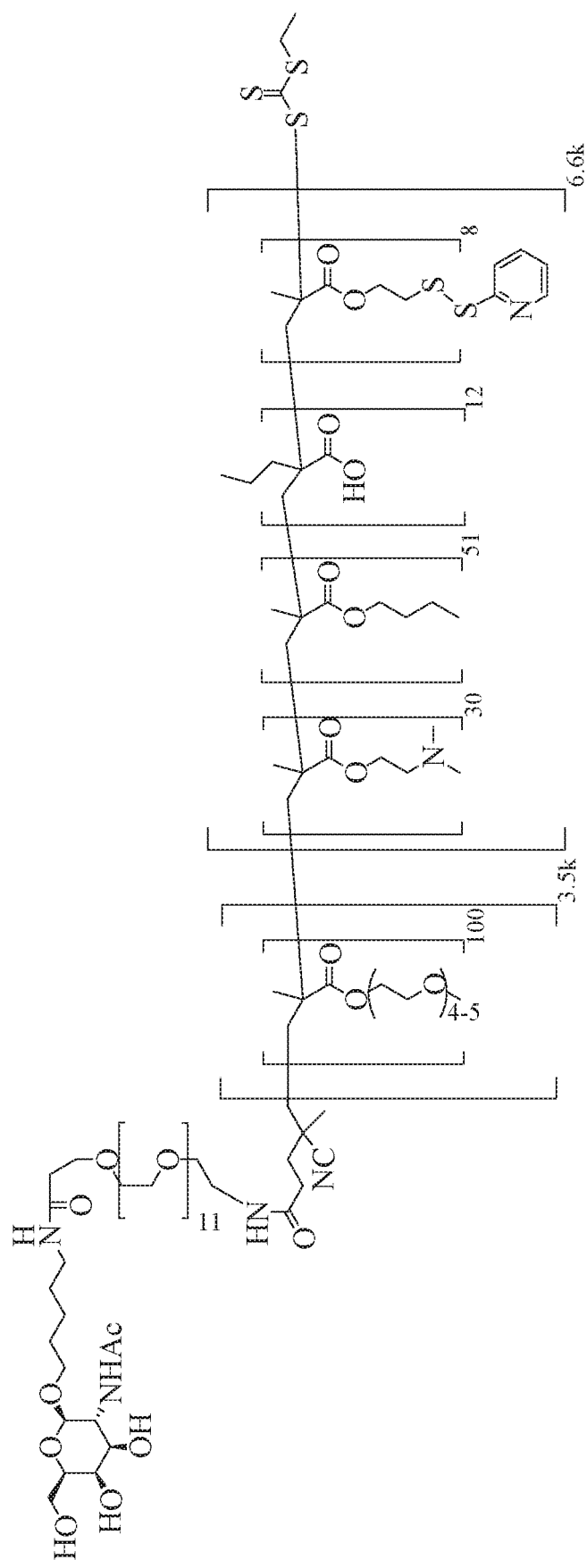
Figure 12B:
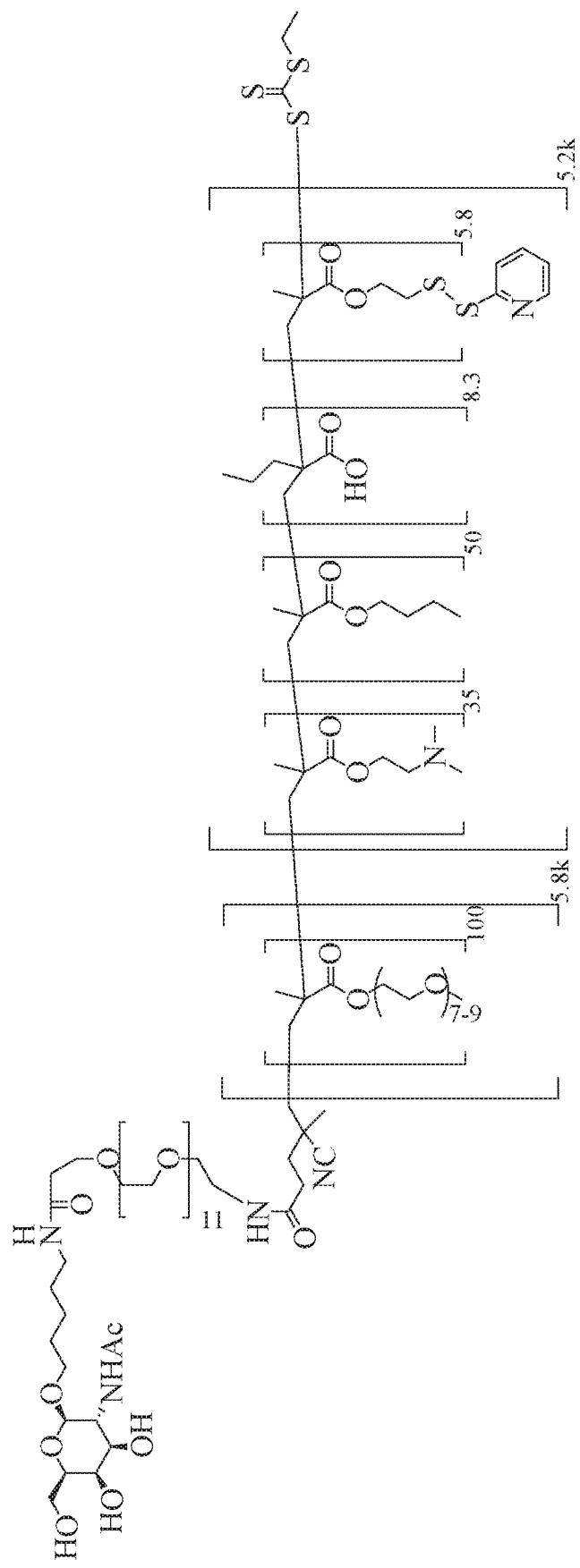
Figure 12C:
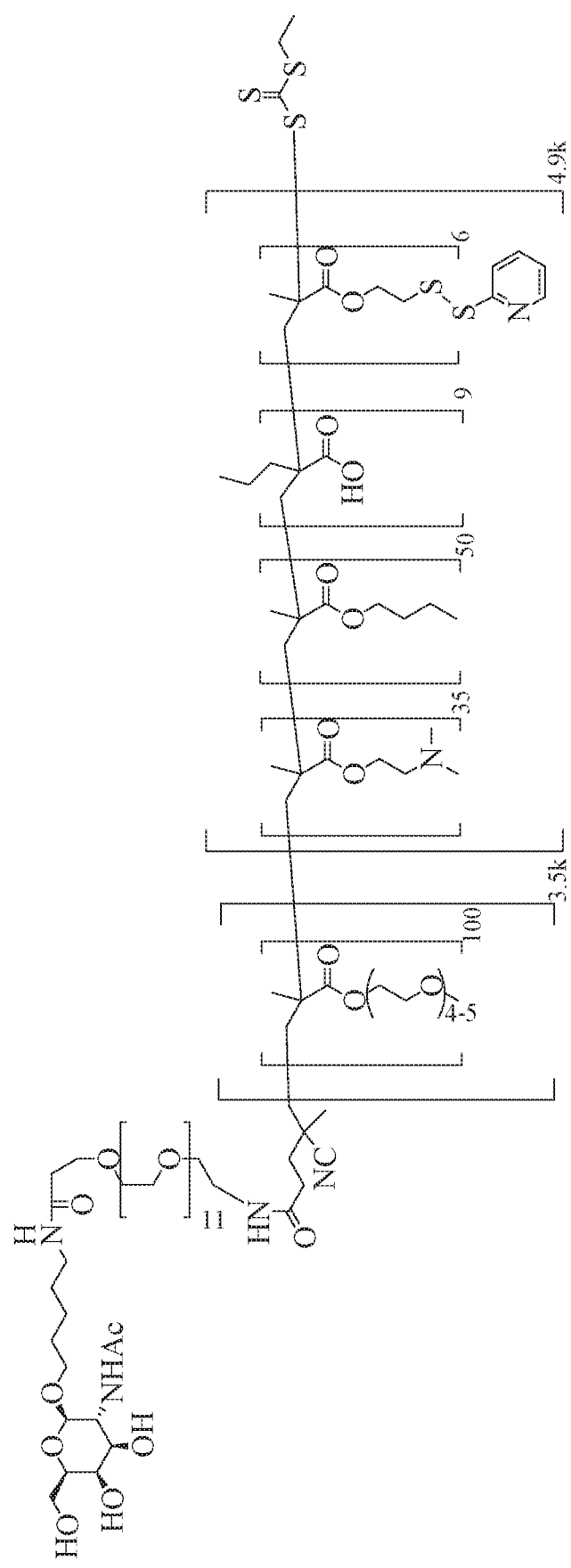
Figure 12C:
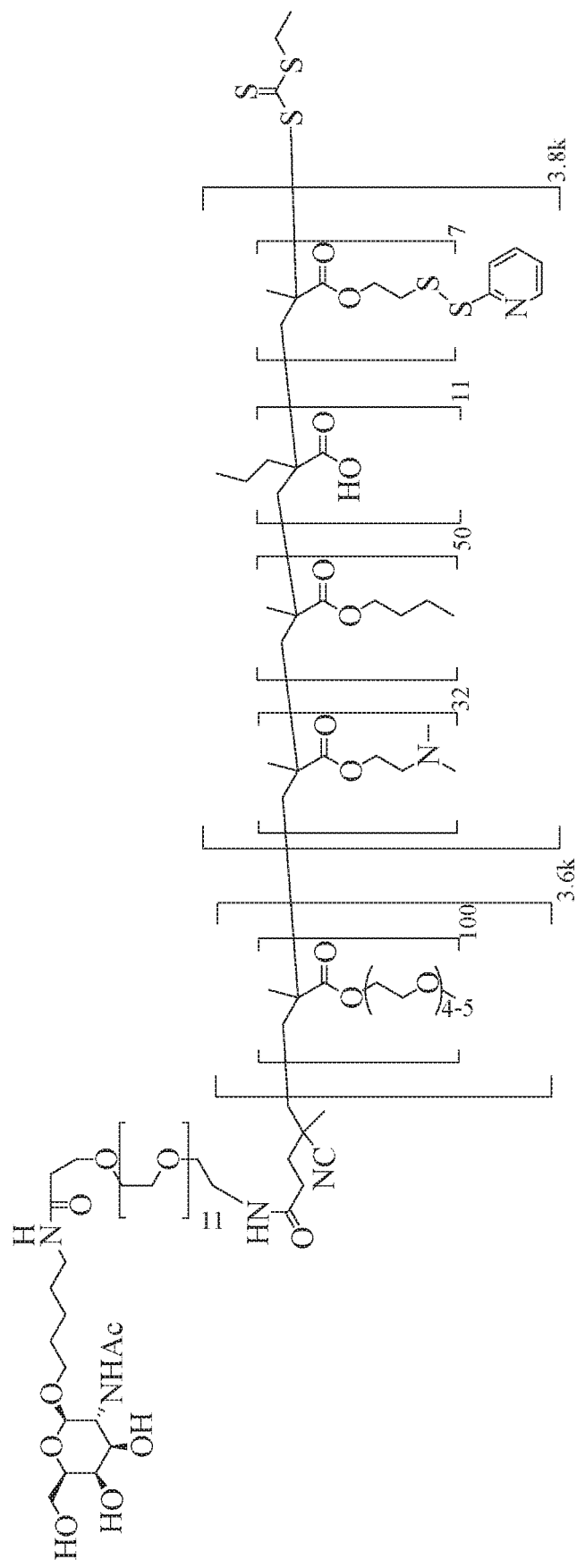

No significant changes were seen in alanine aminotransferase (ALT) levels upon the administration of formulations of si033 with polymer P6, si034 with polymer P6 or a combination of si033 and si034 with polymer P6 as shown in FIGS. 8 and 9.

Example 21: Synthesis of Macro-CTAs

By a process similar to that described in Example 8.1, the following chain transfer agents were prepared:

NAG-C5-PEG$_{36}$-ECT

NAG-C5-PEG$_{24}$-amido-PEG$_{24}$-ECT

2-Morpholinoethyl-amido-ECT

Boc-Aminoxy-PEG$_{11}$-ECT

Boc-Aminoxy-PEG$_{3}$-ECT.

Example 22. Synthesis of Polymer NAG-PEG0.6KDa-[PEGMA(4-5, 100%)]3.45KDa-b-[DMAEMA(35.8%)-BMA(47.5%)-PAA(9.2%)-PDSMA(7.5%)]6.6KDa (P11)

The synthesis of polymer P11 was conducted in two polymerization steps, a first block (conjugation block)-

TABLE 9

Study Details

Figure 13A:
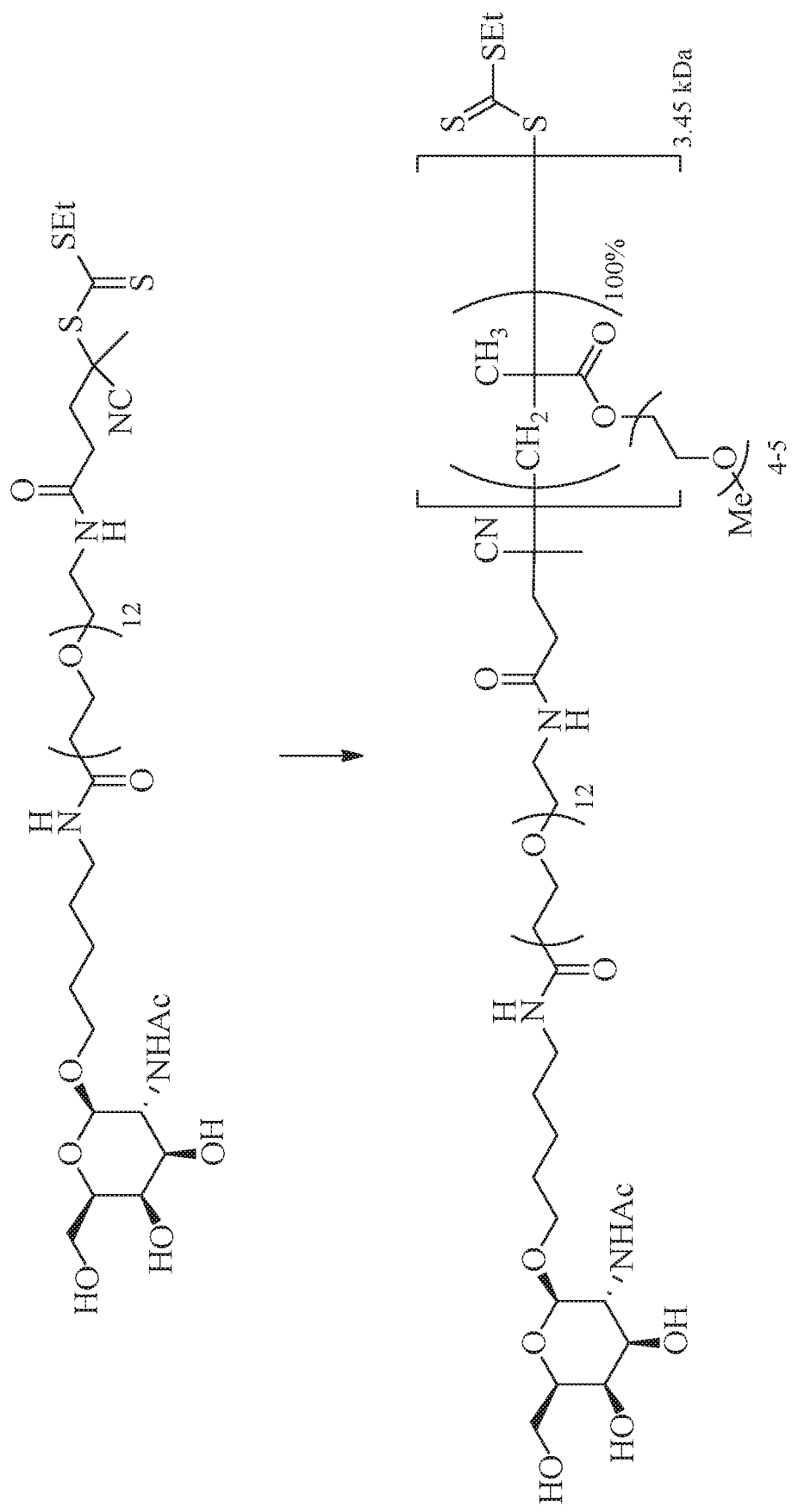
FIGS. 13A and 13B schematically depict the synthesis of an exemplary block copolymer in two polymerization steps: a first block (conjugation block) polymerization (FIG. 13A) and a second block (endosome release block) polymerization (FIG. 13B).
Figure 13B:
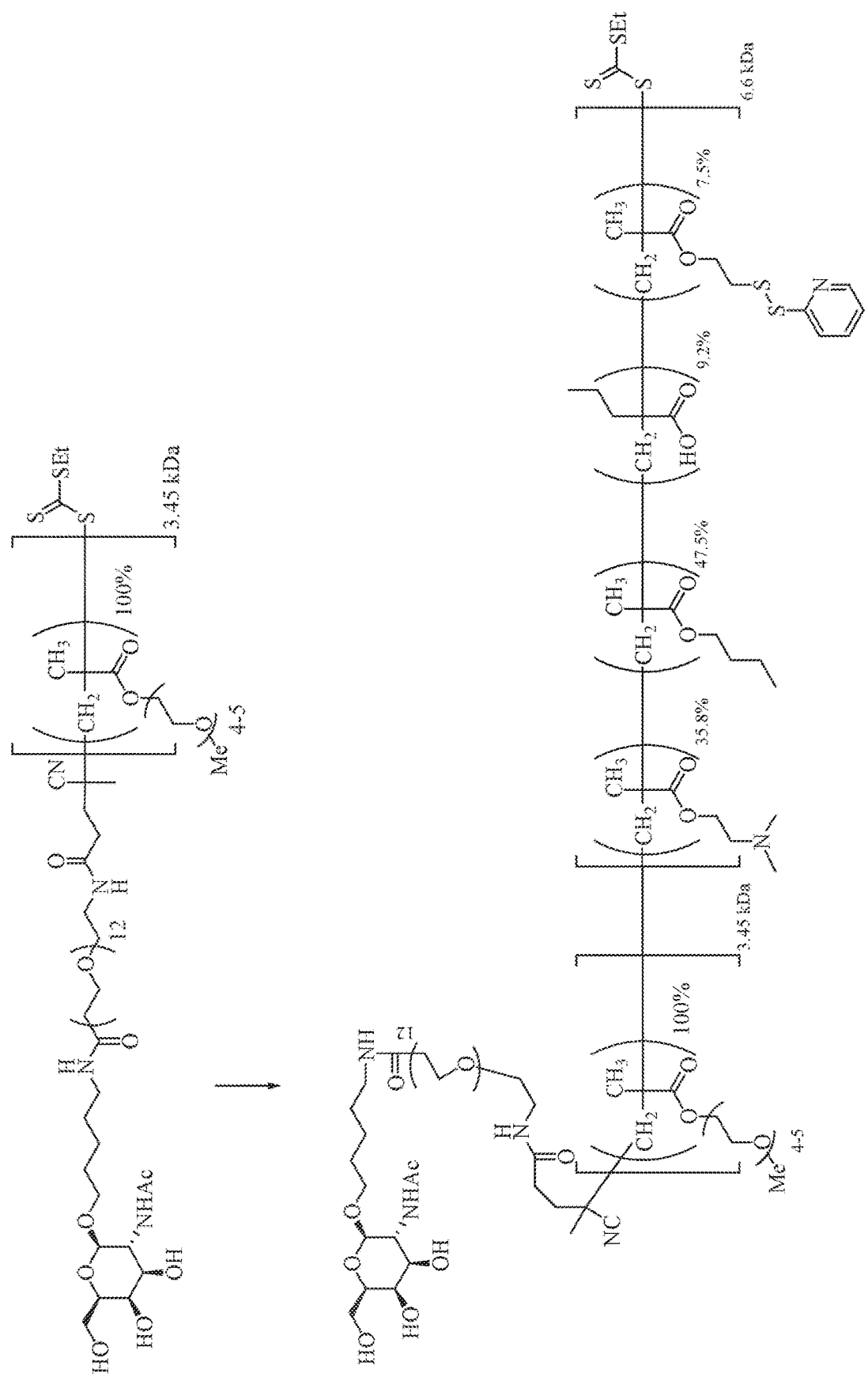

| Group | siRNA | siRNA ID | Polymer | Polymer (mg/kg) | siRNA (mg/kg) | # Doses | Sacrifice Timepoints | # Animals/ Group |
|---|---|---|---|---|---|---|---|---|
| 1 | β-catenin | si033 | PRX231-6 | 75 | 3 | 1 | 24 hr | 6 |
| 2 | | si033 | | 75 | 3 | 1 | 48 hr | 6 |
| 3 | | si033 | | 75 | 3 | 1 | 72 hr | 6 |
| 4 | | si033 | | 75 | 3 | 1 | 96 hr | 6 |
| 5 | | si033 | | 75 | 3 | 1 | 6 days | 6 |
| 6 | | si033 | | 75 | 3 | 1 | 10 days | 6 |
| 7 | MET | si034 | PRX231-6 | 75 | 3 | 1 | 24 hr | 6 |
| 8 | | si034 | | 75 | 3 | 1 | 48 hr | 6 |
| 9 | | si034 | | 75 | 3 | 1 | 96 hr | 6 |
| 10 | | si034 | | 75 | 3 | 1 | 6 days | 6 |
| 11 | | si034 | | 75 | 3 | 1 | 10 days | 5 |
| 12 | Combination of | si033, si034 | PRX231-6 | 75 | 1.5 each | 1 | 48 hr | 6 |
| 13 | β-catenin | si033, si034 | | 75 | 1.5 each | 1 | 96 hr | 6 |
| 14 | and MET | si033, si034 | | 75 | 1.5 each | 1 | 6 days | 6 |
| 15 | | si033, si034 | | 75 | 1.5 each | 1 | 10 days | 6 |
| 16 | Buffer | None | None | N/A | N/A | 1 | 72 hr | 5 |
| 17 | | None | | N/A | N/A | 1 | 10 days | 6 | polymerization (see FIG. 13A) and a second block (endosome release block) polymerization (see FIG. 13B).

First Block (Conjugation Block) Polymerization

TABLE 10

Reagent Table

| Reactant and Product | Lot Number | MW (g/mol) | Equiv. | mmol | Amount Calc. (mg) | Amount Experimental (mg) |
|---|---|---|---|---|---|---|
| NAG-PEG0.6KDa-ECT | MQ-03-12-2 | 1151.45 | 1 | 1.817708 | 2093 | 2093 |
| PEGMA4-5 | MKBN1112V | 300.0 | 15.5 | 28.17448 | 8452 | 8454.2 |
| AIBN (recrystallized Oct. 24, 2013) | 102413 | 164.21 | 0.05 | 0.090885 | 14.92 | c = 1.0703 mg/g Target AIBN soln = 13.9401 g, used 13.9402 g |
| DMF | DX1727-7 | 73.09 | n/a | n/a | 14380 | 14391.9 |

Polymer Synthesis

AIBN/DMF (13.9402 g of 1.0703 mg/g AIBN in DMF) was added to the CTA (2.093 g; 1.817708 mmol) in a 40 mL reaction vessel and mixed to dissolve the CTA. DMF was then added until the total weight of DMF was 14.3919 g. Then PEGMA4-5 (8454.2 mg, 28.18 mmol, filtered through aluminum oxide [activated, basic, Brockmann I]) was added. This mixture was vortexed for several minutes to give a homogeneous stock solution and transferred to a 50 mL round-bottom flask. A $T_0$ sample (40 µL) was pulled and stored at −20° C. for monomer incorporation determination. The solution was then cooled to 0° C. using an ice bath. The solution was degassed by bubbling nitrogen into the solution for 47 min (maintained at 0° C.), followed by flushing the head space with nitrogen for an additional 4 min (total nitrogen time of 51 min). The flask was moved to room temperature for 10 min and then placed in a pre-heated oil bath (stir speed was set at 350 rpm, internal temperature=65° C. (thermocouple)).

After 1 h 45 min, the reaction was stopped by introducing oxygen (three needles inserting into the rubber septa) followed by opening the cap and then placing the flask in an ice bath. A $T_f$ sample (40 µL) was pulled and stored at −20° C. for monomer incorporation determination.

Polymer Purification

The reaction solution was diluted with MeOH (~60 mL), transferred to dialysis membranes (Spectrum Labs, Spectrum Spectra/Por*6 Dialysis Membrane Tubing MWCO: 2000) and dialyzed against MeOH (5×4000 mL) for 7 days. Samples were taken for GPC, HPLC, and NMR analyses.

Analytical Testing:

NMR Analysis

A small aliquot of the dialysis solution (ca. 500-1000 µL) was withdrawn from the dialysis tubing and placed into a tared vial. The solution was then evaporated using a rotary evaporator. Once the solvents were removed the vial was transferred to a high vacuum line and placed under high vacuum for 48 h. Then the compound (24 mg) was dissolved in 800 µL methanol-d4 and a proton NMR spectrum was collected.

The $^1$H NMR of polymer P11 block 1 indicated a polymer was prepared by incorporating PEGMA (4-5). The $^1$H NMR was consistent for proposed structure.

Analytical GPC Analysis

Overview

Polymers were analyzed by gel permeation chromatography (GPC) in DMF/LiBr with a triple detection method using a Viscotek system (GPCmax VE-2001). The GPC analysis used multiple detectors, including a Viscotek RI detector, S3210 UV/Vis, and 270 Dual Detector (light scattering). The 270 Dual Detectors contains a differential viscometer detector, an advanced low angle (7°) light scattering detector (LALS) and right angle light scattering detector (RALS). OmniSEC software was used to calculate the absolute molecular weight of the polymer.

Procedure

Sample Preparation

1. Polystyrene GPC Standard (Polystyrene, 20,000, analytical standard for GPC, Aldrich (Fluka) #81407).
2. Dissolve the GPC standard polymer in degassed DMF/1% LiBr (~3 mg/ml, record actual concentration).
3. Filter through a 0.45 µm nylon filter (Acrodisk 13 mm syringe filter, Pall Life Sciences #4426T) into an autosampler vial.

Polymer samples

1. Dissolve polymer sample in degassed DMF/LiBr (~8 mg/ml, record actual concentration).
2. Filter through a 0.45 µm nylon filter (Acrodisk 13 mm syringe filter, Pall Life Sciences #4426T) into an autosampler vial. Columns and Settings Columns and Parameters:

1. Guard Column: PolarGel-M, 50×7.5 mm (P/N: PL1117-1800)
2. Columns: 2×PolarGel-M, 300×7.5 mm (P/N: PL1117-6800) (PolarGel-M GPC columns are packed with low swell, macro porous copolymer beads that have a surface of balanced polarity, comprising hydrophobic and hydrophilic components, Polymer Labs (Agilent).
3. Eluent: DMF/1% LiBr (w/v), filtered through a 0.2 µm Nylon Filter
4. Flow Rate: 0.7 mL/min
5. Injection Volume: 60, 80, 100 and 120 µL
6. Column Temperature: 50° C.
7. Viscotek detectors: S3210 UV/Vis, RI detector, and 270 Dual Detector
8. Analysis run time=40 min.

Polymer Analysis

One injection of polystyrene (20 KDa, 100 µt, GPC standard polymer) is needed for the polymer analysis. The GPC data is worked up by picking baseline and polymer peaks in the RI and RALS detector traces using OmniSEC software. In the OmniSEC software, a new method is written based on the Polystyrene (20 KDa) standard analysis:
1. Method—New—Blank—Multidetectors—Homopolymers
2. Choose Detectors: RI and RALS
3. Enter Standard Name: Polystyrene (20 KDa)
4. Enter Standard Name
5. RI for solvent=1.43
6. Save method
7. Calibrate method
8. Five injections of each PRX polymer are needed for the polymer analysis (60, 80, 100, 120, and 140 μL).
   a. Open traces for the five polymer injections in the OmniSEC software
   b. Fix baseline and peak pick for each sample
   c. Close all files
   d. Determine Polymer dn/dc
   i. In the OmniSEC software, open trendview: tools—trendview
   ii. Set view to dndc
   iii. Open method from step 4.3aV above
   iv. Open polymer series: file—open
   v. Calculate dn/dc
   vi. Record polymer dn/dc value
9. Determine Polymer Molecular Weight and Polydispersity (PDI)
   In the OmniSEC software, open the polymer trace (100 μL injection)
   In the method, enter the polymer dn/dc value from step 4.3bIIv above
   Calculate the molecular weight ($\Sigma$)
   Record values for Mn, Mw, and PDI. Reported values for PRX polymers will be Mn values.

Analytical GPC Results

Mn=4,600 g/mol, PDI=1.12, dn/dc=0.05932

Monomer Incorporation by HPLC

The analysis of the HPLC results indicate the following monomer incorporation ratios in the polymer: NAG-PEG$_{12}$-[PEGMA$_{100}$%]$_{3.45k}$. The overall conversion of this polymerization reaction was 23.4% with PEGMA incorporation at 100%.

TABLE 11

Monomer Incorporation Calculations

|  | Peak Area 1 | Peak Area 2 | Peak Area 3 | | |
| --- | --- | --- | --- | --- | --- |
| PEGMA 4-5 | 7761198 | 7911522 | 7867785 | | |
| PDSMA | 0 | 0 | 0 | | |
| PEGMA 4-5 | 6032832 | 6040105 | 5957546 | | |
| PDSMA | 0 | 0 | 0 | | |
| % conversion PEGMA 4-5 | 22.27 | 23.65 | 24.28 | | |
| % conversion BPAM | | | | | |
| % conversion PDSMA | 0.00 | 0.00 | 0.00 | | |
| mol PEGMA 4-5 inc. | 0.2227 | 0.2365 | 0.2428 | | |
| mol BPAM inc. | 0 | 0 | 0 | | |
| mol PDSMA inc. | 0 | 0 | 0 | Overall % Conversion | Std Dev |
| Total mol in Polymer | 0.2227 | 0.2365 | 0.2428 | 23.40 | 1.03 |
|  | | | | Average | Std Dev |
| % PEGMA 4-5 (in polymer) | 100.00 | 100.00 | 100.00 | 100.00 | 0.00 |
| % BPAM (in polymer) | 0.00 | 0.00 | 0.00 | 0.00 | 0.00 |
| % PDSMA (in polymer) | 0.00 | 0.00 | 0.00 | 0.00 | 0.00 |

| PEGMA 4-5 Feed | BPAM Feed | PDSMA Feed |
| --- | --- | --- |
| 1 | 0 | 0 |

Isolation of the Final Polymer

Once the final GPC analysis was determined, then the dialysis solution was transferred to a 40 mL reaction vial. The solvent was removed under reduced atmosphere followed by high vacuum (approx. 20 h) to afford 1.980 g of polymer (yield 23.7%).

Second Block (Endosome Release Block) Polymerization

TABLE 12

Reagent Table

| Reactant and Product | Lot Number | FW (g/mol) | D | Eq | mmol | Amt (mg) | Actual Amt (mg) |
| --- | --- | --- | --- | --- | --- | --- | --- |
| Macro-CTA | DR-01-53 | 4600.00 | | 1 | 0.430435 | 1980 | 1980 |

TABLE 12-continued

Reagent Table

| Reactant and Product | Lot Number | FW (g/mol) | D | Eq | mmol | Amt (mg) | Actual Amt (mg) |
|---|---|---|---|---|---|---|---|
| PAA | SRG-255-169C | 114.14 | 0.951 | 28.5 | 12.26739 | 1400.20 | 1419.3 |
| DMAEMA | 11024JE | 157.22 | 0.933 | 28.5 | 12.26739 | 1928.68 | 1924 |
| BMA | MKBL3019V | 142.20 | 0.894 | 56 | 24.10435 | 3427.64 | 3437.7 |
| PDMSA | MQ-03-22-vial 4 | 255.4 |  | 6 | 2.582609 | 659.49 | 663.3 |
| AIBN | 102413 | 164.21 |  | 0.1 | 0.043043 | 7.07 | c = 1.0910 mg/g Target AIBN soln = 6.4801 g, used 6.4837 g |
| DMF | DX1727-7 | 73.09 | 0.944 | n/a | n/a | 14060 | 14148.6 |

Monomer Analytical Analysis

PDSMA was analyzed by GPC immediately prior to use to confirm that no high molecular weight polymer was present as a result of homopolymerization.

Polymer Synthesis

AIBN/DMF solution (6.4837 g/g; 1.0910 mg/g AIBN in DMF) was added to the macro-CTA (polymer P11 block 1, 1.980 g) in a 40 mL reaction vessel. DMF was then added until the total weight of DMF was 14.1486 g and the sample was mixed to dissolve the macro-CTA. BMA (3437.7 mg, 24.10435 mmol, filtered through Aluminum oxide [activated, basic, Brockmann I]), PAA (1419.3 mg, 12.2674 mmol, monomer not purified, 2-propylacrylic acid, lot # SRG-255-169C), DMAEMA (1924 mg, 12.2674 mmol, filtered through Aluminum oxide [activated, basic, Brockmann I], and PDSMA (663.3 mg, 2.5826 mmol, batch MQ-03-22-vial 4) were added to the reaction solution. The mixture was vortexed for several minutes to give a homogeneous stock solution and transferred to a 50 mL round-bottom flask. A $T_0$ sample (40 µL) was pulled and stored at −20° C. for monomer incorporation determination. The solution was then cooled to 0° C. using an ice bath. The solution was degassed by bubbling nitrogen into the solution for 46 min (maintained at 0° C.), followed by flushing the head space with nitrogen for an additional 5 min (total nitrogen time of 51 min). Then the flask was sealed with parafilm and placed into a pre-heated oil bath (stirring speed was 350 rpm, internal temperature=59° C. (thermocouple)).

After 8 h, the reaction was stopped by introducing oxygen (three needles inserting into the rubber septa) followed by opening the cap and then placing the flask in an ice bath. A $T_f$ sample (40 µL) was pulled and stored at −20° C. for monomer incorporation determination.

The reaction was then diluted with approximately 35 mL of acetone and precipitated into a stirred mixture of ether/hexanes (1:3 v/v) in 50 mL centrifuge tubes (10) first and then again into a large beaker with 900 mL ether/hexanes (1:3 v/v).

Polymer Purification

The polymer dissolved with MeOH (100 mL), transferred to four individual dialysis membranes (Spectrum Labs, Spectrum Spectra/Por*6 Dialysis Membrane Tubing MWCO: 2,000) and dialyzed against methanol (4×8000 mL; two 4 liter beakers) for 5 days. After the dialysis against methanol, it was dialyzed against nanopure water using the same membrane (×7 over 5 h). When the dialysis was complete, the solution was transferred to 10 individual 20 mL tared vials, frozen (liquid nitrogen followed by dried ice), and lyophilized for 6 days to afford 3.77 g of the final product (yield=78.2%). The final product was analyzed by UVNis (for PDS content of the polymer, in DMF+TCEP), NMR (in methanol-d4), and GPC (DMF+LiBr). The final product was stored in glass vials with rubber septum that were purged with argon and sealed with parafilm. The vials were stored at −20° C.

Analytical Testing $^1$H NMR of Polymer P11 Block 1—Block 2 $CD_3OD$

NMR results were consistent with proposed structure. There was no evidence of remaining vinyl monomers as indicated by the lack of signals between 5.4 and 6.5 ppm.

Analytical GPC

Results: Mn=11,200 g/mol (100 µL injection), PDI=1.57, dn/dc=0.0624

Monomer Incorporation by HPLC

Analysis of the monomer incorporation by HPLC results indicated the average overall conversion of this polymerization reaction was 30.24% with DMAEMA incorporation at 35.8%, PAA incorporation at 9.2%, BMA incorporation at 47.5%, and PDSMA incorporation at 7.5%. The analysis of the HPLC indicated the following monomer incorporation ratios in the polymer: $NAG\text{-}PEG_{12}\text{-}[PEGMA_{100\%}]_{3.45k}\text{-}[BMA_{47.5\%}\text{-}PAA_{9.2\%}\text{-}DMAEMA_{35.8\%}\text{-}PDSMA_{7.5\%}]_{6.6k}$.

TABLE 13

| Monomer Incorporation Calculations | | | | |
|---|---|---|---|---|
| Enter monomer feed ratios | | | | |
| DMAEMA Feed | PDSMA Feed | PEGMA Feed | PAA Feed | BMA Feed |
| 0.24 | 0.05 | 0 | 0.24 | 0.47 |
| 0.24 | 0.05 | 0 | 0.24 | 0.47 |

Enter peak areas for each monomer; 3 injections required-- injection 4 may be left blank

| | To inj 4 | Peak Areas To inj 2 | To inj 3 | To inj 1 |
|---|---|---|---|---|
| DMAEMA | 3242224 | 3277249 | 3047662 | |
| PDSMA | 1286889 | 1288943 | 1258209 | |
| PAA | 3245906 | 3256478 | 3189947 | |
| BMA | 6297454 | 6256387 | 6229199 | |

| | Tf inj 4 | Tf inj 2 | Tf inj 3 | Tf inj 1 |
|---|---|---|---|---|
| DMAEMA | 1684539 | 1764750 | 1793265 | |
| PDSMA | 684450 | 706950 | 711990 | |
| PAA | 2778065 | 2915338 | 2867467 | |
| BMA | 4215662 | 4440591 | 4387927 | |
| D % conversion | 48.04 | 46.15 | 41.16 | |
| PDS % | 46.81 | 45.15 | 43.41 | |
| P % conversion | 14.41 | 10.48 | 10.11 | |
| B % conversion | 33.06 | 29.02 | 29.56 | |
| mol D inc. | 0.1153 | 0.1108 | 0.0988 | |
| mol PDS inc | 0.0234 | 0.0226 | 0.0217 | |

| | | | | Overall % Conversion | Std Dev |
|---|---|---|---|---|---|
| mol P inc. | 0.0346 | 0.0251 | 0.0243 | | |
| mol B inc. | 0.1554 | 0.1364 | 0.1389 | | |
| Total mol inc. | 0.3287 | 0.2949 | 0.2837 | 30.24 | 2.34 |

| | | | | Average | Std Dev |
|---|---|---|---|---|---|
| % D (in polymer) | 35.1 | 37.6 | 34.8 | 35.8 | 1.5 |
| % PDS (in Poly) | 7.1 | 7.7 | 7.7 | 7.5 | 0.3 |
| % P (in polymer) | 10.5 | 8.5 | 8.6 | 9.2 | 1.1 |
| % B (in polymer) | 47.3 | 46.3 | 49.0 | 47.5 | 1.4 |

Polymer PDS Content

Background Information:

Polymer molecular weight was calculated by analytical GPC. Monomer incorporation was determined by analytical HPLC and was used to determine the theoretical amount of PDS groups incorporated into the polymer during polymer synthesis (PDS/polymer chain). Actual PDS content was determined by UV/Vis spectroscopy following disulfide reduction and liberation of pyridine-2-thione.

The molar absorbtivity of pyridine-2-thione was determined to be $\epsilon=5,695$ $M^{-1}cm^{-1}$ in DMF with $\lambda_{max}=370$ nm. At $\lambda=370$ nm, there was nearly negligible absorption from the CTA or polymer.

Procedure

PRX polymer stock solution at 5-8 mg/mL in DMF was prepared. Actual concentration was recorded. To 200 µL of polymer solution in an eppendorf tube, 6 µL of 0.5 M TCEP solution (Sigma #646547) was added. Following about a 5 min reduction, the solution was spun for about 1 min at max RPM to pellet precipitate.

Absorption was read on a Nanodrop ND-1000 spectrophotometer ($\lambda=370$ nm, path length=1 mm).

Analysis

The amount of pyridyl-2-thione (mol/1) was determined according to the following formula: pyridyl-2-thione (mol/1)=(Abs 370/569.5 $M^{-1}mm^{-1}$).

The polymer concentration used in the assay was calculated according to the following formula: Polymer analysis concentration (mg/ml)=(concentration of PRX polymer stock solution*0.2 ml)/0.206 ml.

The expected amount of pyridyl-2-thione (mol/1) was determined according to the following formula: Theoretical pyridyl-2-thione (mol/1)=Polymer analysis concentration (mg/ml)/PRX Polymer Mn (g/mol)*Theoretical PDS/polymer chain.

% of PDS groups found=[determined pyridyl-2-thione (mol/1)/Theoretical pyridyl-2-thione (mol/1)]*100.

Actual PDS/polymer chain=determined pyridyl-2-thione (mol/1)/Theoretical pyridyl-2-thione (mol/1)]*Theoretical PDS/polymer chain.

Results of analysis of the PDS content of the polymer indicated 2.28 PDS (62% of theoretical) groups per chain.

Conclusions

Polymer P11 was synthesized and released with the following specifications: NAG-PEG$_{12}$-[PEGMA$_{100\%}$]$_{3.45k}$-[BMA$_{47.5\%}$-PAA$_{9.2\%}$-DMAEMA$_{35.8\%}$-PDSMA$_{7.5\%}$]$_{6.6k}$.

By similar methods, the following polymers were synthesized according to the following conditions shown in Tables 14-21, below.

a. Polymer P12: NAG-PEG$_{36}$-[PEGMA300,100%]$_{3.5k}$-b-[BMA$_{50\%}$-PAA$_{9\%}$-DMAEMA$_{35\%}$-PDSMA$_{6\%}$]$_{4.9k}$

TABLE 14

| P12 | Block 1 | Block 2 |
|---|---|---|
| [M/CTA/I] | [15.5/1/0.05] | [120.5/1/0.1] |
| [concentration] | 0.95M | 2.3M |
| Time | 2 h 50 m | 8 h 35 m |
| Internal temp | 65-66° C. | 58-59° C. |

CTA = NAG-C$_5$-PEG$_{36}$-ECT;
I = AIBN b. Polymer P13: NAG-PEG$_{24}$-amido-PEG$_{24}$-[PEGMA300,100%]$_{3.6k}$-b-[BMA$_{50\%}$-PAA$_{11\%}$-DMAEMA$_{32\%}$-PDSMA$_{7\%}$]$_{3.8k}$

TABLE 15

| P13 | Block 1 | Block 2 |
|---|---|---|
| [M/CTA/I] | [15.5/1/0.05] | [123/1/0.1] |
| [concentration] | 0.68M | 2.84M |
| Time | 3 h 45 m | 10 h 15 m |
| Internal temp | 65-66° C. | 58-59° C. |

CTA = NAG-C$_5$-PEG$_{24}$-amido-PEG$_{24}$-ECT;
I = AIBN c. Polymer P14: NAG-PEG$_{12}$-[PEGMA500 (100%)]$_{5.8k}$-b-[DMAEMA$_{35\%}$-BMA$_{50\%}$-PAA$_{8\%}$-PDSMA$_{6\%}$]$_{5.2k}$

TABLE 16

| P14 | Block 1 | Block 2 |
|---|---|---|
| [M/CTA/I] | [15.5/1/0.05] | [123.9/1/0.1] |
| [concentration] | 1.0M | 2.36M |
| Time | 2 h | 10 h |
| Internal temp | 65-66° C. | 58-59° C. |

CTA = NAG-C$_5$-PEG$_{12}$-ECT;
I = AIBN d. Polymer P15: BocNO-PEG$_{11}$[PEGMA (300, 100%)]$_{3.8k}$-b-[DMAEMA$_{32\%}$-BMA$_{47\%}$-PAA$_{14\%}$-PDSMA$_{7\%}$]$_{4.0k}$

TABLE 17

| P15 | Block 1 | Block 2 |
|---|---|---|
| [M/CTA/I] | [16/1/0.05] | [120/1/0.1] |
| [concentration] | 1.16M | 2.39M |
| Time | 1 h 45 m | 5 h 25 m |
| Internal temp | 65-66° C. | 58-59° C. |

CTA = Boc-Aminoxy-PEG$_{11}$-ECT;
I = AIBN e. Polymer P16: BOCNO-PEG$_{11}$-[PEGMA (300, 100%)]$_{3.8k}$-b-[DMAEMA$_{33\%}$-BMA$_{46\%}$-PAA$_{14\%}$-PDSMA$_{7\%}$]4.8k

TABLE 18

| P16 | Block 1 | Block 2 |
|---|---|---|
| [M/CTA/I] | [16/1/0.05] | [119.7/1/0.1] |
| [concentration] | 1.16M | 2.33M |
| Time | 1 h 45 m | 7 h |
| Internal temp | 65-66° C. | 58-59° C. |

CTA = Boc-Aminoxy-PEG$_{11}$-ECT;
I = AIBN f. Polymer P17: BOCNO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$

TABLE 19

| P17 | Block 1 | Block 2 |
|---|---|---|
| [M/CTA/I] | [15.5/1/0.05] | [119.6/1/0.1] |
| [concentration] | 1.01M | 2.58M |
| Time | 2 h 5 m | 10 h |
| Internal temp | 65-66° C. | 58-59° C. |

CTA = Boc-Aminoxy-PEG$_{11}$-ECT;
I = AIBN g. Polymer P18: ECT-[PEGMA (300, 58%)-TFPMA$_{42\%}$]$_{5.14k}$-b-[DMAEMA$_{31\%}$-BMA$_{49\%}$-PAA$_{12\%}$-PDSMA$_{8\%}$]$_{5.03k}$

TABLE 20

| P18 | Block 1 | Block 2 |
|---|---|---|
| [M/CTA/I] | [29.3/1/0.05] | [121/1/0.1] |
| [concentration] | 1.6M | 2.31M |
| Time | 2 h 15 m | 8 h 15 m |
| Internal temp | 65° C. | 58-59° C. |

CTA = ECT;
I = AIBN h. Polymer P19: NAG-PEG$_{12}$-[PEGMA (300, 73%)-TFPMA$_{27\%}$]$_{4.55k}$-b-[DMAEMA$_{36\%}$-BMA$_{46\%}$-PAA$_{10\%}$-PDSMA$_{7\%}$]$_{5.33k}$

TABLE 21

| P19 | Block 1 | Block 2 |
|---|---|---|
| [M/CTA/I] | [20/1/0.05] | [121/1/0.1] |
| [concentration] | 0.97M | 2.45M |
| Time | 2 h 5 m | 9 h |
| Internal temp | 65° C. | 58-59° C. |

CTA = NAG-C$_5$-PEG$_{12}$-ECT;
I = AIBN g. Polymer P30: BOCNO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$

TABLE 22

| P30 | Block 1 | Block 2 |
|---|---|---|
| [M/CTA/I]$^c$ | [16/1/0.05] | [120.5/1/0.1] |
| [concentration] | 31-wt % monomer in solvent | 2.57M |

TABLE 22-continued

| P30 | Block 1 | Block 2 |
|---|---|---|
| Time | 4 h | 10 h 15 m |
| Internal temp (approx.) | 65-66° C. | 58-59° C. |

$^c$M = PEGMA 1000;
CTA = BOC-Aminoxy-PEG$_{11}$-ECT;
I = AIBN h. Polymer P51: NAG-PEG$_{36}$-[PEGMA (500, 100%)]$_{6.19k}$-b-[PMAEMA$_{31.6\%}$-BMA$_{48.4\%}$-PAA$_{13.1\%}$-PDSMA$_{6.8\%}$]$_{4.3k}$

TABLE 23

| P51 | Block 1 | Block 2 |
|---|---|---|
| [M/CTA/I]$^c$ | [15.5/1/0.05] | [121/1/0.1] |
| [concentration] | 0.95M | 2.38M |
| Time | 3 h 45 m | 8 h |
| Internal temp (approx.) | 65-66° C. | 58-59° C. |

$^c$M = PEGMA 500;
CTA = NAG-C$_5$-PEG$_{36}$-ECT;
I = AIBN i. Polymer P52: NAG-PEG$_{36}$-[PEGMA (500, 100%)]$_{6.19k}$-b-[PMAEMA$_{30.8\%}$-BMA$_{50.8\%}$-PAA$_{11.6\%}$-PDSMA$_{6.8\%}$]$_{3.5k}$

TABLE 24

| P52 | Block 1 | Block 2 |
|---|---|---|
| [M/CTA/I]$^c$ | [15.5/1/0.05] | [121/1/0.1] |
| [concentration] | 0.95M | 2.34M |
| Time | 3 h 45 m | 4 h 50 m |
| Internal temp (approx.) | 65-66° C. | 58-59° C. |

$^c$M = PEGMA 500;
CTA = NAG-C$_5$-PEG$_{36}$-ECT;
I = AIBN j. Polymer P53: NAG-PEG$_{48}$-[PEGMA (300, 100%)]$_{3.8k}$-b-[DMAEMA$_{31.4\%}$-BMA$_{49.3\%}$-PAA$_{9\%}$-PDSMA$_{9\%}$]$_{6.3k}$

TABLE 25

| P53 | Block 1 | Block 2 |
|---|---|---|
| [M/CTA/I]$^c$ | [15.5/1/0.05] | [108.4/1/0.1] |
| [concentration] | 0.86M | 2.32M |
| Time | 3 h 50 m | 15 h 30 m |
| Internal temp (approx.) | 65-66° C. | 58-59° C. |

$^c$M = PEGMA 300;
CTA = NAG-C$_5$-PEG$_{48}$-ECT;
I = AIBN k. By similar process, the following tri-NAG polymers were prepared. Monomer % listed is the % monomer in the polymerization reaction
  i. Polymer P54: Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{4.2k}$.
  ii. Polymer P55: Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{3.2k}$.
  iii. Polymer P56: Tri-NAG-PEG$_{12}$-[PEGMA(300, 80%)-PDSMA$_{10\%}$-BPAM$_{10\%}$]$_{6.1k}$-[BMA$_{50\%}$-PAA$_{25\%}$-DMAEMA$_{25\%}$]$_{4.9k}$.
  iv. Polymer P57: Tri-NAG-PEG$_{12}$-[PEGMA(300, 80%)-PDSMA$_{10\%}$-BPAM$_{10\%}$]$_{7k}$-[BMA$_{50\%}$-PAA$_{25\%}$-DMAEMA$_{25\%}$]$_{27.8k}$.

Example 23. Procedure for Synthesis of Polymer-Cationic Peptide Conjugates

In the reaction vial, the polymer was dissolved in solvent (MeOH or DMF) at a concentration of 10 mM polymeric PDS, to which a stir bar was added. The resulting solution was stirred at moderate speed on a stir plate. Concurrently, peptide was dissolved in solvent (MeOH or DMF) at an approximate concentration of 10 mM. The concentration of peptide thiol was then determined by Ellman's assay. Using the thiol concentration determined from Ellman's assay, the peptide stock solution was then adjusted to twice the reaction concentration by adding additional solvent. The conjugation reaction was then conducted by slowly (~2.5 mL/min) adding an appropriate volume (to afford the desired amount of peptide/polymer) of the peptide stock solution to the polymer solution in the reaction vessel, while stirring. After the entire amount of peptide had been added, the reaction was allowed to proceed until the peptide had been consumed. Progress of the conjugation was monitored by HPLC for release of pyridal-2-thione and consumption of peptide.

The HPLC assay for release of pyridal-2-thione and consumption of peptide was as follows: a small aliquot (60 uL) of the reaction solution was diluted (H2O+0.1% TFA) so the peptide concentration was 0.7 mM. The diluted solution was then split into two equal volumes. Into one of the volumes a 10% volume of 0.5 M aqueous TCEP was added, and mixed to fully release pyridal-2-thione. Both aliquots were then applied to the HPLC with UV monitoring at 210 nm and 370 nm. Loss of UV signal in elution peak corresponding to free peptide in the untreated reaction solution was used to indicate reaction progression. Comparison of the UV signal corresponding to pyridal-2-thione between the untreated and TCEP treated samples was used to determine the effective conjugation of the peptide to the polymeric precursor. Completion of conjugation (consumption of >95% of the added peptide) was usually reached in less than 1 hr.

After the conjugation reaction had reached completion, dipyridal disulfide (1 eq to the amount of PDS groups on the original polymer) was added and the solution and incubated an additional 30 minutes. The reaction solution was then diluted 2 fold with acetone and the conjugate was precipitated with hexanes/Ether (3:1). The precipitate was collected by centrifugation and decanted. The pellet was then dissolved in acetone and the conjugate was washed by precipitation an additional two times. After the final precipitation, the isolated pellet was placed under high vacuum for 1 hour to further remove residual solvents. The dried conjugate was then dissolved in H$_2$0 and Lyophilized. Following lyophilization, the product was weighed to determine the yield and a small fraction (~5 mg) was taken and dissolved in MeOH (100 mg/mL) then diluted with H$_2$O+0.1% TFA to approximately 1 mg/mL of total peptide. The resulting solution was analyzed by HPLC to analyze for any peptide species.

Analysis of the final material includes the % peptide loading on the polymer, the amount of peptide/polymer chain, formation of peptide side products (peptide dimer), and final amount of unconjugated peptide in the final lyophilized conjugate.

According to the above procedure the following polymer-peptide conjugates were prepared:

Polymer P20 is the $CK_{10}NH_2$ conjugate of NAG-PEG$_{12}$-[PEGMA (300, 100%)]$_{3.45k}$-b-[BMA$_{47.5\%}$-PAA$_{9.2\%}$-DMAEMA$_{35.8\%}$-PDSMA$_{7.5\%}$]$_{6.6k}$—at 0.80 peptides/polymer;

Polymer P21 is the $CK_{10}NH_2$ conjugate of: NAG-PEG$_{12}$-[PEGMA500 (100%)]$_{5.8k}$-b-[DMAEMA$_{35\%}$-BMA$_{50\%}$-PAA$_{8\%}$-PDSMA$_{6\%}$]$_{5.2k}$—at 1.06 peptides/polymer;

Polymer P22 is the $CK_{10}NH_2$ conjugate of NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$—at 0.96 peptides/polymer;

Polymer P23 is the $CK_{10}NH_2$ conjugate of NAG-PEG$_{24}$-amido-PEG$_{24}$-[PEGMA300, 100%]$_{3.6k}$-b-[BMA$_{50\%}$-PAA$_{11\%}$-DMAEMA$_{32\%}$-PDSMA$_{7\%}$]$_{3.8k}$—at 0.94 peptides/polymer;

Polymer P24 is the $CK_{10}NH_2$ conjugate of NAG-C5-PEG$_{24}$-amido-PEG$_{24}$-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$—at 0.69 peptides/polymer;

Polymer P25 is the $CK_{10}NH_2$ conjugate of NAG-C5-PEG5k-Ph-aldehyde(oxime)NO-PEG$_{11}$-[PEGMA (300, 100%)]$_{3.8k}$-b-[DMAEMA$_{32\%}$-BMA-$_{47\%}$-PAA$_{14\%}$-PDSMA$_{7\%}$]$_{4.0k}$—at 0.75 peptides/polymer;

Polymer P26 is the $CK_{10}NH_2$ conjugate of ECT-[PEGMA (300, 58%)-NAG-C5-PEG$_{36}$ (42%)]$_{19.9k}$-b-[DMAEMA$_{31\%}$-BMA$_{49\%}$-PAA$_{12\%}$-PDSMA$_{8\%}$]$_{5.03k}$—at 0.48 peptides/polymer;

Polymer P27 is the $CK_{10}NH_2$ conjugate of NAG-PEG$_{12}$-[PEGMA (300, 73%)-NAG-C5-PEG$_{36}$ (18%)-TFPMA$_{5\%}$]$_{11k}$-b-[DMAEMA$_{36\%}$-BMA$_{46\%}$-PAA$_{10\%}$-PDSMA$_{7\%}$]$_{5.33k}$—at 0.78 peptides/polymer;

Polymer P31 is the $CK_{10}NH_2$ conjugate of NAG-C5-PEG10k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$—at 0.99 peptides/polymer;

Polymer P32 is the $CK_{10}NH_2$ conjugate of NAG-C5-PEG20k-Ph-aldehyde(oxime)NO-PEG$_{11}$-[PEGMA (300, 100%)]$_{3.8k}$-b-[DMAEMA$_{32\%}$-BMA$_{47\%}$-PAA$_{14\%}$-PDSMA$_{7\%}$]$_{4.0k}$—at 1.25 peptides/polymer;

Polymer P33 is the $CK_{10}NH_2$ conjugate of NAG-C5-PEG24-amido-PEG$_{24}$-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$—at 1.29 peptides/polymer;

Polymer P34 is the $CK_{10}NH_2$ conjugate of NAG-C5-PEG5k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$—at 0.82 peptides/polymer;

Polymer P35 is the $CK_{10}NH_2$ conjugate of NAG-C5-PEG10k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$—at 0.97 peptides/polymer;

Polymer P36 is the $CK_{10}NH_2$ conjugate of NAG-C5-PEG20k-Ph-aldehyde(oxime)NO-PEG$_{11}$-[PEGMA (500, 100%)]$_{5.8k}$-b-[DMAEMA$_{35\%}$-BMA$_{48\%}$-PAA$_{9\%}$-PDSMA$_{8\%}$]$_{5.3k}$—at 1.5 peptides/polymer;

Polymer P37 is the $CK_{10}NH_2$ conjugate of NAG-C5-PEG24-amido-PEG$_{24}$-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$—at 1.06 peptides/polymer;

Polymer P38 is the $CK_{10}NH_2$ conjugate of NAG-C5-PEG5k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$—at 1.12 peptides/polymer;

Polymer P39 is the $CK_{10}NH_2$ conjugate of NAG-C5-PEG10k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$—at 0.88 peptides/polymer;

Polymer P40 is the $CK_{10}NH_2$ conjugate of NAG-C5-PEG20k-Ph-aldehyde(oxime)NO-PEG$_{11}$-[PEGMA (1000, 100%)]$_{9.1k}$-[DMAEMA$_{32.3\%}$-BMA$_{48.4\%}$-PAA$_{11.8\%}$-PDSMA$_{7.5\%}$]$_{8.15k}$—at 0.98 peptides/polymer;

Polymer P58 is the $CK_{10}NH_2$ conjugate of NAG-PEG$_{36}$-[PEGMA (500, 100%)]$_{6.19k}$-b-[DMAEMA$_{31.6\%}$-BMA$_{48.4\%}$-PAA$_{13.1\%}$-PDSMA$_{6.8\%}$]$_{4.3k}$—at 0.95 peptides/polymer;

Polymer P59 is the $CK_{10}NH_2$ conjugate of NAG-PEG$_{36}$-[PEGMA (500, 100%)]$_{6.19k}$-b-[DMAEMA$_{30.8\%}$-BMA$_{50.8\%}$-PAA$_{11.6\%}$-PDSMA$_{6.8\%}$]$_{3.5k}$—at 0.87 peptides/polymer;

Polymer P60 is the $CR_{10}NH_2$ conjugate of NAG-PEG$_{48}$-[PEGMA (300,100%)]$_{3.8k}$-b-[BMA$_{49.3\%}$-PAA$_{9\%}$-DMAEMA$_{31.4\%}$-PDSMA$_{9\%}$]$_{6.3k}$—at 0.91 peptides/polymer;

Polymer P61 is the $CR_{10}NH_2$ conjugate of NAG-PEG$_{12}$-[PEGMA(500, 100%)]$_{5.8k}$-b-[DMAEMA$_{35\%}$-BMA$_{50\%}$-PAA$_{8\%}$-PDSMA$_{6\%}$]$_{5.2k}$—at 0.97 peptides/polymer;

Polymer P62 is the $CR_{10}NH_2$ conjugate of NAG-PEG$_{36}$-[PEGMA300, 100%]$_{3.5k}$-b-[BMA$_{50\%}$-PAA$_{9\%}$-DMAEMA$_{35\%}$-PDSMA$_{6\%}$]$_{4.9k}$—at 0.94 peptides/polymer;

Polymer P63 is the $CK_{10}NH_2$ conjugate of Tri-NAG-PEG$_{12}$-[PEGMA(300, 80%)-PDSMA$_{10\%}$-BPAM$_{10\%}$]$_{7k}$-[BMA$_{50\%}$-PAA$_{25\%}$-DMAEMA$_{25\%}$]$_{27.8k}$—at 0.64 peptides/polymer (monomer % listed is the % monomer in the polymerization reaction);

Polymer P64 is the $CK_{10}NH_2$ conjugate of Tri-NAG-PEG$_{12}$-[PEGMA(300, 80%)-PDSMA$_{10\%}$-BPAM$_{10\%}$]$_{6.1k}$-[BMA$_{50\%}$-PAA$_{25\%}$-DMAEMA$_{25\%}$]$_{4.9k}$—at 0.85 peptides/polymer (monomer % listed is the % monomer in the polymerization reaction);

Polymer P65 is the $CK_{10}NH_2$ conjugate of Tri-NAG-PEG$_{12}$-[PEGMA(300, 80%)-PDSMA$_{10\%}$-BPAM$_{10\%}$]$_{6.4k}$-[BMA$_{50\%}$-PAA$_{25}$%-DMAEMA$_{25\%}$]$_{3.2k}$—at 0.70 peptides/polymer (monomer % listed is the % monomer in the polymerization reaction);

Polymer P66 is the $CK_{10}NH_2$ conjugate of Tri-NAG-PEG$_{12}$-[PEGMA(300, 80%)-PDSMA$_{10\%}$-BPAM$_{10\%}$]$_{6.4k}$-[BMA$_{50\%}$-PAA$_{25\%}$-DMAEMA$_{25\%}$]$_{42k}$—at 1.1 peptides/polymer (monomer % listed is the % monomer in the polymerization reaction).

Example 24. Preparation for the Oxime Ligation on Polymers

The boc-protected hydroxyl amine polymer (0.19 mmol) was dissolved in an excess of neat TFA (4 mL) and stirred for one hour to deprotect the hydroxyl amine. The TFA was then removed from the polymer under reduced atmosphere (by RotoVap, 30 min). The resulting polymer was used without further purification. The oxime ligation reaction was started by dissolving 2.5 equivalents of the NAG-PEGx-Ph-aldehyde (0.5 mmol) in a minimum of DMSO (~2 mL), and the resulting solution was then added to the hydroxyl amine polymer. A small aliquot was taken for GPC and HPLC analysis to determine the initial NAG-PEGx-PH-aldehyde content in the reaction. The ligation reaction was allowed to proceed for 16 hours. After 16 hours an aliquot of the reaction mixture was taken for final GPC and HPLC determination of NAG-PEGx-content. The reaction was then precipitated in cold Hexanes/Ether (2:1) to recover the oxime ligated polymer. The precipitate was collected by centrifugation, decanting solvent from the pellet. The pellet was then washed an additional two times by dissolving in acetone and precipitating in cold Hexanes/Ether. The final pellet was placed on high Vac overnight to remove residual solvent.

According to the above procedure the following polymers were prepared:

Polymer P28 is the oxime ligated polymer between NAG-C5-PEG24-amido-PEG24-PH-aldehyde and polymer P15;

Polymer P29 is the oxime ligated polymer between NAG-C5-PEG5k-PH-aldehyde and polymer P15;

Polymer P41 is the oxime ligated polymer between NAG-C5-PEG10k-Ph-aldehyde and polymer P15;

Polymer P42 is the oxime ligated polymer between NAG-C5-PEG20k-Ph-aldehyde and polymer P15;

Polymer P43 is the oxime ligated polymer between NAG-C5-PEG24-amido-PEG24-Ph-aldehyde and polymer P30;

Polymer P44 is the oxime ligated polymer between NAG-C5-PEG5k-Ph-aldehyde and polymer P30;

Polymer P45 is the oxime ligated polymer between NAG-C5-PEG10k-Ph-aldehyde and polymer P30;

Polymer P46 is the oxime ligated polymer between NAG-C5-PEG20k-Ph-aldehyde and polymer P30;

Polymer P47 is the oxime ligated polymer between NAG-C5-PEG24-amido-PEG24-Ph-aldehyde and polymer P17;

Polymer P48 is the oxime ligated polymer between NAG-C5-PEG5k-Ph-aldehyde and polymer P17;

Polymer P49 is the oxime ligated polymer between NAG-C5-PEG10k-Ph-aldehyde and polymer P17;

Polymer P50 is the oxime ligated polymer between NAG-C5-PEG20k-Ph-aldehyde and polymer P17.

Example 25: Formulation of Polymers with FLuc mRNA

Polymers are solubilized in 300 mM sucrose/20 mM phosphate buffer, pH 7.4 (SUP) plus 1% Tween 80 with agitation at 20 mg/mL for 1 hour. FLuc (firefly luciferase) mRNA stock solution at 1 mg/mL in 10 mM Tris-HCL (pH7.5) from TriLink Biotechnologies is diluted to 0.2 mg/mL in SUP buffer. Using a microfluidics device, the polymer and mRNA solutions are mixed at a 1:1 volume, at 12 mL/minute, and at an N/P ratio typically around 20. The final concentrations of the polymer and mRNA are typically at 10 mg/mL and 0.1 mg/mL respectively in 0.5% Tween 80/SUP buffer. The formulations are incubated at room temperature for approximately 60 minutes prior to injecting mice.

The formulation particle size is measured by adding 10 µl of formulation to 90 µL of SUP buffer into a disposable micro-cuvette and analyzed using the Malvern Instrument ZETASIZER NANO-ZS. The formulation zeta-potential at pH 7.4 is measured by adding 10 µl of formulation to 740 µL of SUP buffer into a disposable 1 mL cuvette. The zeta dip cell is inserted into the 1 mL cuvette and the formulation is analyzed using the ZETASIZER NANO-ZS. The zeta-potential is also measured at pH 4 as described above by adding 10 µl of formulation to 740 µL of 20 mM acetate buffer pH 4 containing 5% glucose. The ability of the polymer formulation to compact the mRNA is measured in a 96 well plate using a SYBR Gold dye accessibility assay. Typically, 50 µL of the polymer formulation at 0.01 mg/mL mRNA is added to 150 µL of diluted SYBR Gold stock solution (1 µL of Stock SYBR Gold in 3 mL of SUP buffer) and incubated for 15 minutes at room temperature with agitation. The fluorescence is read at an excitation wavelength of 495 nm and emission wavelength of 538 nm. The percent dye accessibility is calculated by dividing the fluorescence intensity of the formulated mRNA by the fluorescence intensity of the free mRNA×100.

Example 26: In Vivo Testing of Polymer-mRNA Formulations

FLuc mRNA was formulated with polymers P20, P22, or P23 as described in Example 25.

Female CD-1 mice (7-10 weeks old) were used for in vivo testing of the polymer-FLuc mRNA formulations. The formulations were dosed intravenously at 1 mg/kg of mRNA and 100 mg/kg of total polymer dose, with 5 mice injected per group. Mice injected with vehicle only (SUP buffer) wa used as a control. All mice were given a final dose volume of approximately 0.25 ml or 10 mL/kg based on individual body weights.

In vivo luminescence on live mice was detected using an IVIS Lumina II Imaging System (PerkinElmer, Hopkinton, Mass.) in connection with the Living Image Software (version 4.3, PerkinElmer). Each mouse was injected with 250 µL of D-luciferin potassium salt (PerkinElmer, 15 mg/mL, dissolved in PBS without magnesium and calcium) intraperitoneally 10 minutes prior to imaging. Mice were sedated with 2% isoflurane gas anesthesia right before imaging and subsequently placed in the imaging chamber. The image acquisition was operated using the luminescent option in Living Image Software with the exposure time set at auto or desired length (e.g., 20 seconds). The images were analyzed in Living Image Software using Region of Interest (ROI) tool to quantify the luminescence of each animal, which was expressed as total flux (photons/second).

FLuc mRNA was quantified in liver tissue and blood using a quantitative PCR assay. Mice were sedated at the designated time points with 2% isoflurane gas anesthesia and then 200 µL of blood is collected retro-orbitally. Whole blood was immediately diluted into 1 ml of TRIzol Reagent (Life Technologies) mixed well and then placed on ice. Following animal sacrifice, 50-100 mg of liver tissue was placed in a sterile tube and flash frozen in liquid nitrogen. Frozen liver samples were taken up in a sufficient volume of TRIzol Reagent to 100 mg/mL based on recorded liver weight and immediately homogenized using a FastPrep 24 manifold. The liver sample was then mixed with 10% by volume of 1-Bromo-3-chloropropane and centrifuged for 10 minutes at 4° C. to extract total RNA. 50 µL of the total extract was subjected to RNA purification using the MagMax Microarray protocol and eluted into 100 µL elution buffer. Blood RNA was isolated using the same method except that 100 µL of the extract was used for purification.

RNA samples were individually normalized to 100 ng/µl of total liver RNA and blood RNA was normalized to 50 ng/µL. 10 µL of normalized input RNA was reverse transcribed using the High Capacity Reverse Transcription reagents (Life Technologies). The cDNA product was diluted 1:5 for analysis by qPCR. A standard curve for luciferase was generated using free mRNA diluted to 0.05 mg/mL and then six ten-fold serial dilutions. The standard curve was reverse transcribed and diluted in the same fashion as assay samples.

Reverse Transcription cDNA product was analyzed for luciferase and GAPDH using TaqMan gene expression assays. 8 μL of the diluted cDNA was mixed with 10 μL of TaqMan Gene Expression Master Mix (Life Technologies) and 1 μL of each primer/probe set and run with standard cycling conditions. The standard curve was used to determine absolute quantities of FLuc mRNA in assay samples.

Table 26 displays luminescence values in the liver for animals treated with P20+FLuc mRNA, P22+FLuc mRNA, P23+FLuc mRNA, or buffer. Data was acquired at 3 hours post dose. Luminescence values are shown as a geomean from 5 animals in each group. All 3 polymer-mRNA formulations demonstrated strong luminescence signal in the liver compared to buffer. Polymers P22 and P23 demonstrated 5-10 fold greater luminescence signal in the liver compared to P20.

TABLE 26

Luminescence results at 3 hours post dose

|  | Polymer Dose (mg/kg) | mRNA Dose (mg/kg) | Total Flux (photons/sec) | |
|---|---|---|---|---|
|  |  |  | Geomean | STDEV |
| Buffer | 0 | 0 | 2.13E+05 | 1.32E+05 |
| P20 + FLuc mRNA | 100 | 1 | 7.82E+06 | 4.14E+07 |
| P22 + FLuc mRNA | 50 | 1 | 4.67E+06 | 2.71E+07 |
|  | 75 | 1 | 1.02E+08 | 2.29E+08 |
|  | 100 | 1 | 1.18E+08 | 5.27E+07 |
| P23 + FLuc mRNA | 50 | 1 | 1.42E+07 | 1.75E+07 |
|  | 75 | 1 | 5.97E+07 | 1.98E+08 |
|  | 100 | 1 | 3.51E+07 | 1.64E+08 |

Table 27 displays % dose FLuc mRNA in the liver and Table 28 displays % dose in blood for animals treated with P20+FLuc mRNA, P22+FLuc mRNA, P23+FLuc mRNA, buffer, or unformulated mRNA. Data was acquired at 1 and 30 minutes post dose. % mRNA dose values are shown as an average from 5 animals in each group. While neither buffer nor unformulated mRNA had any detection in liver or blood, mRNA was detected in all 3 polymer-mRNA formulations. Polymers P22 and P23 demonstrated approximately 20-fold greater FLuc mRNA delivered to the liver compared to P20 at 1 minute post dose. P20 had significantly higher levels of FLuc mRNA in blood at 1 minute compared to P22 and P23.

TABLE 27

Percent FLuc mRNA dose in liver at 1 and 30 minutes post dose

|  | Polymer Dose (mg/kg) | mRNA Dose (mg/kg) | Time Point | FLuc mRNA (% dose) | |
|---|---|---|---|---|---|
|  |  |  |  | Average | STDEV |
| Buffer | 0 | 0 | 1 min | 0.0% | 0.0% |
| Fluc mRNA | 0 | 1 | 1 min | 0.0% | 0.0% |
| P20 + FLuc mRNA | 75 | 0.75 | 1 min | 0.6% | 0.1% |
|  |  |  | 30 min | 0.1% | 0.0% |
| P22 + FLuc mRNA | 75 | 0.75 | 1 min | 10.2% | 8.8% |
|  |  |  | 30 min | 0.6% | 0.3% |
| P23 + FLuc mRNA | 75 | 0.75 | 1 min | 14.4% | 2.8% |
|  |  |  | 30 min | 0.4% | 0.3% |

TABLE 28

Percent FLuc mRNA dose in blood at 1 and 30 minutes post dose

|  | Polymer Dose (mg/kg) | mRNA Dose (mg/kg) | Time Point | FLuc mRNA (% dose) | |
|---|---|---|---|---|---|
|  |  |  |  | Average | STDEV |
| Buffer | 0 | 0 | 1 min | 0.0% | 0.0% |
| FLuc mRNA | 0 | 1 | 1 min | 0.0% | 0.0% |
| P20 + FLuc mRNA | 75 | 0.75 | 1 min | 24.2% | 9.5% |
|  |  |  | 30 min | 0.2% | 0.1% |
| P22 + FLuc mRNA | 75 | 0.75 | 1 min | 3.5% | 7.0% |
|  |  |  | 30 min | 0.1% | 0.0% |
| P23 + FLuc mRNA | 75 | 0.75 | 1 min | 0.3% | 0.1% |
|  |  |  | 30 min | 0.0% | 0.0% |

Example 27: In Vivo Testing of Polymer-mRNA Formulations

FLuc mRNA was formulated with polymers P20 and P21 as described in Example 25. Mice were injected with polymer-FLuc mRNA formulation and examined for luciferase expression and FLuc mRNA quantification in liver and blood as described in Example 26. Table 29 displays luminescence values in the liver for animals treated with polymer+FLuc mRNA. Both polymers demonstrated strong luminescence signal in the liver compared to buffer. Polymer P21 demonstrated ~10 fold greater luminescence signal in the liver compared to PRX398.

TABLE 29

Luminescence results at 3 hours post dose

|  | Polymer Dose (mg/kg) | mRNA Dose (mg/kg) | Total Flux (photons/sec) | |
|---|---|---|---|---|
|  |  |  | Geomean | STDEV |
| Buffer | 0 | 0 | 2.37E+05 | 1.33E+05 |
| P20 + Fluc mRNA | 100 | 1 | 3.80E+06 | 1.03E+07 |
| P21 + Fluc mRNA | 75 | 1 | 2.91E+07 | 1.57E+08 |
|  | 100 | 1 | 4.69E+07 | 1.26E+08 |

Table 30 displays % dose FLuc mRNA in the liver and Table 31 displays % dose in blood for animals treated with polymer P21+FLuc mRNA. mRNA was detected in liver and blood with P21 polymer-mRNA formulation. Polymer P21 showed a similar amount of FLuc mRNA delivered to the liver as compared to polymer P20 at 1 and 30 minutes post dose shown in Example 26. Polymer P21 had significantly higher levels of FLuc mRNA in blood at 1 and 30 minute compared to polymer P20 in Example 26. This may indicate increased circulatory stability in the blood with polymer P21.

TABLE 30

Percent FLuc mRNA dose in liver at 1 and 30 minutes post dose

|  | Polymer Dose (mg/kg) | mRNA Dose (mg/kg) | Time Point | Fluc mRNA (% dose) | |
|---|---|---|---|---|---|
|  |  |  |  | Average | STDEV |
| Buffer | 0 | 0 | 1 min | 0.0% | 0.0% |
| P21 + Fluc mRNA | 75 | 1 | 1 min | 0.8% | 0.4% |
|  |  |  | 30 min | 0.1% | 0.0% |

TABLE 31

Percent FLuc mRNA dose in blood at 1 and 30 minutes post dose

| | Polymer Dose (mg/kg) | mRNA Dose (mg/kg) | Time Point | Fluc mRNA (% dose) | |
|---|---|---|---|---|---|
| | | | | Average | STDEV |
| Buffer | 0 | 0 | 1 min | 0.0% | 0.0% |
| P21 + Fluc mRNA | 75 | 1 | 1 min | 79.7% | 22.4% |
| | | | 30 min | 2.4% | 1.4% |

Example 28: Formulation of Polymers with FLuc mRNA

Polymers are solubilized in 20 mM HEPES/5% glucose, pH 7.4 (HEPES/glucose) plus 20% ethanol with agitation typically between 20-40 mg/mL for 1 hour at room temperature and then incubated overnight at 4° C. FLuc (firefly luciferase) mRNA stock solution at 1 mg/mL in 10 mM Tris-HCL (pH7.5) from TriLink Biotechnologies is diluted to 0.2 mg/mL in HEPES/glucose buffer. Using a microfluidics device, the polymer and mRNA solutions are mixed at a 1:1 volume, at 12 mL/minute, and at an N/P ratio typically between 10 and 20. The final concentrations of the polymer and mRNA are typically at 2-20 mg/mL and 0.1 mg/mL respectively in HEPES/glucose with 10% ethanol buffer. The formulations are incubated at room temperature for approximately 60 minutes prior to injecting mice.

The formulation particle size is measured by adding 10 µl of formulation to 90 µL of HEPES/glucose buffer into a disposable micro-cuvette and analyzed using the Malvern Instrument ZETASIZER NANO-ZS. The formulation zeta-potential at pH 7.4 is measured by adding 10 µl of formulation to 740 µL of HEPES/glucose buffer into a disposable 1 mL cuvette. The zeta dip cell is inserted into the 1 mL cuvette and the formulation is analyzed using the ZETASIZER NANO-ZS. The zeta-potential is also measured at pH 4 as described above by adding 10 µl of formulation to 740 µL of 20 mM acetate buffer pH 4 containing 5% glucose. The ability of the polymer formulation to compact the mRNA is measured in a 96 well plate using a SYBR Gold dye accessibility assay. Typically, 50 µL of the polymer formulation at 0.01 mg/mL mRNA is added to 150 µL of diluted SYBR Gold stock solution (1 µL of Stock SYBR Gold in 3 mL of HEPES/glucose buffer) and incubated for 15 minutes at room temperature with agitation. The fluorescence is read at an excitation wavelength of 495 nm and emission wavelength of 538 nm. The percent dye accessibility is calculated by dividing the fluorescence intensity of the formulated mRNA by the fluorescence intensity of the free mRNA×100.

Example 29: In Vivo Testing of Polymer-mRNA Formulations

FLuc mRNA was formulated with each of the following polymers: P20, P24, P31, P32, P58, P59, P62, P61, P27, P33, P34, P35, P36, P37, P38, P39, P40, P64, P65, and P66. Polymers were formulated as described in Example 28, except for one study comparing polymers P58 and P59 to polymer P20, in which these polymers were formulated as described in Example 25. Mice were injected with polymer-FLuc mRNA formulations and examined for luciferase expression as described in Example 26.

Table 32 displays luminescence values in the liver for animals treated with polymer+FLuc mRNA in an experiment comparing polymers P24, P31, and P32 to polymer P20. Polymers demonstrated strong luminescence signal in the liver compared to buffer. Polymer P24 demonstrated ~7 fold greater luminescence signal in the liver compared to polymer P20.

Table 33 displays luminescence values in the liver for animals treated with polymer+FLuc mRNA in an experiment comparing polymers P58 and P59 to polymer P20. Polymers demonstrated strong luminescence signal in the liver compared to buffer. Polymer P58 demonstrated ~20 fold greater luminescence signal in the liver compared to polymer P20.

Table 34 displays luminescence values in the liver for animals treated with polymer+FLuc mRNA in an experiment comparing polymers P62, P61, and P27 to polymer P20. Polymers demonstrated strong luminescence signal in the liver compared to buffer. Polymer P27 demonstrated ~5 fold greater luminescence signal in the liver compared to polymer P20.

Table 35 displays luminescence values in the liver for animals treated with polymer+FLuc mRNA in an experiment comparing polymers P33, P34, P35, and P36 to polymer P20. Polymers demonstrated strong luminescence signal in the liver compared to buffer. Polymers P33, P34, and P35 demonstrated ~12-30 fold greater luminescence signal in the liver compared to polymer P20.

Table 36 displays luminescence values in the liver for animals treated with polymer+FLuc mRNA in an experiment comparing polymers P37, P38, P39, and P40 to polymer P20. Polymers demonstrated strong luminescence signal in the liver compared to buffer. Polymer P37 demonstrated ~4 fold greater luminescence signal in the liver compared to polymer P20.

Table 37 displays luminescence values in the liver for animals treated with polymer+FLuc mRNA in an experiment comparing polymers P64, P65, and P66 to polymer P20. Polymers demonstrated strong luminescence signal in the liver compared to buffer. Polymers P64 and P66 demonstrated ~4 fold greater luminescence signal in the liver compared to polymer P20.

TABLE 32

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| Buffer | 0 | 0 | 2.08E+05 | NA |
| P20 + Fluc mRNA | 100 | 1 | 2.83E+07 | 6.91E+07 |
| P24 + Fluc mRNA | 53 | 1 | 1.83E+08 | 1.92E+08 |
| | 80 | 1 | 1.62E+07 | 1.41E+08 |
| P31 + Fluc mRNA | 62 | 1 | 1.76E+07 | 6.20E+08 |
| | 93 | 1 | 1.21E+08 | 1.59E+08 |
| P32 + Fluc mRNA | 74 | 1 | 1.30E+06 | 9.23E+06 |
| | 112 | 1 | 1.17E+06 | 4.78E+06 |

TABLE 33

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| Buffer | 0 | 0 | 2.61E+05 | NA |
| P20 + Fluc mRNA | 100 | 1 | 2.58E+06 | 7.47E+06 |
| P58 + Fluc mRNA | 100 | 1 | 5.09E+07 | 9.71E+07 |
| P59 + Fluc mRNA | 100 | 1 | 1.68E+07 | 8.95E+07 |

TABLE 34

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| Buffer | 0 | 0 | 1.70E+05 | NA |
| P20 + Fluc mRNA | 100 | 1 | 1.53E+07 | 4.75E+07 |
| P62 + Fluc mRNA | 50 | 1 | 5.95E+05 | 1.40E+06 |
| P61 + Fluc mRNA | 75 | 1 | 3.51E+07 | 2.01E+08 |
| P27 + Fluc mRNA | 108 | 1 | 7.48E+07 | 7.19E+07 |

TABLE 35

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| Buffer | 0 | 0 | 1.20E+05 | NA |
| P20 + Fluc mRNA | 100 | 1 | 8.81E+06 | 9.94E+06 |
| P33 + Fluc mRNA | 38 | 1 | 2.74E+08 | 6.22E+08 |
| | 77 | 1 | 3.91E+07 | 2.52E+08 |
| P34 + Fluc mRNA | 68 | 1 | 1.08E+08 | 1.95E+08 |
| | 102 | 1 | 1.11E+08 | 1.38E+08 |
| P35 + Fluc mRNA | 74 | 1 | 1.81E+08 | 2.04E+08 |
| | 111 | 1 | 3.85E+07 | 2.97E+07 |
| P36 + Fluc mRNA | 69 | 1 | 9.78E+06 | 1.97E+08 |
| | 104 | 1 | 4.70E+07 | 5.43E+08 |

TABLE 36

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| Buffer | 0 | 0 | 2.27E+05 | NA |
| P20 + Fluc mRNA | 100 | 1 | 2.77E+07 | 7.04E+07 |
| P37 + Fluc mRNA | 63 | 1 | 1.15E+08 | 2.48E+08 |
| | 95 | 1 | 2.94E+08 | 3.87E+08 |
| P38 + Fluc mRNA | 68 | 1 | 4.31E+07 | 3.63E+08 |
| | 101 | 1 | 5.75E+07 | 1.72E+08 |
| P39 + Fluc mRNA | 102 | 1 | 2.16E+07 | 1.57E+08 |
| | 153 | 1 | 1.18E+07 | 5.91E+07 |

TABLE 36-continued

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| P40 + Fluc mRNA | 123 | 1 | 9.98E+05 | 3.90E+06 |
| | 185 | 1 | 1.49E+07 | 7.13E+07 |

TABLE 37

Luminescence results at 3 hours post dose

| | Polymer Dose (mg/kg) | mRNA Dose (mg/kg) | Total Flux (photons/sec) | |
|---|---|---|---|---|
| | | | Geomean | STDEV |
| Buffer | 0 | 0 | 1.98E+05 | NA |
| P20 + Fluc mRNA | 100 | 1 | 1.53E+07 | 4.75E+07 |
| P64 + Fluc mRNA | 77 | 1 | 6.01E+07 | 3.33E+08 |
| | 103 | 1 | 4.74E+07 | 3.87E+08 |
| P65 + Fluc mRNA | 76 | 1 | 2.64E+07 | 9.63E+07 |
| | 102 | 1 | 2.85E+07 | 1.69E+08 |
| P66 + Fluc mRNA | 66 | 1 | 5.82E+07 | 1.82E+08 |
| | 88 | 1 | 2.00E+07 | 4.99E+07 |

Example 30: Treatment of OTCD with Polymer-mRNA Formulations in OTC-spf$^{ash}$ Mice OTC-spf$^{ash}$ (sparse fur and abnormal skin and hair) mice contain an R129H mutation which results in reduced levels of OTC protein and have only 5-10% of the normal level of enzyme activity in liver (see Hodges et al., *PNAS* 86:4142-4146, 1989). The OTC-spf$^{ash}$ mouse model has elevated urine orotic acid levels compared to wild-type littermate mice.

Groups of 5-10 OTC-spf$^{ash}$ mice are treated by intravenous route of administration with synthetic OTC mRNA formulated with polymer that targets hepatocytes in the liver, thereby achieving expression and activity of OTC. Mice are treated with vehicle control or OTC mRNA from 0.1-5 mg/kg. Either single or repeat dosing is performed with a variety of dosing intervals (e.g. twice daily, daily, every 2 days, etc.). Urine is collected pre-dose as well as at different time points ranging from 3 hours to 48 hours post final dose on the short term or up to 2 weeks post dose for duration of expression. At these time points, mice are sacrificed and livers are collected and sampled to evaluate OTC protein expression by western analysis immunofluorescence of liver tissue section, and OTC enzyme activity. Urine is analyzed for orotic acid levels normalized to creatinine levels.

Results are compared to vehicle-treated OTC deficient mice. In addition, results are compared to wild-type litter mate mice that have normal levels of OTC protein expression, enzyme activity and urine orotic acid levels. Efficacy is shown by detectable levels of OTC protein expression evaluated by western and immunofluorescence that are above the level detected in vehicle treated mice, enzyme activity that is at least 15% of normal levels, and urine orotic acid levels are reduced at least 50% compared to vehicle control treated mice.

Example 31: Treatment of OTCD with Polymer-mRNA Formulations in OTC-spf Mice OTC-spf mice contain an H117N mutation, which results in reduced levels of enzyme activity to 5-10% of normal levels (see Rosenberg et al., *Science* 222:426-428, 1983). The OTC-spf mouse model has elevated urine orotic acid levels compared to wild-type littermate mice.

Groups of 5-10 OTC-spf mice are treated by intravenous route of administration with synthetic OTC mRNA formulated with polymer that targets hepatocytes in the liver, thereby achieving expression and activity of OTC. Mice are treated with vehicle control or OTC mRNA from 0.1-5 mg/kg. Either single or repeat dosing is performed with a variety of dosing intervals (e.g. twice daily, daily, every 2 days, etc.). Urine is collected pre-dose as well as at different time points ranging from 3 hours to 48 hours post final dose on the short term or up to 2 weeks post dose for duration of expression. At these time points, mice are sacrificed and livers are collected and sampled to evaluate OTC protein expression by western analysis immunofluorescence of liver tissue section, and OTC enzyme activity. Urine is analyzed for orotic acid levels normalized to creatinine levels.

Results are compared to vehicle-treated OTC deficient mice. In addition, results are compared to wild-type litter mate mice that have normal levels of OTC protein expression, enzyme activity and urine orotic acid levels. Efficacy is shown by detectable levels of OTC protein expression evaluated by western and immunofluorescence that are above the level detected in vehicle treated mice, enzyme activity that is at least 15% of normal levels, and urine orotic acid levels are reduced at least 50% compared to vehicle control treated mice.

Example 32: Treatment of OTCD with Polymer-mRNA Formulations in a Hyperammonemia Mouse Model An additional model for OTC deficiency is inducing hyperammonemia in OTC-spf or OTC-spf$^{ash}$ mice (see Cunningham et al., *Mol Ther* 19(5): 854-859, 2011). These mice are treated with OTC siRNA or AAV2/8 vector/OTC shRNA to knockdown residual endogenous OTC expression and activity. Plasma ammonia levels are elevated and mice die approximately 2-14 days.

Groups of 5-10 hyperammonemia-induced mice are treated by intravenous route of administration with synthetic OTC mRNA formulated with polymer that targets hepatocytes in the liver, thereby achieving expression and activity of OTC. Mice are treated with vehicle control or OTC mRNA from 0.1-5 mg/kg. Either single or repeat dosing is performed with a variety of dosing intervals (e.g. twice daily, daily, every 2 days, etc.). Animals are monitored for ataxia, a clinical sign of hyperammonemia, and >10% body weight loss over 24 hours starting at 24 hours and up to 4 weeks post dose. Blood and urine are collected from mice that develop ataxia to examine plasma ammonia levels and orotic acid levels. Immediately following, mice are sacrificed and livers are collected and sampled to evaluate OTC protein expression by western analysis, immunofluorescence of liver tissue sections, and OTC enzyme activity.

Results are compared to vehicle-treated OTC deficient mice. In addition, results are compared to wild-type litter mate mice that have normal levels of OTC protein expression, enzyme activity and urine orotic acid levels. Efficacy is shown by increased survival compared to vehicle control treated mice and at least 50% reduction in plasma ammonia levels. Efficacy is also indicated by detectable levels of OTC protein expression evaluated by western and immunofluorescence that is above the level detected in vehicle treated mice, enzyme activity that is at least 15% of normal levels, and urine orotic acid levels are reduced at least 50% compared to vehicle control treated mice.

Example 33: Treatment of MMA with Polymer-mRNA Formulations in Mut$^{-/-}$ Mice or Mut$^{-/-}$; Tg$^{INS-MCK-Mut}$ Mice Groups of 5-10 Mut$^{-/-}$; Tg$^{INS-MCK-Mut}$ mice are treated by intravenous route of administration with synthetic mRNA formulated polymer that targets hepatocytes in the liver, thereby achieving expression and activity of MUT protein. Mice are treated with vehicle control or Mut mRNA from 0.1-5 mg/kg. Either single or repeat dosing is performed with a variety of dosing intervals (e.g. twice daily, daily, every 2 days, etc.). Plasma is collected to examine methylmalonic acid levels at different time points ranging from 3 hours to 72 hours post final dose on the short term or up to 2 weeks post dose for duration of expression. A $^{13}$C propionate oxidation/breathe assay is performed at different time points ranging from 24-72 hours post dose or longer time points up to 2 weeks post dose to examine in vivo metabolic effects of MUT protein expression. At these time points, mice are sacrificed and livers are collected and sampled to evaluate MUT protein expression by western analysis and immunofluorescence of liver tissue sections.

Results are compared to vehicle-treated mice as well as to wild-type litter mate mice that have normal levels of MUT protein expression, methylmalonic acid levels in plasma, and $^{13}$C propionate oxidation. Efficacy is shown by detectable levels of MUT protein expression evaluated by western and immunofluorescence that is above the level detected in vehicle treated mice. Plasma methylmalonic acid levels are normally <5 µM in wild-type littermate mice whereas Mut$^{-/-}$; Tg$^{INS-MCK-Mut}$ mice have 200-400 µM methylmalonic acid levels. Efficacy by plasma methylmalonic acid levels is a correction towards levels seen in wild-type littermate mice. Efficacy is also detected by a significant increase in $^{13}$C propionate oxidation compared to vehicle control treated mice.

Example 34: Treatment of PA with Polymer-mRNA Formulations in Pcca$^{-/-}$ (A138T) Mice Groups of 5-10 Pcca$^{-/-}$ (A138T) mice are treated by intravenous route of administration with synthetic mRNA formulated polymer that targets hepatocytes in the liver, thereby achieving expression and activity of PCC enzyme. Mice are treated with vehicle control or Pcca mRNA from 0.1-5 mg/kg. Either single or repeat dosing is performed with a variety of dosing intervals (e.g. twice daily, daily, every 2 days, etc.). Blood is collected to examine propionylcarnitine/acetylcarnitine ratio, methylcitrate, and plasma ammonia levels at different time points ranging from 3 hours to 72 hours post final dose on the short term or up to 2 weeks post dose for duration of expression. At these time points, mice are sacrificed and livers are collected and sampled to measure PCC enzyme activity and protein expression.

Results are compared to vehicle-treated mice as well as to wild-type litter mate mice that have normal PCC enzyme activity, metabolite levels in blood, and protein expression. Efficacy is shown by detectable levels of PCCA protein evaluated by western that is above the level detected in vehicle treated mice. PCC enzyme activity is normally ~2% of wild-type levels in affected mice. PCC enzyme activity at 10-20% of wild-type levels or higher is seen as efficacious.

Reduction in propionylcarnitine/acetylcarnitine ratio, methylcitrate, and plasma ammonia levels also demonstrate efficacy.

Example 35: Reaction of NAG-C5-PEG$_{36}$NH2 with Polymer P19: NAG-PEG-$_{12}$-[PEGMA (300, 73%)-TFPMA (27%)]4.55 KDa-b-[DMAEMA (36%)-BMA (46%)-PAA (10%)-PDSMA (7%)]5.33 KDa To polymer P19 (175 mgs, 0.000016 mole) in a 40ml glass vial was added DMF (1 mL) at RT under argon. To the solution was added NAG-C5-PEG$_{36}$NH2 (250 mgs, 0.000128 mole) and the mixture was stirred until a solution was obtained (15 min). TEA (19 ul, 0.000156 mole) was added and the yellow solution was heated to 60 C and held at that temperature for 48 hrs. The reaction was then treated with 3-amino-1-propanol (17 uL) and heating at 60 C was continued for 7 hrs. The reaction was diluted with Acetone (2 mL) and the product was precipitated with Et2O/Hexanes (1:3, 40 mL). The precipitation was repeated twice more. The resultant pellet was dried under high vacuum for 15 hrs.

The resulting pellet was dissolved in MeOH (3 mL) and the solution was treated with 0.5M TCEP (500 ul, 10 equiv). After 30 min the yellow solution was treated with DPDS (112 mgs, 20 equiv). The reaction was agitated for 60 min then the solution was diluted with MeOH (12 ml) and was dialyzed from MeOH thrice. The contents of the dialysis bag were concentrated on the rotavap and the residue dried for 16 hrs. HNMR showed ~4 out of 5.5 TFP units were displaced by NAGPEG$_{36}$NH2, to afford polymer P30: NAG-PEG$_{12}$-[PEGMA (300, 73%)-NAG-C5-PEG$_{36}$ (18%)-TFPMA (5%)]11 KDa-b-[DMAEMA (36%)-BMA (46%)-PAA (10%)-PDSMA (7%)]5.33 KDa.

By similar process, polymer P18: ECT-[PEGMA (300, 58)-TFPMA (42)] 5.14 KDa-b-[DMAEMA (31)-BMA (49)-PAA (12)-PDSMA (8)] 5.03 KDa, was modified with NAG-C5-PEG$_{36}$NH2, to afford polymer P31 ECT-[PEGMA (300, 58)-NAG-C5-PEG$_{36}$ (42)] 19.9 KDa-b-[DMAEMA (31)-BMA (49)-PAA (12)-PDSMA (8)] 5.03 KDa.

Example 36: Synthesis of Tri-NAG CTA

Part 1: Synthesis of Fmoc-Amido-Triacid

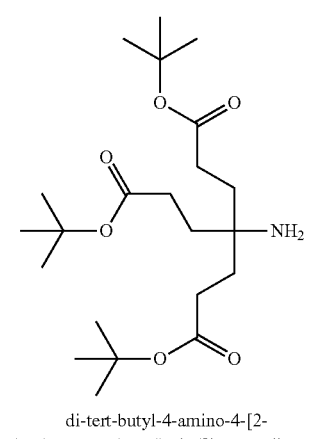

di-tert-butyl-4-amino-4-[2-(tertbutoxycarbonyl)ethyl]heptanedionate
Chemical Formula: C$_{22}$H$_{41}$NO$_6$
Molecular Weight: 415.56

1.) FmocCl, Et$_3$N THF
2.) TFA

-continued

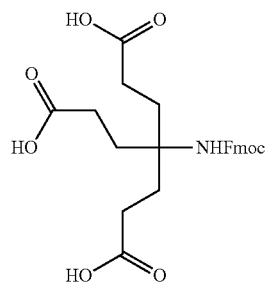

Chemical Formula: C$_{37}$H$_{51}$NO$_8$
Molecular Weight: 637.80

Procedure:

To a 100 mL round bottom flask was added FmocCl (3.14 g, 12.2 mmol). This material was dissolved in THF (50 mL). In a separate 250 mL round bottom flask was added di-tert-butyl-4-amino-4-[2-(tertbutoxycarbonyl)ethyl]heptanedionate (5.00 g, 12.0 mmol, tris t-butyl amine) which was then dissolved in THF (50 mL). The FmocCl solution was then added to the solution of tris t-butyl amine in one portion. Immediately following the addition, triethylamine (1.79 mL, 12.8 mmol) was added to the reaction mixture. Upon the addition of triethylamine a precipitate formed in the flask. The reaction was left to stir under argon atmosphere at room temperature for 30 minutes.

The crude reaction mixture was concentrated using rotary evaporation. The product was used as a crude mixture for the next reaction in the synthetic sequence (assuming quantitative yield).

To the crude reaction mixture was added TFA (25 mL). A white solid remained in the reaction mixture. This mixture was concentrated by rotary evaporation until approximately 5 mL remained. To the mixture was added water (1 mL) to react any trifluoroacetic anhydride and convert it to carboxylic acid. The mixture was concentrated by rotary evaporation and high vacuum, resulting in white solid. This solid was triturated with ethyl acetate and the solid was centrifuged. The solid was triturated and centrifuged until 6.4 g (84%, two steps) colorless solid with good purity was recovered.

Part 2: Synthesis of Fmoc-Amido-tri-pentafluorophenyl ester

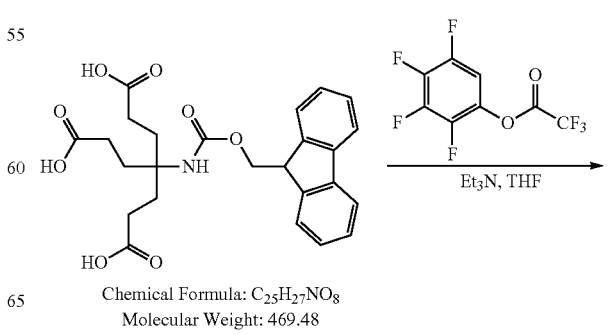

Chemical Formula: C$_{25}$H$_{27}$NO$_8$
Molecular Weight: 469.48

Et$_3$N, THF

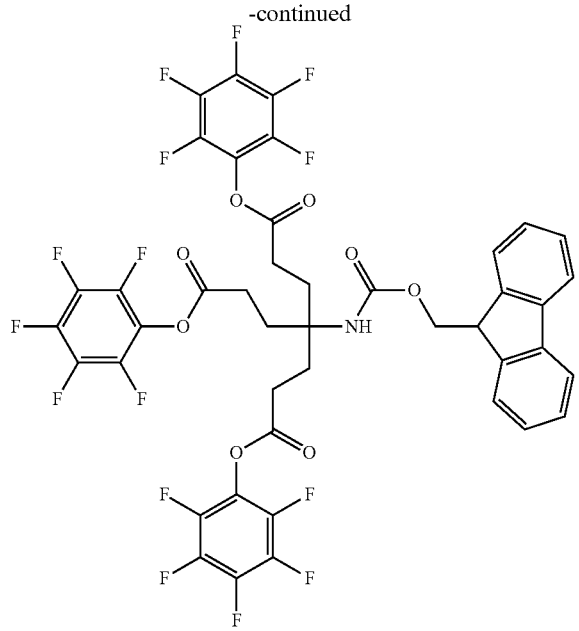

Chemical Formula: C₄₃H₂₄F₁₅NO₈
Molecular weight: 967.63

Procedure:

To a 250 mL one-neck round bottom flask was added TL-02-19 (3.3 g, 7.0 mmol, thoroughly dried overnight on high vacuum) followed by anhydrous THF (60 mL, lot # B0313244). This mixture was stirred under a flow of argon gas and then cooled to 0° C. for 5 min. Then trifluoroacetic acid pentafluorophenyl ester (4.0 mL, 23.2 mmol, lot #69096MJ) was added drop wise followed by triethylamine (3.24 mL, 23.2 mmol, lot # B0518226). The reaction was then warmed to room temperature under a flow of argon gas.

The reaction progress can be followed by TLC (SiO₂, 100% CH₂Cl₂) by looking for the disappearance of the starting material TL-02-19 (Rf=0.0) and the appearance of the PFP activated product MD-03-20 (Rf=0.49). After stirring for 2.0 h at room temperature the starting material was completely consumed by TLC.

Once the starting material was consumed by TLC the crude reaction was evaporated using a rotary evaporator to remove all the THF. Once the crude reaction was condensed to a viscous oil the mixture was dissolved with CH₂Cl₂ (150 mL) and extracted using saturated aqueous NaHCO₃ (3×50 mL). The organic layer was separated, dried over Na₂SO₄, filtered and evaporated providing 6.0 g (89%) of the final product as a white solid. All solvents and volatile reagents were thoroughly removed using high vacuum (0.5 mmHg) overnight before the crude product was used in the next synthetic step. No characterization of the final product was preformed other than TLC analysis (TLC conditions described above). The TLC analysis of the final product showed the material was only one compound (Rf=0.49). Ninhydrin TLC based (300 mg ninhydrin dissolved in 100 mL EtOH and 3 mL AcOH) analysis showed that there was no Fmoc deprotected product produced via this process.

Part 3: Synthesis of Fmoc-Amido Triacid-2

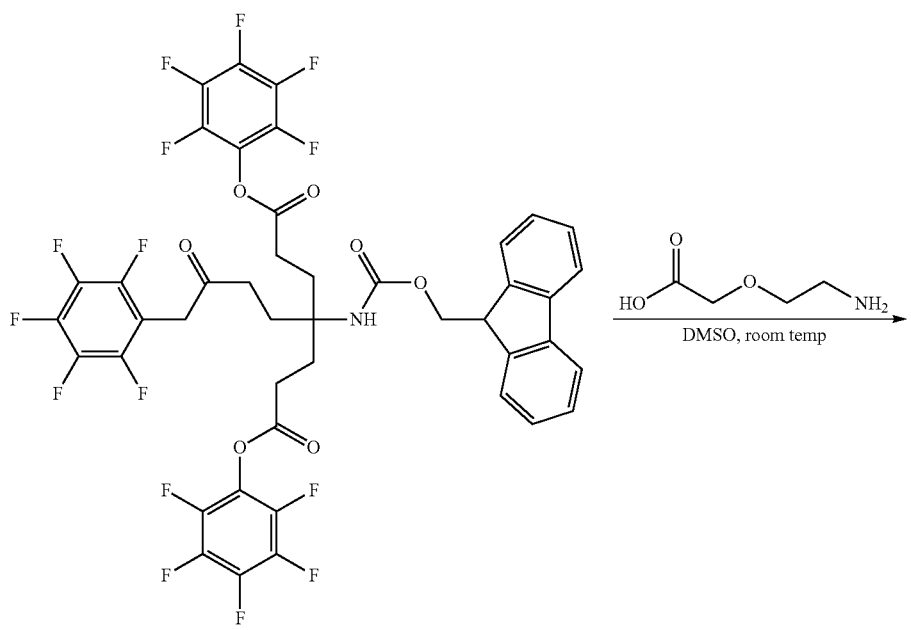

Chemical Formula: C₄₃H₂₄F₁₅NO₈
Molecular weight: 967.63

-continued

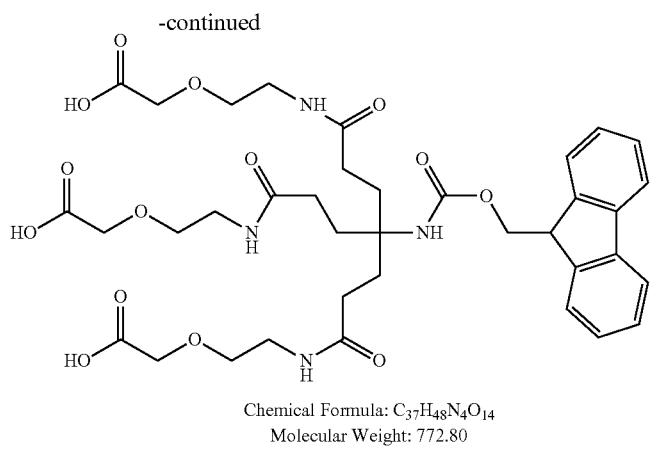

Chemical Formula: $C_{37}H_{48}N_4O_{14}$
Molecular Weight: 772.80

Procedure:

To a 250 mL one-neck round-bottom flask was added MD-03-20 (6.0 g, 6.2 mmol) followed by anhydrous DMSO (50 mL). This mixture was stirred at room temperature under a flow of inert argon gas until MD-03-20 was completely dissolved. Then (2-amino-ethoxy)-acetic acid (2.26 g, 18.97 mmol, compound acquired from Chess Fine Organics) was added directly to the reaction mixture. The (2-amino-ethoxy)-acetic acid slowly dissolved into the reaction mixture. After all reagents were dissolved the mixture was stirred at room temperature under a flow of argon gas for 2 h.

The reaction progress can be followed by analytical HPLC by diluting the reaction mixture (10 μL) into DMSO (700 μL) and injecting 10 μL of that diluted mixture (FIG. 1). The HPLC analysis was determined using Shimadzu LD-20AB with the UV detector set to 210 nm through a C18 analytical reverse phase column (ES Industries Chromega Columns, Sonoma C18 catalog number 155B21-SMA-C18 (2), 100 Å, 25.0 cm×4.6 mm, column heated to 30.0° C., $CH_3CN/H_2O$ containing 0.01% TFA, isocratic gradient at 10% $CH_3CN$ for 2 min, then linear gradient from 10% to 60% $CH_3CN$ over 20 min, total flow rate of 1.0 mL/min). The desired tri acid product has a retention time of 16.45 min, the pentafluorophenol (PFP) leaving group was found at 22.1 min, and the loss of Fmoc was detected at 24.7 min.

After reacting 2 h at room temperature the reaction was complete. The crude reaction was directly purified using C18 preparative reverse phase HPLC by Shimadzu (Phenomenex, Luna 5 C18(2), part number 00G-4252-P0-AX, 100 Å, 25.0 cm×21.2 mm, with a SecurityGuard PREP Cartridge, C18 15×21.2 mm ID, part number AJ0-7839, $CH_3CN/H_2O$ with 0.01% TFA, isocratic gradient at 10% $CH_3CN$ for 5 min, then linear gradient from 10% to 35% $CH_3CN$ over 15 min, then linear gradient from 35% to 40% $CH_3CN$ over 5 min, then isocratic gradient at 40% $CH_3CN$ for 2 min, total flow rate of 20.0 mL/min, column at room temperature). Roughly 1.5 mL of the crude reaction mixture in DMSO (~100 mg/mL) were injected each HPLC run. Using the HPLC purification conditions above the desired product eluted between 24.5 and 25.5 min. The fraction(s) associated with the desired product were pooled together, and the solvent thoroughly evaporated using a rotary evaporator. Then the final product was transferred to a flask using MeOH and all solvents were completely removed using high vacuum (pressure <0.5 mmHg) overnight providing 3.13 g (65%) of the desired product as a white solid.

The final product was dissolved in MeOH (ca. 1. mg/mL) and analyzed by C18 analytical reverse phase HPLC. The HPLC analysis was determined using Shimadzu LD-20AB with the UV detector set to 210 nm through a C18 analytical reverse phase column (ES Industries Chromega Columns, Sonoma C18 catalog number 155B21-SMA-C18(2), 100 Å, 25.0 cm×4.6 mm, column heated to 30.0° C., $CH_3CN/H_2O$ containing 0.01% TFA, isocratic gradient at 10% $CH_3CN$ for 2 min, then linear gradient from 10% to 60% $CH_3CN$ over 20 min, total flow rate of 1.0 mL/min). The final product has a retention time of 16.45 min.

The final product was also analyzed using a 300 MHz $^1H$ NMR with $CD_3OD$ as solvent and is consistent with the structure. The final product was also analyzed using Bruker Esquire Ion Trap Mass Spectrometer showing the M+Na ion (m/z=795.8) and the 2M+Na ion (m/z=1568.6).

Part 4: Synthesis of NAG(OAc)4-C5 Amine

1. Reaction 1: Synthesis of Ac-Galactosamine-$C_5$-NHBoc (MQ-02-70)

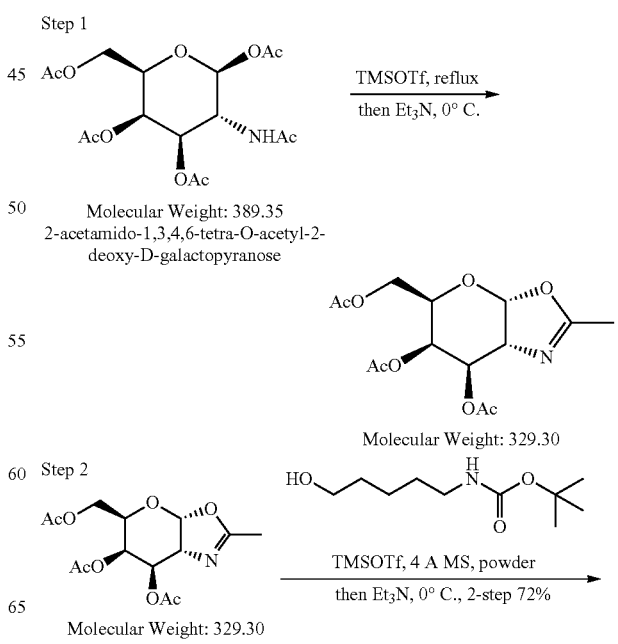

-continued

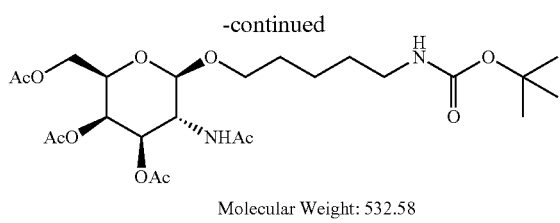

Molecular Weight: 532.58

Raw Materials
Step 1

TABLE 38

| | MW (density g/mL) | Weight | Moles | equiv | Vol (mL) | Lot# | Supplier |
|---|---|---|---|---|---|---|---|
| 2-acetamido-1,3,4,6-tetra-O-acetyl-2-deoxy-D-galactopyranose | 389.35 | 19.2 g | 0.049 | 1 | | MA07898110 | Carbosynth |
| DCM, anhydrous | | | | | 300 | BOON0138 | Acros 34846-1000 |
| Trimethylsilyltrifluoromethane-sulfonate (TMSOTf) | 222.26 (1.23) | | 0.118 | 2.4 | 21.4 | BCBB3628V | Fluka 91741-50 mL |
| Triethylamine (TEA) | 101.2 (0.726) | | 0.0686 | 1.4 | 9.64 | SHBC1859V | Aldrich T0886-100 mL |

Step 2

TABLE 39

| | MW (density g/mL) | Weight | Moles | equiv | Vol (mL) | Lot# | Supplier |
|---|---|---|---|---|---|---|---|
| Oxazoline intermediate | 329.20 | 17.57 | 0.049 | 1 | | | |
| 5-(tbutoxycarbonylamino)-1-pentanol | 203.4 | 14.75 g | 0.0725 | 1.48 | | SQCQJ-TM | TCI B2869 >97% |
| DCM, anhydrous | | | | | 300 | BOON0138 | Acros 34846-1000 |
| Trimethylsilyltrifluoromethane-sulfonate (TMSOTf) | 222.26 (1.23) | | 0.024 | 0.49 | 4.34 | BCBB3628V | Fluka 91741-50 mL |
| Triethylamine (TEA) | 101.2 (0.726) | | 0.034 | 0.7 | 4.82 | SHBC1859V | Aldrich T0886-100 mL |

Synthesis
Step 1

Anhydrous DCM (300 mL) was added to 2-acetamido-1,3,4,6-tetra-O-acetyl-2-deoxy-D-galactopyranose (19.2 g, 0.049 mole) in an oven-dried 500 mL round-bottom flask (RBF) at RT under argon. TMSOTf (21.4 mL, 0.118 mole, 2.4 equiv) was then added in one portion to the thin suspension at RT. The RBF was fitted with a reflux condenser and was heated in an oil bath to bring the reaction to reflux. After 4.5 hr, thin layer chromatography (TLC) (80% EtOAc/Hexanes, visualization using $KMnO_4$ dip, product is less polar than starting material, product Rf=0.40; SM Rf=0.33) showed reaction completion. Heating was stopped and the reaction flask was allowed to reach RT. The reaction flask was placed in an ice bath for 15 min and the reaction was quenched with triethylamine (9.64 mL, 0.069 mole, 1.4 equiv), and the resulting solution was stirred for 15 min. The DCM layer was then washed with sat $NaHCO_3$ (2×125 mL), brine (1×150 mL), $H_2O$ (1×150 mL) and dried over $Na_2SO_4$ (34 g) with stirring for 1 hr. The golden yellow solution was filtered and concentrated under reduced atmosphere (bath temp 29° C.). This material can be stored at −20° C. without any deleterious effects. The residue was placed under high vacuum for 2 hr to give a thick syrup (17.57 g) which was used as is in the next step.

Step 2

Anhydrous DCM (200 mL) was added to the oxazoline intermediate (obtained in step 1) at RT under argon. When complete dissolution was achieved a solution of 5-(t-butoxycarbonylamino)-1-pentanol) dissolved in anhydrous DCM (100 mL) was added. 4 Å molecular sieves (powdered, used as received from supplier) were added at RT and the suspension was stirred for 1 hr under argon. TMSOTf (4.34 mL, 0.024 mole, 0.49 equiv) was added in one portion at RT and the suspension was stirred at RT overnight. After 21 hr at RT the reaction flask was placed in an ice bath for 25 min, then triethylamine (4.82 mL, 0.034 mole, 0.7 equiv) was added over 1 min. After 30 min the ice bath was removed and the reaction was allowed to reach RT over 30 min. The reaction suspension was filtered through a pad of celite and the celite was washed with additional DCM (75 mL). The combined DCM layer was washed with $H_2O$ (1×150 mL), sat $NaHCO_3$ (1×150 mL), $H_2O$ (1×150 mL) and dried over $Na_2SO_4$ (23 g) for 1 hr. The solution was filtered and DCM was removed under reduced atmosphere. The residue was dried under high vacuum for 7 hr.

Flash Chromatography
Column Specifications
Dry silica gel: 1250 mL

Slurrying solvent: 50% EtOAc/Hexanes
Column dimensions: 11.5 cm×14 cm (Diameter×Height)
Flow rate: ~3 L/hr
Eluent:

| | |
|---|---|
| 50% EtOAc/Hexanes | 3 L |
| 80% EtOAc/Hexanes | 5 L |
| 100% EtOAc/Hexanes | 2 L |

Elution and Fraction Collection

After 5.5 L had eluted, fraction collection was started. A total of 17×250 mL fractions were collected. The pure product was in fractions 2 to 15. The pure fraction was concentrated on a rotavap to give a white waxy solid. The solid was dried under high vacuum for 24 hr to give 18.71 g (72% yield for 2 steps) of Ac-Galactosamine-$C_5$-NHBoc (MQ-02-70).

$^1$H-NMR (CD$_3$OD, 400 MHz) of Ac-Galactoseamin-$C_5$-NHBoc (MQ-02-70): Results: NMR looks consistent for proposed structure.

Part 5: Synthesis of Fmoc-amido-tri-NAG(OAc)$_4$

Sugar Deprotection:

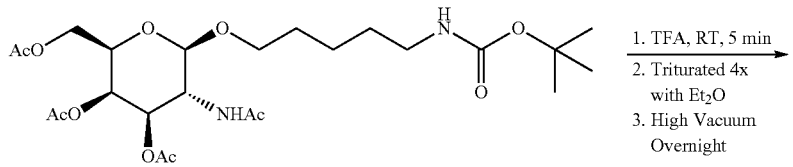

1. TFA, RT, 5 min
2. Triturated 4x with Et$_2$O
3. High Vacuum Overnight

TL-01-74
Molecular Weight: 532.58

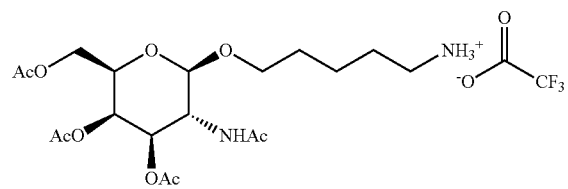

TL-01-74 deprotected
Molecular Weight: 546.49

Coupling Reaction:

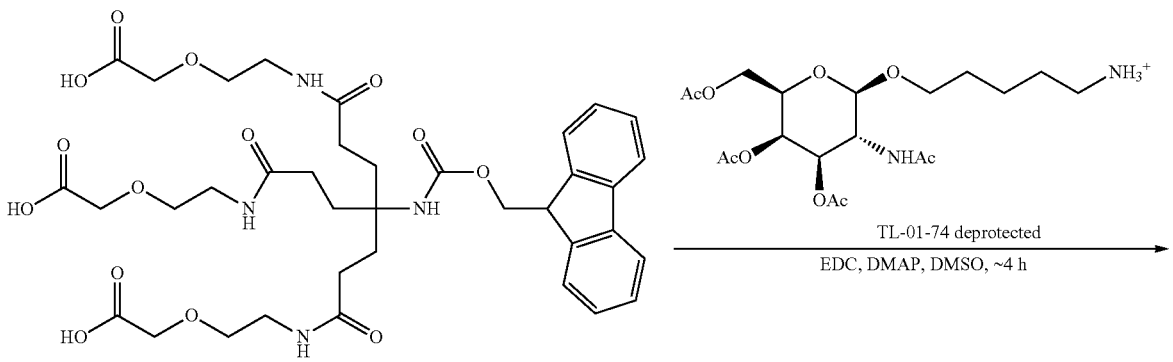

MD-03-21 HPLC very pure
Chemical Formula: $C_{37}H_{48}N_4O_{14}$
Molecular Weight: 772.80

TL-01-74 deprotected
EDC, DMAP, DMSO, ~4 h

-continued

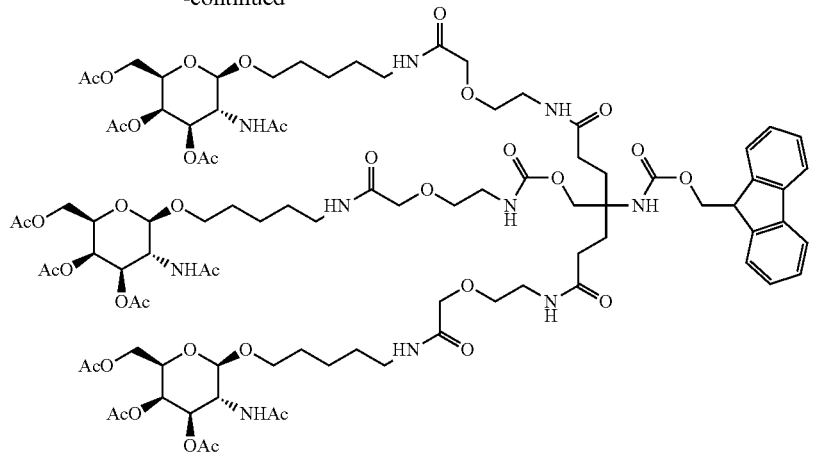

MD-03-24
Chemical Formula: $C_{94}H_{138}N_{10}O_{38}$
Molecular Weight: 2016.15

Procedure:
Step 1. Sugar Deprotection:

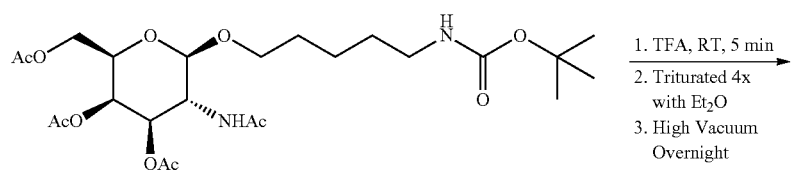

TL-01-74
Molecular Weight: 532.58

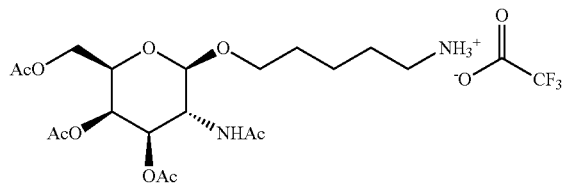

TL-01-74 deprotected
Molecular Weight: 546.49

To a 250 mL one-neck round-bottom flask was added TL-01-74 (9.08 g, 17.1 mmol) followed by trifluoroacetic acid (50 mL, TFA). Once all of the carbohydrate was completely dissolved the TFA was evaporated using a rotary evaporator until a light yellow oil is produced. The carbohydrate was triturated with diethyl ether (Et$_2$O, 4×75 mL). Following the final trituration, the remaining was removed using a rotary evaporator then the crude carbohydrate is placed onto a high vacuum line (pressure ~0.5. mmHg) overnight. After high vacuum overnight the process provided 8.75 g (94%) of the deprotected sugar.

Step 2. Coupling Reaction
Coupling Reaction:

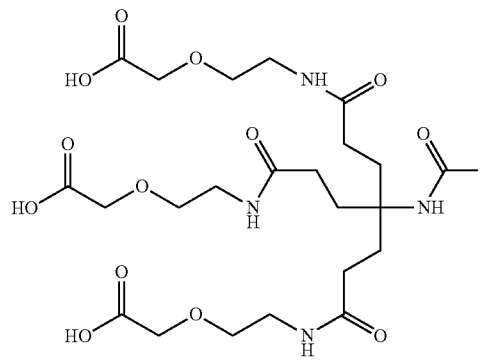

MD-03-21 HPLC very pure
Chemical Formula: $C_{37}H_{48}N_4O_{14}$
Molecular Weight: 772.80

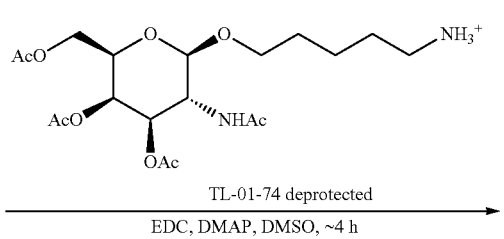

TL-01-74 deprotected
EDC, DMAP, DMSO, ~4 h

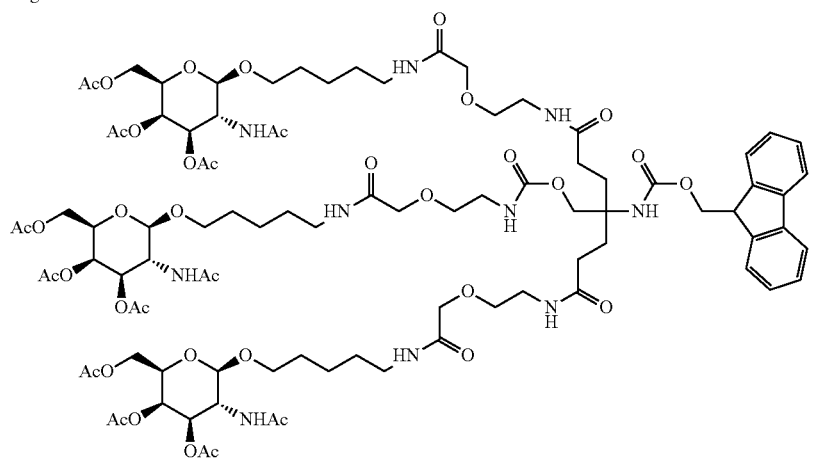

MD-03-24
Chemical Formula: $C_{94}H_{138}N_{10}O_{38}$
Molecular Weight: 2016.15

To a 100 mL one-neck round bottom flask was added the purified triacid MD-03-21 (1.33 g, 1.72 mmol). Then the sugar TL-01-74 deprotected (8.47 g, 15.5 mmol) dissolved in anhydrous DMSO (15 mL) was added to the reaction vial containing the triacid (MD-03-21). Any residual sugar was washed with additional DMSO (5 mL) and transferred into the reaction mixture. Then 4-(dimethylamino)pyridine (11.0 mg, 0.09 mmol, DMAP) was added to the reaction followed by N-hydroxysuccinimide (1.78 g, 15.5 mmol, NHS). This mixture was stirred vigorously at room temperature while N-(3-dimethylaminopropyl)-N'-ethylcarbodiimide (2.75 mL, 15.5 mmol, EDC) was added dropwise to the reaction over ca. 5 min.

The reaction progress can be followed by analytical HPLC by diluting the reaction mixture (10 μL) into a solution of MeOH (500 μL) with H$_2$O (200 μL L) and injecting 50 μL of that diluted mixture. The HPLC analysis was determined using Shimadzu LD-20AB with the UV detector set to 210 nm through a C18 analytical reverse phase column (ES Industries Chromega Columns, Sonoma C18 catalog number 155B21-SMA-C18(2), 100 Å, 25.0 cm×4.6 mm, column heated to 30.0° C., CH$_3$CN/H$_2$O containing 0.01% TFA, isocratic gradient at 10% CH$_3$CN for 2 min, then linear gradient from 10% to 60% CH$_3$CN over 20 min, total flow rate of 1.0 mL/min). The triacid starting material MD-03-21 has a retention time of 16.4 min and the desired product MD-03-24 has a retention time of 19.8 min using the above HPLC analysis. The intermediate where only one sugar has been added has a retention time of 17.9 min while the intermediate where two sugars are added has a retention time of 19.0 min. This reaction used the free amine form of EDC which can cause the removal of Fmoc protecting group. In this particular process only a small amount of the product where Fmoc was deprotected was detected using this HPLC analysis. This Fmoc fragment had a retention time of 26.6 min. Furthermore, the other fragment from Fmoc removal, the tri-sugar without Fmoc, has a retention time of 13.5 min using the above HPLC conditions.

Analysis after 3-4 hrs indicated the reaction was not complete, and additional N-(3-dimethylaminopropyl)-N'-ethylcarbodiimide (900 μL, 5.1 mmol, EDC) was added. After the additional 900 μL of EDC was added the reaction was still incomplete by HPLC analysis. Subsequently, incremental additions of EDC were made throughout the day until most of the starting material and intermediates were consumed by HPLC. The reaction was quenched after a total of 1800 μL (10.2 mmol) of additional EDC had been added to the reaction mixture (therefore, the total amount of EDC needed to drive this reaction to completion was 4.55 mL (25.7 mmol)). The reaction was quenched by the addition of H₂O (30 mL) and MeOH (20 mL), and the quenched reaction was then frozen at −80° C. until HPLC purification.

The quenched reaction was thawed and the crude product was purified using C18 preparative reverse phase HPLC by Shimadzu (Phenomenex, Luna 5 C18(2), part number 00G-4252-P0-AX, 100 Å, 25.0 cm×21.2 mm, with a Security-Guard PREP Cartridge, C18 15×21.2 mm ID, part number AJ0-7839, CH₃CN/H₂O without any additive, isocratic gradient at 30% CH₃CN for 5 min, then linear gradient from 30% to 53% CH₃CN over 20 min, total flow rate of 20.0 mL/min, column at room temperature). Roughly 1.0 mL of the crude compound dissolved in H₂O, DMSO and MeOH (3:2:2 v/v; ca. 50 mg/mL) were injected each HPLC run. Using the HPLC purification conditions above the desired product MD-03-24 eluted between 20.1 and 21.2 min. The fraction(s) associated with the desired product were pooled together. All the fractions containing the desired product were combined and the solvent thoroughly evaporated using a rotary evaporator. Then the product was transferred to a vial and all solvents were completely removed using high vacuum for >2 hours providing 2.34 g (67%) of the desired product as a white solid.

The final product was dissolved in MeOH (ca. 1. mg/mL) and analyzed by C18 analytical reverse phase HPLC using the HPLC conditions described above.

The final product was also analyzed using a 300 MHz $^1$H NMR with CD₃OD as solvent, and is consistent for the structure. The glycosidic linkage was 100% pure beta as determined by the NMR analysis of the anomeric hydrogen signal (4.54 ppm, doublet, J=8.4 Hz, 3 hydrogen) since this signal has a large coupling constant (i.e., 8.4 Hz). The anomeric hydrogen signal at 4.54 ppm integrates to 3 protons and the aromatic signals from the Fmoc protecting group between 7.30 and 7.85 ppm integrate to 8 protons providing high confidence that there are exactly 3 N-acetyl-galactosamine molecules in this structure.

The final product was also analyzed using Bruker Esquire Ion Trap Mass Spectrometer, indicating a M+1=2039, and an M+K=2054.9

Part 6: Synthesis of Tri-NAG(OAc)₄-PEG₁₂-ECT

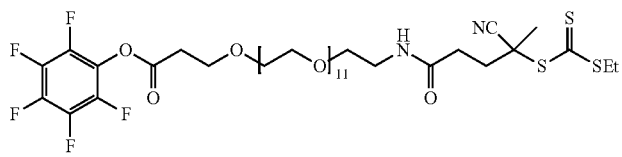

MD-03-30
Chemical Formula: C₄₂H₆₅F₅N₂O₁₅S₃
Molecular Weight: 1029.16

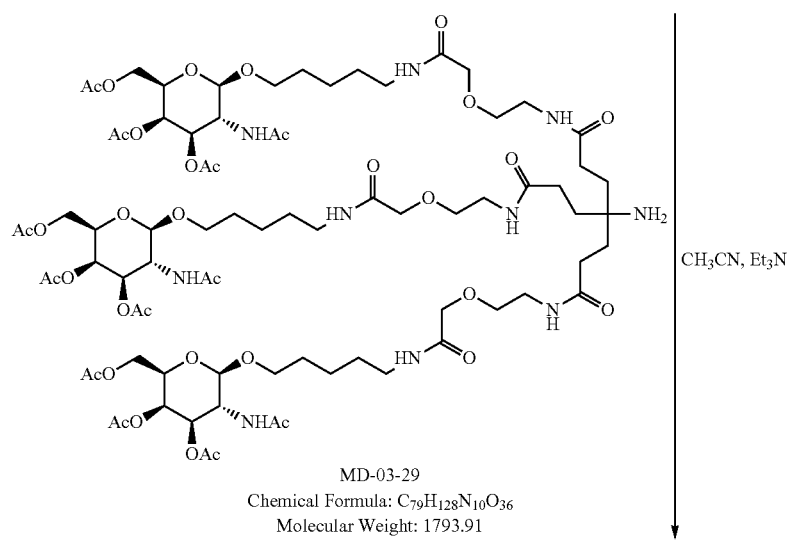

MD-03-29
Chemical Formula: C₇₉H₁₂₈N₁₀O₃₆
Molecular Weight: 1793.91

CH₃CN, Et₃N

-continued

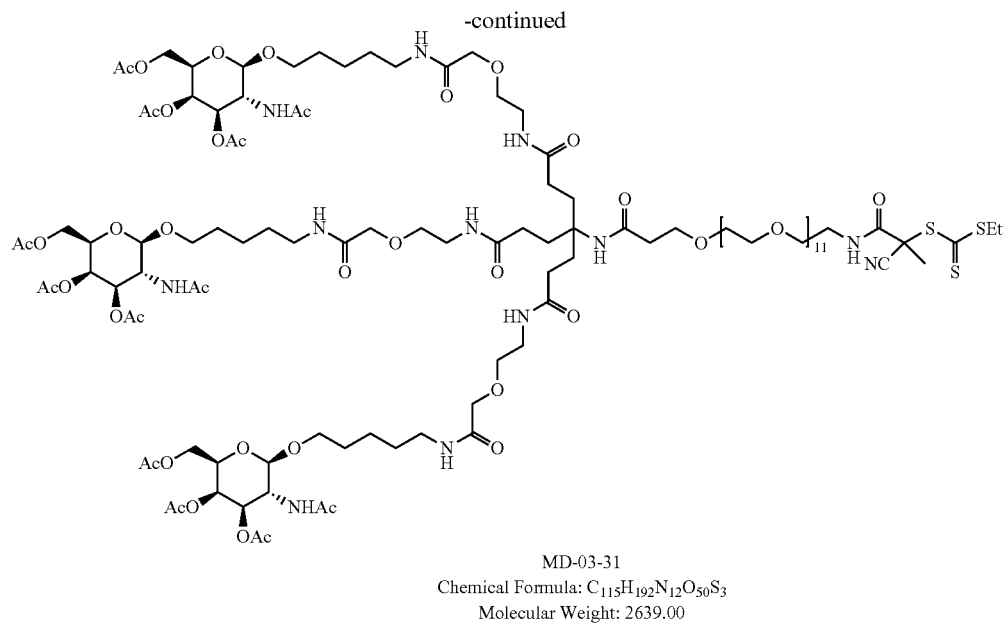

MD-03-31
Chemical Formula: $C_{115}H_{192}N_{12}O_{50}S_3$
Molecular Weight: 2639.00

Procedure:

To a 100 mL one-neck round-bottom flask was added MD-03-30 (700 mg, 0.68 mmol, extracted product) followed by anhydrous acetonitrile (2.5 mL, Lot #: B00J7229) and triethylamine (285 µL, 2.04 mmol, Lot #: A0270061). The mixture was stirred under a flow of argon gas until all of MD-03-30 was dissolved. Then the flask was cooled to 0° C. with an ice bath. To a separate flask was added MD-03-29 (1.13 g, 0.62 mmol) followed by anhydrous acetonitrile (2.5 mL, Lot #: B00J7229). This solution was stirred under a flow of argon until MD-03-29 was completely dissolved. Then the solution containing MD-03-29 was added to the reaction mixture at 0° C. drop wise over 5 min. The reaction was allowed to warm to room temperature and then it was stirred at room temperature overnight.

After reacting for 2 days the crude reaction was thoroughly evaporated using a rotary evaporator then placed under high vacuum >1 hour. After the reaction was completely evaporated the crude product was dissolved in DMSO (ca. 15 mL) and purified using C18 preparative reverse phase HPLC by Shimadzu (Phenomenex, Luna 5 C18(2), part number 00G-4252-P0-AX, 100 Å, 25.0 cm×21.2 mm, with a SecurityGuard PREP Cartridge, C18 15×21.2 mm ID, part number AJ0-7839, $CH_3CN/H_2O$ without any additive, isocratic gradient at 30% $CH_3CN$ for 5 min, then linear gradient from 30% to 53% $CH_3CN$ over 20 min, total flow rate of 20.0 mL/min, column at room temperature). Roughly 1.0 mL of the crude compound dissolved in DMSO (ca. 100 mg/mL) were injected each HPLC run. Using the HPLC purification conditions above the desired product MD-03-31 eluted between 21.6 and 23.0 min. The fraction(s) associated with the desired product were pooled together, and the water/$CH_3CN$ solvent was completely removed after each HPLC run using a rotary evaporator. The temperature of the water bath on the rotary evaporated was not allowed to reach a temperature higher than 30° C. in order to help preserve trithiocarbonate group on the CTA. After the crude reaction was completely purified and all fractions were combined with the solvents removed by rotary evaporation the condensed orange oil final product was dissolved in MeOH and transferred equally to three glass vials. The glass vials where placed under high vacuum (pressure <0.5 mmHg) overnight. The combined yield of the final product after overnight vacuum was 612 mg (37%). The bright orange oily solid product was covered with inert argon gas, the lid was screwed on tight, the vials were further sealed with parafilm and stored in the −80° C. refrigerator until used by the polymer synthesis group.

The final product was dissolved in MeOH (ca. 1. mg/mL) and analyzed by C18 analytical reverse phase HPLC—the desired product had a retention time of 20.77 min. 1H-NMR (400 MHz, $CD_3OD$) was consistent for product. The final product was also analyzed using Bruker Esquire Ion Trap Mass Spectrometer: M+2Na=1342.2 m/z, M+2H+Na=885.7 m/z.

Thus, embodiments of the block copolymers are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

We claim:

1. A synthetic oligonucleotide comprising: a nucleic acid sequence encoding a functional human ornithine transcarbamylase (OTC), wherein the nucleic acid sequence comprises a codon optimized mRNA sequence at least 95% identical to nucleic acids 48-1112 of SEQ ID NO: 114.

2. The synthetic oligonucleotide of claim 1, wherein the functional human OTC comprises an amino acid sequence having at least 95%, at least 96%, at least 97%, at least 98%, at least 99%, at least 99.5% or 100% sequence identity with amino acid residues 35-354 of SEQ ID NO:107.

3. The synthetic oligonucleotide of claim 2, wherein the functional human OTC further comprises a mitochondrial leader sequence.

4. The synthetic oligonucleotide of claim 1, wherein the functional human OTC comprises the amino acid sequence of SEQ ID NO:107.

5. The synthetic oligonucleotide of claim 1, wherein the codon optimized mRNA sequence comprises nucleic acids 48-1112 of SEQ ID NO: 114.

6. The synthetic oligonucleotide of claim 1 which comprises a sequence at least 95% identical to SEQ ID NO: 114.

7. The synthetic oligonucleotide of claim 1 which comprises a sequence at least 96%, at least 97%, at least 98%, at least 99%, at least 99.5% or 100% identical to SEQ ID NO: 114.

8. The synthetic oligonucleotide of claim 1 which comprises the sequence of SEQ ID NO: 114.

9. A composition comprising:
(a) the synthetic oligonucleotide of claim 1; and
(b) a pharmaceutically acceptable diluent or carrier.

10. The composition of claim 9, further comprising a peptide, polymer, and/or a lipid.

11. The composition of claim 10, wherein the polymer comprises a block copolymer.

12. The composition of claim 9, wherein the functional human OTC comprises the amino acid sequence of SEQ ID NO:107.

13. The composition of claim 9, wherein the codon optimized mRNA sequence comprises nucleic acids 48-1112 of SEQ ID NO: 114.

14. The composition of claim 9, wherein the synthetic oligonucleotide comprises a sequence at least 95%, at least 96%, at least 97%, at least 98%, at least 99%, at least 99.5% or 100% identical to SEQ ID NO: 114.

15. An oligonucleotide construct comprising:
(a) a nucleic acid sequence encoding a functional human ornithine transcarbamylase (OTC), wherein the nucleic acid sequence comprises a codon optimized mRNA sequence at least about 95% identical to nucleic acids 48-1112 of SEQ ID NO: 114; and
(b) a 3' polyA tail.

16. The oligonucleotide construct of claim 15, wherein the functional human OTC comprises the amino acid sequence of SEQ ID NO:107.

17. The oligonucleotide construct of claim 15, wherein the codon optimized mRNA sequence comprises nucleic acids 48-1112 of SEQ ID NO: 114.

18. The oligonucleotide construct of claim 15 which comprises a sequence at least 95%, at least 96%, at least 97%, at least 98%, at least 99%, at least 99.5% or 100% identical to SEQ ID NO: 114.

19. A method for increasing the amount of ornithine transcarbamylase (OTC) in a liver cell comprising transfecting to the liver cell a composition comprising an oligonucleotide construct comprising a nucleic acid sequence encoding a functional human OTC and a mitochondrial leader sequence, wherein the nucleic acid sequence comprises a codon optimized mRNA sequence at least about 95% identical to nucleic acids 48-1112 of SEQ ID NO: 114, wherein when the liver cell is in a subject the composition is administered to the subject intravenously, such that the amount of OTC in the liver cell is increased.

20. The method of claim 19, wherein the functional human OTC comprises the amino acid sequence of SEQ ID NO:107.

21. The method of claim 19, wherein the codon optimized mRNA sequence comprises nucleic acids 48-1112 of SEQ ID NO: 114.

22. The method of claim 19, wherein the oligonucleotide construct comprises a sequence at least 95%, at least 96%, at least 97%, at least 98%, at least 99%, at least 99.5% or 100% identical to SEQ ID NO: 114.

23. The method of claim 19, wherein the composition further comprises a peptide, polymer, and/or a lipid.

24. The method of claim 23, wherein the polymer comprises a block copolymer.

25. A method for treating ornithine transcarbamylase deficiency (OTCD) or treating or reducing the risk of hyperammonemia in a subject with OTCD comprising intravenously administering to a subject in need thereof a therapeutically effective amount of a composition comprising an oligonucleotide construct comprising a nucleic acid sequence encoding a functional human ornithine transcarbamylase (OTC) and a mitochondrial leader sequence, wherein the nucleic acid sequence comprises a codon optimized mRNA sequence at least about 95% identical to nucleic acids 48-1112 of SEQ ID NO: 114, wherein an effective amount of the nucleic acid is transfected into the liver, such that the OTCD is treated, the hyperammonemia is treated, and/or the risk of hyperammonemia is reduced in the subject.

26. The method of claim 25, wherein the codon optimized mRNA sequence comprises nucleic acids 48-1112 of SEQ ID NO: 114.

27. The method of claim 25, wherein the oligonucleotide construct comprises a sequence at least 95%, at least 96%, at least 97%, at least 98%, at least 99%, at least 99.5% or 100% identical to SEQ ID NO: 114.

28. The method of claim 25, wherein the composition further comprises a peptide, polymer, and/or a lipid.

29. The method of claim 25, wherein the subject is a human.

30. The method of claim 25, wherein the functional human OTC comprises the amino acid sequence of SEQ ID NO: 107.

* * * * *

SEQUENCE LISTING

<160> NUMBER OF SEQ ID NOS: 122

<210> SEQ ID NO 1
<211> LENGTH: 21
<212> TYPE: DNA

```
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 1
acgacaaaug ugugcgauct t                                              21

<210> SEQ ID NO 2
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 2
gcgcguugac uuauucaugt t                                              21

<210> SEQ ID NO 3
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
```

```
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 3
gcgccgugau gaauaucgat t                                              21

<210> SEQ ID NO 4
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 4
ucgccgaaau acgguccuat t                                              21

<210> SEQ ID NO 5
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 5
gccgaaauac gguccuaugt t                                              21

<210> SEQ ID NO 6
```

```
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 6
guaagugccc gaaguguaat t                                              21

<210> SEQ ID NO 7
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 7
gugcaguauc cucugacagt t                                              21

<210> SEQ ID NO 8
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
```

```
              nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 8
cugguguccc ggauaucagt t                                            21

<210> SEQ ID NO 9
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 9
ucuaguuguc gacaccuact t                                            21

<210> SEQ ID NO 10
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 10
auggcucuag uugucgacat t                                            21
```

```
<210> SEQ ID NO 11
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 11
auuucgccga aauacgguct t                                             21

<210> SEQ ID NO 12
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 12
ggcucuaguu gucgacacct t                                             21

<210> SEQ ID NO 13
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
```

```
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 13
aacugguguc ccggauauct t                                            21

<210> SEQ ID NO 14
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 14
gucaauucag cgaaguccut t                                            21

<210> SEQ ID NO 15
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 15
```

```
cucuaguugu cgacaccuat t                                              21
```

```
<210> SEQ ID NO 16
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 16
gcgaucggag gaaugccugt t                                              21
```

```
<210> SEQ ID NO 17
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 17
aaauacgguc cuauggcugt t                                              21
```

```
<210> SEQ ID NO 18
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
```

```
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 18
uuuacuucuu gacgguccat t                                              21

<210> SEQ ID NO 19
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 19
ucauggguca auucagcgat t                                              21

<210> SEQ ID NO 20
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"
```

```
<400> SEQUENCE: 20
ugugcgaucg gaggaaugct t                                              21

<210> SEQ ID NO 21
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 21
gcgcgccgug augaauauct t                                              21

<210> SEQ ID NO 22
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 22
uuucgccgaa auacgguect t                                              21

<210> SEQ ID NO 23
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
```

```
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 23
ugguuucucg aucaggacct t                                            21

<210> SEQ ID NO 24
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 24
uuaugcacgg uccccaaugt t                                            21

<210> SEQ ID NO 25
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
```

```
<223> OTHER INFORMATION: /mod_base = "5'-phosphorothioate thymidine"

<400> SEQUENCE: 25
cgaaauacgg uccuauggct t                                              21

<210> SEQ ID NO 26
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 26
uggugccacg acaaaugugt t                                              21

<210> SEQ ID NO 27
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 27
gaucgcacac auuugucgut t                                              21

<210> SEQ ID NO 28
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
```

```
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 28
caugaauaag ucaacgcgct t                                             21

<210> SEQ ID NO 29
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 29
ucgauauuca ucacggcgct t                                             21

<210> SEQ ID NO 30
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
```

-continued

```
<221> NAME/KEY: modified_base
<222> LOCATION: (21)..(21)
<223> OTHER INFORMATION: /mod_base = "5'-phosphorothioate thymidine"

<400> SEQUENCE: 30
uaggaccgua uuucggcgat t                                              21

<210> SEQ ID NO 31
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 31
cauaggaccg uauuucggct t                                              21

<210> SEQ ID NO 32
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 32
uuacacuucg ggcacuuact t                                              21

<210> SEQ ID NO 33
<211> LENGTH: 21
<212> TYPE: DNA
<213> ORGANISM: Artificial sequence
<220> FEATURE:
<223> OTHER INFORMATION: Description of the artificial sequence:
```

```
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 33
cugucagagg auacugcact t                                              21

<210> SEQ ID NO 34
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 34
cugauauccg ggacaccagt t                                              21

<210> SEQ ID NO 35
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
```

```
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 35
guaggugucg acaacuagat t                                              21

<210> SEQ ID NO 36
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 36
ugucgacaac uagagccaut t                                              21

<210> SEQ ID NO 37
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 37
gaccguauuu cggcgaaaut t                                              21

<210> SEQ ID NO 38
<211> LENGTH: 21
<212> TYPE: DNA
<213> ORGANISM: Artificial sequence
```

```
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 38
ggugucgaca acuagagcct t                                              21

<210> SEQ ID NO 39
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 39
gauauccggg acaccaguut t                                              21

<210> SEQ ID NO 40
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
```

```
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 40
aggacuucgc ugaauugact t                                               21

<210> SEQ ID NO 41
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 41
uaggugucga caacuagagt t                                               21

<210> SEQ ID NO 42
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 42
caggcauucc uccgaucgct t                                               21

<210> SEQ ID NO 43
<211> LENGTH: 21
```

```
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 43
cagccauagg accguauuut t                                              21

<210> SEQ ID NO 44
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 44
uggaccguca agaaguaaat t                                              21

<210> SEQ ID NO 45
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
```

```
-continued

<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 45
ucgcugaauu gacccaugat t                                              21

<210> SEQ ID NO 46
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 46
gcauuccucc gaucgcacat t                                              21

<210> SEQ ID NO 47
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 47
gauauucauc acggcgcgct t                                              21
```

```
<210> SEQ ID NO 48
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 48
ggaccguauu ucggcgaaat t                                            21

<210> SEQ ID NO 49
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 49
gguccugauc gagaaaccat t                                            21

<210> SEQ ID NO 50
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
```

```
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 50
cauuggggac cgugcauaat t                                              21

<210> SEQ ID NO 51
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 51
gccauaggac cguauuucgt t                                              21

<210> SEQ ID NO 52
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 52
cacauuuguc guggcaccat t                                              21
```

```
<210> SEQ ID NO 53
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 53
cagggguccu cugugaacut t                                            21

<210> SEQ ID NO 54
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 54
ugcucuucgu caucugacct t                                            21

<210> SEQ ID NO 55
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
```

```
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 55
gcucuucguc aucugaccat t                                                  21

<210> SEQ ID NO 56
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 56
ggagcuaaaa uggcagugct t                                                  21

<210> SEQ ID NO 57
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 57
```
ccugugcagc uggaauucut t                                              21

<210> SEQ ID NO 58
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 58
agaguagcug caggggucct t                                              21

<210> SEQ ID NO 59
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 59
cugacuaucc aguugauggt t                                              21

<210> SEQ ID NO 60
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate

```
        group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 60
ccauuccauu guuugugcat t                                           21

<210> SEQ ID NO 61
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 61
auaccauucc auuguuugut t                                           21

<210> SEQ ID NO 62
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"
```

-continued

<400> SEQUENCE: 62
gcaggggucc ucugugaact t                                              21

<210> SEQ ID NO 63
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 63
ccaggaccuc auggaugggt t                                              21

<210> SEQ ID NO 64
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 64
uaccauucca uuguuugugt t                                              21

<210> SEQ ID NO 65
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base

```
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 65
ugugaacuug cucaggacat t                                          21

<210> SEQ ID NO 66
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 66
uggauaucgc caggaugaut t                                          21

<210> SEQ ID NO 67
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
```

<222> LOCATION: (21)..(21)
<223> OTHER INFORMATION: /mod_base = "5'-phosphorothioate thymidine"

<400> SEQUENCE: 67
ugacuaucca guugaugggt t                                              21

<210> SEQ ID NO 68
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 68
accaugcaga auacaaaugt t                                              21

<210> SEQ ID NO 69
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 69
acuguuggau ugauucgaat t                                              21

<210> SEQ ID NO 70
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA

```
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 70
cuauccaguu gaugggcugt t                                              21

<210> SEQ ID NO 71
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 71
gacuauccag uugaugggct t                                              21

<210> SEQ ID NO 72
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
```

```
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 72
gcugacuauc caguugaugt t                                              21

<210> SEQ ID NO 73
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 73
aauaccauuc cauuguuugt t                                              21

<210> SEQ ID NO 74
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 74
acccuggugc ugacuaucct t                                              21

<210> SEQ ID NO 75
<211> LENGTH: 21
<212> TYPE: DNA
<213> ORGANISM: Artificial sequence
<220> FEATURE:
```

```
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 75
ugcuuuauuc ucccauugat t                                              21

<210> SEQ ID NO 76
<211> LENGTH: 21
<212> TYPE: DNA
<213> ORGANISM: Artificial sequence
<220> FEATURE:
<223> OTHER INFORMATION: Description of the artificial sequence:
      sense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-O-methyl corresponding
      nucleoside"
<220> FEATURE:
<221> NAME/KEY: modified_base
<222> LOCATION: (3)..(5)
<223> OTHER INFORMATION: /mod_base = "2'-deoxy-2'-fluoro corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 76
aggagcuaaa auggcagugt t                                              21

<210> SEQ ID NO 77
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
```

<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 77
aguucacaga ggaccccugt t                                              21

<210> SEQ ID NO 78
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 78
ggucagauga cgaagagcat t                                              21

<210> SEQ ID NO 79
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 79
uggucagaug acgaagagct t                                              21

<210> SEQ ID NO 80
<211> LENGTH: 21
<212> TYPE: DNA

```
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 80
gcacugccau uuuagcucct t                                         21

<210> SEQ ID NO 81
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 81
agaauuccag cugcacaggt t                                         21

<210> SEQ ID NO 82
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
```

```
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 82
ggaccccugc agcuacucut t                                              21

<210> SEQ ID NO 83
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 83
ccaucaacug gauagucagt t                                              21

<210> SEQ ID NO 84
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 84
ugcacaaaca auggaauggt t                                              21

<210> SEQ ID NO 85
```

<211> LENGTH: 21
<212> TYPE: DNA
<213> ORGANISM: Artificial sequence
<220> FEATURE:
<223> OTHER INFORMATION: Description of the artificial sequence:
    antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
    group"
<220> FEATURE:
<221> NAME/KEY: modified_base
<222> LOCATION: (1)..(2)
<223> OTHER INFORMATION: /mod_base = "2'-deoxy-2'-fluoro corresponding
    nucleoside"
<220> FEATURE:
<221> NAME/KEY: modified_base
<222> LOCATION: (3)..(5)
<223> OTHER INFORMATION: /mod_base = "2'-O-methyl corresponding
    nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 85
acaaacaaug gaaugguaut t                                              21

<210> SEQ ID NO 86
<211> LENGTH: 21
<212> TYPE: DNA
<213> ORGANISM: Artificial sequence
<220> FEATURE:
<223> OTHER INFORMATION: Description of the artificial sequence:
    antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
    group"
<220> FEATURE:
<221> NAME/KEY: modified_base
<222> LOCATION: (1)..(2)
<223> OTHER INFORMATION: /mod_base = "2'-deoxy-2'-fluoro corresponding
    nucleoside"
<220> FEATURE:
<221> NAME/KEY: modified_base
<222> LOCATION: (3)..(5)
<223> OTHER INFORMATION: /mod_base = "2'-O-methyl corresponding
    nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 86
guucacagag gaccccugct t                                              21

<210> SEQ ID NO 87
<211> LENGTH: 21
<212> TYPE: DNA
<213> ORGANISM: Artificial sequence
<220> FEATURE:
<223> OTHER INFORMATION: Description of the artificial sequence:
    antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
    group"
<220> FEATURE:
<221> NAME/KEY: modified_base
<222> LOCATION: (1)..(2)
<223> OTHER INFORMATION: /mod_base = "2'-deoxy-2'-fluoro corresponding

```
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 87
cccauccaug agguccuggt t                                              21

<210> SEQ ID NO 88
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 88
cacaaacaau ggaaugguat t                                              21

<210> SEQ ID NO 89
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 89
uguccugagc aaguucacat t                                              21
```

```
<210> SEQ ID NO 90
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 90
aucauccugg cgauauccat t                                             21

<210> SEQ ID NO 91
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 91
cccaucaacu ggauagucat t                                             21

<210> SEQ ID NO 92
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
```

```
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 92
cauuuguauu cugcauggut t                                          21

<210> SEQ ID NO 93
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 93
uucgaaucaa uccaacagut t                                          21

<210> SEQ ID NO 94
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 94
```
cagcccauca acuggauagt t                                            21

<210> SEQ ID NO 95
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 95
gcccaucaac uggauaguct t                                            21

<210> SEQ ID NO 96
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 96
caucaacugg auagucagct t                                            21

<210> SEQ ID NO 97
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"

```
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 97
caaacaaugg aaugguauut t                                              21

<210> SEQ ID NO 98
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 98
ggauagucag caccagggut t                                              21

<210> SEQ ID NO 99
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"
```

```
<400> SEQUENCE: 99
ucaaugggag aauaaagcat t                                              21

<210> SEQ ID NO 100
<211> LENGTH: 21
<212> TYPE: DNA
<213> ORGANISM: Artificial sequence
<220> FEATURE:
<223> OTHER INFORMATION: Description of the artificial sequence:
      antisense strand of dsRNA
<220> FEATURE:
<221> NAME/KEY: modified_base
<222> LOCATION: (1)..(1)
<223> OTHER INFORMATION: /mod_base = "nucleoside: lacks 5'-phosphate
      group"
<220> FEATURE:
<221> NAME/KEY: modified_base
<222> LOCATION: (1)..(2)
<223> OTHER INFORMATION: /mod_base = "2'-deoxy-2'-fluoro corresponding
      nucleoside"
<220> FEATURE:
<221> NAME/KEY: modified_base
<222> LOCATION: (3)..(5)
<223> OTHER INFORMATION: /mod_base = "2'-O-methyl corresponding
      nucleoside"
<220> FEATURE:
<221> NAME/KEY: modified_base
<222> LOCATION: (21)..(21)
<223> OTHER INFORMATION: /mod_base = "5'-phosphorothioate thymidine"

<400> SEQUENCE: 100
cacugccauu uuagcuccut t                                              21

<210> SEQ ID NO 101
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 101

Cys Lys Lys Lys Lys Lys Lys Lys Lys Lys Lys
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 102

Cys Arg Arg Arg Arg Arg Arg Arg Arg Arg Arg
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 103

Cys Lys Lys Lys Lys Lys Lys Lys Lys Lys Lys
1               5                   10

<210> SEQ ID NO 104
<211> LENGTH: 11
<212> TYPE: PRT
```

<213> ORGANISM: Artificial Sequence
<220> FEATURE:
<223> OTHER INFORMATION: Synthetic polypeptide

<400> SEQUENCE: 104

Cys Arg Arg Arg Arg Arg Arg Arg Arg Arg
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 105

Leu Leu Leu Leu Leu Leu Leu Leu Leu Leu Cys
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 106

Arg Arg Arg Arg Arg Arg Arg Arg Arg Arg Cys
1               5                   10

<210> SEQ ID NO 107
<211> LENGTH: 354
<212> TYPE: PRT
<213> ORGANISM: Homo sapiens

<400> SEQUENCE: 107

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
                20                  25                  30

Asn Lys Val Gln Leu Lys Gly Arg Asp Leu Leu Thr Leu Lys Asn Phe
            35                  40                  45

Thr Gly Glu Glu Ile Lys Tyr Met Leu Trp Leu Ser Ala Asp Leu Lys
        50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

```
Trp Ile Gly Asp Gly Asn Asn Ile Leu His Ser Ile Met Met Ser Ala
            195                 200                 205

Ala Lys Phe Gly Met His Leu Gln Ala Ala Thr Pro Lys Gly Tyr Glu
        210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
            245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
        290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
            325                 330                 335

Val Met Val Ser Leu Leu Thr Asp Tyr Ser Pro Gln Leu Gln Lys Pro
            340                 345                 350

Lys Phe

<210> SEQ ID NO 108
<211> LENGTH: 354
<212> TYPE: PRT
<213> ORGANISM: Artificial Sequence
<220> FEATURE:
<223> OTHER INFORMATION: Human ornithine transcarbamylase with mouse
      mitochondrial leader sequence

<400> SEQUENCE: 108

Met Leu Ser Asn Leu Arg Ile Leu Leu Asn Asn Ala Ala Leu Arg Lys
1               5                   10                  15

Gly His Thr Ser Val Val Arg His Phe Trp Cys Gly Lys Pro Val Gln
            20                  25                  30

Ser Gln Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190
```

Trp Ile Gly Asp Gly Asn Asn Ile Leu His Ser Ile Met Met Ser Ala
            195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
    275                 280                 285

Lys Thr Ala Lys Val Ala Ala Ser Asp Trp Thr Phe Leu His Cys Leu
290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 109
<211> LENGTH: 1262
<212> TYPE: DNA
<213> ORGANISM: Artificial Sequence
<220> FEATURE:
<223> OTHER INFORMATION: cDNA encoding human ornithine transcarbamylase,
      codon-optimized for mouse expression
<220> FEATURE:
<221> NAME/KEY: promoter
<222> LOCATION: (1)..(20)
<223> OTHER INFORMATION: T7 promoter

<400> SEQUENCE: 109
taatacgact cactataggg aaataagaga gaaagaaga gtaagaagaa atataagagc      60
caccatgctg ttcaacctca gaatcctcct caataacgcc gcctttagaa acggtcataa    120
cttcatggtc agaaacttta gatgtggtca gcctctccag aacaaagtgc agctcaaggg   180
gcgggacctg ctcaccctga aaatttcac aggcgaggaa atcaagtaca tgctctggct    240
gtctgccgat ctgaagttca ggatcaagca gaagggcgaa tatctcccac tgctccaggg   300
gaaaagtctg ggtatgatct tcgaaaagcg gagtactagg accagactgt caacagagac   360
tggattcgct ctgctcggag acacccatg ctttctgacc acacaggaca ttcatctcgg    420
tgtgaacgag tcactgaccg acacagctcg agtcctcagc tccatggcag atgccgtgct   480
ggcaagggtc tacaaacaga gtgaccctcga taccctggct aaggaagcaa gcatccccat   540
cattaatgga ctctccgacc tgtatcaccc tatccagatt ctggccgatt acctcacccct   600 gcaggagcat tattctagtc tgaaagggct cacactgagc tggattggcg acggaaacaa   660
tatcctgcac tccattatga tgtctgccgc taagtttggc atgcatctgc aggcagccac   720
accaaaagga tacgaacccg atgcttccgt gactaagctg gccgaacagt atgctaaaga   780
gaacggaact aagctgctcc tgaccaatga ccccctggag gctgcacacg ggggtaacgt   840
cctgatcact gataccctgga tttccatggg ccaggaggaa gagaagaaaa agcgcctgca   900
ggcattccag ggataccagg tgacaatgaa aactgccaag gtcgccgctt ctgattggac   960

```
ttttctccat tgtctgcccc gaaagcctga agaggtggac gatgaggtct tctattcacc    1020
tcggagcctg gtgtttccag aagccgagaa tcgcaagtgg acaatcatgg cagtgatggt    1080
gtccctcctc acagactatt ccccacagct ccagaagccc aagttttgag cggccgctta    1140
attaagctgc cttctgcggg gcttgccttc tggccatgcc cttcttctct cccttgcacc    1200
tgtacctctt ggtctttgaa taaagcctga gtaggaagtc tagagtttaa acatttaaat    1260
ct                                                                    1262
```

<210> SEQ ID NO 110
<211> LENGTH: 1262
<212> TYPE: DNA
<213> ORGANISM: Artificial Sequence
<220> FEATURE:
<223> OTHER INFORMATION: cDNA encoding human ornithine transcarbamylase
      with mouse mitochondrial leader sequence, codon-optimized for
      mouse expression
<220> FEATURE:
<221> NAME/KEY: promoter
<222> LOCATION: (1)..(20)
<223> OTHER INFORMATION: T7 promoter

<400> SEQUENCE: 110

```
taatacgact cactataggg aaataagaga gaaagaaga gtaagaagaa atataagagc      60
caccatgctc tctaacctca ggattctgct caacaacgct gctctgcgga aggccatac    120 ctctgtcgtc aggcacttct ggtgtgggaa acccgtgcag agccaggtgc agctcaaggg    180
gcgggacctg ctcaccctga aaaatttcac aggcgaggaa atcaagtaca tgctctggct    240
gtctgccgat ctgaagttca ggatcaagca gaagggcgaa tatctcccac tgctccaggg    300
gaaaagtctg gtatgatct tcgaaaagcg gagtactagg accagactgt caacagagac    360
tggattcgct ctgctcggag gacacccatg ctttctgacc acacaggaca ttcatctcgg    420
tgtgaacgag tcactgaccg acacagctcg agtcctcagc tccatggcag atgccgtgct    480
ggcaagggtc tacaaacaga gtgacctcga taccctggct aaggaagcaa gcatccccat    540
cattaatgga ctctccgacc tgtatcaccc tatccagatt ctggccgatt acctcaccct    600
gcaggagcat tattctagtc tgaaagggct cacactgagc tggattggcg acggaaacaa    660
tatcctgcac tccattatga tgtctgccgc taagtttggc atgcatctgc aggcagccac    720
accaaaagga tacgaacccg atgcttccgt gactaagctg gccgaacagt atgctaaaga    780
gaacggaact aagctgctcc tgaccaatga ccccctggag gctgcacacg ggggtaacgt    840
cctgatcact gatacctgga tttccatggg ccaggaggaa gagaagaaaa agcgcctgca    900
ggcattccag ggataccagg tgacaatgaa aactgccaag gtcgccgctt ctgattggac    960
ttttctccat tgtctgcccc gaaagcctga agaggtggac gatgaggtct tctattcacc   1020
tcggagcctg gtgtttccag aagccgagaa tcgcaagtgg acaatcatgg cagtgatggt   1080
gtccctcctc acagactatt ccccacagct ccagaagccc aagttttgag cggccgctta   1140
attaagctgc cttctgcggg gcttgccttc tggccatgcc cttcttctct cccttgcacc   1200
tgtacctctt ggtctttgaa taaagcctga gtaggaagtc tagagtttaa acatttaaat   1260
ct                                                                   1262
```

<210> SEQ ID NO 111
<211> LENGTH: 1262
<212> TYPE: DNA
<213> ORGANISM: Artificial Sequence
<220> FEATURE:
<223> OTHER INFORMATION: cDNA encoding human ornithine transcarbamylase, codon-optimized for human expression
<220> FEATURE:
<221> NAME/KEY: promoter
<222> LOCATION: (1)..(20)
<223> OTHER INFORMATION: T7 promoter

<400> SEQUENCE: 111

| | | | | | |
|---|---|---|---|---|---|
| taatacgact | cactataggg | aaataagaga | gaaagaaga | gtaagaagaa | atataagagc | 60 |
| caccatgctg | tttaacctga | ggattctgct | gaacaacgct | gcttttcgga | acggccacaa | 120 |
| ctttatggtg | cggaactttc | ggtgcggaca | gccactgcag | aacaaagtgc | agctgaaggg | 180 |
| gagggacctg | ctgaccctga | aaatttcac | aggagaggaa | atcaagtaca | tgctgtggct | 240 |
| gtctgccgat | ctgaagttcc | ggatcaagca | gaagggcgaa | tatctgccac | tgctgcaggg | 300 |
| caaaagtctg | gggatgatct | tcgaaaagag | gagtactcgg | accagactgt | caacagagac | 360 |
| tggattcgct | ctgctgggag | gacacccatg | ctttctgacc | acacaggaca | ttcatctggg | 420 |
| cgtgaacgag | tcactgaccg | acacagctcg | agtcctgagc | tccatggcag | atgccgtgct | 480 |
| ggcacgggtc | tacaaacaga | gcgacctgga | taccctggct | aaggaagcaa | gcatccccat | 540 |
| cattaatggg | ctgtccgacc | tgtatcaccc | tatccagatt | ctggccgatt | acctgaccct | 600 |
| gcaggagcat | tattctagtc | tgaaaggcct | gacactgagc | tggattgggg | acggaaacaa | 660 |
| tatcctgcac | tccattatga | tgtctgccgc | taagtttgga | atgcatctgc | aggcagccac | 720 |
| accaaaaggc | tacgaacccg | atgccagtgt | gactaagctg | gccgaacagt | atgctaaaga | 780 |
| gaacggcact | aagctgctgc | tgaccaatga | ccctctggag | gctgcacacg | gaggcaacgt | 840 |
| cctgatcact | gatacctgga | tttccatggg | ccaggaggaa | gagaagaaaa | agcgcctgca | 900 |
| ggcattccag | gggtaccagg | tgacaatgaa | aactgccaag | gtcgccgctt | ctgattggac | 960 |
| tttctgcat | tgtctgcccc | gaaaacctga | agaggtggac | gatgaggtct | tctattcacc | 1020 |
| taggagcctg | gtgttttccag | aagccgagaa | tcgcaagtgg | acaatcatgg | ctgtgatggt | 1080 |
| gtccctgctg | actgattatt | cccccccagct | gcagaaacct | aagttctgag | cggccgctta | 1140 |
| attaagctgc | cttctgcggg | gcttgccttc | tggccatgcc | cttcttctct | cccttgcacc | 1200 |
| tgtacctctt | ggtctttgaa | taaagcctga | gtaggaagtc | tagagtttaa | acatttaaat | 1260 |
| ct | | | | | | 1262 |

<210> SEQ ID NO 112
<211> LENGTH: 1221
<212> TYPE: RNA
<213> ORGANISM: Artificial Sequence
<220> FEATURE:
<223> OTHER INFORMATION: mRNA encoding human ornithine transcarbamylase,
      codon-optimized for mouse expression

<400> SEQUENCE: 112

| | | | | | |
|---|---|---|---|---|---|
| gggaaauaag | agagaaaaga | agaguaagaa | gaaauauaag | agccaccaug | cuguucaacc | 60 |
| ucagaauccu | ccucaauaac | gccgccuuua | gaaacgguca | uaacuucaug | ucagaaaacu | 120 |
| uuagaugugg | ucagccucuc | cagaacaaag | ugcagcucaa | ggggcgggac | cugcucaccc | 180 |
| ugaaaaauuu | cacaggcgag | gaaaucaagu | acaugcucug | gcugucugcc | gaucugaagu | 240 |
| ucaggaucaa | gcagaagggc | gaauaucucc | cacugcucca | ggggaaaagu | cugggugauga | 300 |
| ucuucgaaaa | gcggaguacu | aggaccagac | ugucaacaga | gacuggauuc | gcucugcucg | 360 |
| gagacacccc | augcuuucug | accacacagg | acauucaucu | cggugugaac | gagucacuga | 420 |
| ccgacacagc | ucgaguccuc | agcuccaugg | cagaugccgu | gcuggcaagg | gucuacaaac | 480 |

| | |
|---|---|
| agagugaccu cgauacccug gcuaaggaag caagcauccc caucauuaau ggacucuccg | 540 |
| accuguauca cccuauccag auucuggccg auuaccucac ccugcaggag cauuauucua | 600 |
| gucugaaagg gcucacacug agcuggauug gcgacggaaa caauauccug cacuccauua | 660 |
| ugaugucugc cgcuaaguuu ggcaugcauc ugcaggcagc cacaccaaaa ggauacgaac | 720 |
| ccgaugcuuc cgugacuaag cuggccgaac aguaugcuaa agagaacgga acuaagcugc | 780 |
| uccugaccaa ugaccccug gaggcugcac acggggguaa cguccugauc acugauaccu | 840 |
| ggauucccau gggccaggag gaagagaaga aaaagcgccu gcaggcauuc cagggauacc | 900 |
| aggugacaau gaaaacugcc aaggucgccg cuucugauug gacuuuucuc cauugucugc | 960 |
| cccgaaagcc ugaagaggug gacgaugagg ucuucuauuc accucggagc cuggguguuuc | 1020 |
| cagaagccga gaaucgcaag uggacaauca uggcagugau ggugucccuc cucacagacu | 1080 |
| auucccccaca gcuccagaag cccaaguuuu gagcggccgc uuaauuaagc ugccuucugc | 1140 |
| ggggcuugcc uucuggccau gcccuucuuc ucucccuugc accuguaccu cuuggucuuu | 1200 |
| gaauaaagcc ugaguaggaa g | 1221 |

<210> SEQ ID NO 113
<211> LENGTH: 1221
<212> TYPE: RNA
<213> ORGANISM: Artificial Sequence
<220> FEATURE:
<223> OTHER INFORMATION: mRNA encoding human ornithine transcarbamylase
      with mouse mitochondrial leader sequence, codon-optimized for
      mouse expression

<400> SEQUENCE: 113

| | |
|---|---|
| gggaaauaag agagaaaaga agaguaagaa gaaauauaag agccaccaug cucucuaacc | 60 |
| ucaggauucu gcucaacaac gcugcucugc ggaaaggcca uaccucuguc gucaggcacu | 120 |
| ucuggugugg gaaacccgug cagagccagg ugcagcucaa ggggcgggac cugcucaccc | 180 |
| ugaaaaauuu cacaggcgag gaaaucaagu acaugcucug gcugucugcc gaucugaagu | 240 |
| ucaggaucaa gcagaagggc gaauaucucc cacugcucca ggggaaaagu cuggguauga | 300 |
| ucuucgaaaa gcggaguacu aggaccgac ugucaacaga gacuggauuc gcucugcucg | 360 |
| gaggacaccc augcuuucug accacacagg acauucaucu cggugugaac gagucacuga | 420 |
| ccgacacagc ucgaguccuc agcuccaugg cagaugccgu gcuggcaagg gucuacaaac | 480 |
| agagugaccu cgauacccug gcuaaggaag caagcauccc caucauuaau ggacucuccg | 540 |
| accuguauca cccuauccag auucuggccg auuaccucac ccugcaggag cauuauucua | 600 |
| gucugaaagg gcucacacug agcuggauug gcgacggaaa caauauccug cacuccauua | 660 |
| ugaugucugc cgcuaaguuu ggcaugcauc ugcaggcagc cacaccaaaa ggauacgaac | 720 |
| ccgaugcuuc cgugacuaag cuggccgaac aguaugcuaa agagaacgga acuaagcugc | 780 |
| uccugaccaa ugaccccug gaggcugcac acggggguaa cguccugauc acugauaccu | 840 |
| ggauucccau gggccaggag gaagagaaga aaaagcgccu gcaggcauuc cagggauacc | 900 |
| aggugacaau gaaaacugcc aaggucgccg cuucugauug gacuuuucuc cauugucugc | 960 |
| cccgaaagcc ugaagaggug gacgaugagg ucuucuauuc accucggagc cuggguguuuc | 1020 |
| cagaagccga gaaucgcaag uggacaauca uggcagugau ggugucccuc cucacagacu | 1080 |
| auucccccaca gcuccagaag cccaaguuuu gagcggccgc uuaauuaagc ugccuucugc | 1140 |
| ggggcuugcc uucuggccau gcccuucuuc ucucccuugc accuguaccu cuuggucuuu | 1200 |
| gaauaaagcc ugaguaggaa g | 1221 |

<210> SEQ ID NO 114
<211> LENGTH: 1221
<212> TYPE: RNA
<213> ORGANISM: Artificial Sequence
<220> FEATURE:
<223> OTHER INFORMATION: mRNA encoding human ornithine transcarbamylase,
      codon-optimized for human expression

<400> SEQUENCE: 114

```
gggaaauaag agagaaaaga agaguaagaa gaaauauaag agccaccaug cuguuuaacc      60
ugaggauucu gcugaacaac gcugcuuuuc ggaacggcca caacuuuaug gugcggaacu     120
uucggugcgg acagccacug cagaacaaag ugcagcugaa ggggagggac cugcugaccc     180
ugaaaaauuu cacaggagag gaaaucaagu acaugcugug gcugucugcc gaucugaagu     240
uccggaucaa gcagaagggc gaauaucugc cacugcugca gggcaaaagu cggggauga     300
ucuucgaaaa gaggaguacu cggaccagac ugucaacaga gacuggauuc gcucugcugg     360
gaggacaccc augcuuucug accacacagg acauucaucu gggcgugaac gagucacuga     420
ccgacacagc ucgagucccu agcuccaugg cagaugccgu gcuggcacgg gucuacaaac     480
agagcgaccu ggauacccug gcuaaggaag caagcauccc caucauuaau gggcugcccg     540
accuguauca cccuauccag auucuggccg auuaccugac ccugcaggag cauuauucua     600
gucugaaagg ccugacacug agcuggauug gggacggaaa caauauccug cacuccauua     660
ugaugucugc cgcuaaguuu ggaaugcauc ugcaggcagc cacaccaaaa ggcuacgaac     720
ccgaugccag ugugacuaag cuggccgaac aguaugcuaa agagaacggc acuaagcugc     780
ugcugaccaa ugacccucug gaggcugcac acggaggcaa cguccugauc acugauaccu     840
ggauuuccau gggccaggag gaagagaaga aaaagcgccu gcaggcauuc caggggguacc    900
aggugacaau gaaaacugcc aaggucgccg cuucugauug gacuuucug cauugucugc     960
cccgaaaacc ugaagaggug gacgaugagg ucuucuauuc accuaggagc cugguguuuc    1020
cagaagccga gaaucgcaag uggacaauca uggcugugau ggugucccug cugacugauu    1080
auucccccca gcugcagaaa ccuaaguucu gagcggccgc uuaauuaagc ugccuucugc    1140
ggggcuugcc uucuggccau gcccuucuuc ucucccuugc accuguaccu cuugguucuuu    1200
gaauaaagcc ugaguaggaa g                                              1221
```

<210> SEQ ID NO 115
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 115

```
Leu Leu Leu Leu Leu Leu Leu Leu Leu Leu Cys
1               5                   10
```

<210> SEQ ID NO 116
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 116

```
Arg Arg Arg Arg Arg Arg Arg Arg Arg Arg Cys
1               5                   10
```

<210> SEQ ID NO 117
<211> LENGTH: 750
<212> TYPE: PRT
<213> ORGANISM: Homo sapiens

<400> SEQUENCE: 117

```
Met Leu Arg Ala Lys Asn Gln Leu Phe Leu Ser Pro His Tyr Leu
1               5                   10                  15

Arg Gln Val Lys Glu Ser Ser Gly Ser Arg Leu Ile Gln Gln Arg Leu
            20                  25                  30

Leu His Gln Gln Gln Pro Leu His Pro Glu Trp Ala Ala Leu Ala Lys
        35                  40                  45

Lys Gln Leu Lys Gly Lys Asn Pro Glu Asp Leu Ile Trp His Thr Pro
    50                  55                  60

Glu Gly Ile Ser Ile Lys Pro Leu Tyr Ser Lys Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
            100                 105                 110

Phe Ser Thr Val Glu Glu Ser Asn Lys Phe Tyr Lys Asp Asn Ile Lys
        115                 120                 125

Ala Gly Gln Gln Gly Leu Ser Val Ala Phe Asp Leu Ala Thr His Arg
    130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
                165                 170                 175

Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
        195                 200                 205

Pro Lys Glu Lys Leu Thr Gly Thr Ile Gln Asn Asp Ile Leu Lys Glu
    210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
        275                 280                 285

Arg Thr Gly Leu Gln Ala Gly Leu Thr Ile Asp Glu Phe Ala Pro Arg
    290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335

Phe Gln Pro Lys Asn Ser Lys Ser Leu Leu Arg Ala His Cys Gln
            340                 345                 350

Thr Ser Gly Trp Ser Leu Thr Glu Gln Asp Pro Tyr Asn Asn Ile Val
        355                 360                 365

Arg Thr Ala Ile Glu Ala Met Ala Ala Val Phe Gly Gly Thr Gln Ser
```

370                 375                 380
Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Ile Gln Glu Glu Ser
                405                 410                 415

Gly Ile Pro Lys Val Ala Asp Pro Trp Gly Gly Ser Tyr Met Met Glu
                420                 425                 430

Cys Leu Thr Asn Asp Val Tyr Asp Ala Ala Leu Lys Leu Ile Asn Glu
            435                 440                 445

Ile Glu Glu Met Gly Gly Met Ala Lys Ala Val Ala Glu Gly Ile Pro
        450                 455                 460

Lys Leu Arg Ile Glu Glu Cys Ala Ala Arg Arg Gln Ala Arg Ile Asp
465                 470                 475                 480

Ser Gly Ser Glu Val Ile Val Gly Val Asn Lys Tyr Gln Leu Glu Lys
                485                 490                 495

Glu Asp Ala Val Glu Val Leu Ala Ile Asp Asn Thr Ser Val Arg Asn
                500                 505                 510

Arg Gln Ile Glu Lys Leu Lys Lys Ile Lys Ser Ser Arg Asp Gln Ala
            515                 520                 525

Leu Ala Glu Arg Cys Leu Ala Ala Leu Thr Glu Cys Ala Ala Ser Gly
        530                 535                 540

Asp Gly Asn Ile Leu Ala Leu Ala Val Asp Ala Ser Arg Ala Arg Cys
545                 550                 555                 560

Thr Val Gly Glu Ile Thr Asp Ala Leu Lys Lys Val Phe Gly Glu His
                565                 570                 575

Lys Ala Asn Asp Arg Met Val Ser Gly Ala Tyr Arg Gln Glu Phe Gly
                580                 585                 590

Glu Ser Lys Glu Ile Thr Ser Ala Ile Lys Arg Val His Lys Phe Met
            595                 600                 605

Glu Arg Glu Gly Arg Arg Pro Arg Leu Leu Val Ala Lys Met Gly Gln
        610                 615                 620

Asp Gly His Asp Arg Gly Ala Lys Val Ile Ala Thr Gly Phe Ala Asp
625                 630                 635                 640

Leu Gly Phe Asp Val Asp Ile Gly Pro Leu Phe Gln Thr Pro Arg Glu
                645                 650                 655

Val Ala Gln Gln Ala Val Asp Ala Asp Val His Ala Val Gly Ile Ser
                660                 665                 670

Thr Leu Ala Ala Gly His Lys Thr Leu Val Pro Glu Leu Ile Lys Glu
            675                 680                 685

Leu Asn Ser Leu Gly Arg Pro Asp Ile Leu Val Met Cys Gly Gly Val
        690                 695                 700

Ile Pro Pro Gln Asp Tyr Glu Phe Leu Phe Glu Val Gly Val Ser Asn
705                 710                 715                 720

Val Phe Gly Pro Gly Thr Arg Ile Pro Lys Ala Ala Val Gln Val Leu
                725                 730                 735

Asp Asp Ile Glu Lys Cys Leu Glu Lys Lys Gln Gln Ser Val
            740                 745                 750

<210> SEQ ID NO 118
<211> LENGTH: 2409
<212> TYPE: RNA
<213> ORGANISM: Artificial Sequence
<220> FEATURE:
<223> OTHER INFORMATION: mRNA encoding human methylmalonyl-coenzyme A
    mutase

<400> SEQUENCE: 118

```
gggaauuaag agagaaaaga agaguaagaa gaaauauaag agccaccaug uuaagagcua    60
agaaucagcu uuuuuacuu ucaccucauu accugaggca gguaaaagaa ucaucaggcu   120
ccaggcucau acagcaacga cuucuacacc agcaacagcc ccuucaccca gaaugggcug   180
cccugguaa aaagcagcug aaaggcaaaa acccagaaga ccuaauaugg cacaccccgg   240
aagggaucuc uauaaaaccc uuguauucca agagagauac uauggacuua ccugaagaac   300
uuccaggagu gaagccauuc acacguggac cauauccuac caugauacc uuuaggcccu   360
ggaccauccg ccaguaugcu gguuuuagua cugguggaaga aagcaauaag uucuauaagg   420
acaacauuaa ggcuggucag cagggauuau caguugccuu ugaucuggcg acacaucgug   480
gcuaugauuc agacaacccu cgaguucgug gugauguugg aauggcugga guugcuauug   540
acacugugga agauaccaaa auucuuuuug auggaauucc uuuagaaaaa augucaguuu   600
ccaugacuau gaauggagca guuauuccag uucuugcaaa uuuuauagua acuggagaag   660
aacaaggugu accuaaagag aagcuuacug guaccaucca aaaugauaua cuaaaggaau   720
uuaugguucg aaauacauac auuuuuccuc cagaaccauc caugaaaauu auugcugaca   780
uauuugaaua uacagcaaag cacaugccaa aauuuaauuc aauucaauu aguggauacc   840
auaugcagga agcaggggcu gaugccauuc uggagcuggc cuauacuuua gcaugaugau   900
uggaguacuc uagaacugga cuccaggcug ccugacaau ugaugaauuu gcaccaaggu   960
ugucuuucuu cugggggaauu ggaaugaauu ucuauaugga aauagcaaag augagagcug  1020
guagaagacu cugggcucac uuaauagaga aaauguuuca gccuaaaaac ucaaaaucuc  1080
uucuucuaag agcacacugu cagacaucug gauggucacu uacgagcag gaucccuaca  1140
auaauauugu ccguacugca auagaagcaa uggcagcagu auuuggaggg acucagucuu  1200
ugcacacaaa uucuuuugau gaagcuuugg guuugcaaac ugugaaaagu gcucgaauug  1260
ccaggaacac acaaaucauc auucaagaag aaucugggau ucccaaagug gcugauccuu  1320
ggggaggguc uuuacaugau gaaugucuca caaaugaugu uuaugaugcu gcuuaaaagc  1380
ucauuaauga aauugaagaa augggugaa uggccaaagc uguagcugag ggaauaccua  1440
aacuucgaau ugaagaaugu gcugcccgaa gacaagcuag aauagauucu gguucugaag  1500
uaauuguugg aguaaauaag uaccaguugg aaaaagaaga cgcugaagaa guucggcaa  1560
uugauaauac uucagugcga acaggcagaa uugaaaaacu aagaagauc aaauccagca  1620
gggaucaagc uuugggugaa cguuugcuug cugcacuaac cgaaugugcu gcuagcggag  1680
auggaaauau ccuggcucuu gcaguggaug caucucgggc aagauguaca gugggagaaa  1740
ucacagaugc ccugaaaaag guauuuggug aacauaaagc gaaugaucga auggugagug  1800
gagcauaucg ccaggaauuu ggagaaagua agagauaac aucugcuauc aagagggcuu  1860
auaaauucau ggaacgugaa ggcucgcagac cucgcuucu uguagcaaaa augggacaag  1920
auggccauga cagaggagca aaaguuauug cuacaggauu ugcugaucuu gguuuugaug  1980
uggacauagg cccucuuuuc cagacucccuc gugaaugggc ccagcaggcu guggaugcgg  2040
augugcaugc ugugggcaua agcacccucg cugcuggca uaaaacccua guccugaac  2100
ucaucaaaga acuuaacuccc cuuggacggc cagauauucu ugcaugugu ggagggguga  2160
uaccacccuca ggauuaugaa uuucuguuug aaguggugu uccaaugua uuuggucccug  2220
ggacucgaau uccaaaggcu gccguucagg ugcuugauga uauugagaag uguuuggaaa  2280
```

-continued

```
agaagcagca aucuguauaa gcggccgcuu aauuaagcug ccuucugcgg ggcuugccuu    2340
cuggccaugc ccuucuucuc ucccuugcac cuguaccucu uggucuuuga auaaagccug    2400
aguaggaag                                                           2409
```

```
<210> SEQ ID NO 119
<211> LENGTH: 728
<212> TYPE: PRT
<213> ORGANISM: Homo sapiens

<400> SEQUENCE: 119

Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys His Val Leu Tyr Tyr Ser Arg Gln Cys Leu Met Val Ser
        35                  40                  45

Arg Asn Leu Gly Ser Val Gly Tyr Asp Pro Asn Glu Lys Thr Phe Asp
    50                  55                  60

Lys Ile Leu Val Ala Asn Arg Gly Glu Ile Ala Cys Arg Val Ile Arg
65                  70                  75                  80

Thr Cys Lys Lys Met Gly Ile Lys Thr Val Ala Ile His Ser Asp Val
                85                  90                  95

Asp Ala Ser Ser Val His Val Lys Met Ala Asp Glu Ala Val Cys Val
            100                 105                 110

Gly Pro Ala Pro Thr Ser Lys Ser Tyr Leu Asn Met Asp Ala Ile Met
        115                 120                 125

Glu Ala Ile Lys Lys Thr Arg Ala Gln Ala Val His Pro Gly Tyr Gly
    130                 135                 140

Phe Leu Ser Glu Asn Lys Glu Phe Ala Arg Cys Leu Ala Ala Glu Asp
145                 150                 155                 160

Val Val Phe Ile Gly Pro Asp Thr His Ala Ile Gln Ala Met Gly Asp
                165                 170                 175

Lys Ile Glu Ser Lys Leu Leu Ala Lys Lys Ala Glu Val Asn Thr Ile
            180                 185                 190

Pro Gly Phe Asp Gly Val Val Lys Asp Ala Glu Glu Ala Val Arg Ile
        195                 200                 205

Ala Arg Glu Ile Gly Tyr Pro Val Met Ile Lys Ala Ser Ala Gly Gly
    210                 215                 220

Gly Gly Lys Gly Met Arg Ile Ala Trp Asp Asp Glu Glu Thr Arg Asp
225                 230                 235                 240

Gly Phe Arg Leu Ser Ser Gln Glu Ala Ala Ser Ser Phe Gly Asp Asp
                245                 250                 255

Arg Leu Leu Ile Glu Lys Phe Ile Asp Asn Pro Arg His Ile Glu Ile
            260                 265                 270

Gln Val Leu Gly Asp Lys His Gly Asn Ala Leu Trp Leu Asn Glu Arg
        275                 280                 285

Glu Cys Ser Ile Gln Arg Arg Asn Gln Lys Val Val Glu Glu Ala Pro
    290                 295                 300

Ser Ile Phe Leu Asp Ala Glu Thr Arg Arg Ala Met Gly Glu Gln Ala
305                 310                 315                 320

Val Ala Leu Ala Arg Ala Val Lys Tyr Ser Ser Ala Gly Thr Val Glu
                325                 330                 335

Phe Leu Val Asp Ser Lys Lys Asn Phe Tyr Phe Leu Glu Met Asn Thr
            340                 345                 350
```

Arg Leu Gln Val Glu His Pro Val Thr Glu Cys Ile Thr Gly Leu Asp
        355                 360                 365

Leu Val Gln Glu Met Ile Arg Val Ala Lys Gly Tyr Pro Leu Arg His
    370                 375                 380

Lys Gln Ala Asp Ile Arg Ile Asn Gly Trp Ala Val Glu Cys Arg Val
385                 390                 395                 400

Tyr Ala Glu Asp Pro Tyr Lys Ser Phe Gly Leu Pro Ser Ile Gly Arg
                405                 410                 415

Leu Ser Gln Tyr Gln Glu Pro Leu His Leu Pro Gly Val Arg Val Asp
            420                 425                 430

Ser Gly Ile Gln Pro Gly Ser Asp Ile Ser Ile Tyr Tyr Asp Pro Met
        435                 440                 445

Ile Ser Lys Leu Ile Thr Tyr Gly Ser Asp Arg Thr Glu Ala Leu Lys
    450                 455                 460

Arg Met Ala Asp Ala Leu Asp Asn Tyr Val Ile Arg Gly Val Thr His
465                 470                 475                 480

Asn Ile Ala Leu Leu Arg Glu Val Ile Asn Ser Arg Phe Val Lys
                485                 490                 495

Gly Asp Ile Ser Thr Lys Phe Leu Ser Asp Val Tyr Pro Asp Gly Phe
                500                 505                 510

Lys Gly His Met Leu Thr Lys Ser Glu Lys Asn Gln Leu Leu Ala Ile
            515                 520                 525

Ala Ser Ser Leu Phe Val Ala Phe Gln Leu Arg Ala Gln His Phe Gln
        530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Val Ala Ser Asn
                565                 570                 575

Asn Gly Ser Val Phe Ser Val Glu Val Asp Gly Ser Lys Leu Asn Val
                580                 585                 590

Thr Ser Thr Trp Asn Leu Ala Ser Pro Leu Leu Ser Val Ser Val Asp
            595                 600                 605

Gly Thr Gln Arg Thr Val Gln Cys Leu Ser Arg Glu Ala Gly Gly Asn
        610                 615                 620

Met Ser Ile Gln Phe Leu Gly Thr Val Tyr Lys Val Asn Ile Leu Thr
625                 630                 635                 640

Arg Leu Ala Ala Glu Leu Asn Lys Phe Met Leu Glu Lys Val Thr Glu
                645                 650                 655

Asp Thr Ser Ser Val Leu Arg Ser Pro Met Pro Gly Val Val Val Ala
                660                 665                 670

Val Ser Val Lys Pro Gly Asp Ala Val Ala Glu Gly Gln Glu Ile Cys
            675                 680                 685

Val Ile Glu Ala Met Lys Met Gln Asn Ser Met Thr Ala Gly Lys Thr
        690                 695                 700

Gly Thr Val Lys Ser Val His Cys Gln Ala Gly Asp Thr Val Gly Glu
705                 710                 715                 720

Gly Asp Leu Leu Val Glu Leu Glu
                725

<210> SEQ ID NO 120
<211> LENGTH: 2343
<212> TYPE: RNA
<213> ORGANISM: Artificial Sequence
<220> FEATURE:

<223> OTHER INFORMATION: mRNA encoding human propionyl CoA carboxylase, alpha polypeptide (PCCA)

<400> SEQUENCE: 120

```
gggaaauaag agagaaaaga agaguaagaa gaaauauaag agccaccaug gcggggucu      60
ggucgggac agcaccgcug gucgcugccg gacggcgugg gcgguggccg ccgcagcagc     120
ugaugcugag cgcggcgcug cggacccuga agcauguucu guacuauuca agacagugcu    180
uaaugguguc ccguaaucuu gguucagugg gauaugaucc uaaugaaaaa acuuuugaua    240
aaauucuugu ugcuaauaga ggagaaauug caugucgggu auuagaacu ugcaagaaga     300
ugggcauuaa gacaguugcc auccacagug auguugaugc uaguucuguu caugugaaaa    360
uggcggauga ggcugucugu guuggcccag cucccaccag uaaaagcuac cucaacaugg    420
augccaucau ggaagccauu aagaaaacca gggcccaagc uguacauccu gguuauggau    480
uccuuucaga aacaaagaa uuugccagau guuggcagc agaagauguc guuucauug       540
gaccugacac acaugcuauu caagccaugg gcgacaagau ugaaagcaaa uuauuagcua    600
agaaagcaga gguuaauaca aucccuggcu uugauggagu agucaaggau gcagaagaag    660
cugucagaau ugcaagggaa auuggcuacc cugucaugau caaggccuca gcaggugug    720
gugggaaagg caugcgcauu gcuugggaug augaagagac cagggauggu uuuagauugu    780
caucucaaga agcugcuucu aguuuuggcg augauagacu acuaauagaa aaauuuauug    840
auaauccucg ucauauagaa auccagguuc uaggugauaa acaugggaau gcuuuauggc    900
uuaaugaaag agagugcuca auucagaaa gaaucagaa ggugguggag aagcaccaa       960
gcauuuuuuu ggaugcggag acucgaagag cgaugggaga acaagcugua gcucuugcca   1020
gagcaguaaa auauuccucu gcugggaccg uggaguuccu uguggacucu aagaagaauu   1080
uuuauuucuu ggaaaugaau acaagacucc agguugagca uccugucaca gaaugcauua   1140
cuggccugga ccuagucag gaaaugaucc guguugcuaa gggcuacccu ucucaggcaca   1200
aacaagcuga uauucgcauc aacggcuggg caguugaaug ucggguuuau gcugaggacc   1260
ccuacaaguc uuuuggguua ccaucuauug ggagauugc ucaguaccaa gaaccguuac     1320
aucuaccugg uguccgagug gacagugga uccaaccagg aagugauauu agcauuuauu    1380
augauccuau gauuucaaaa cuaaucacau auggcucuga uagaacugag gcacugaaga    1440
gaauggcaga ugcacuggau aacuauguua ucgaggugua ucacauaau auugcauuac    1500
uucgagaggu gauaaucaac ucacgcuuug uaaaggaga caucagcacu aaauuucucu    1560
ccgaugugua uccugauggc uucaaaggac acaugcuaac caagagugag aagaaccagu    1620
uauuggcaau agcaucauca uuguuugugg cauccaguu aagagcacaa cauuuucaag    1680
aaauucaag aaugccuguu auuaaaccag acauagccaa cugggagcuc ucaguaaaau    1740
ugcaugauaa aguucauacc guaguagcau caaacaaugg ucagugeuuc ucgguggaag    1800
uugauggguc gaaacuaaau gugaccagca cguggaaccu ggcuucgccc uuauugucug    1860
ucagcguuga uggcacucag aggacugucc agugcuuuc ucgagaagca gguggaaaca    1920
ugagcauuca guucuuggu acaguguaca aggugaauau cuuaaccaga cuugccgcag    1980
aauugaacaa auuuaugcug aaaaaguga cugaggacac aagcaguguu cugcguucc     2040
cgaugcccgg aguggugug gccgucucug ucaagccugg acgcgggua gcagaagguc    2100
aagaaauuug ugugauugaa gccaugaaaa ugcagauau augcacagcu gggaaaacug    2160
gcacggugaa aucugugcac ugucaagcug agacacagu uggagaaggg gaucugcucg    2220
```

```
uggagcugga augagcggcc gcuuaauuaa gcugccuucu gcggggcuug ccuucuggcc    2280
augcccuucu ucucucccuu gcaccuguac cucuuggucu uugaauaaag ccugaguagg    2340
aag                                                                 2343
```

<210> SEQ ID NO 121
<211> LENGTH: 539
<212> TYPE: PRT
<213> ORGANISM: Homo sapiens

<400> SEQUENCE: 121

```
Met Ala Ala Ala Leu Arg Val Ala Ala Gly Ala Arg Leu Ser Val
1               5                   10                  15

Leu Ala Ser Gly Leu Arg Ala Ala Val Arg Ser Leu Cys Ser Gln Ala
                20                  25                  30

Thr Ser Val Asn Glu Arg Ile Glu Asn Lys Arg Thr Ala Leu Leu
            35                  40                  45

Gly Gly Gly Gln Arg Arg Ile Asp Ala Gln His Lys Arg Gly Lys Leu
        50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                    85                  90                  95

Ala Asp Lys Asn Lys Phe Pro Gly Asp Ser Val Val Thr Gly Arg Gly
                100                 105                 110

Arg Ile Asn Gly Arg Leu Val Tyr Val Phe Ser Gln Asp Phe Thr Val
            115                 120                 125

Phe Gly Gly Ser Leu Ser Gly Ala His Ala Gln Lys Ile Cys Lys Ile
        130                 135                 140

Met Asp Gln Ala Ile Thr Val Gly Ala Pro Val Ile Gly Leu Asn Asp
145                 150                 155                 160

Ser Gly Gly Ala Arg Ile Gln Glu Gly Val Glu Ser Leu Ala Gly Tyr
                    165                 170                 175

Ala Asp Ile Phe Leu Arg Asn Val Thr Ala Ser Gly Val Ile Pro Gln
                180                 185                 190

Ile Ser Leu Ile Met Gly Pro Cys Ala Gly Gly Ala Val Tyr Ser Pro
            195                 200                 205

Ala Leu Thr Asp Phe Thr Phe Met Val Lys Asp Thr Ser Tyr Leu Phe
        210                 215                 220

Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
                    245                 250                 255

Ala His Arg Ala Phe Glu Asn Asp Val Asp Ala Leu Cys Asn Leu Arg
                260                 265                 270

Asp Phe Phe Asn Tyr Leu Pro Leu Ser Ser Gln Asp Pro Ala Pro Val
            275                 280                 285

Arg Glu Cys His Asp Pro Ser Asp Arg Leu Val Pro Glu Leu Asp Thr
        290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                    325                 330                 335

Ala Lys Asn Ile Ile Val Gly Phe Ala Arg Met Asn Gly Arg Thr Val
                340                 345                 350
```

```
Gly Ile Val Gly Asn Gln Pro Lys Val Ala Ser Gly Cys Leu Asp Ile
            355                 360                 365

Asn Ser Ser Val Lys Gly Ala Arg Phe Val Arg Phe Cys Asp Ala Phe
        370                 375                 380

Asn Ile Pro Leu Ile Thr Phe Val Asp Val Pro Gly Phe Leu Pro Gly
385                 390                 395                 400

Thr Ala Gln Glu Tyr Gly Gly Ile Ile Arg His Gly Ala Lys Leu Leu
                405                 410                 415

Tyr Ala Phe Ala Glu Ala Thr Val Pro Lys Val Thr Val Ile Thr Arg
            420                 425                 430

Lys Ala Tyr Gly Gly Ala Tyr Asp Val Met Ser Ser Lys His Leu Cys
            435                 440                 445

Gly Asp Thr Asn Tyr Ala Trp Pro Thr Ala Glu Ile Ala Val Met Gly
450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
            515                 520                 525

Arg Pro Trp Arg Lys His Ala Asn Ile Pro Leu
            530                 535

<210> SEQ ID NO 122
<211> LENGTH: 1776
<212> TYPE: RNA
<213> ORGANISM: Artificial Sequence
<220> FEATURE:
<223> OTHER INFORMATION: mRNA encoding human propionyl CoA carboxylase,
      beta polypeptide (PCCB)

<400> SEQUENCE: 122
gggaauaaag agagaaaaga agaguaagaa gaaauauaag agccaccaug gcggcggcau      60
uacggguggc ggcggucggg gcaaggcuca gcguucuggc gagcggucuc cgcgccgcgg    120
uccgcagccu uugcagccag gccaccucug uuaacgaacg caucgaaaac aagcgccgga    180
ccgcgcugcu ggggaggggc caacgccgua uugacgcgca gcacaagcga ggaaagcuaa    240
cagccaggga gaggaucagu cucuugcugg acccuggcag cuuuguugag agcgacaugu    300
uuguggaaca cagaugugca gauuuuggaa uggcugcuga uaagaauaag uuccuggag     360 acagcguggu cacuggacga ggccgaauca auggaagauu gguuuaugc uucagucagg    420 auuuuacagu uuuuggaggc agucugcag gagcacaugc ccaaaagauc ugcaaaauca    480
uggaccaggc cauaacgug ggggcuccag ugauugggcu gaaugacucu gggggagcac    540
ggauccaaga aggaguggag ucuuuggcug gcuaugcaga caucuuucug aggaauguua    600
cggcauccgg agucaucccu cagauuucuc ugaucauggg cccaugugcu ggugggccg    660 ucuacucccc agcccuaaca gacuucacgu ucauggguaaa ggacaccucc uaccuguuca    720
ucacuggccc ugauguugug aagucugucc aaugaggga uguuacccag gaggagcucg    780
guggugccaa gacccacacc accaugucag guguggccca cagagcuuuu gaaaaugaug    840
uugaugccuu guguaaucuc cgggauuucu ucaacuaccu gccccugagc agucaggacc    900
cggcucccgu ccgugagugc cacgaucccra ugaccgucuc gguuccugag cuugacacaa    960
```

```
uugucccuuu ggaaucaacc aaagccuaca acauggugga caucauacac ucuguuguug    1020
augagcguga auuuuuugag aucaugccca auuaugccaa gaacaucauu guugguuuug    1080
caagaaugaa ugggaggacu guuggaauug uuggcaacca accuaaggug gccucaggau    1140
gcuuggauau uaauucaucu gugaaagggg cucguuuugu cagauucugu gaugcauuca    1200
auauuccacu caucacuuuu guugaugucc cuggcuuucu accuggcaca gcacaggaau    1260 acggggcau cauccggcau ggugccaagc uucucuacgc auuugcugag gcaacuguac     1320
ccaaagucac agucaucacc aggaaggccu auggaggugc cuaugauguc augagcucua    1380
agcaccuuug uggugauacc aacuaugccu ggcccaccgc agagauugca gucaugggag   1440
caaagggcgc uguggagauc aucuucaaag ggcaugagaa uguggaagcu gcucaggcag    1500
aguacaucga gaaguuugcc aacccuuucc cugcagcagu gcgaggguuu ggaugaca     1560 ucauccaacc uucuuccaca cgugcccgaa ucugcuguga ccuggauguc uuggccagca    1620
agaagguaca acguccuugg agaaaacaug caaauauucc auuguaagcg gccgcuuaau   1680
uaagcugccu ucugcgggggc uugccuucug gccaugcccu ucuucucucc cuugcaccug  1740
uaccucuugg ucuuugaaua aagccugagu aggaag                              1776
```